US009950001B2

(12) United States Patent
Dowdy et al.

(10) Patent No.: US 9,950,001 B2
(45) Date of Patent: Apr. 24, 2018

(54) POLYNUCLEOTIDES HAVING BIOREVERSIBLE GROUPS

(71) Applicant: The Regents of the University of California, Oakland, CA (US)

(72) Inventors: Steven F. Dowdy, La Jolla, CA (US); Bryan R. Meade, San Diego, CA (US); Khirud Gogoi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 191 days.

(21) Appl. No.: 14/422,970

(22) PCT Filed: Aug. 20, 2013

(86) PCT No.: PCT/US2013/055675
§ 371 (c)(1),
(2) Date: Feb. 20, 2015

(87) PCT Pub. No.: WO2014/031575
PCT Pub. Date: Feb. 27, 2014

(65) Prior Publication Data
US 2015/0238516 A1 Aug. 27, 2015

Related U.S. Application Data

(60) Provisional application No. 61/691,175, filed on Aug. 20, 2012.

(51) Int. Cl.
*A61K 31/713* (2006.01)
*A61K 31/7125* (2006.01)
*C07H 21/00* (2006.01)
*C07H 21/02* (2006.01)
*C12N 15/11* (2006.01)
*C12N 15/113* (2010.01)
*A61K 47/64* (2017.01)

(52) U.S. Cl.
CPC ........ *A61K 31/713* (2013.01); *A61K 31/7125* (2013.01); *A61K 47/645* (2017.08); *C07H 21/00* (2013.01); *C07H 21/02* (2013.01); *C12N 15/111* (2013.01); *C12N 15/113* (2013.01); *C12N 2310/14* (2013.01); *C12N 2310/351* (2013.01); *C12N 2320/32* (2013.01); *C12N 2810/40* (2013.01); *Y02P 20/55* (2015.11)

(58) Field of Classification Search
None
See application file for complete search history.

(56) References Cited

U.S. PATENT DOCUMENTS

| 3,673,612 | A | 7/1972 | Merrill et al. |
|---|---|---|---|
| 4,806,463 | A | 2/1989 | Goodchild et al. |
| 4,888,278 | A | 12/1989 | Singer et al. |
| 5,489,525 | A | 2/1996 | Pastan |
| 5,547,932 | A | 8/1996 | Curiel et al. |
| 5,622,867 | A | 4/1997 | Livesey et al. |
| 5,652,122 | A | 7/1997 | Frankel et al. |
| 5,670,617 | A | 9/1997 | Frankel et al. |
| 5,674,980 | A | 10/1997 | Frankel et al. |
| 5,733,523 | A | 3/1998 | Kuijpers et al. |
| 5,747,641 | A | 5/1998 | Frankel et al. |
| 5,804,604 | A | 9/1998 | Frankel et al. |
| 5,891,641 | A | 4/1999 | Prusiner et al. |
| 5,955,591 | A | 9/1999 | Imbach et al. |
| 6,022,735 | A | 2/2000 | Curiel et al. |
| 6,077,663 | A | 6/2000 | Curiel |
| 6,124,445 | A | 9/2000 | Imbach et al. |
| 6,214,366 | B1 | 4/2001 | Prusiner et al. |
| 6,221,355 | B1 | 4/2001 | Dowdy et al. |
| 6,309,663 | B1 | 10/2001 | Patel et al. |
| 6,316,003 | B1 | 11/2001 | Frankel et al. |
| 6,348,185 | B1 | 2/2002 | Piwnica-Worms et al. |
| 6,376,248 | B1 | 4/2002 | Hawley-Nelson et al. |
| 6,399,589 | B1 | 6/2002 | Gosselin et al. |
| 6,407,077 | B1 | 6/2002 | Gosselin et al. |
| 6,423,334 | B1 | 7/2002 | Brayden et al. |
| 6,468,986 | B1 | 10/2002 | Zuckermann et al. |

(Continued)

FOREIGN PATENT DOCUMENTS

| JP | H04-500687 A | 2/1992 |
|---|---|---|
| JP | 2003-501487 | 1/2003 |

(Continued)

OTHER PUBLICATIONS

Sjakste et al., "Tightly bound to DNA proteins: Possible universal substrates for intranuclear processes" Gene (2012) vol. 492 pp. 54-64 (Year: 2012).*
Gohlke, Pascale, Extended European Search Report, European Application No. EP13831273, dated Feb. 9, 2016.
Breslow, Ronald et al., "Recognition and catalysis in nucleic acid chemistry," Proc. Natl. Acad. Sci. USA, vol. 90, Feb. 1993, pp. 1201-1207.
Chauhan et al., "PTD-Fusion Peptide as a Delivery Vehicle for siRNA to Target HIV Reservoirs", Molecular Therapy, Nature Publishing Group, vol. 13, Jan. 1, 2006, p. S277.
Dagland et al., "Fluoride-Labile Protecting Groups for the Synthesis of Base-Sensitive Methyl-SATE Oligonucleotide Prodrugs," Eur. J. Org. Chem, pp. 2327-2335, 2003.
Dias et al. "DNA-lipid systems. A physical chemistry study," Brazilian J. of Medicinal and Biological Research, 35:509-522, 2002.

(Continued)

Primary Examiner — Eric Olson
(74) Attorney, Agent, or Firm — Gavrilovich, Dodd & Lindsey LLP

(57) ABSTRACT

The disclosure provides methods and compositions for delivering polynucleotides into cells. The disclosure provides transiently protected polynucleotides comprising an anionic charge-neutralizing moiety/group, which may also confer additional functionality. These compounds can enter the cytosol of cells by endocytic or macropinocytic mechanisms. The transient protecting group is bioreversible, i.e., once inside a cell, it is designed to be removed by enzymatic activity or by passive intracellular methods (e.g., changes in pH or reductive environment).

67 Claims, 45 Drawing Sheets

(56) References Cited

U.S. PATENT DOCUMENTS

| | | | |
|---|---|---|---|
| 6,531,590 B1* | 3/2003 | Manoharan | C07H 21/00 435/91.1 |
| 6,610,841 B1 | 8/2003 | Warren | |
| 6,645,501 B2 | 11/2003 | Dowdy et al. | |
| 6,720,355 B2 | 4/2004 | Prusiner et al. | |
| 6,762,169 B1* | 7/2004 | Manoharan | A61K 47/64 435/440 |
| 6,835,810 B2 | 12/2004 | Hwu | |
| 6,841,535 B2 | 1/2005 | Divita et al. | |
| 6,903,077 B1 | 6/2005 | Heintz | |
| 7,084,248 B2 | 8/2006 | Summerton | |
| 7,101,844 B2 | 9/2006 | Kim et al. | |
| 7,166,692 B2 | 1/2007 | Karas | |
| 7,297,759 B2 | 11/2007 | Park et al. | |
| 7,329,638 B2 | 2/2008 | Yang et al. | |
| 7,354,737 B2 | 4/2008 | Lee et al. | |
| 7,420,031 B2 | 9/2008 | Karas | |
| 7,491,805 B2 | 2/2009 | Vargeese et al. | |
| 7,514,530 B2 | 4/2009 | Divita et al. | |
| 7,585,834 B2 | 9/2009 | Wender et al. | |
| 7,807,780 B2 | 10/2010 | Waugh et al. | |
| 8,691,971 B2 | 4/2014 | Petersen | |
| 2003/0125242 A1 | 7/2003 | Rosenecker et al. | |
| 2003/0143732 A1 | 7/2003 | Fosnaugh et al. | |
| 2003/0153743 A1 | 8/2003 | Manoharan et al. | |
| 2004/0127441 A1 | 7/2004 | Gleave et al. | |
| 2004/0204377 A1 | 10/2004 | Rana | |
| 2005/0032186 A1 | 2/2005 | Kim et al. | |
| 2005/0042603 A1 | 2/2005 | Wang | |
| 2005/0074884 A1 | 4/2005 | Robbins et al. | |
| 2005/0147993 A1 | 7/2005 | Khan | |
| 2005/0196414 A1 | 9/2005 | Drake et al. | |
| 2005/0239687 A1 | 10/2005 | Divita et al. | |
| 2005/0260756 A1 | 11/2005 | Troy et al. | |
| 2006/0030003 A1 | 2/2006 | Simon | |
| 2006/0035815 A1 | 2/2006 | Chen et al. | |
| 2006/0040882 A1 | 2/2006 | Chen et al. | |
| 2006/0178297 A1 | 8/2006 | Troy et al. | |
| 2006/0182736 A1 | 8/2006 | Kim et al. | |
| 2006/0205665 A1 | 10/2006 | Bonny | |
| 2006/0222657 A1 | 10/2006 | Dowdy et al. | |
| 2008/0027025 A1 | 1/2008 | Dowdy et al. | |
| 2008/0153737 A1 | 6/2008 | Lieberman et al. | |
| 2009/0093026 A1 | 4/2009 | Dowdy et al. | |
| 2009/0098049 A1 | 4/2009 | Dowdy et al. | |
| 2011/0294869 A1 | 12/2011 | Petersen | |
| 2012/0142763 A1* | 6/2012 | Dowdy | A61K 48/0091 514/44 R |

FOREIGN PATENT DOCUMENTS

| | | |
|---|---|---|
| WO | 91/14696 A1 | 10/1991 |
| WO | 97/06183 A1 | 2/1997 |
| WO | 97/47637 A1 | 12/1997 |
| WO | 9807734 A1 | 2/1998 |
| WO | 99/55717 A1 | 11/1999 |
| WO | 00/40723 A1 | 7/2000 |
| WO | 2004/007721 A1 | 1/2004 |
| WO | 2004/048545 A2 | 6/2004 |
| WO | 2005/084158 A2 | 9/2005 |
| WO | 2005/115479 A2 | 12/2005 |
| WO | 2005/117991 A2 | 12/2005 |
| WO | 2006000721 A1 | 1/2006 |
| WO | 2008/008476 A2 | 1/2008 |
| WO | 2010/129853 A2 | 11/2010 |
| WO | 2011005761 A1 | 1/2011 |

OTHER PUBLICATIONS

Ferreira et al., "Lewis acid deprotection of silyl-protected oligonucleotides and base-sensitive oligonucleotide analogs," Tetrahedron Lett., 45:6287-6290, 2004.

Hecker et al., "Prodrugs of Phosphate and Phosphonates," J. Med. Chem., 51:2328-2345, 2008.

Kosonen, Markus et al., "Hydrolysis and intramolecular transesterification of ribonucleoside 3'-phosphotriesters: the effect of alkyl groups on the general and specific acid-base-catalyzed reactions of 5'-O-pivaloyluridin-3-yl dialkyl phosphates," J. Chem. Soc., Perkin Trans. 2, 1998, pp. 663-670.

Letsinger et al., "Cationic Oligonucleotides," J. Am. Chem. Soc., 110:4470-4471, 1988.

McGuigan et al., "Intracellular Delivery of Bioactive AZT Nucleotides by Aryl Phosphate Derivatives of AZT," J. Med. Chem. 36: 1048-1052, 1993.

Meade, Bryan R., "Synthesis of bioreversible, phosphotriester-modified siRNA oligonucleotides," University of California, San Diego, http://roger.ucsd.edu:80/record=b6938126-S9, Nov. 9, 2010.

Murakami et al., Chemistry and Biology, 34(7):454-460, 1996.

Paoella et al., "Electrostatic Mechanism for DNA Bending by bZIP Proteins", Biochemistry, vol. 36, 1997, pp. 10033-10038.

Schmidt et al., "The RNA Cleavage by Hybridase .4. Oligonucleotide Probes with 2'-Deoxy-2'-Fluoronucleosides and Arabinofuranosylcytosine," Bioorganicheskaya Khimiya, 17 (6): 823-830, 1991.

Schlienger et al., "S-Acyl-2-thioethyl Aryl Phosphotriester Derivatives as Mononucleotide Prodrugs," J. Med. Chem., 43:4570-4574, 2000.

Shafiee et al., "New bis(SATE) Prodrug of AZT 5'Monophosphate: In vitro Anti-HIV Activity, Stability, and Potential Oral Absorption," J. of Pharmaceutical Sciences, 90(4):448-463, 2001.

Tosquellas et al., "The pro-oligonucleotide approach: solid phase synthesis and preliminary evaluation of model pro-dodecathymidylates," Nucleic Acids Res., 26(9):2069-2074, 1998.

Villard et al., "Phenyl phosphotriester derivatives of AZT: Variations upon the SATE Moiety," Bioorganic & Medicinal Chemistry, 16:7321-7329, 2008.

Wagner et al., "Pronucleotides:Toward the InVivo Delivery of Antiviral and Anticancer Nucleotides," Med. Res. Rev., 20(6):417-451, 2000.

Alvarez et al., "Photocleavable Protecting Groups as Nucleobase Protections Allowed the Solid-Phase Synthesis of Base-Sensitive SATE-Prooligonucleotides", J. Org. Chem., 1999, 64, 6319-6328.

Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," Pharmaceutical Research, vol. 19, No. 6, Jun. 2002.

Baharlou, Simin, International Preliminary Report on Patentability and Written Opinion, dated Jan. 13, 2009, International Application No. PCT/US07/15966.

Baharlou, Simin, International Preliminary Examination Report, PCT/US2010/036905, International Bureau of WIPO, dated Dec. 6, 2011.

Barka et al., "Transduction of TAT-HA-Beta-galactosidase Fusion Protein into Salivary Gland-derived Cells and Organ Cultures of the Devolping Gland, and into Rat Submandibular Gland in Vivo", The Journal of Histochemistry and Cytochemistry, 2000, vol. 48, No. 11, pp. 1453-1460.

Behike, Mark A., "Progress Towards in Vivo Use of siRNAs", Molecular Therapy, Apr. 2006, 13(4), pp. 644-670.

Bell-Harris Valerie. Written Opinion of the International Search Authority (US) for International Application No. PCT/US2007/15966. dated Jun. 16, 2008.

Brooks, Hilary et al., "Tat peptide-mediated cellular delivery: back to basics", Adv. Drug. Del. Reviews, 2005, vol. 57, Iss. 4, pp. 559-577.

Carpick et al., "Characterization of the Solution Complex between the Interferon-induced, Double-stranded RNA-activated Protein Kinase and HIV-1 Trans-activating Region RNA", The Journal of Biological Chemistry, vol. 272, No. 14, Apr. 4, 1997, pp. 9510-9516.

Communication Pursuant to Rules 161(2) and 162 EPC, European Patent Application No. 13831273.1, dated Jun. 1, 2015.

Da Ros et al., "Oligonucleotides and Oligonucleotide Conjugates: A New Approach for Cancer Treatment", Current Medicinal Chemistry, 2005, 12, 71-88.

Davidson, Thomas J. et al., "Highly Efficient Small Interfering RNA Delivery to Primary Mammalian Neurons Induces MicroRNA-Like

(56) References Cited

OTHER PUBLICATIONS

Effects before mRNA Degradation", The Journal of Neuroscience, Nov. 10, 2004, 24(45), 10040-10046.
Desai, Anand, International Search Report, dated Jun. 1, 2007, International Application No. PCT/US04/20837.
Falnes et al., "Ability of the Tat basic domain and VP22 to mediate cell binding, but not membrane translocation of the diptheria toxin A-fragment", Biochemistry 40: 4349-4358 (2001).
Fittipaldi, Antonio et al., "Transcellular protein transduction using the Tat protein of HIV-1", Advanced Drug Delivery Reviews, 57 (2005) 597-608.
Grotzinger, Thilo, Extended European Search Report, European Patent Application No. 07750474.4, dated Feb. 3, 2010.
Inoue, Akiko, Japanese Patent Office Action, Application No. 2009-519541, Japanese Patent Office, dated Oct. 22, 2013.
Jia, First Office Action, Application No. 2013102901292120, Japanese Patent Office, dated Nov. 1, 2013.
Jing, Xi, Application No. 200780013087.4, The State Intellectual Property Office of the People's Republic of China, Jun. 5, 2012.
Lao, Fang, Chinese Office Action, Appl. No. 200780030587.9, State Intellectual Property Office of China, dated Sep. 3, 2010.
Lao, Fang, Chinese Office Action, Appl. No. 200780030587.9, State Intellectual Property Office of China, dated Dec. 19, 2011.
Lao, Fang, Chinese Office Action, Appl. No. 200780030587.9, State Intellectual Property Office of China, dated Dec. 14, 2012.
Lao, Fang, Chinese Office Action, Appl. No. 200780030587.9, State Intellectual Property Office of China, dated Jun. 3, 2013.
Lecaillon, Jennifer, Extended European Search Report, European Patent Application No. 10783926.8, dated Apr. 19, 2013.
Martin, Molly et al., "Peptide-guided Gene Delivery", The AAPS Journal 2007; 9 (1), E18-E29.
Michiue, Hiroyuki et al., "The NH2 Terminus of Influenza Virus Hemagglutinin-2 Subunit Peptides Enhances the Antitumor Potency of Polyarginine-meidated p53 Protein Transduction", The Journal of Biological Chemistry, vol. 280, No. 9, pp. 8285-8289.
Mosher, Tera, Canadian Office Action, Appl. No. 2,659,103, Canadian Intellectual Property Office, dated Feb. 27, 2014.
Navarro-Quiroga et al., "Improved neurotensin-vector-mediated gene transfer by the coupling of hemagglutinin HA2 fusogenic peptide and Vp1 SV40 nuclear localization signal", Molecular Brain Research 105: 86-97 (2002).
Park et al., "9-Polylysine Protein Transduction Domain: Enhanced Penetration Efficiency of Superoxide Dismutase Mammalian Cells and Skin," Mol. Cells 13(2): pp. 202-208 (Apr. 2002).
Rudolph, Carsten et al., "Oligomers of the Arginine-rich Motif of the HIV-1 TAT Protein Are Capable of Transferring Plasmid DNA into Cells", The Journal of Biological Chemistry, vol. 278, No. 8, Mar. 28, 2003, pp. 11411-11418.
Ryter, Jodi M. et al., "Molecular basis of double-stranded RNA-protein interactions: structure of a dsRNA-binding domain complexed with dsRNA", The EMBO Journal, vol. 17, No. 24, pp. 7505-7513, 1998.
Scherr et al., "Gene silencing mediated by small interfering RNAs in mammalian cells," Current Medicinal Chemistry, Feb. 2003, pp. 245-256, vol. 10, No. 3.
Shin, Dana H., U.S. Office Action, U.S. Appl. No. 13/375,451, United States Patent & Trademark Office, dated Mar. 13, 2013.
Shin, Dana H., U.S. Office Action, U.S. Appl. No. 13/375,451, United States Patent & Trademark Office, dated Aug. 2, 2013.
Shin, Dana H., U.S. Office Action, U.S. Appl. No. 13/375,451, United States Patent & Trademark Office, dated Nov. 12, 2013.
Shin, Dana H., U.S. Office Action, U.S. Appl. No. 13/375,451, United States Patent & Trademark Office, dated Jan. 17, 2014.
Takenobu et al., "Development of p53 protein transduction therapy using membrane-permeable peptides and the application to oral cancer cells", Molecular Cancer Therapeutics 1: 1043-1049 (2002).
Tian, Bin et al., "The Double-Stranded-Rna-Binding Motif: Interference and Much More", Nature Reviews/Molecular Cell Biology, vol. 5, Dec. 2004, 1013-1023.
Tsuru, Takeshi, Notice of Reasons for Rejection, Japanese Patent Application No. 2008-554412, dated Sep. 25, 2012.
Uehara, Katsunori, Japanese Office Action, Appl. 2009-519541, Japanese Patent Office, dated Jan. 8, 2013.
Violini et al., "Evidence for a plasma membrane-mediated permeability barrier to Tat basic domain in well-differentiated epithelial cells: lack of correlation with heparan sulfate", Biochemistry 41: 12652-12661 (2002).
Xia et al., "The HIV Tat protein transduction domain improves the biodistribution of beta-glucoronidase expressed from recombinant viral vectors," Nature Biotechnology 19: 640-644 (2001).
Yang et al., "HIV-1 TAT-mediated protein transduction and subcellular localiztion using novel expression vector", FEBS Letters 532: 36-44 (2002).
Baharlou, Simin, International Preliminary Report on Patentability and Written Opinion, PCT/US2013/055675, The International Bureau of WIPO, dated Mar. 5, 2015.
Office Action, Chinese Patent Application No. 201380054525.7, dated Aug. 2, 2017.
Farooqui et al., Effect of Structural Variations in Cholesterol-Conjugated Oligonucleotides on Inhibitory Activity toward HIV-1, Bioconjug. Chem., 1991, vol. 2, No. 6, pp. 422-426.
Jeong Ji Hoon et al., "siRNA Conjugate Delivery Systems", Bioconjugate Chem., 2009, 20, pp. 5-14.
Juliano, R.L. et al., "The Chemistry and Biology of Oligonucleotide Conjugates", Accounts of Chemical Research, 2012, vol. 45, No. 7, pp. 1067-1076.
Letsinger et al., "Cholesteryl-conjugated oligonucleotides: Synthesis, properties, and activity as inhibitors of replication of human immunodeficiency virus in cell culture", Proc. Natl. Acad. Sci. USA, Sep. 1989, vol. 86, pp. 6553-6556.
Nomura, Hideo, Application No. 2015-528564, Japanese Patent Office, dated Jul. 25, 2017.

\* cited by examiner

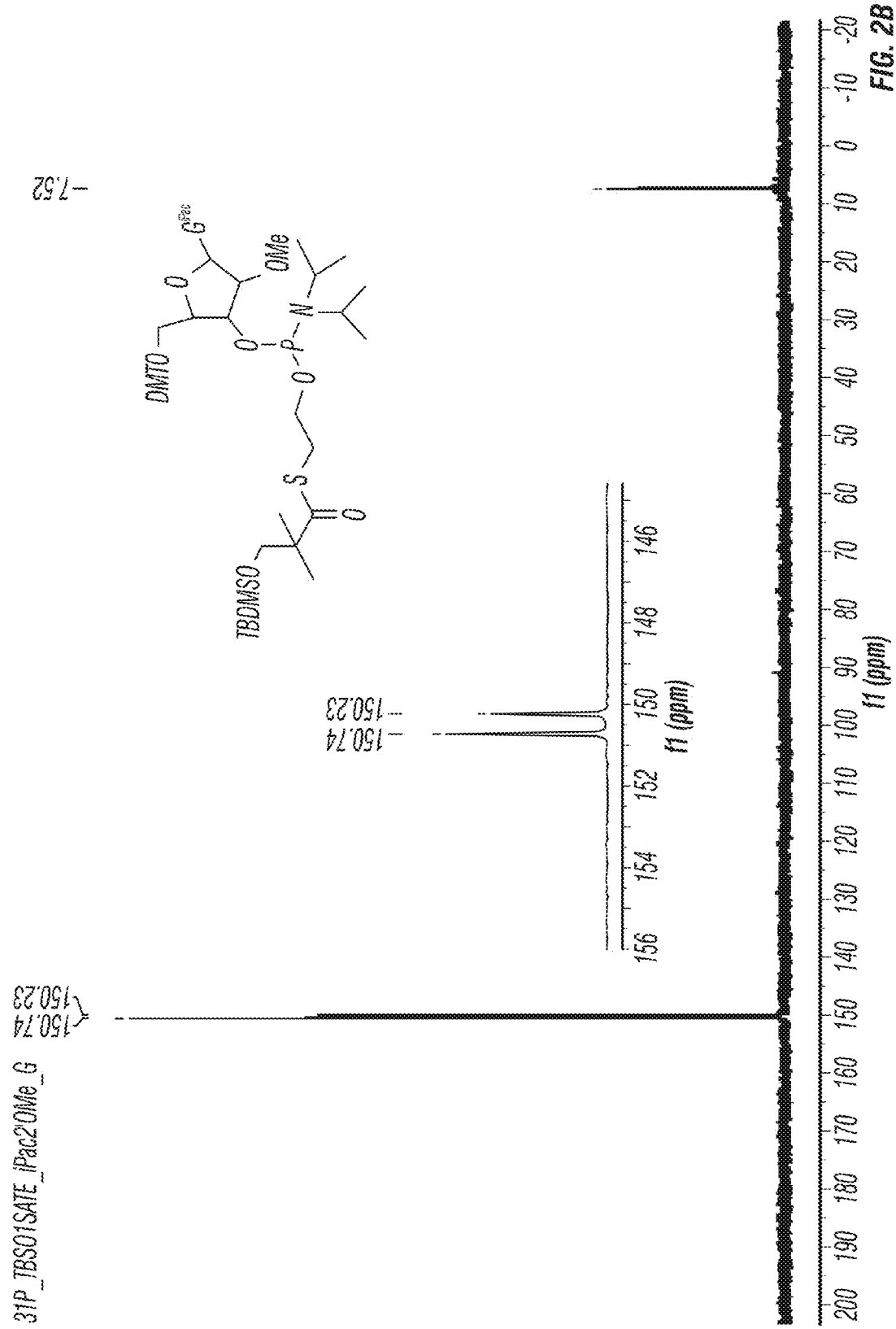

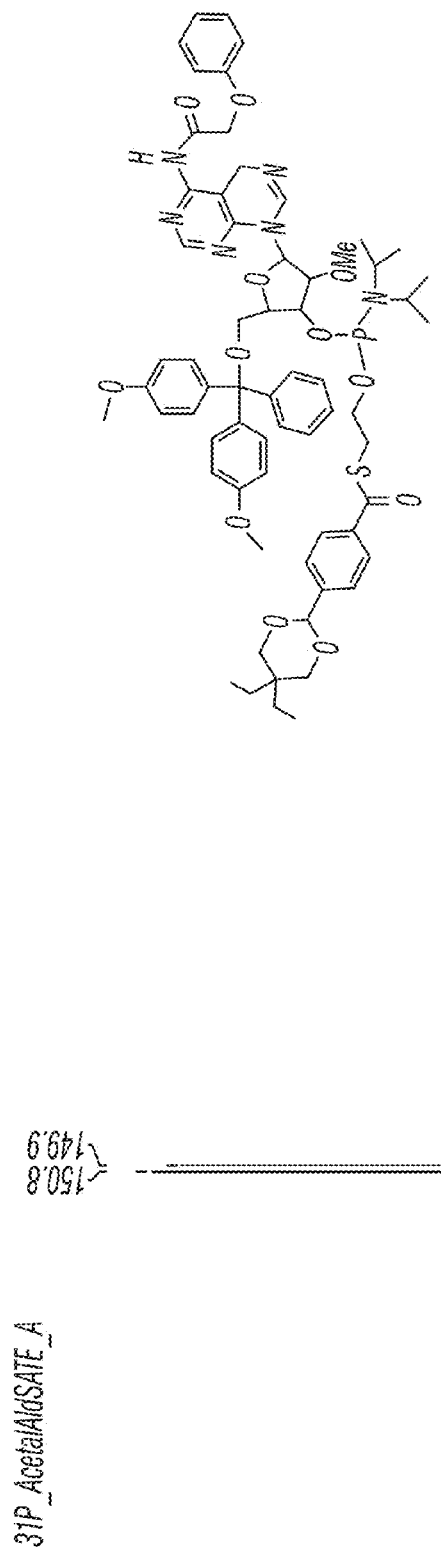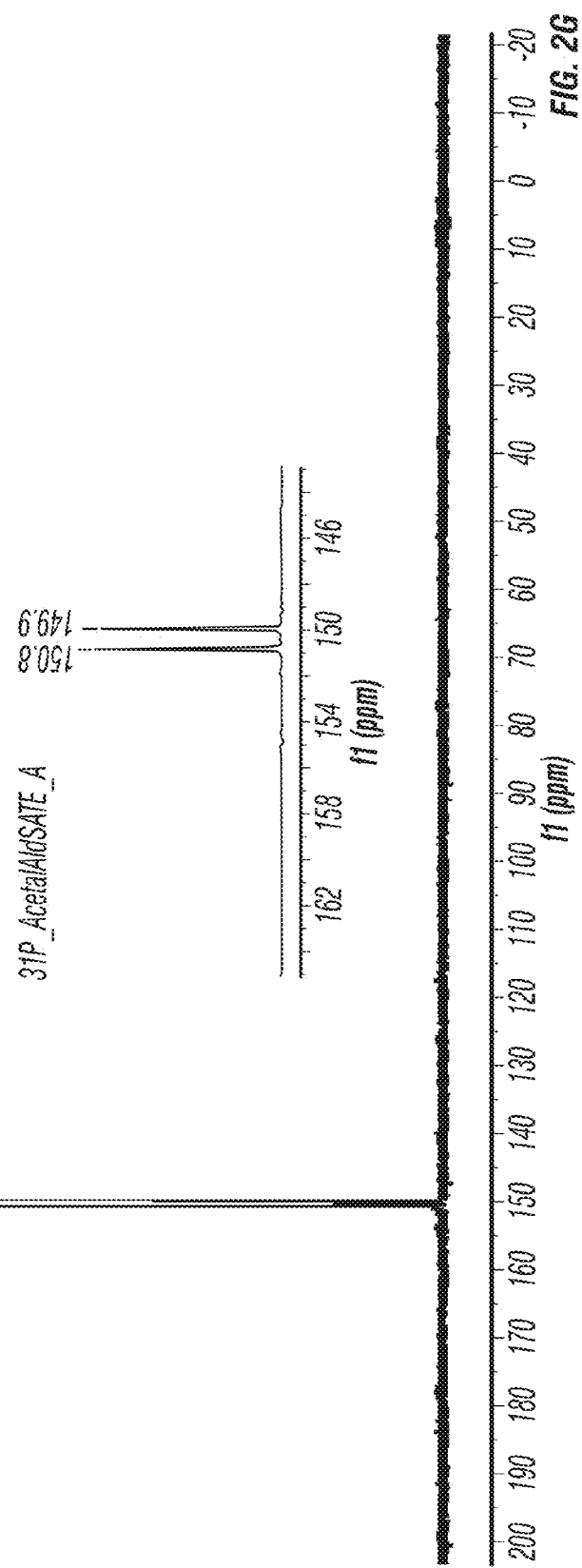
FIG. 2G

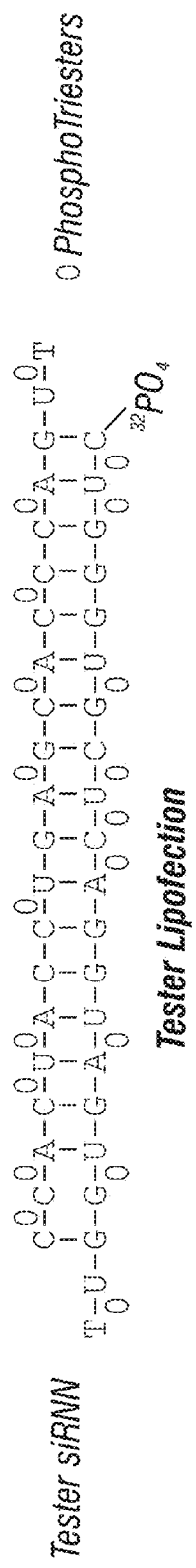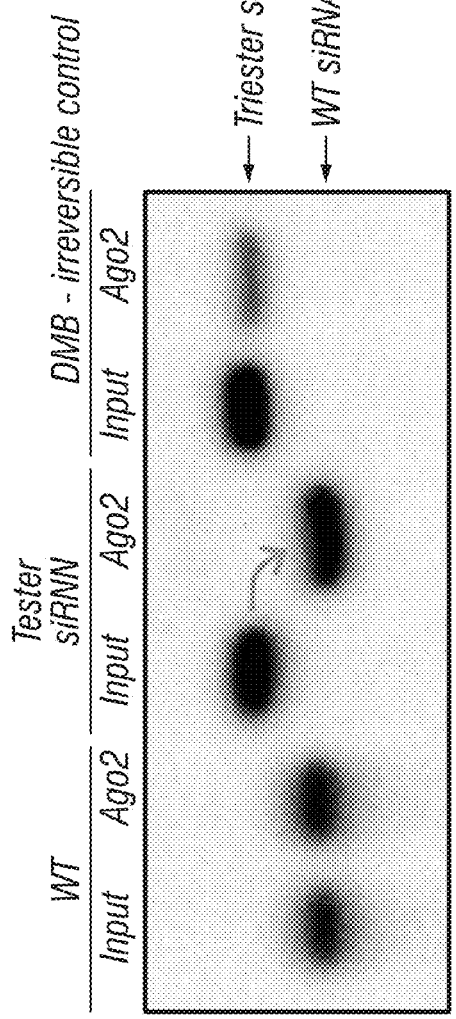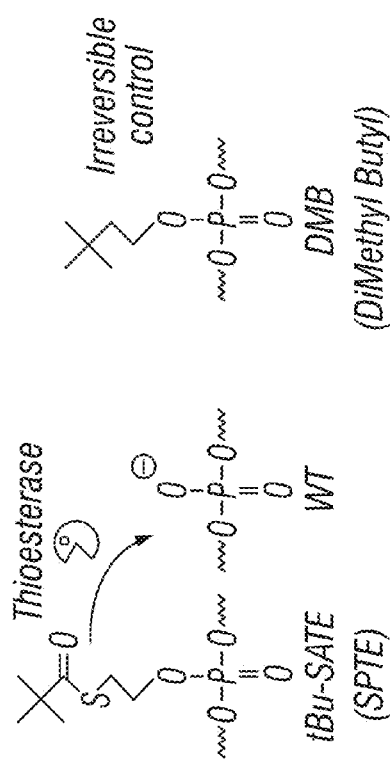
FIG. 3

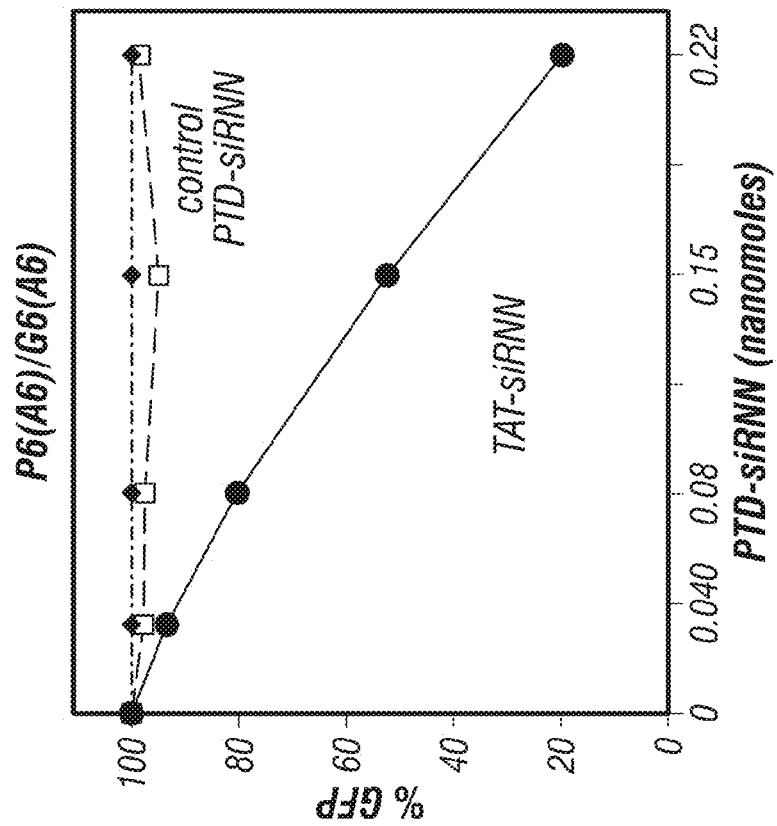
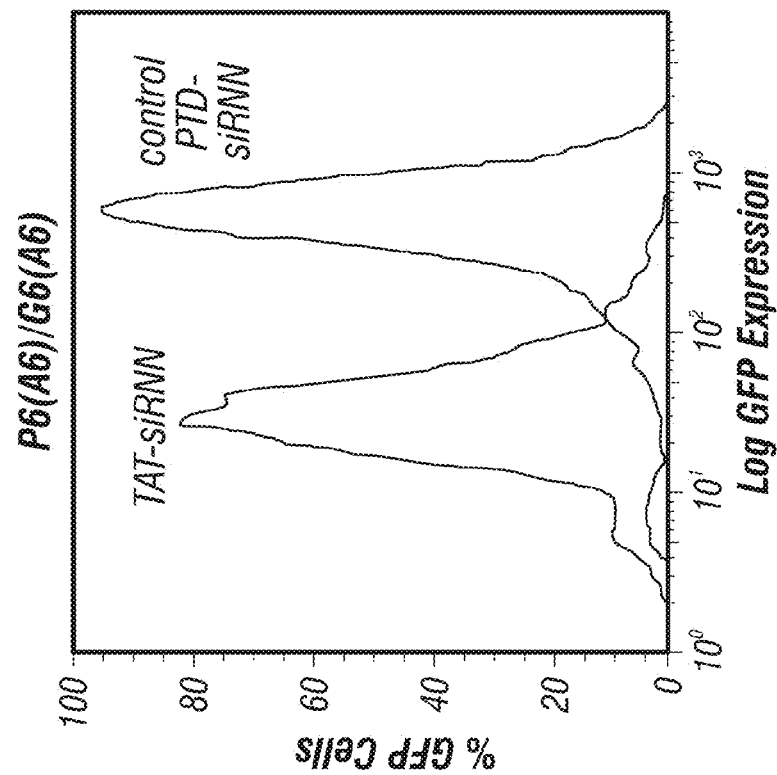
FIG. 7 (Cont'd)

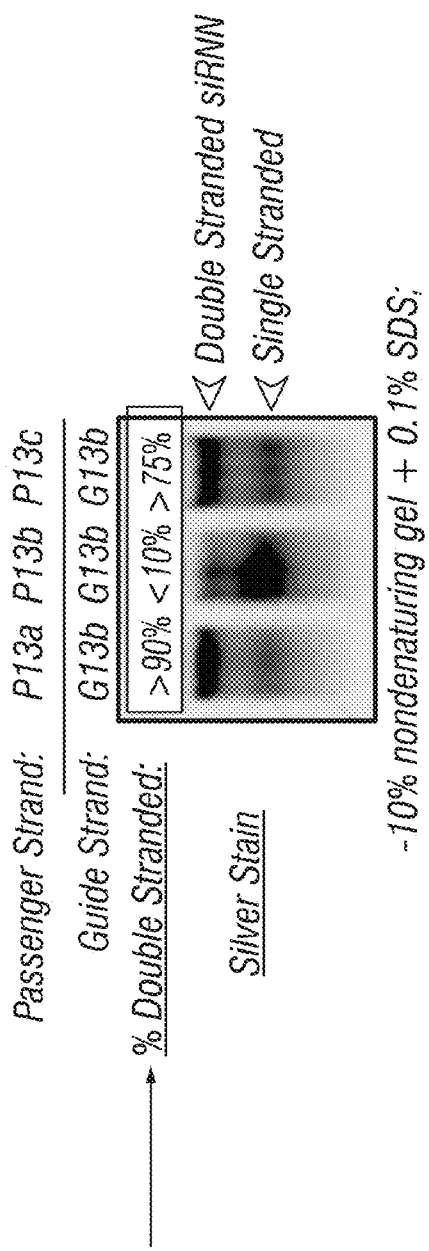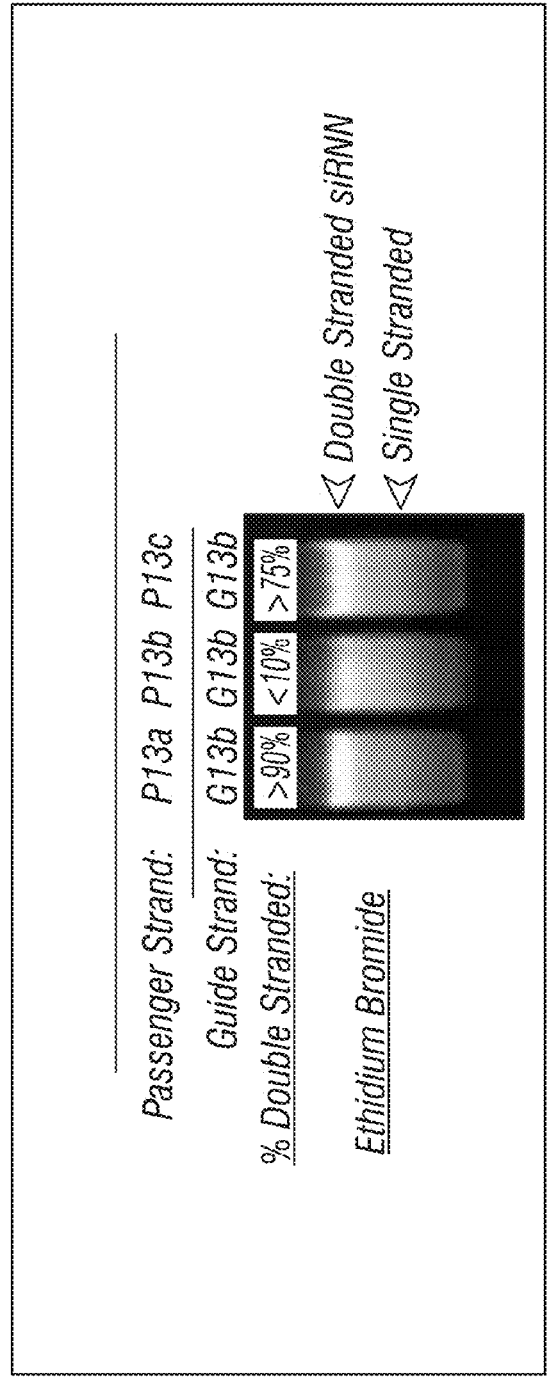
FIG. 8

Below shows the matrix of Passenger (P) strands duplexed (hybridized) to Guide (G) strands, analyzed by silver stained gels.
Example P11c = 11x O-Sate triesters, version "c" as to their locations.
For % examples = see previous page.  N.D. = Not Done

| | $P^{WT}$ | P9a | P11a | P11b | P11c | P11d | P11e | P12a | P13a | P13b | P13c | P15a |
|---|---|---|---|---|---|---|---|---|---|---|---|---|
| $G^{WT}$ | >90% | >90% | >90% | >90% | >90% | >90% | >90% | >90% | >90% | >90% | >90% | >90% |
| G9a | >90% | >90% | N.D. | N.D. | >90% | >90% | >90% | >90% | >90% | N.D. | N.D. | N.D. |
| G11a | >90% | >90% | >90% | N.D. | N.D. | >90% | N.D. | N.D. | N.D. | N.D. | N.D. | N.D. |
| G11b | >90% | >90% | >90% | >90% | N.D. | >90% | N.D. | N.D. | N.D. | N.D. | N.D. | N.D. |
| G11c | >90% | >90% | N.D. | N.D. | >90% | >90% | >90% | N.D. | >90% | >90% | >90% | ~50% |
| G13a | >90% | >90% | N.D. | N.D. | N.D. | >90% | >90% | N.D. | >90% | >90% | ~50% | <10% |
| G13b | >90% | >90% | N.D. | N.D. | N.D. | >90% | >90% | N.D. | >90% | <10% | >75% | <10% |
| G14a | >90% | >90% | N.D. | N.D. | N.D. | >90% | >90% | N.D. | ~50% | ~50% | ~50% | 0% |
| G14b | >90% | >90% | N.D. | N.D. | N.D. | >90% | >90% | N.D. | ~50% | ~50% | ~50% | 0% |
| G15a | >90% | >90% | N.D. | N.D. | N.D. | <10% | ~50% | N.D. | <10% | <10% | <10% | 0% |
| G16a | >90% | N.D. | N.D. | N.D. | N.D. | N.D. | N.D. | N.D. | N.D. | N.D. | N.D. | 0% |

FIG. 9

Passenger Strands for dsRNN Analysis $P^{WT}$
P9a = 1, 2, 4, 5, 7, 11, 13, 15, 17
P11a = 10, 11, 12, 13, 14, 15, 16, 17, 18, 19, 20
P11b = 1, 2, 3, 4, 5, 6, 7, 8, 9, 10, 11
P11c = 7, 9, 11, 13, 14, 15, 16, 17, 18, 19, 20
P11d = 1, 2, 4, 5, 7, 9, 11, 13, 15, 17, 19
P11e = 1, 2, 4, 5, 7, 11, 13, 15, 17, 19, 20
P12a = 1, 2, 4, 5, 7, 11, 13, 14, 15, 17, 19
P13a = 4, 5, 7, 9, 11, 13, 14, 15, 16, 17, 18, 19, 20
P13b = 2, 4, 5, 7, 9, 11, 13, 14, 15, 16, 17, 19, 20
P13c = 1, 5, 7, 8, 9, 13, 14, 15, 16, 17, 18, 19, 20
P15a = 1, 2, 4, 5, 7, 9, 11, 13, 14, 15, 16, 17, 18, 19, 20

Guide Strands for dsRNN Analysis $G^{WT}$
G9a = 1, 2, 6, 8, 9, 10, 14, 17, 20
G11a = 10, 11, 12, 13, 14, 15, 16, 17, 18, 19, 20
G11b = 1, 2, 3, 4, 5, 6, 7, 8, 9, 10, 11
G11c = 1, 2, 6, 8, 9, 10, 11, 14, 15, 17, 20
G13a = 1, 2, 6, 8, 9, 10, 14, 15, 16, 17, 18, 19, 20
G13b = 1, 2, 6, 8, 9, 10, 11, 13, 14, 15, 17, 19, 20
G14a = 1, 2, 6, 8, 9, 10, 11, 14, 15, 16, 17, 19, 20
G14b = 1, 2, 6, 8, 9, 10, 11, 13, 14, 15, 16, 17, 19, 20
G15a = 1, 2, 4, 6, 8, 9, 10, 11, 13, 14, 15, 16, 17, 19, 20
G16a = 1, 2, 4, 5, 6, 8, 9, 10, 11, 13, 14, 15, 16, 17, 19, 20

Note: All Triesters on this page are O-SATEs

| | $P^{WT}$ | P3(A3)a | P3(A3)b | P4(A4)a | P4(A4)b | P4(A4)c | P4(A4)d | P4(A4)e |
|---|---|---|---|---|---|---|---|---|
| $G^{WT}$ | >90% | >90% | >90% | >90% | >90% | >90% | >90% | >90% |
| G6(S6)a | >90% | >90% | >90% | >90% | >90% | >90% | >90% | >90% |
| G6a | >90% | >90% | >90% | >90% | >90% | >90% | >90% | >90% |
| G3(A3)a | >90% | >90% | >90% | >90% | >90% | >90% | >90% | >90% |
| G4(A4)a | >90% | >90% | >90% | >90% | >90% | >90% | >90% | >90% |
| G6(A6)a | >90% | >90% | >90% | >90% | >90% | >90% | >90% | >90% |

| | P5(A5)a | P6(A6)a | P6(A4S2)a | P6(S6)a |
|---|---|---|---|---|
| $G^{WT}$ | >90% | >90% | >90% | >90% |
| G6(S6)a | >90% | >90% | >90% | >90% |
| G6a | >90% | >90% | >90% | >90% |
| G3(A3)a | >90% | >90% | >90% | >90% |
| G4(A4)a | >90% | >90% | >90% | >90% |
| G6(A6)a | >90% | >90% | >90% | >90% |

FIG. 10

Ald-SATE Passenger Strands $P^{WT}$
P3(A3)a = 1-A, 13-A, 20-A
P3(A3)b = 1-A, 5-A, 20-A
P4(A4)a = 1-A, 5-A, 13-A, 20-A
P4(A4)b = 1-A, 5-A, 16-A, 20-A
P4(A4)c = 1-A, 13-A, 16-A, 20-A
P4(A4)d = 1-A, 5-A, 13-A, 16-A
P4(A4)e = 5-A, 13-A, 16-A, 20-A
P5(A5)a = 1-A, 5-A, 13-A, 16-A, 20-A
P6(A6)a = 1-A, 5-A, 9-A, 13-A, 16-A, 20-A
P6(A4S2)a = 1-A, 5-A, 9-S, 13-A, 16-S, 20-A

Ald-SATE Guide Strands $G^{WT}$
G3(A3)a = 1-A, 14-A, 20-A
G4(A4)a = 1-A, 6-A, 14-A, 20-A
G6(A6)a = 2-A, 6-A, 10-A, 14-A, 17-A, 20-A

Complement Strands for Ald-SATE Oligos

P6(S6)a = 1-S, 5-S, 9-S, 13-S, 16-S, 20-S
G6a = 2, 6, 10, 14, 17, 20 (note this is by definition ALL O-SATEs)
G6(S6)a = 2-S, 6-S, 10-S, 14-S, 17-S, 20-S A = Ald-SATE Phosphotriester
S = SPTE Phosphotriester

*FIG. 10 (Cont'd)*

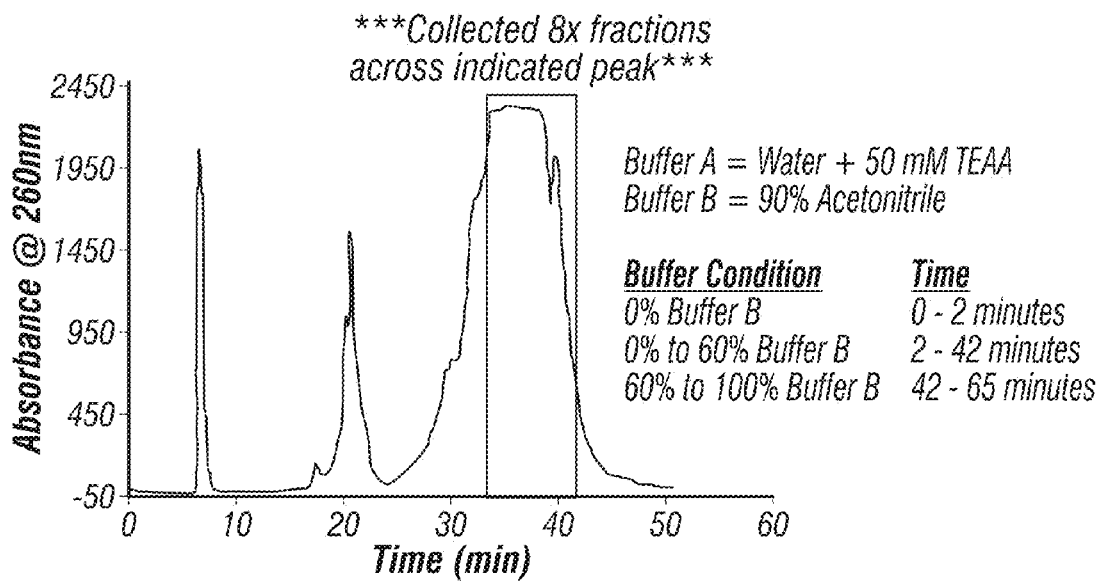
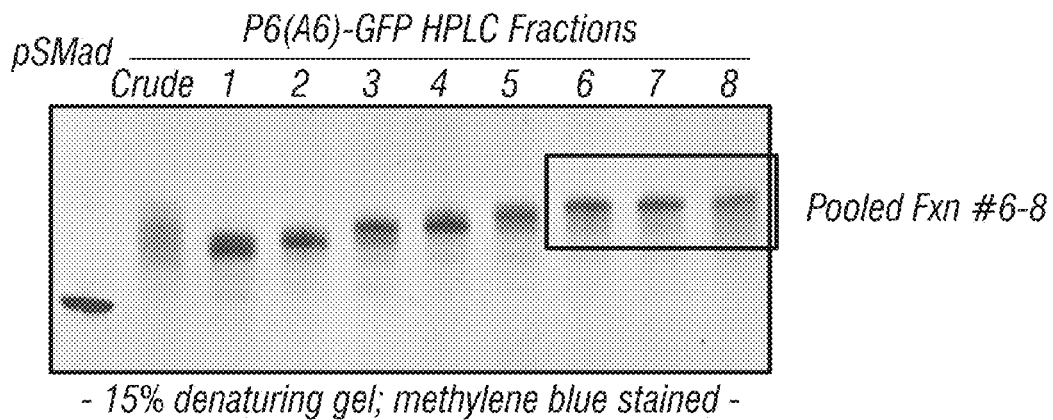
FIG. 11

```
                            SEQUENCE LISTING

<160> NUMBER OF SEQ ID NOS: 31

<210> SEQ ID NO 1
<211> LENGTH: 9
<212> TYPE: PRT
<213> ORGANISM: Artificial Sequence
<220> FEATURE:
<223> OTHER INFORMATION: Protein Transduction Domain derived from TAT

<400> SEQUENCE: 1

Arg Lys Lys Arg Arg Gln Arg Arg Arg
1               5

<210> SEQ ID NO 2
<211> LENGTH: 16
<212> TYPE: PRT
<213> ORGANISM: Artificial Sequence
<220> FEATURE:
<223> OTHER INFORMATION: Penetratin

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 21
<212> TYPE: PRT
<213> ORGANISM: Artificial Sequence
<220> FEATURE:
<223> OTHER INFORMATION: Buforin II

<400> SEQUENCE: 3

Thr Arg Ser Ser Arg Ala Gly Leu Gln Phe Pro Val Gly Arg Val His
1               5                   10                  15

Arg Leu Leu Arg Lys
            20

<210> SEQ ID NO 4
<211> LENGTH: 26
<212> TYPE: PRT
<213> ORGANISM: Artificial Sequence
<220> FEATURE:
<223> OTHER INFORMATION: Transportan

<400> SEQUENCE: 4

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 5
<211> LENGTH: 18
<212> TYPE: PRT
<213> ORGANISM: Artificial Sequence
<220> FEATURE:
<223> OTHER INFORMATION: MAP (Model Amphipathic Peptide)

<400> SEQUENCE: 5

Lys Leu Ala Leu Lys Leu Ala Leu Lys Ala Leu Lys Ala Ala Leu Lys
1               5                   10                  15
```

Leu Ala

```
<210> SEQ ID NO 6
<211> LENGTH: 16
<212> TYPE: PRT
<213> ORGANISM: Artificial Sequence
<220> FEATURE:
<223> OTHER INFORMATION: K-FGF

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Ku70

<400> SEQUENCE: 7

Val Pro Met Leu Lys Pro Met Leu Lys Glu
1               5                   10

<210> SEQ ID NO 8
<211> LENGTH: 28
<212> TYPE: PRT
<213> ORGANISM: Artificial Sequence
<220> FEATURE:
<223> OTHER INFORMATION: Prion domain

<400> SEQUENCE: 8

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 9
<211> LENGTH: 18
<212> TYPE: PRT
<213> ORGANISM: Artificial Sequence
<220> FEATURE:
<223> OTHER INFORMATION: pVEC

<400> SEQUENCE: 9

Leu Leu Ile Ile Leu Arg Arg Arg Ile Arg Lys Gln Ala His Ala His
1               5                   10                  15

Ser Lys

<210> SEQ ID NO 10
<211> LENGTH: 21
<212> TYPE: PRT
<213> ORGANISM: Artificial Sequence
<220> FEATURE:
<223> OTHER INFORMATION: Pep-1

<400> SEQUENCE: 10

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 11
<211> LENGTH: 18
<212> TYPE: PRT
```

```
<213> ORGANISM: Artificial Sequence
<220> FEATURE:
<223> OTHER INFORMATION: SynB1

<400> SEQUENCE: 11

Arg Gly Gly Arg Leu Ser Tyr Ser Arg Arg Arg Phe Ser Thr Ser Thr
1               5                   10                  15

Gly Arg

<210> SEQ ID NO 12
<211> LENGTH: 15
<212> TYPE: PRT
<213> ORGANISM: Artificial Sequence
<220> FEATURE:
<223> OTHER INFORMATION: Pep-7 (phage display)

<400> SEQUENCE: 12

Ser Asp Leu Trp Glu Met Met Met Val Ser Leu Ala Cys Gln Tyr
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: HN-1 (phage display)

<400> SEQUENCE: 13

Thr Ser Pro Leu Asn Ile His Asn Gly Gln Lys Leu
1               5                   10

<210> SEQ ID NO 14
<211> LENGTH: 8
<212> TYPE: PRT
<213> ORGANISM: Artificial Sequence
<220> FEATURE:
<223> OTHER INFORMATION: PTD consensus sequence
<220> FEATURE:
<221> NAME/KEY: MISC_FEATURE
<222> LOCATION: (1)..(1)
<223> OTHER INFORMATION: B is a basic amino acid
<220> FEATURE:
<221> NAME/KEY: MISC_FEATURE
<222> LOCATION: (2)..(4)
<223> OTHER INFORMATION: Xaa is an alpha-helix enhancing amino acid
<220> FEATURE:
<221> NAME/KEY: MISC_FEATURE
<222> LOCATION: (5)..(5)
<223> OTHER INFORMATION: B is a basic amino acid
<220> FEATURE:
<221> NAME/KEY: MISC_FEATURE
<222> LOCATION: (6)..(7)
<223> OTHER INFORMATION: Xaa is any alpha-helix enhancing amino acid
<220> FEATURE:
<221> NAME/KEY: MISC_FEATURE
<222> LOCATION: (8)..(8)
<223> OTHER INFORMATION: B is a basic amino acid

<400> SEQUENCE: 14

Asx Xaa Xaa Xaa Asx Xaa Xaa Asx
1               5

<210> SEQ ID NO 15
<211> LENGTH: 8
<212> TYPE: PRT
<213> ORGANISM: Artificial Sequence
<220> FEATURE:
<223> OTHER INFORMATION: PTD consensus sequence
<220> FEATURE:
<221> NAME/KEY: MISC_FEATURE
```

-continued

```
<222> LOCATION: (1)..(1)
<223> OTHER INFORMATION: B is a basic amino acid
<220> FEATURE:
<221> NAME/KEY: MISC_FEATURE
<222> LOCATION: (2)..(3)
<223> OTHER INFORMATION: Xaa is an alpha-helix enhancing amino acid
<220> FEATURE:
<221> NAME/KEY: MISC_FEATURE
<222> LOCATION: (4)..(5)
<223> OTHER INFORMATION: B is a basic amino acid
<220> FEATURE:
<221> NAME/KEY: MISC_FEATURE
<222> LOCATION: (6)..(7)
<223> OTHER INFORMATION: Xaa is an alpha-helix enhancing amino acid
<220> FEATURE:
<221> NAME/KEY: MISC_FEATURE
<222> LOCATION: (8)..(8)
<223> OTHER INFORMATION: B is a basic amino acid

<400> SEQUENCE: 15

Asx Xaa Xaa Asx Asx Xaa Xaa Asx
1               5

<210> SEQ ID NO 16
<211> LENGTH: 7
<212> TYPE: PRT
<213> ORGANISM: Artificial Sequence
<220> FEATURE:
<223> OTHER INFORMATION: PTD from a prion

<400> SEQUENCE: 16

Lys Lys Arg Pro Lys Pro Gly
1               5

<210> SEQ ID NO 17
<211> LENGTH: 11
<212> TYPE: PRT
<213> ORGANISM: Artificial Sequence
<220> FEATURE:
<223> OTHER INFORMATION: PTD Consensus sequence
<220> FEATURE:
<221> NAME/KEY: MISC_FEATURE
<222> LOCATION: (1)..(2)
<223> OTHER INFORMATION: Xaa is an alpha-helix enhancing amino acid
<220> FEATURE:
<221> NAME/KEY: MISC_FEATURE
<222> LOCATION: (4)..(4)
<223> OTHER INFORMATION: Xaa is an alpha-helix enhancing amino acid
<220> FEATURE:
<221> NAME/KEY: MISC_FEATURE
<222> LOCATION: (5)..(5)
<223> OTHER INFORMATION: Xaa is proline or an alpha-helix enhancing
      amino acid
<220> FEATURE:
<221> NAME/KEY: MISC_FEATURE
<222> LOCATION: (6)..(6)
<223> OTHER INFORMATION: Xaa is a basic amino acid or an alpha-helix
      enhancing amino acid
<220> FEATURE:
<221> NAME/KEY: MISC_FEATURE
<222> LOCATION: (7)..(7)
<223> OTHER INFORMATION: Xaa is a basic amino acid
<220> FEATURE:
<221> NAME/KEY: MISC_FEATURE
<222> LOCATION: (8)..(8)
<223> OTHER INFORMATION: Xaa is proline or an alpha-helix
      enhancing amino acid
<220> FEATURE:
<221> NAME/KEY: MISC_FEATURE
<222> LOCATION: (9)..(9)
<223> OTHER INFORMATION: Xaa is an alpha-helix enhancing amino acid
<220> FEATURE:
<221> NAME/KEY: MISC_FEATURE
<222> LOCATION: (10)..(10)
<223> OTHER INFORMATION: Xaa is a basic amino acid
```

```
<220> FEATURE:
<221> NAME/KEY: MISC_FEATURE
<222> LOCATION: (11)..(11)
<223> OTHER INFORMATION: Xaa is a basic amino acid  or an alpha-helix
      enhancing amino acid

<400> SEQUENCE: 17

Xaa Xaa Arg Xaa Xaa Xaa Xaa Xaa Xaa Xaa Xaa
1               5                   10

<210> SEQ ID NO 18
<211> LENGTH: 5
<212> TYPE: PRT
<213> ORGANISM: Artificial Sequence
<220> FEATURE:
<223> OTHER INFORMATION: PTD Consensus Sequence
<220> FEATURE:
<221> NAME/KEY: MISC_FEATURE
<222> LOCATION: (2)..(2)
<223> OTHER INFORMATION: Xaa is R or K
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is R or K

<400> SEQUENCE: 18

Lys Xaa Arg Xaa Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Peptide Linker

<400> SEQUENCE: 19

Gly Gly Gly Gly Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Peptide Linker
<220> FEATURE:
<221> NAME/KEY: REPEAT
<222> LOCATION: (1)..(5)
<223> OTHER INFORMATION: The sequence repeats 'n' times

<400> SEQUENCE: 20

Gly Gly Gly Gly Ser
1               5

<210> SEQ ID NO 21
<211> LENGTH: 12
<212> TYPE: PRT
<213> ORGANISM: Artificial Sequence
<220> FEATURE:
<223> OTHER INFORMATION: Peptide Linker

<400> SEQUENCE: 21

Gly Lys Ser Ser Gly Ser Gly Ser Glu Ser Lys Ser
1               5                   10
```

```
<210> SEQ ID NO 22
<211> LENGTH: 14
<212> TYPE: PRT
<213> ORGANISM: Artificial Sequence
<220> FEATURE:
<223> OTHER INFORMATION: Peptide Linker

<400> SEQUENCE: 22

Gly Ser Thr Ser Gly Ser Gly Lys Ser Ser Glu Gly Lys Gly
1               5                   10

<210> SEQ ID NO 23
<211> LENGTH: 18
<212> TYPE: PRT
<213> ORGANISM: Artificial Sequence
<220> FEATURE:
<223> OTHER INFORMATION: Peptide Linker

<400> SEQUENCE: 23

Gly Ser Thr Ser Gly Ser Gly Lys Ser Ser Glu Gly Ser Gly Ser Thr
1               5                   10                  15

Lys Gly

<210> SEQ ID NO 24
<211> LENGTH: 18
<212> TYPE: PRT
<213> ORGANISM: Artificial Sequence
<220> FEATURE:
<223> OTHER INFORMATION: Peptide Linker

<400> SEQUENCE: 24

Gly Ser Thr Ser Gly Ser Gly Lys Pro Gly Ser Gly Glu Gly Ser Thr
1               5                   10                  15

Lys Gly

<210> SEQ ID NO 25
<211> LENGTH: 14
<212> TYPE: PRT
<213> ORGANISM: Artificial Sequence
<220> FEATURE:
<223> OTHER INFORMATION: Peptide Linker

<400> SEQUENCE: 25

Glu Gly Lys Ser Ser Gly Ser Gly Ser Glu Ser Lys Glu Phe
1               5                   10

<210> SEQ ID NO 26
<211> LENGTH: 20
<212> TYPE: RNA
<213> ORGANISM: Artificial Sequence
<220> FEATURE:
<223> OTHER INFORMATION: Tester siRNN sequence

<400> SEQUENCE: 26
ccacuaccug agcacccagu                                              20

<210> SEQ ID NO 27
<211> LENGTH: 21
<212> TYPE: RNA
<213> ORGANISM: Artificial Sequence
<220> FEATURE:
<223> OTHER INFORMATION: Tester siRNN passenger strand

<400> SEQUENCE: 27
ccacuaccug agcacccagu u                                            21
```

```
<210> SEQ ID NO 28
<211> LENGTH: 21
<212> TYPE: RNA
<213> ORGANISM: Artificial Sequence
<220> FEATURE:
<223> OTHER INFORMATION: Tester siRNN guide strand

<400> SEQUENCE: 28
cugggugcuc agguaguggu u                                              21

<210> SEQ ID NO 29
<211> LENGTH: 20
<212> TYPE: RNA
<213> ORGANISM: Artificial Sequence
<220> FEATURE:
<223> OTHER INFORMATION: Tester siRNN complement strand

<400> SEQUENCE: 29
uggugaugga cucguggguc                                                20

<210> SEQ ID NO 30
<211> LENGTH: 21
<212> TYPE: DNA
<213> ORGANISM: Artificial Sequence
<220> FEATURE:
<223> OTHER INFORMATION: Tester siRNN

<400> SEQUENCE: 30
ccaggauuac aagauucaau t                                              21

<210> SEQ ID NO 31
<211> LENGTH: 21
<212> TYPE: DNA
<213> ORGANISM: Artificial Sequence
<220> FEATURE:
<223> OTHER INFORMATION: Tester siRNN complementary strand

<400> SEQUENCE: 31
tugguccuaa uguucuaagu u                                              21
```

POLYNUCLEOTIDES HAVING BIOREVERSIBLE GROUPS

CROSS REFERENCE TO RELATED APPLICATIONS

This application is a U.S. National Stage Application filed under 35 U.S.C. § 371 and claims priority to International Application No. PCT/US2013/055675, filed Aug. 20, 2013, which claims priority to U.S. Provisional Application Ser. No. 61/691,175, filed Aug. 20, 2012, the disclosures of which are incorporated herein by reference.

TECHNICAL FIELD

This invention relates to compositions and methods for transfecting cells.

BACKGROUND

Nucleic acid delivery to cells both in vitro and in vivo has been performed using various recombinant viral vectors, lipid delivery systems and electroporation. Such techniques have sought to treat various diseases and disorders by knocking-out gene expression, providing genetic constructs for gene therapy or to study various biological systems.

Polyanionic polymers such as polynucleotides do not readily diffuse across cell membranes. In order to overcome this problem for cultured cells, cationic lipids are typically combined with anionic polynucleotides to assist uptake. Unfortunately, this complex is generally toxic to cells, which means that both the exposure time and concentration of cationic lipid must be carefully controlled to insure transfection of viable cells.

The discovery of RNA interference (RNAi) as a cellular mechanism that selectively degrades mRNAs allows for both the targeted manipulation of cellular phenotypes in cell culture and the potential for development of directed therapeutics (Behlke, Mol. Ther. 13, 644-670, 2006; Xie et al., Drug Discov. Today 11, 67-73, 2006). However, because of their size and negative (anionic) charged nature, siRNAs are macromolecules with no ability to enter cells. Indeed, siRNAs are 25× in excess of Lipinski's "Rule of 5s" for cellular delivery of membrane diffusible molecules that generally limits size to less than 500 Da. Consequently, in the absence of a delivery vehicle or transfection agent, naked siRNAs do not enter cells, even at millimolar concentrations (Barquinero et al., Gene Ther. 11 Suppl 1, S3-9, 2004). Significant attention has been focused on the use of cationic lipids that both condense the siRNA and punch holes in the cellular membrane to solve the siRNA delivery problem. Although widely used, transfection reagents fail to achieve efficient delivery into many cell types, especially primary cells and hematopoietic cell lineages (T and B cells, macrophage). Moreover, lipofection reagents often result in varying degrees of cytotoxicity ranging from mild in tumor cells to high in primary cells.

SUMMARY

The disclosure provides methods and compositions for delivering polynucleotides into cells. The disclosure provides transiently protected polynucleotides comprising an anionic charge-neutralizing moiety/group, which may also confer additional functionality as described herein. These compounds can enter the cytosol of cells by endocytic or macropinocytic mechanisms. In one embodiment, the transient protecting group is bioreversible, i.e., once inside a cell, it is designed to be removed by enzymatic activity or by passive intracellular methods (e.g., changes in pH or reductive environment). Accordingly, the disclosure provides polynucleotides useful as therapeutics, diagnostics and as tools for research.

The disclosure provides a polynucleotide construct comprising a component (i) selected from the group consisting of a peptide, a polypeptide, a carbohydrate, a neutral organic polymer, a positively charged polymer, a therapeutic agent, a targeting moiety, an endosomal escape moiety, and any combination thereof, wherein component (i) is linked to the polynucleotide construct through a bioreversible group attached to an internucleotide bridging group. The polynucleotide construct may further comprise at least one second component (ii) selected from the group consisting of a bioreversible group which comprises a hydrophilic functional group, a bioreversible group which comprises a conjugating moiety, and a bioreversible group which comprises a conjugating moiety and a hydrophilic group, wherein the conjugating moiety may further comprise a protecting group. In one embodiment, the bioreversible group comprises a thioester. In yet another embodiment of any of the preceding embodiments the component (i) allows the polynucleotide construct to be transported intracellularly, whereupon the bioreversible group is cleaved. In yet another embodiment of any of the preceding embodiments, the construct can further comprise at least one third component (iii) selected from the group consisting of a small molecule, a peptide, a polypeptide, a carbohydrate, a neutral organic polymer, a positively charged polymer, a therapeutic agent, a targeting moiety, an endosomal escape moiety, or any combination thereof, wherein the component (iii) is conjugated to an internucleotide bridging group or terminal nucleotide group intracellularly bioreversible group. In a further embodiment, component (iii) is the small molecule. In yet a further embodiment, the small molecule is an optionally substituted $C_{1-6}$ alkyl. In one embodiment, the polynucleotide construct has the structure of Formula II:

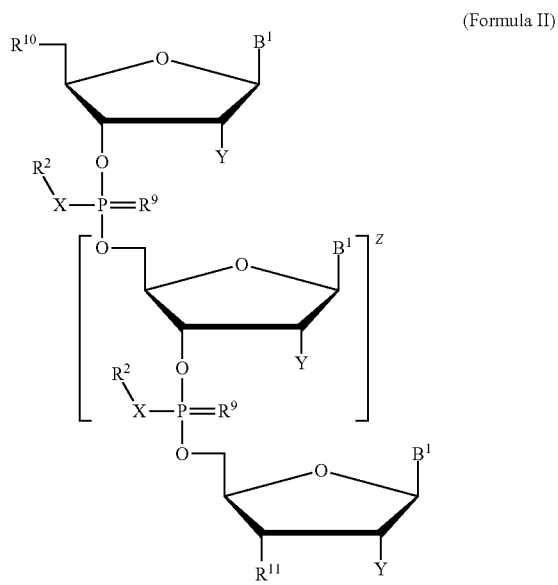

(Formula II)

or a salt thereof, wherein one $R^2$ comprises the component (i), Z is a number from 0 to 150; each $B^1$ is individually a nucleobase; each X is individually selected from the group consisting of O, S and NR⁵; each Y is individually selected from the group consisting of a hydrogen, hydroxyl, halo, optionally substituted $C_{1-6}$ alkoxy, or a protected hydroxyl group; each $R^2$ is individually absent, a hydrogen, or a first bioreversible group that comprises a hydrophilic functional group, a second bioreversible group that comprises a conjugating moiety, or a third bioreversible group that comprises an auxiliary moiety selected from the group consisting of a small molecule, a peptide, a polypeptide, a carbohydrate, a neutral organic polymer, a positively charged polymer, a therapeutic agent, a targeting moiety, an endosomal escape moiety, or combination thereof, wherein the conjugating moiety or the hydrophilic functional group is optionally protected with a protecting group; each $R^5$ is individually selected from the group consisting of H, an optionally substituted $C_{1-6}$ alkyl, S-pivaloyl thioethanol, hydroxyl, an optionally substituted $C_{1-6}$ alkoxy, an optionally substituted $C_{3-8}$ cycloalkyl, an optionally substituted $C_{6-12}$ aryl, and an optionally substituted $C_{2-9}$ heterocyclyl; each $R^9$ is individually either an O or S; $R^{10}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, a 5' cap, phosphothiol, an optionally substituted $C_{1-6}$ alkyl, an amino containing group, a biotin containing group, a digoxigenin containing group, a cholesterol containing group, a dye containing group, a quencher containing group, a peptide, a polypeptide, a carbohydrate, a neutral organic polymer, a positively charged polymer, a therapeutic agent, a targeting moiety, an endosomal escape moiety, and any combination thereof; and $R^{11}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, an optionally substituted $C_{1-6}$ alkyl, an amino containing group, a biotin containing group, a digoxigenin containing group, a cholesterol containing group, a dye containing group, a quencher containing group, a phosphothiol, a peptide, a polypeptide, a carbohydrate, a neutral organic polymer, a positively charged polymer, a therapeutic agent, a targeting moiety, an endosomal escape moiety, and any combination thereof. In a certain embodiment, each X is O or S. In yet another embodiment, the construct has one or more strands of nucleotides comprising the structure of Formula II(a):

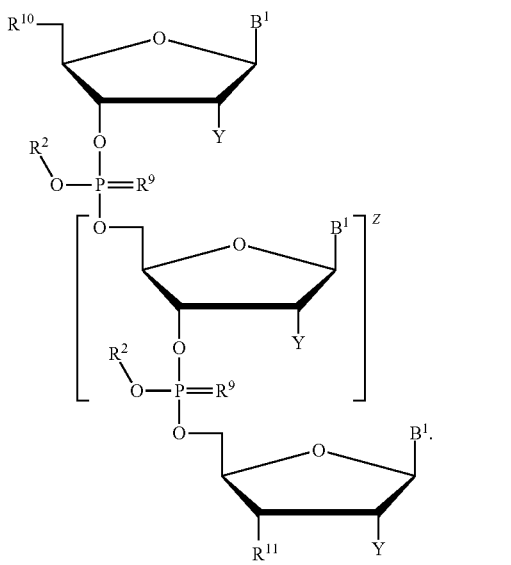

(Formula II(a))

In a further embodiment, when, in the polynucleotide construct above, $R^2$ is the first, second, or third bioreversible group, Y is other than hydroxyl, e.g., F or OMe. In yet another embodiment of any of the preceding embodiments, component (i) bound to the bioreversible group has structural Formula V:

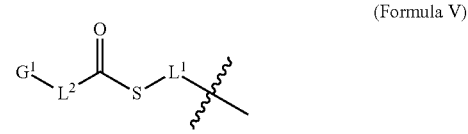

(Formula V)

wherein, $G^1$ is the peptide, the polypeptide, the carbohydrate, the neutral organic polymer, the positively charged polymer, the therapeutic agent, the targeting moiety, the endosomal escape moiety, or combination thereof; $L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and $L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S. In yet another embodiment of any of the preceding embodiments, component (ii) bound to the bioreversible group has structural Formula V:

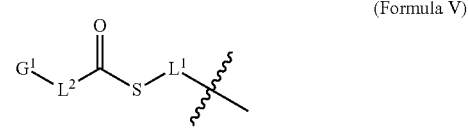

(Formula V)

wherein, $G^1$ is the conjugating moiety or hydrophilic functional group; $L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and $L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S. In yet another embodiment of any of the preceding embodiments, $L^1$ is

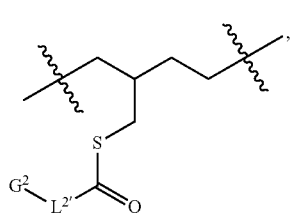

wherein $L^{2'}$ is a covalent bond or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S; $G^2$ is a conjugating moiety, a hydrophilic functional group, a small molecule, a peptide, a polypeptide, a carbohydrate, a neutral organic polymer, a positively charged polymer, a therapeutic agent, a targeting moiety, an endosomal escape moiety, or combination thereof. In yet another embodiment of any of the preceding embodiments, the construct may further comprise a structure of Formula V':

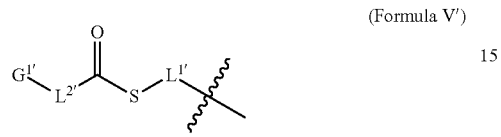

(Formula V')

wherein, $G^{1'}$ is a conjugating moiety, a hydrophilic functional group, a small molecule, a peptide, a polypeptide, a carbohydrate, a neutral organic polymer, a positively charged polymer, a therapeutic agent, a targeting moiety, an endosomal escape moiety, or combination thereof; $L^{1'}$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and $L^{2'}$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S. In yet a further embodiment structural Formula V or V' is selected from the group consisting of:

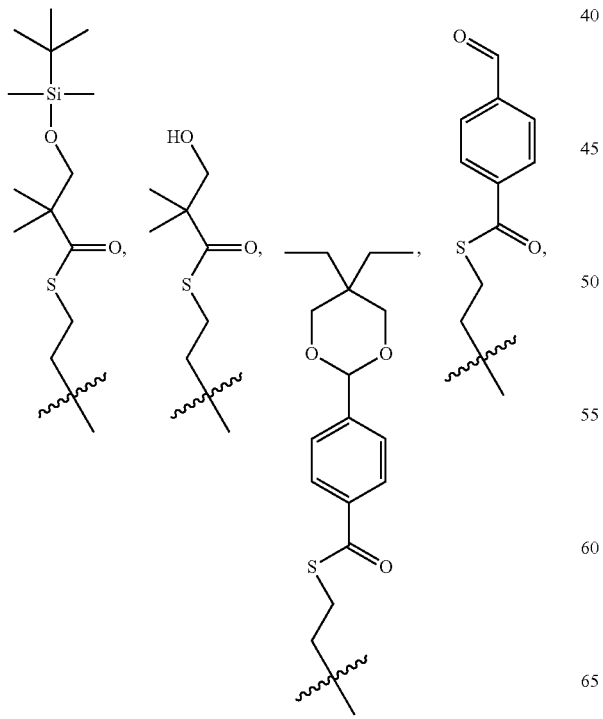

-continued

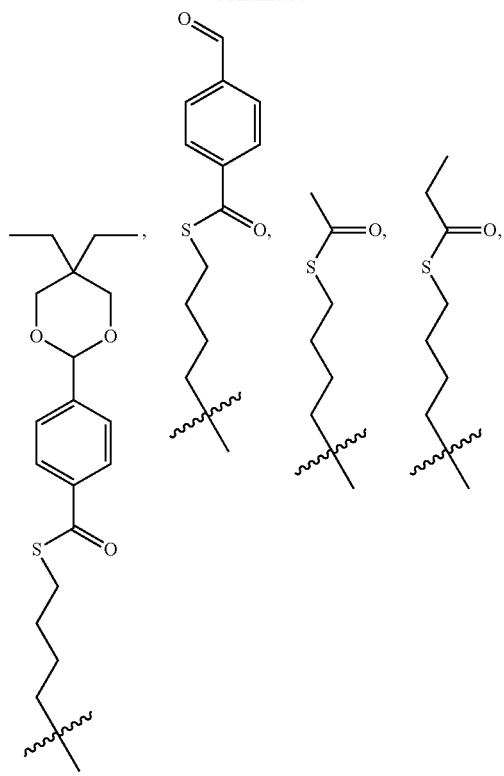

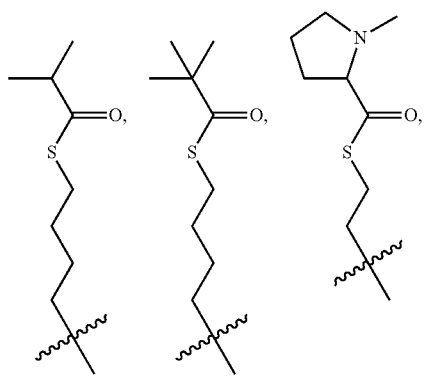

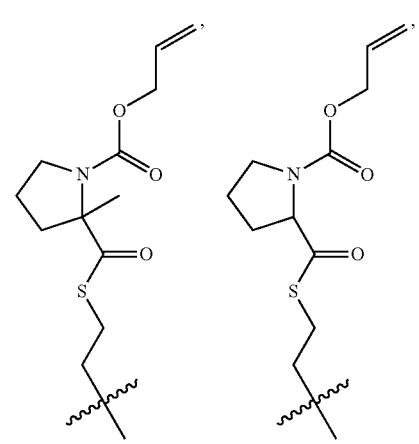

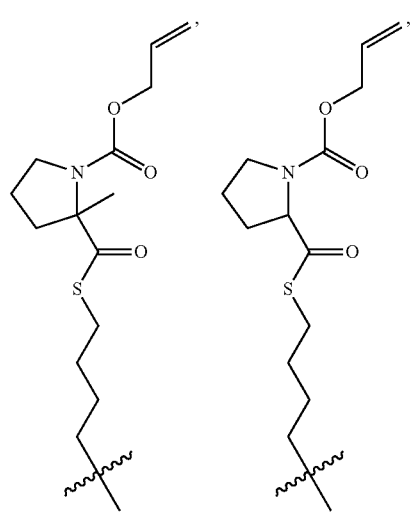
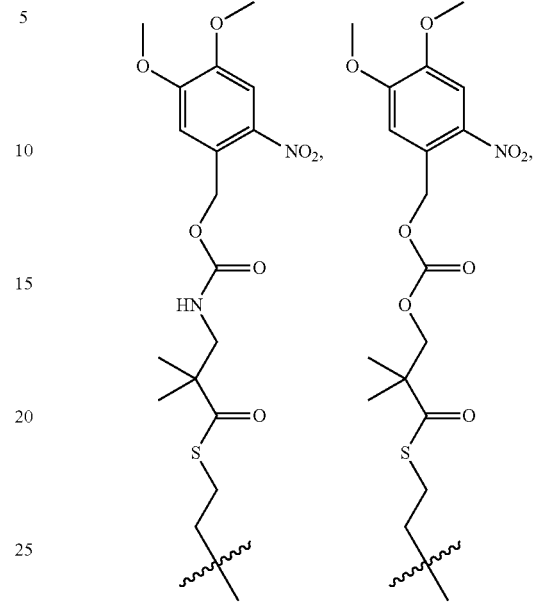
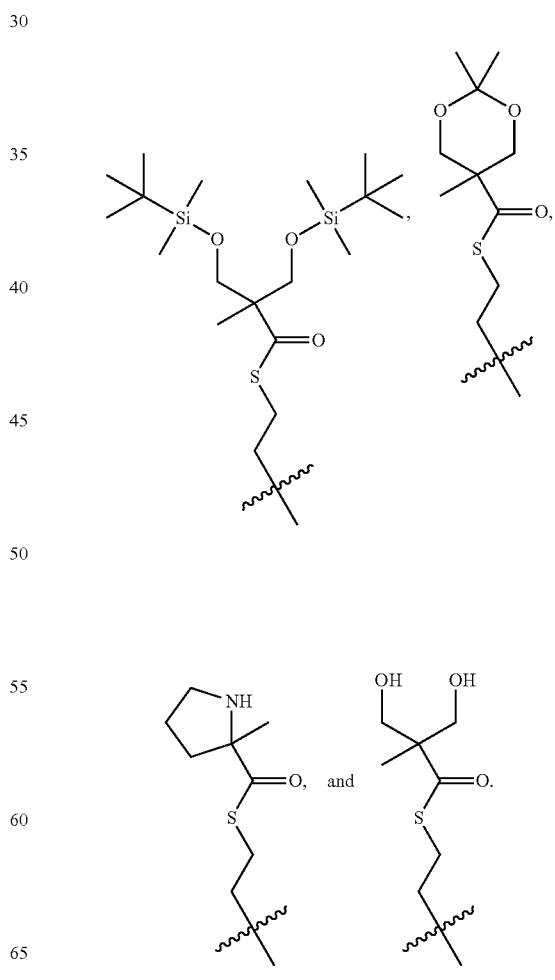

In yet a further embodiment, structural Formula V or V' is selected from the group consisting of:
In yet a further embodiment, structural Formula V or V' is selected from the group consisting of:
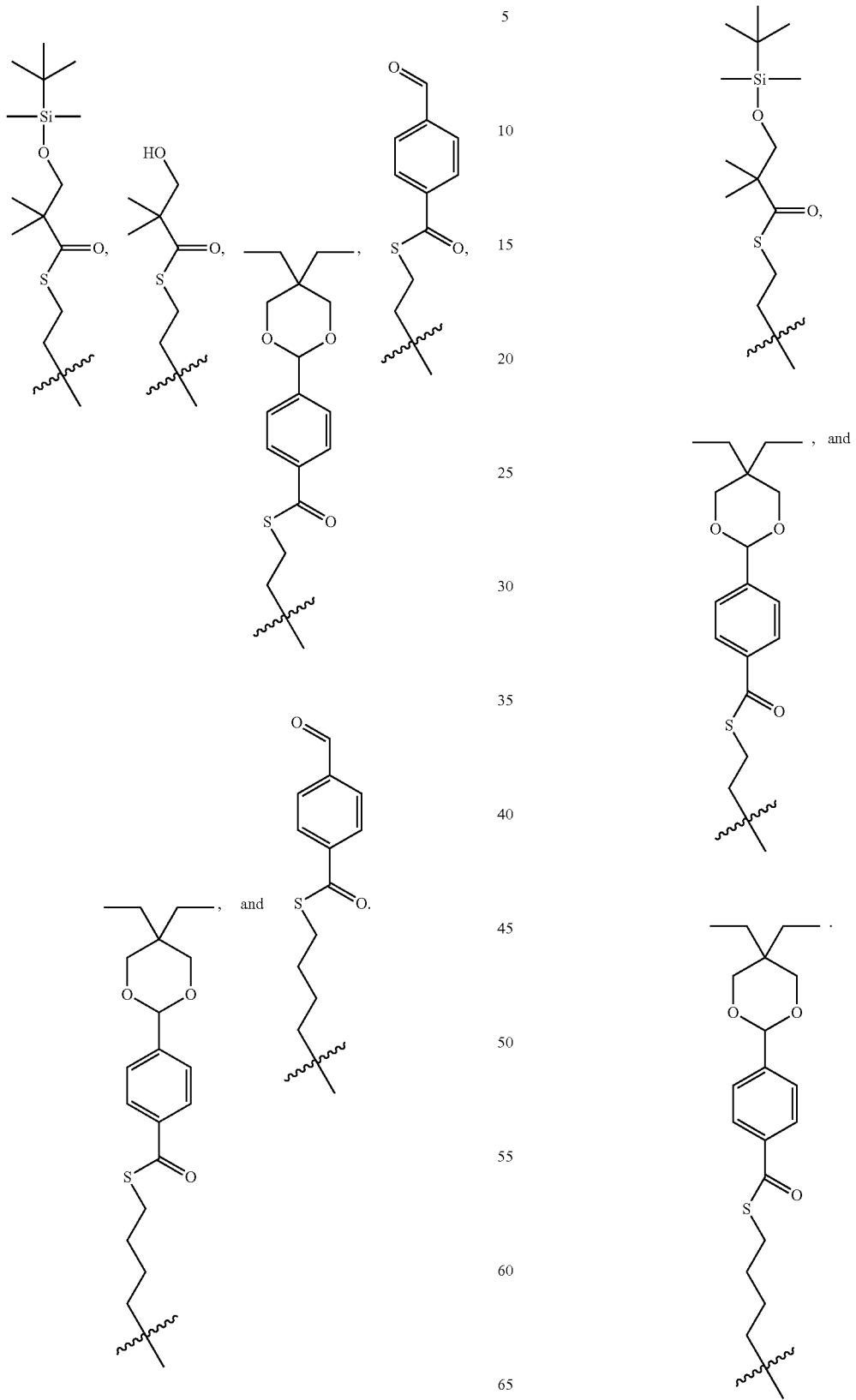

In yet another embodiment, structural Formula V or V' is selected from the group consisting of:

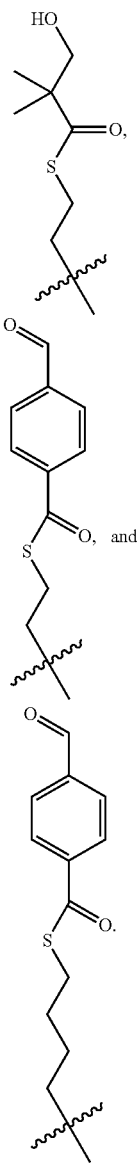

In a further embodiment, structural Formula V' is selected from the group consisting of:

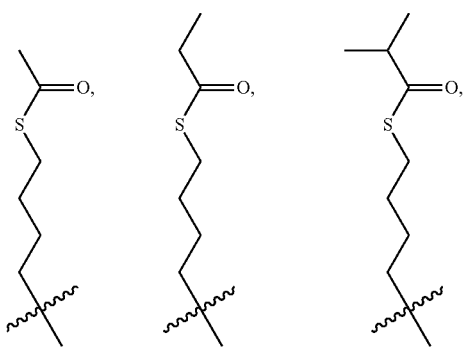

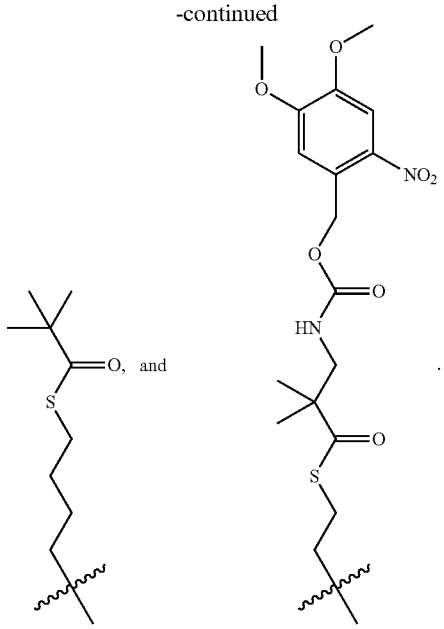

In any number of various embodiments above, $L^1$ is an optionally substituted $C_{2-10}$ alkylene. In another embodiment, $L^1$ is unsubstituted or substituted $C_2$, $C_4$, or $C_5$ alkylene. In yet another embodiment, $L^2$ is a covalent bond. In a further embodiment, $L^2$ is optionally substituted $C_{1-10}$ alkylene or optionally substituted $C_{6-12}$ arylene. In yet other embodiments, $G^1$ is hydroxyl or $G^1$ is the conjugating moiety. In yet another embodiment, the conjugating moiety is —CHO, thiol, or —$N_3$. In further embodiments of any of the foregoing, $G^1$ comprises the peptide, the polypeptide, the carbohydrate, the neutral organic polymer, the positively charged polymer, the therapeutic agent, the targeting moiety, the endosomal escape moiety, or any combination thereof. In another embodiment, $G^1$ is bound to $L^2$ via a bond formed by a reaction selected from the group consisting of a pericyclic reaction; an alkylation or arylation of a hydroxyl, thiol, or amino moiety; and a reaction of a hydroxyl, thiol, or amino nucleophile with an electrophile. In one embodiment, $L^2$ is not a bond, and $G^1$ is bound to $L^2$ via an amide bond, a sulfonamide bond, a carboxylic ester, a thioester, an optionally substituted $C_{6-12}$ aryl or $C_{2-9}$ heteroaryl; an imine; a hydrazone; an oxime; or a succinimide. In a further embodiment of any number of the foregoing embodiments, one or more hydrophilic functional groups and/or conjugating moieties of $R^2$ are protected with protecting groups. In yet another embodiment of any of the preceding embodiments, the peptide, the polypeptide, the protein, the carbohydrate, the neutral organic polymer, the positively charged polymer, the therapeutic agent, the targeting moiety, the endosomal escape moiety, or combination thereof is linked to the bioreversible group through a condensation reaction with an aldehyde conjugating moiety to form an imine, enamine or hydrazone bond. In yet another embodiment of any of the preceding embodiments, the peptide, the polypeptide, the protein, the carbohydrate, the neutral organic polymer, the positively charged polymer, the therapeutic agent, the targeting moiety, the endosomal escape moiety, or combination thereof is linked to the bioreversible group by one or more nitrogen containing conjugating moieties having the structure of Formula III:

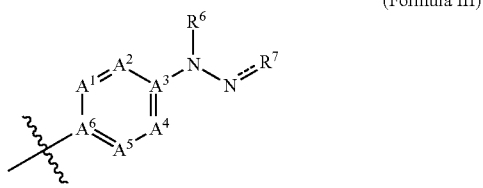

(Formula III)

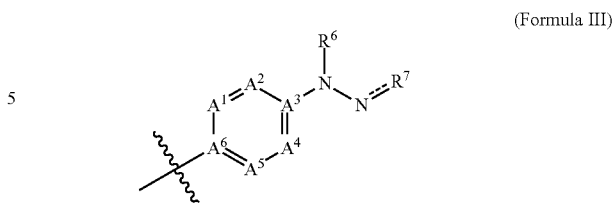

(Formula III)

wherein, $A^1$, $A^2$, $A^4$, and $A^5$ are each individually a N or $CR^8$; $A^3$ and $A^6$ are C; $R^6$-$R^7$ are each individually a H, optionally substituted $C_{1-6}$ alkyl, optionally substituted $C_{2-6}$ alkenyl, optionally substituted imine, and optionally substituted enamine; and each $R^8$ is individually a H, optionally substituted $C_{1-6}$ alkyl, optionally substituted $C_{2-6}$ alkenyl, optionally substituted $C_{2-6}$ alkynyl, halo, hydroxyl, —CHO, optionally substituted $C_{1-6}$ acyl, carboxyl, cyano, nitro, optionally substituted amino, thiol, optionally substituted $C_{2-9}$ heterocyclyl, optionally substituted $C_{6-12}$ aryl, optionally substituted $C_{3-8}$ cycloalkyl, and optionally substituted $C_{4-8}$ cycloalkenyl. In yet another embodiment of any of the preceding embodiments, at most 25%, 50%, 75% or 90% of the bioreversible groups are linked to the peptide, the polypeptide, the carbohydrate, the neutral organic polymer, the positively charged polymer, the therapeutic agent, the targeting moiety, the endosomal escape moiety, or combination thereof. In a specific embodiment, of any of the foregoing, component (i) comprises a delivery domain. In a further embodiment, the delivery domain comprises one or more a peptide transduction domains (PTDs). In one embodiment, the one or more PTDs are linked to the bioreversible group through an imine, enamine, or hydrazone bond. For example, the one or more PTDs are linked to the bioreversible group to form structural Formula IV:

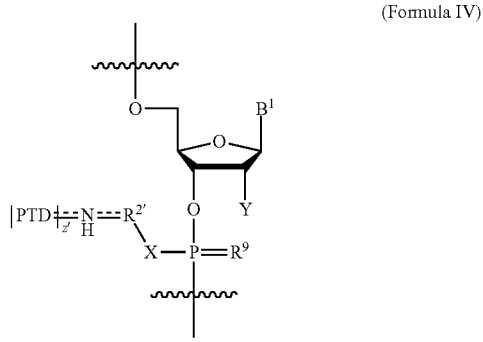

(Formula IV)

wherein, $R^{2'}$ is the residue of the bioreversible group bound to the PTD; z' is a number from 1 to 10, wherein, when z' is greater than 1, the PTDs may be linked together through poly($C_{1-4}$ alkyleneoxide) groups having 1-10 repeating units. In a specific embodiment, the one or more PTDs are trans-activating transcriptional activator (TAT) peptides. In various embodiments of the foregoing, the PTD is linked to the bioreversible group through a complementary conjugating moiety comprising the structure of Formula III:

wherein, $A^1$, $A^2$, $A^4$, and $A^5$ are each individually a N or $CR^8$; $A^3$ and $A^6$ are C; $R^6$-$R^7$ are each individually a H, optionally substituted $C_{1-6}$ alkyl, optionally substituted $C_{2-6}$ alkenyl, optionally substituted imine, and optionally substituted enamine; and each $R^8$ is individually a H, optionally substituted $C_{1-6}$ alkyl, optionally substituted $C_{2-6}$ alkenyl, optionally substituted $C_{2-6}$ alkynyl, halo, hydroxyl, —CHO, optionally substituted $C_{1-6}$ acyl, carboxyl, cyano, nitro, optionally substituted amino, thiol, optionally substituted $C_{2-9}$ heterocyclyl, optionally substituted $C_{6-12}$ aryl, optionally substituted $C_{3-8}$ cycloalkyl, and optionally substituted $C_{4-8}$ cycloalkenyl. In one embodiment, the bioreversible group prior to conjugation is selected from the group consisting of:

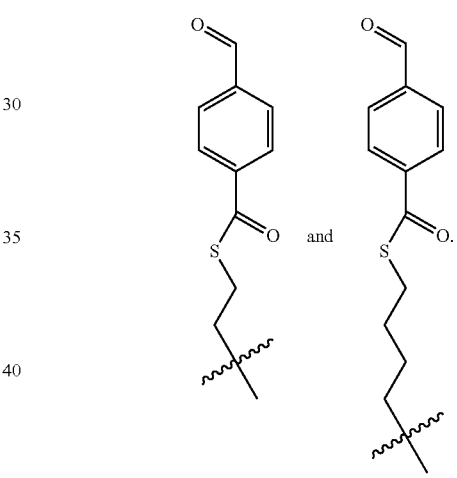

In another embodiment, the PTD comprises a cationic peptide sequence having 5-10 arginine and/or lysine residues over 5-15 amino acids. For example, the PTD can comprise the sequence RKKRRQRRR (SEQ ID NO: 1). In a further embodiment, component (i) comprises a PTD conjugated to poly(ethylene glycol) (PEG) having 1-10 repeating units. In some specific embodiments, component (i) comprises a sequence selected from the group consisting of: PEG-(PTD); GG-(PTD)-PEG-(PTD); PEG-(PTD)-PEG-(PTD); GG-(PTD)-PEG-PEG-PEG-(PTD); PEG-(PTD)-PEG-PEG-PEG-(PTD); GG-(PTD)-PEG-(PTD)-PEG-(PTD); and GG-(PTD)-PEG-PEG-PEG-(PTD)-PEG-PEG-PEG-(PTD); wherein PEG is a poly(ethyleneglycol) linker having one to ten repeat units. In another embodiment, component (i) comprises a targeting moiety. In some embodiments, the targeting moiety is a ligand, carbohydrate, antibody, FAb, ScFv, or single-domain antibody. In yet another embodiment of any of the preceding embodiments, the polynucleotide construct comprises a non-natural nucleobase. In yet another embodiment, the construct comprises only naturally occurring nucleobases. In any of the foregoing embodiments, the nucleobases are selected from cytosine, guanine, adenine, uracil, and thymidine. In another embodiment, no more than 75% or 65% of the nucleotides in the polynucleotide construct have the bioreversible group. In any of the foregoing embodiments, the polynucleotide construct comprises 2-40 or 5-10 bioreversible groups. In yet another embodiment of any of the preceding embodiments, the polynucleotide construct has 10-32 nucleotides (e.g., 17-30 nucleotides). When more than one bioreversible is present in a construct, such groups may be the same or different. In particular, the construct may include a mixture of bioreversible groups with a peptide, a polypeptide, a carbohydrate, a neutral organic polymer, a positively charged polymer, a therapeutic agent, a targeting moiety, an endosomal escape moiety, or combination thereof and bioreversible groups with $C_{1-6}$ alkyl or hydroxyl-substituted $C_{1-6}$ alkyl small molecule groups.

In other embodiments, the polynucleotide construct has the structure of Formula II(a):

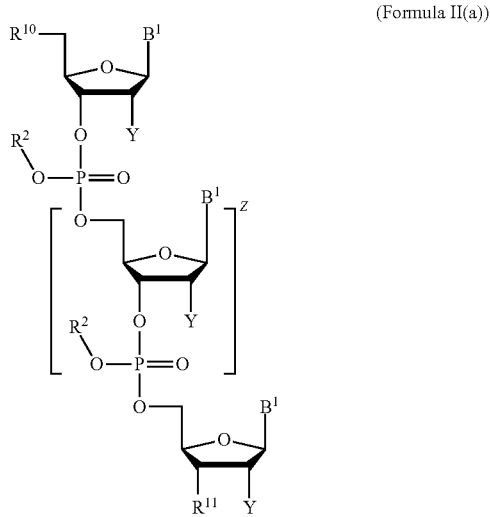

(Formula II(a))

or a salt thereof, wherein one $R^2$ comprises the component (i), Z is a number from 0 to 30; each $B^1$ is individually a nucleobase; each Y is individually selected from the group consisting of hydroxyl, halo, or $C_{1-6}$ alkoxy; each $R^2$ is individually absent; a hydrogen; a group of Formula V:

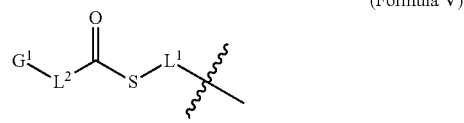

(Formula V)

wherein, $G^1$ is the peptide, the polypeptide, the neutral organic polymer, or any combination thereof; $L^1$ is an optionally substituted $C_{2-6}$ alkylene, optionally substituted $C_{2-6}$ alkenylene, or optionally substituted $C_{2-6}$ alkynylene, wherein each of alkylene, alkenylene, or alkynylene is optionally interrupted with 1 or 2 oxygen atoms; and $L^2$ is a covalent bond, or is selected from optionally substituted $C_{1-6}$ alkylene; optionally substituted $C_{2-6}$ alkenylene; optionally substituted $C_{2-6}$ alkynylene; and optionally substituted $C_{6-10}$ arylene; or a group of

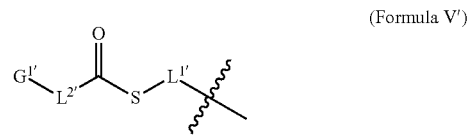

(Formula V')

wherein, $G^{1'}$ is hydrogen, aldehyde or protected aldehyde, hydroxyl, protected hydroxyl, amine, protected amine, or 5- or 6-membered heterocyclic amine optionally substituted with a protecting group or $C_{1-6}$ alkyl; $L^{1'}$ is an optionally substituted $C_{2-6}$ alkylene, wherein each alkylene is optionally interrupted with 1 or 2 oxygen atoms; and $L^{2'}$ is a covalent bond, or is selected from optionally substituted $C_{1-6}$ alkylene and optionally substituted $C_{6-10}$ arylene; $R^{10}$ is selected from the group consisting of H, hydroxyl, optionally substituted $C_{1-6}$ alkoxy, a protected hydroxyl group, a monophosphate, a disphosphate, a triphosphate, a 5' cap, phosphothiol, an optionally substituted $C_{1-6}$ alkyl, an amino containing group, a peptide, a polypeptide, neutral organic polymer, and any combination of a peptide, polypeptide, and neutral organic polymer; and $R^{11}$ is selected from the group consisting of H, hydroxyl, optionally substituted $C_{1-6}$ alkoxy, a protected hydroxyl group, a monophosphate, a disphosphate, a triphosphate, an optionally substituted $C_{1-6}$ alkyl, a peptide, a polypeptide, neutral organic polymer, and any combination of a peptide, polypeptide, and neutral organic polymer. In further embodiments, for a nucleotide in which $R^2$ is a group of formula V or V', Y is F or OMe. Structural Formula V' is optionally selected from the group consisting of:

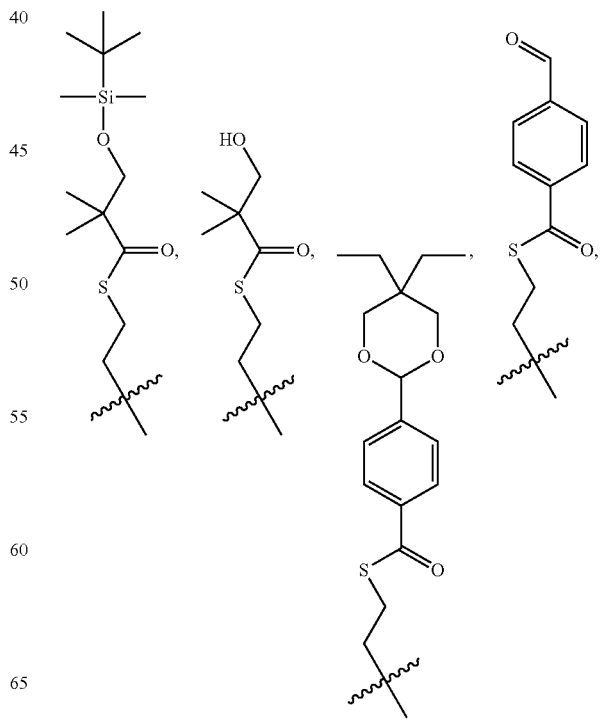

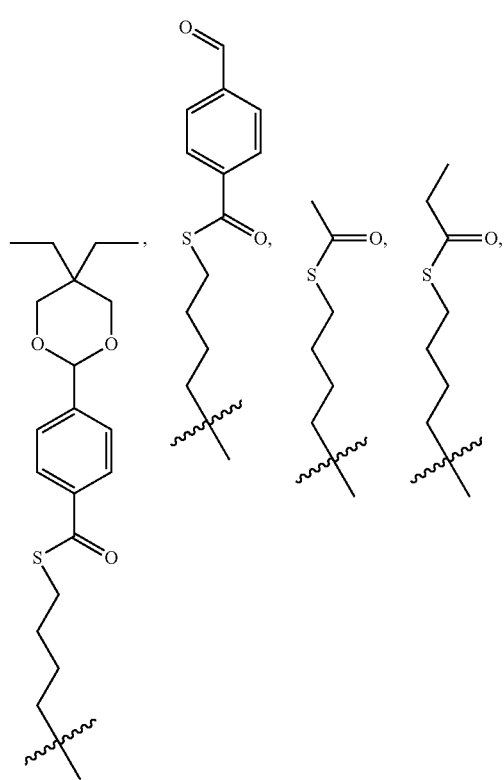
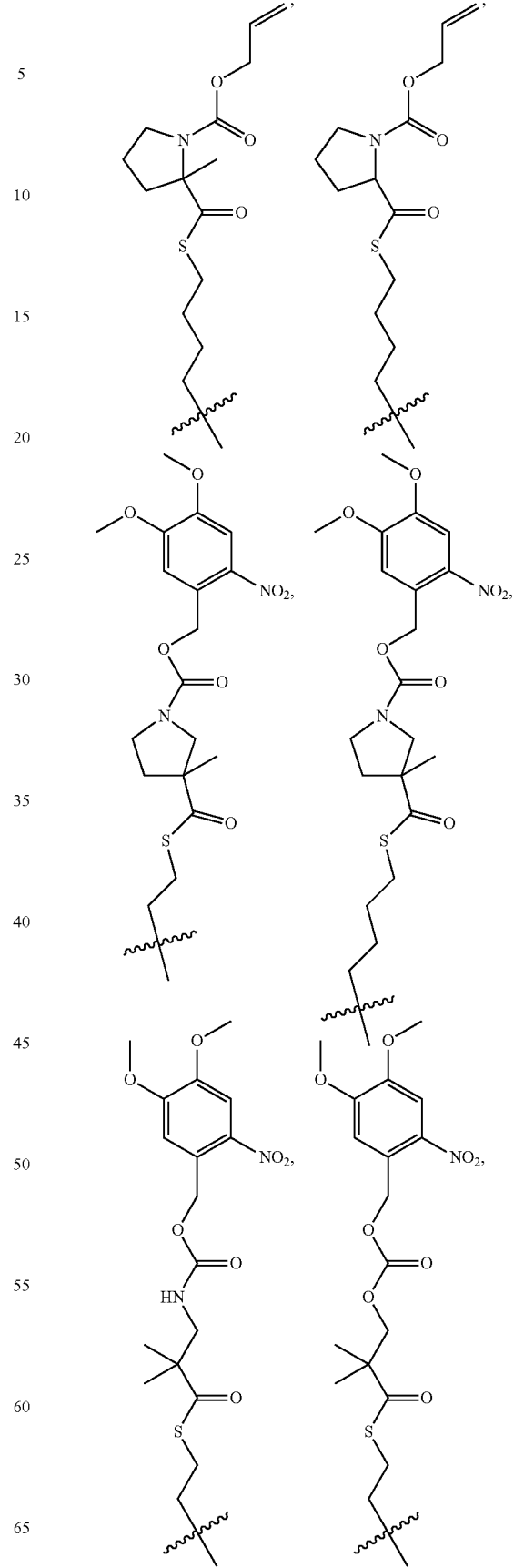

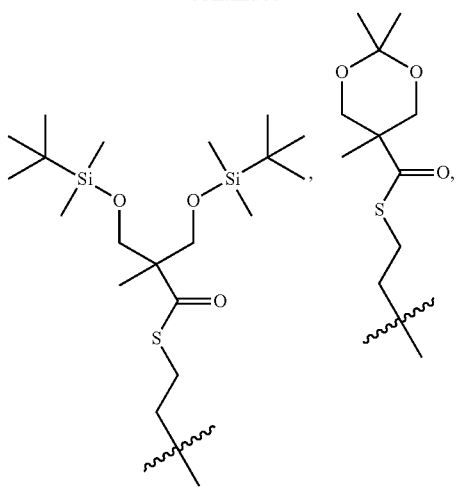

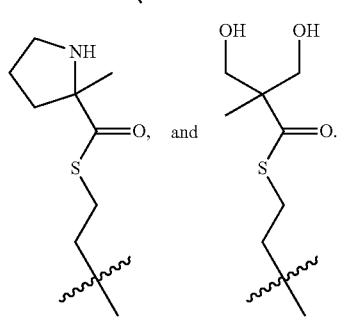

In other embodiments, $G^1$ comprises a delivery domain, comprising one or more a peptide transduction domains (PTDs), as described herein.

The disclosure also provides a polynucleotide construct comprising one or more bioreversible groups that comprise a hydroxyl substituted $C_{1-6}$ alkyl group attached to an internucleotide bridging group or that comprise a conjugating moiety, such as —CHO, $N_3$, or thiol, attached to an internucleotide bridging group or terminal nucleotide group. The disclosure also provides a polynucleotide construct comprising one or more bioreversible groups selected from the group consisting of:

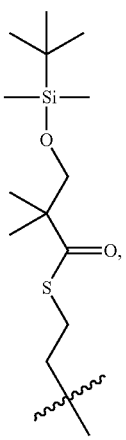
(i)

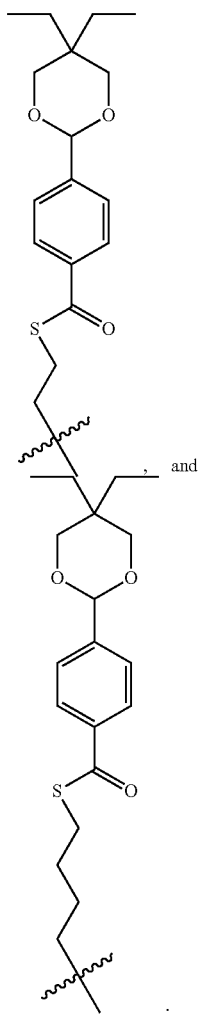
(ii)

(iii)

and attached to an internucleotide bridging group or a terminal nucleotide group. In one embodiment, the polynucleotide construct has the structure of Formula II:

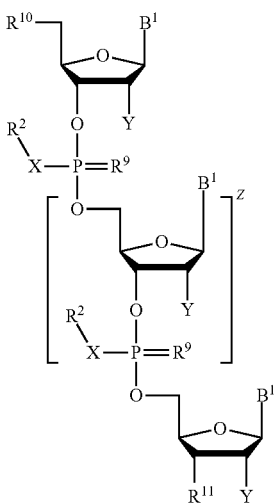
(Formula II)

or a salt thereof, wherein Z is a number from 0 to 150; each $B^1$ is individually a nucleobase; each X is individually selected from the group consisting of O, S and $NR^5$; each Y is individually selected from the group consisting of a hydrogen, hydroxyl, halo, optionally substituted $C_{1-6}$ alkoxy, or a protected hydroxyl group; each $R^2$ is individually absent, a hydrogen, bioreversible group (i), bioreversible group (ii), or bioreversible group (iii); each $R^5$ is individually selected from the group consisting of H, an optionally substituted $C_{1-6}$ alkyl, S-pivaloyl thioethanol, hydroxyl, an optionally substituted $C_{1-6}$ alkoxy, an optionally substituted $C_{3-8}$ cycloalkyl, an optionally substituted $C_{6-12}$ aryl, and an optionally substituted $C_{2-9}$ heterocyclyl; each $R^9$ is individually either an O or S; $R^{10}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, a 5' cap, phosphothiol, an optionally substituted $C_{1-6}$ alkyl, an amino containing group, a biotin containing group, a digoxigenin containing group, a cholesterol containing group, a dye containing group, a quencher containing group, a peptide, a polypeptide, a carbohydrate, a neutral organic polymer, a positively charged polymer, a therapeutic agent, a targeting moiety, an endosomal escape moiety, and any combination thereof; and $R^{11}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, an optionally substituted $C_{1-6}$ alkyl, an amino containing group, a biotin containing group, a digoxigenin containing group, a cholesterol containing group, a dye containing group, a quencher containing group, a phosphothiol, a peptide, a polypeptide, a carbohydrate, a neutral organic polymer, a positively charged polymer, a therapeutic agent, a targeting moiety, an endosomal escape moiety, and any combination thereof, provided that at least one $R^2$ is the bioreversible group (i), (ii), or (iii). In a certain embodiment, X is O or S. In yet another embodiment, the polynucleotide construct comprises one or more strands of nucleotides having the structure of Formula II(a):

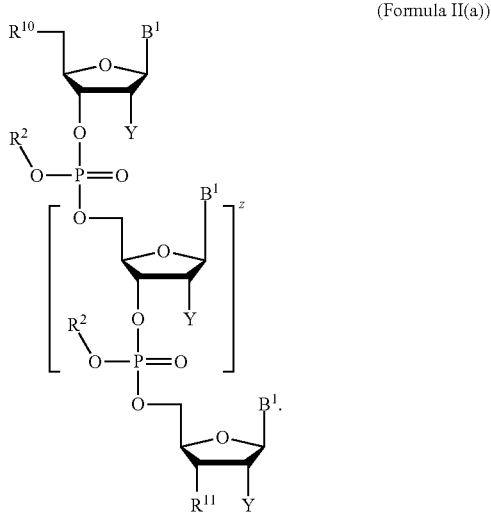

(Formula II(a))

In one embodiment, for a nucleotide in which $R^2$ is the bioreversible group (i), (ii), or (iii), Y is other than hydroxyl, e.g., F or OMe. In yet another embodiment, the polynucleotide construct comprises a mixture of $R^2$ groups, wherein one or more $R^2$ groups are absent or H; one or more $R^2$ groups are bioreversible group (i); and one or more $R^2$ groups are bioreversible group (ii) or (iii). In yet another embodiment, the ratio of $R^2$ groups that are absent or H, to $R^2$ groups that are bioreversible groups (i), (ii), or (iii), is from 1:10 to 10:1. In yet another embodiment, the ratio of $R^2$ groups that are absent or H, to $R^2$ groups that are bioreversible groups (i), (ii), or (iii), is from 1:5 to 5:1. In yet a further embodiment, the ratio of $R^2$ groups that are absent or H, to $R^2$ groups that are bioreversible groups (i), (ii), or (iii), is from 1:4 to 4:1. In yet another embodiment, the ratio of $R^2$ groups that are absent or H, to $R^2$ groups that are bioreversible groups (i), (ii), or (iii), is from 1:3 to 3:1. In still a further embodiment, the ratio of $R^2$ groups that are absent or H, to $R^2$ groups that are bioreversible groups (i), (ii), or (iii), is from 1:2 to 2:1. In a specific embodiment, the ratio of $R^2$ groups that are absent or H, to $R^2$ groups that are bioreversible groups (i), (ii), or (iii), is 1:1. In another embodiment, the ratio of $R^2$ groups that are bioreversible group (i) to $R^2$ groups that are bioreversible groups (ii) or (iii) is from 1:10 to 10:1. In yet another embodiment, the ratio of $R^2$ groups that are bioreversible group (i) to $R^2$ groups that are bioreversible groups (ii) or (iii) is from 1:5 to 5:1. In still another embodiment, the ratio of $R^2$ groups that are bioreversible group (i) to $R^2$ groups that are bioreversible groups (ii) or (iii) is from 1:4 to 4:1. In yet another embodiment, the ratio of $R^2$ groups that are bioreversible group (i) to $R^2$ groups that are bioreversible groups (ii) or (iii) is from 1:3 to 3:1. In yet another embodiment, the ratio of $R^2$ groups that are bioreversible group (i) to $R^2$ groups that are bioreversible groups (ii) or (iii) is from 1:2 to 2:1. In a specific embodiment, the ratio of $R^2$ groups that are bioreversible group (i) to $R^2$ groups that are bioreversible groups (ii) or (iii) is 1:1.

The disclosure also provides a hybridized polynucleotide comprising the polynucleotide construct of any of the foregoing embodiments hybridized to a complementary polynucleotide. In one embodiment, the complementary polynucleotide comprises an intracellularly bioreversible group conjugated to an internucleotide bridging group or terminal nucleotide group. In yet another embodiment, the polynucleotide construct and the complementary polynucleotide each comprise no more than 9 bioreversible groups. In one embodiment, no more than 75% of the total number of nucleotides have bioreversible groups. In another embodiment, the complementary strand and the polynucleotide construct each have between 10-32 (e.g., 19-25) nucleotides. In one embodiment, the hybridized polynucleotide is a siRNA. In another embodiment, the polynucleotide construct is the guide strand, and the complementary polynucleotide is the passenger strand. In another embodiment, the passenger strand comprises a phosphotriester having a moiety that is not cleavable by an intracellular enzyme. In a further embodiment, the moiety that is not cleavable by the intracellular enzyme is optionally substituted $C_{1-6}$ alkyl.

The disclosure also provides a pharmaceutical composition comprising a polynucleotide construct or polynucleotide of any of the foregoing embodiments and a pharmaceutically acceptable excipient.

The disclosure also provides a method of reducing the expression of a protein, comprising administering the construct or hybridized polynucleotide described above to a cell in an amount sufficient to induce an antisense or RNAi mediated reduction of gene expression.

The disclosure also provides a nucleotide construct comprising a structure of Formula (I):

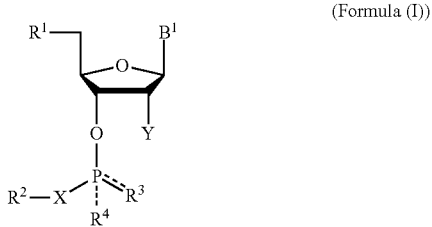

(Formula (I))

or a salt thereof wherein, $B^1$ is a nucleobase; X is an O, S, or $NR^5$; Y is a halo, optionally substituted $C_{1-6}$ alkoxy, or a protected hydroxyl group; $R^1$ is hydroxyl, optionally substituted $C_{1-6}$ alkoxy, a protected hydroxyl group, a monophosphate, a disphosphate, a triphosphate, a tetraphosphate, or a pentaphosphate; $R^2$ is a bioreversible group that comprises an auxiliary moiety selected from the group consisting of peptide, a polypeptide, a carbohydrate, a neutral organic polymer, a positively charged polymer, a therapeutic agent, a targeting moiety, an endosomal escape moiety, and any combination thereof, wherein the auxiliary moiety is linked to the bioreversible group by one or more covalent bonds; $R^3$ is an O, S, or an optionally substituted amino; $R^4$ is an H, hydroxyl, optionally substituted $C_{1-6}$ alkoxy, a protected hydroxyl group, a monophosphate, a disphosphate, a triphosphate, a tetraphosphate, a pentaphosphate, or absent when $R^3$ is an optionally substituted amino; and $R^5$ is H, an optionally substituted $C_{1-6}$ alkyl, S-pivaloyl thioethanol, a hydroxyl, an optionally substituted $C_{1-6}$ alkoxy, an optionally substituted $C_{3-8}$ cycloalkyl, an optionally substituted $C_{6-12}$ aryl, or an optionally substituted $C_{2-9}$ heterocyclyl. In a certain embodiment, X is O or S. In one embodiment, the nucleotide construct comprises a structure of Formula I(a):

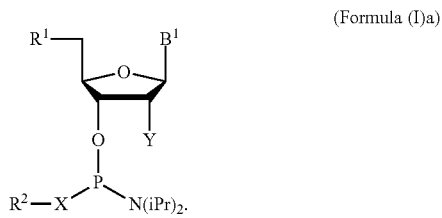

(Formula (I)a)

In one embodiment, $R^1$ is a 4,4'-dimethoxytrityl group (DMT) protected hydroxyl group. In another embodiment, $R^2$ comprises structural Formula V:

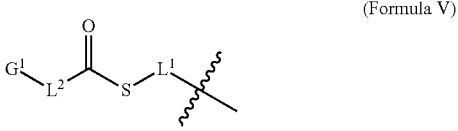

(Formula V)

wherein, $G^1$ is the peptide, the polypeptide, the carbohydrate, the neutral organic polymer, the positively charged polymer, the therapeutic agent, the targeting moiety, the endosomal escape moiety, or any combination thereof; $L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and $L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S. In yet another embodiment, $L^1$ is optionally substituted $C_{2-10}$ alkylene. In yet a further embodiment, $L^1$ is unsubstituted or substituted $C_2$, $C_4$, or $C_5$ alkylene. In yet another embodiment, $L^2$ is a covalent bond. In another embodiment, $L^2$ is optionally substituted $C_{1-10}$ alkylene or optionally substituted $C_{6-12}$ arylene. In yet another embodiment, $L^2$ is not a bond, and $G^1$ is bound to $L^2$ via a bond formed by a reaction selected from the group consisting of a pericyclic reaction; an alkylation or arylation of a hydroxyl, thiol, or amino moiety; and a reaction of a hydroxyl, thiol, or amino nucleophile with an electrophile. In one embodiment, $L^2$ is not a bond, and $G^1$ is bound to $L^2$ via an amide bond, a sulfonamide bond, a carboxylic ester, a thioester, an optionally substituted aryl or heteroaryl, an imine, a hydrazone, an oxime or a succinimide. In particular, $G^1$ is the peptide, the polypeptide, the neutral organic polymer, or any combination thereof; $L^1$ is an optionally substituted $C_{2-6}$ alkylene, optionally substituted $C_{2-6}$ alkenylene, or optionally substituted $C_{2-6}$ alkynylene, wherein each of alkylene, alkenylene, or alkynylene is optionally interrupted with 1 or 2 oxygen atoms; and $L^2$ is a covalent bond, or is selected from optionally substituted $C_{1-6}$ alkylene; optionally substituted $C_{2-6}$ alkenylene; optionally substituted $C_{2-6}$ alkynylene; and optionally substituted $C_{6-10}$ arylene. In these embodiments, $G^1$ may include a delivery domain, e.g., comprising one or more a peptide transduction domains (PTDs). The neutral organic polymer of $G^1$ is optionally poly(ethyleneglycol). In yet another embodiment, $L^1$ is

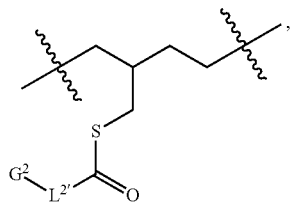

wherein $L^{2'}$ is a covalent bond or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S; $G^2$ is a conjugating moiety, a hydrophilic functional group, a small molecule, a peptide, a polypeptide, a carbohydrate, a neutral organic polymer, a positively charged polymer, a therapeutic agent, a targeting moiety, a endosomal escape moiety, or combination thereof. In one embodiment, X is O. In another embodiment, the peptide, the polypeptide, the protein, the carbohydrate, the neutral organic polymer, the positively charged polymer, the therapeutic agent, the targeting moiety, the endosomal escape moiety, or combination thereof is linked to the bioreversible group through a condensation reaction with the aldehyde group to form an imine, enamine, or hydrazone bond. In yet another embodiment, the peptide, the polypeptide, the protein, the carbohydrate, the neutral organic polymer, the positively charged polymer, the therapeutic agent, the targeting moiety, the endosomal escape moiety, or combination thereof is linked to the bioreversible group by one or more nitrogen containing complementary conjugating moieties having the structure of Formula III:

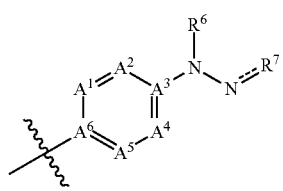
(Formula III)

wherein, $A^1$, $A^2$, $A^4$, and $A^5$ are each individually a N or $CR^8$; $A^3$ and $A^6$ are C; $R^6$-$R^7$ are each individually a H, optionally substituted $C_{1-6}$ alkyl, optionally substituted $C_{2-6}$ alkenyl, optionally substituted imine, and optionally substituted enamine; and each $R^8$ is individually a H, optionally substituted $C_{1-6}$ alkyl, optionally substituted $C_{1-6}$ alkenyl, optionally substituted $C_{2-6}$ alkynyl, halide, hydroxyl, —CHO, optionally substituted $C_{1-6}$ acyl, carboxylic acid, cyano, nitro, optionally substituted amino, thiol, optionally substituted $C_{2-9}$ heterocyclyl, optionally substituted $C_{6-12}$ aryl, optionally substituted $C_{3-8}$ cycloalkyl, and optionally substituted $C_{4-8}$ cycloalkenyl. In one embodiment, $R^2$ comprises a delivery domain. In a further embodiment, the delivery domain comprises one or more peptide transduction domains (PTDs). In yet a further embodiment, the nucleotide construct comprises a structure of Formula I(c):

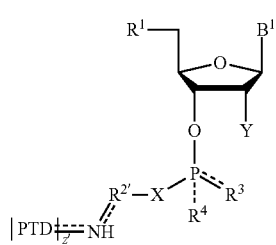
(Formula I(c))

wherein $R^{2'}$ is the residue of the bioreversible group bound to the PTD; and z' is a number from 1 to 10, wherein when z' is greater than 1, the PTDs are linked together through poly($C_{1-4}$ alkyleneoxide) groups having 1-10 repeating units. In another embodiment, the PTD is a cationic peptide sequence having 5-10 arginine and/or lysine residues over 5-15 amino acids. In a specific embodiment, the PTD comprises the sequence RKKRRQRRR (SEQ ID NO: 1). In yet another embodiment, the delivery domain comprises a PTD conjugated to poly(ethylene glycol) have 1-10 repeating units. For example, the delivery domain comprises a structure selected from the group consisting of: PEG-(PTD); GG-(PTD)-PEG-(PTD); PEG-(PTD)-PEG-(PTD); GG-(PTD)-PEG-PEG-PEG-(PTD); PEG-(PTD)-PEG-PEG-PEG-(PTD); GG-(PTD)-PEG-(PTD)-PEG-(PTD); and GG-(PTD)-PEG-PEG-PEG-(PTD)-PEG-PEG-PEG-(PTD); wherein PEG is a poly(ethyleneglycol) linker having one to ten repeat units. In yet another embodiment, $R^2$ comprises the targeting moiety. For example, the targeting moiety can comprise a ligand, carbohydrate, antibody, FAb, ScFv, or single-domain antibody. In yet another embodiment of any of the foregoing, $B^1$ is a non-natural nucleotide base. In a further embodiment, $B^1$ is a naturally occurring nucleotide base. For example, $B^1$ can be cytosine, guanine, adenine, uracil, or thymidine.

The disclosure also provides a nucleotide construct comprising a structure of Formula (I):

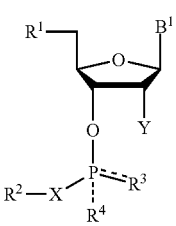
(Formula (I))

or a salt thereof, wherein, $B^1$ is a nucleobase; X is an O, S, or $NR^5$; Y is a halo, optionally substituted $C_{1-6}$ alkoxy, or a protected hydroxyl group; $R^1$ is hydroxyl, optionally substituted $C_{1-6}$ alkoxy, a protected hydroxyl group, a monophosphate, a disphosphate, a triphosphate a tetraphosphate, or a pentaphosphate; $R^2$ is

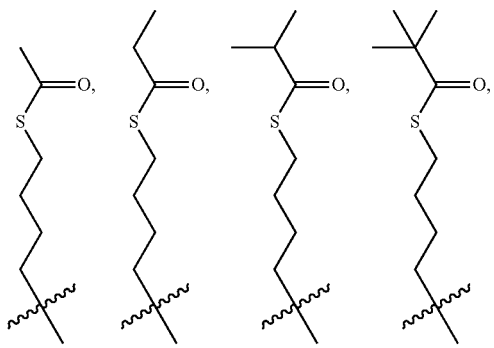

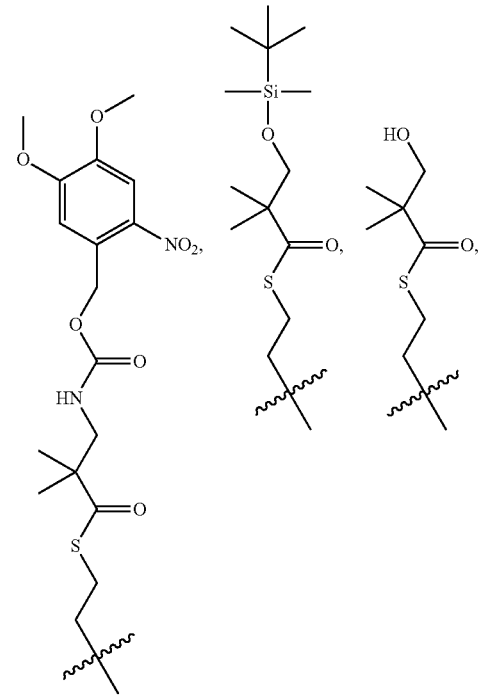

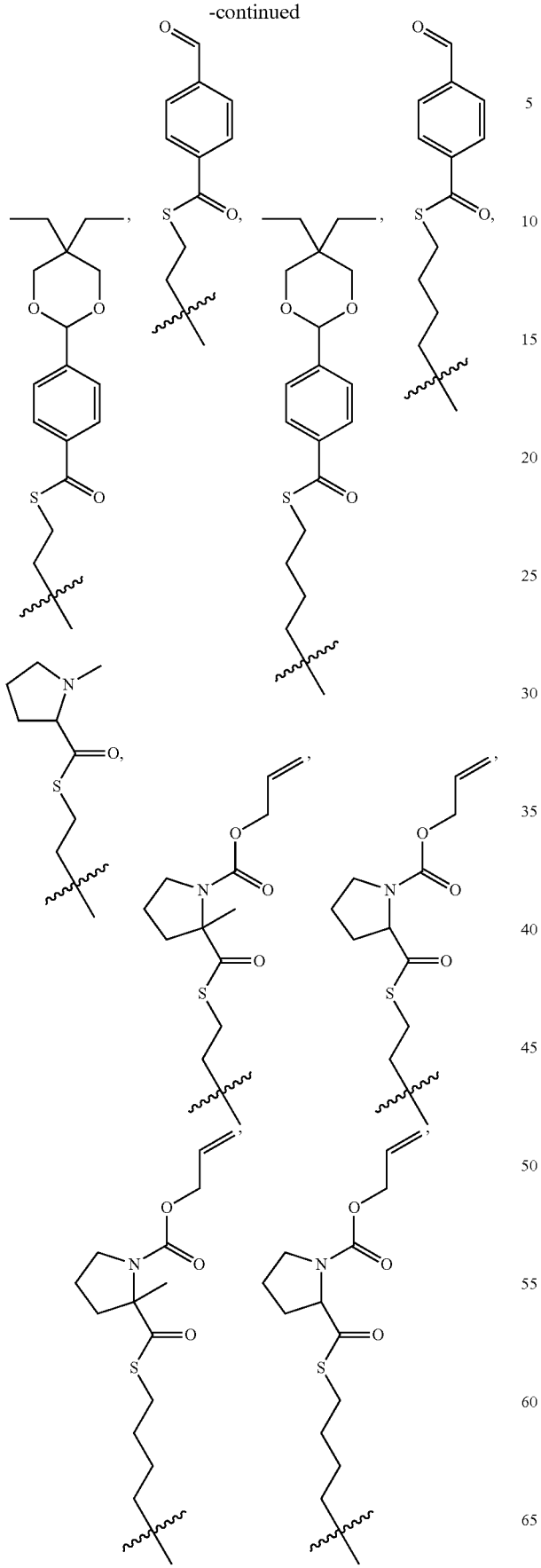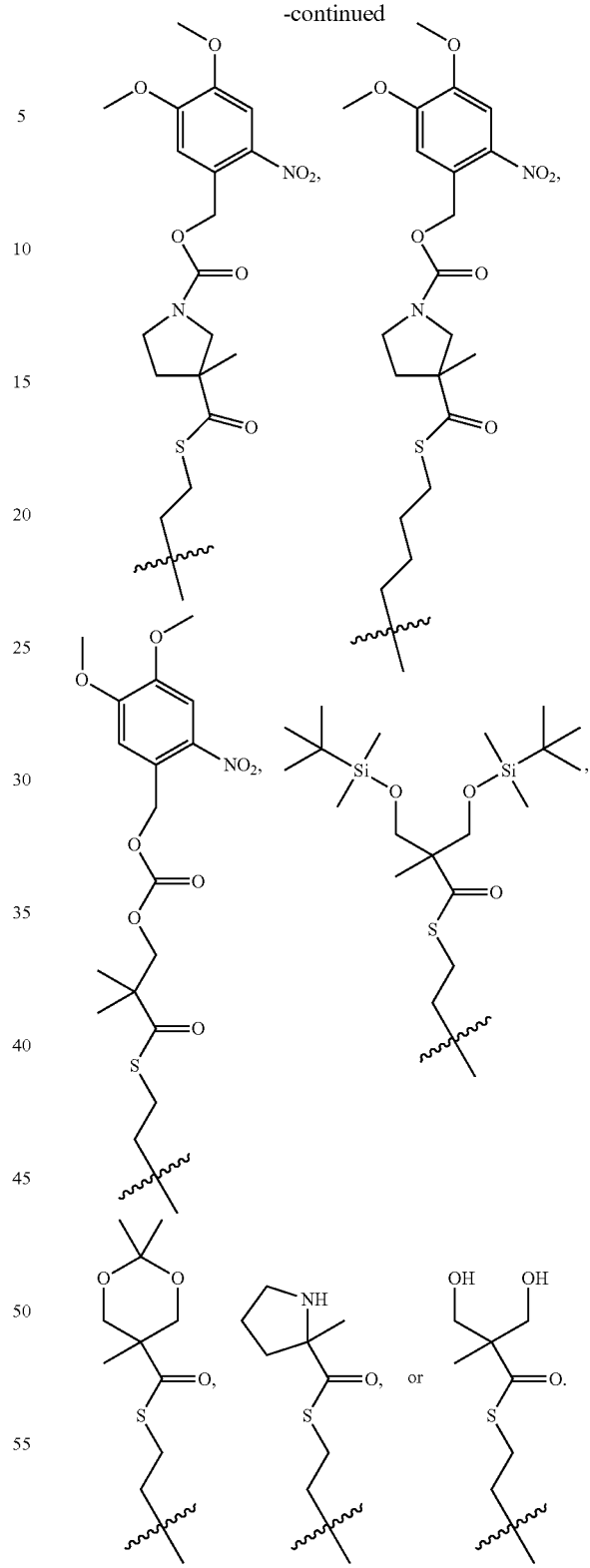
$R^3$ is an O, S, or an optionally substituted amino; $R^4$ is an H, hydroxyl, optionally substituted $C_{1-6}$ alkoxy, a protected hydroxyl group, a monophosphate, a disphosphate, a triphosphate, a tetraphosphate, a pentaphosphate, or absent when $R^3$ is an optionally substituted amino; and $R^5$ is H, an optionally substituted $C_{1-6}$ alkyl, S-pivaloyl thioethanol, a hydroxyl, an optionally substituted $C_{1-6}$ alkoxy, an optionally substituted $C_{3-8}$ cycloalkyl, an optionally substituted $C_{6-12}$ aryl, or an optionally substituted $C_{2-9}$ heterocyclyl. In a certain embodiment, X is O or S.

The disclosure also provides a method of manufacturing a polynucleotide construct, comprising (1) de-blocking a first nucleoside or nucleotide which comprises a DMT protecting group at the 5' position, by removing the DMT group under acidic conditions in an aprotic solvent system, wherein the first nucleoside or nucleotide may be fixed to a solid support at the 3' position or alternatively the 3' position is protected with non-acid labile hydroxyl protecting group and the first nucleoside or nucleotide is in solution; (2) coupling the de-blocked first nucleoside or nucleotide with either an activated nucleotide of as set forth above or activated nucleotide comprising a phosphoramidite at the 3' position in the presence of an acidic azole catalyst; (3) oxidizing the coupled nucleotides with an oxidizing agent in a solvent system comprising a protic solvent and a weak base; (4) de-blocking the coupled nucleotides by removing a DMT group at the 5' position of the coupled nucleotides under acidic conditions in an aprotic solvent system; and wherein steps (2)-(4) are repeated from 1 to 149 times, and wherein the polynucleotide construct comprises at least one nucleotide construct as described above. In one embodiment, the first nucleoside or nucleotide of step (1) has been attached to a solid support, and wherein the resulting polynucleotide construct is cleaved from the solid support after the last de-blocking step. In another embodiment, the steps are carried out using a computer controlled instrument. In yet another embodiment, post synthesis of the polynucleotide construct, if a nucleobase comprises one or more protecting groups, then the protecting groups are removed; and/or for any bioreversible groups which comprise a hydrophilic functional group or conjugating moiety that is protected by a protecting group, then the protecting group is removed. In yet another embodiment, post synthesis of the polynucleotide construct, a small molecule, a peptide, a polypeptide, a carbohydrate, a neutral organic polymer, a positively charged polymer, a therapeutic agent, a targeting moiety, and/or an endosomal escape moiety is linked to one or more conjugating moieties of one or more bioreversible groups.

The disclosure also provides a kit comprising a vessel or vessels containing a peptide, a polypeptide, a protein, a carbohydrate, a neutral organic polymer, a positively charged polymer, a therapeutic agent, a targeting moiety, an endosomal escape moiety, or any combination thereof that have one or more conjugating moieties which can condense with an aldehyde group to form one or more covalent bonds and the polynucleotide construct as described above.

The disclosure includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the compounds of the disclosure are contemplated herein. In particular, the presence of bioreversible groups on certain internucleotide bridging groups or terminal nucleotide groups may produce various diastereomers and mixtures thereof. Unless otherwise stated, all tautomeric forms of the compounds of the disclosure are contemplated herein. The disclosure includes all pharmaceutically acceptable isotopically-labeled compounds of the disclosure, wherein one or more atoms are replaced by atoms having the same atomic number, but an atomic mass or mass number different from the atomic mass or mass number usually found in nature. Examples of isotopes suitable for inclusion in the compounds of the disclosure comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "activated carbonyl," as used herein, represents a functional group having the formula of —C(O)$R^4$ where $R^4$ is a $C_{1-6}$ alkoxy group, OH, or halide.

The term "activated phosphorus center," as used herein, represents a trivalent phosphorus (III) or a pentavalent phosphorus (V) center wherein at least one of the substituents is a $C_{1-6}$ alkoxy group. Desirably, the alkoxy group is —OCH$_3$ or —OCH$_2$CH$_3$.

The term "activated silicon center," as used herein, represents a tetrasubstituted silicon center wherein at least one of the substituents is a $C_{1-6}$ alkoxy group. Desirably, the alkoxy group is —OCH$_3$ or —OCH$_2$CH$_3$.

The term "activated sulfur center," as used herein, represents a tetravalent sulfur wherein at least one of the substituents is a $C_{1-6}$ alkoxy group. Desirably, the alkoxy group is —OCH$_3$ or —OCH$_2$CH$_3$.

The term "acyl," as used herein, represents a hydrogen or an alkyl group (e.g., a haloalkyl group) that is attached to the parent molecular group through a carbonyl group and is exemplified by formyl (i.e., a carboxyaldehyde group), acetyl, propionyl, butanoyl and the like. Exemplary unsubstituted acyl groups include from 1 to 7 carbons. In some embodiments, the alkyl group is further substituted with 1, 2, 3, or 4 substituents as described herein.

The term "alkaryl," as used herein, represents an aryl group attached to the parent molecular group through an alkylene group. Exemplary unsubstituted alkaryl groups are from 7 to 16 carbons. In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "alkenyl," as used herein, represents monovalent straight or branched chain hydrocarbon groups of, unless otherwise specified, from 2 to 6 carbons and cycloalkenyl groups of 4 to 8 carbons containing one or more carbon-carbon double bonds and is exemplified by ethenyl, 1-propenyl, 2-propenyl, 2-methyl-1-propenyl, 1-butenyl, 2-butenyl, and the like. Alkenyl groups may be optionally substituted with 1, 2, 3, or 4 substituent groups that are selected, independently, from aryl, cycloalkyl, or heterocyclyl (e.g., heteroaryl) or any of the exemplary alkyl substituent groups described herein. In addition, when an alkenyl group is present in a bioreversible group of the disclosure it may be substituted with a thioester or disulfide group that is bound to a conjugating moiety, a hydrophilic functional group, or an auxiliary moiety as defined herein.

The term "alkoxy," as used herein, represents a chemical substituent of formula —OR, where R is a $C_{1-6}$ alkyl group, unless otherwise specified. In some embodiments, the alkyl group can be further substituted with 1, 2, 3, or 4 substituent groups as defined herein.

The term "alkyl," as used herein, is inclusive of both straight chain, branched chain, and cycloalkyl saturated hydrocarbon groups from 1 to 6 carbons, unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) alkoxy; (2) alkylsulfinyl; (3) amino; (4) arylalkoxy; (5) azido; (6) halo; (7) (heterocyclyl)oxy; (8) hydroxy; (9) nitro; (10) oxo (e.g., carboxyaldehyde or acyl); (11) spirocyclyl; (12) thioalkoxy; (13) thiol; (14) —$CO_2R^A$, where $R^A$ is selected from the group consisting of (a) alkyl, (b) aryl, (c) hydrogen, and (d) alkaryl; (15) —$C(O)NR^BR^C$, where each of $R^B$ and $R^C$ is, independently, selected from the group consisting of (a) hydrogen, (b) alkyl, (c) aryl, and (d) alkaryl; (16) —$SO_2R^D$, where $R^D$ is selected from the group consisting of (a) alkyl, (b) aryl, and (c) alkaryl; (17) —$SO_2NR^ER^F$, where each of $R^E$ and $R^F$ is, independently, selected from the group consisting of (a) hydrogen, (b) alkyl, (c) aryl and (d) alkaryl; (18) silyl; (19) cyano; and (20) —$S(O)R^H$ where $R^H$ is selected from the group consisting of (a) hydrogen, (b) alkyl, (c) aryl, and (d) alkaryl. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of at least two hydrogen atoms, and is exemplified by methylene, ethylene, isopropylene, and the like.

The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, or 10. In some embodiments, the alkylene can be further substituted with 1, 2, 3, or 4 substituent groups as defined herein for an alkyl group. Similarly, the suffix "ene" designates a divalent radical of the corresponding monovalent radical as defined herein. For example, arylene, heterocyclylene, alkenylene, and alkynylene are divalent forms of aryl, heterocyclyl, alkenyl, and alkynyl. In addition, when an alkyl or alkylene, alkenyl or alkenylene, or alkynyl or alkynyl group is present in a bioreversible group of the disclosure it may be substituted with an ester, thioester, or disulfide group that is bound to a conjugating moiety, a hydrophilic functional group, or an auxiliary moiety as defined herein.

The term "alkynyl," as used herein, represents monovalent straight or branched chain hydrocarbon groups from two to six carbon atoms containing at least one carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —$N(R^{N1})_2$ or —$N(=NR^{N1})(NR^{N1})_2$ wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl, and wherein each $R^{N2}$ is, independently, H, alkyl, or aryl. In one embodiment, amino is —$NH_2$, or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl. The $R^{N1}$ groups may themselves be unsubstituted or substituted as described herein. In addition, when an alkynyl group is present in a bioreversible group of the disclosure it may be substituted with an ester, thioester, or disulfide group that is bound to a conjugating moiety, a hydrophilic functional group, or an auxiliary moiety as defined herein.

The term "antibody," as used herein, is used in the broadest sense and specifically covers, for example, single monoclonal antibodies, antibody compositions with polyepitopic specificity, single chain antibodies, and fragments of antibodies (e.g., antigen binding fragment or Fc region). "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they recognize antigens and/or exhibit any of the desired agonistic or antagonistic properties described herein. Antibodies or fragments may be humanized, human, or chimeric.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) acyl (e.g., carboxyaldehyde); (2) alkyl (e.g., alkoxyalkyl, alkylsulfinylalkyl, aminoalkyl, azidoalkyl, (carboxyaldehyde) alkyl, haloalkyl (e.g., perfluoroalkyl), hydroxyalkyl, nitroalkyl, or thioalkoxyalkyl); (3) alkoxy (e.g., perfluoroalkoxy); (4) alkylsulfinyl; (5) aryl; (6) amino; (7) alkaryl; (8)

azido; (9) cycloalkyl; (10) alkcycloalkyl; (11) halo; (12) heterocyclyl (e.g., heteroaryl); (13) (heterocyclyl)oxy; (14) hydroxy; (15) nitro; (16) thioalkoxy; (17) —(CH$_2$)$_q$CO$_2$R$^A$, where q is an integer from zero to four, and R$^A$ is selected from the group consisting of (a) alkyl, (b) aryl, (c) hydrogen, and (d) alkaryl; (18) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) alkaryl; (19) —(CH$_2$)$_q$SO$_2$R$^D$, where q is an integer from zero to four and where R$^D$ is selected from the group consisting of (a) alkyl, (b) aryl, and (c) alkaryl; (20) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) alkaryl; (21) thiol; (22) aryloxy; (23) cycloalkoxy; (24) arylalkoxy; (25) alkheterocyclyl (e.g., alkheteroaryl); (26) silyl; (27) cyano; and (28) —S(O)R$^H$ where R$^H$ is selected from the group consisting of (a) hydrogen, (b) alkyl, (c) aryl, and (d) alkaryl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group. In addition, when an aryl group is present in a bioreversible group of the disclosure it may be substituted with an ester, thioester, or disulfide group that is bound to a conjugating moiety, a hydrophilic functional group, or an auxiliary moiety as defined herein.

The term "auxiliary moiety" refers to any moiety, including, but not limited to, a small molecule, a peptide, a polypeptide, a carbohydrate, a neutral organic polymer, a positively charged polymer, a therapeutic agent, a targeting moiety, an endosomal escape moiety, and any combination thereof, which can be conjugated to a nucleic acid construct disclosed herein. Generally, but not always the case, an "auxiliary moiety" is linked or attached to a nucleic acid construct disclosed herein by forming one or more covalent bonds to one or more conjugating groups present on a bioreversible group. However, in alternative embodiments an "auxiliary moiety" may be linked or attached to a nucleic acid construct disclosed herein by forming one or more covalent bonds to any portion of the nucleic acid construct in addition to conjugating groups present on a bioreversible group, such as to the 2', 3' or 5' positions of a nucleotide sugar molecule, or on any portion of a nucleobase. Although the name for a particular auxiliary moiety may imply a free molecule, it will be understood that such a free molecule is attached to a nucleic acid construct. One skilled in the art will readily understand appropriate points of attachment of a particular auxiliary moiety to a nucleic acid construct.

The term "azido," as used herein, represents an N$_3$ group.

The term "bioreversible group," as used herein, represents a moiety comprising a functional group that can be actively cleaved intracellularly, e.g., via the action of one or more intracellular enzymes (e.g., an intracellular thioesterase or an intracellar reductase) or passively cleaved intracellularly, such as by exposing the group to the intracellular environment or a condition present in the cell (e.g., pH, reductive or oxidative environment, or reaction with intracellular species, such as glutathione). Exemplary bioreversible groups comprise thioesters or disulfides.

The term "carbene" as used herein, represents a functional group that is a divalent carbon species having six valence electrons and the structure =C: or —CR$^B$: wherein R$^B$ is selected from H, optionally substituted C$_{1-12}$ alkyl, optionally substituted C$_{6-12}$ aryl, optionally substituted C$_{1-12}$ alk C$_{6-12}$ aryl or optionally substituted carbonyl; and C is a carbon with two electrons that are not part of a covalent bond. The two electrons may be paired (e.g., singlet carbene) or unpaired (e.g., triplet carbene).

The term "carbocyclic," as used herein, represents an optionally substituted C$_3$-C$_{12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbohydrate," as used herein, represents a compound which comprises one or more monosaccharide units having at least 5 carbon atoms (which may be linear, branched or cyclic) with an oxygen, nitrogen or sulfur atom bonded to each carbon atom. The term "carbohydrate" therefore encompasses monosaccharides, disaccharides, trisaccharides, tetrasaccharides, oligosaccharides, and polysaccharides. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C$_{5-6}$ sugars; di- and trisaccharides include sugars having two or three monosaccharide units (e.g., C$_{5-6}$ sugars).

The term "carbonyl," as used herein, represents a C(O) group. Examples of functional groups which comprise a "carbonyl" include esters, ketones, aldehydes, anhydrides, acyl chlorides, amides, carboxylic acids, and carboxlyates.

The term "component of a coupling reaction," as used herein, represents a molecular species capable of participating in a coupling reaction. Components of coupling reactions include hydridosilanes, alkenes, and alkynes.

The term "component of a cycloaddition reaction," as used herein, represents a molecular species capable of participating in a cycloaddition reaction. In cycloaddition reactions in which bond formation involves [4n+2]π electrons where n is 1, one component will provide 2π electrons, and another component will provide 4π electrons. Representative components of cycloaddition reactions that provide 2π electrons include alkenes and alkynes. Representative components of cycloaddition reactions that provide 4π electrons include 1,3-dienes, α,β-unsaturated carbonyls, and azides.

The term "conjugating moiety," as used herein, represents a functional group that is capable of forming one or more covalent bonds to another auxiliary moiety (e.g., a functional group that is a nucleophile, electrophile, a component in a cycloaddition reaction, or a component in a coupling reaction) under appropriate conditions. Examples of such groups are provided herein.

The term "coupling reaction," as used herein, represents a reaction of two components in which one component includes a nonpolar σ bond such as Si—H or C—H and the second component includes a π bond such as an alkene or an alkyne that results in either the net addition of the σ bond across the π bond to form C—H, Si—C, or C—C bonds or the formation of a single covalent bond between the two components. One coupling reaction is the addition of Si—H across an alkene (also known as hydrosilylation). Other coupling reactions include Stille coupling, Suzuki coupling, Sonogashira coupling, Hiyama coupling, and the Heck reaction. Catalysts may be used to promote the coupling reaction. Typical catalysts are those which include Pt(0), Pt(II), or Pt(IV).

The term "cycloaddition reaction" as used herein, represents reaction of two components in which [4n+2]π electrons are involved in bond formation when there is either no activation, activation by a chemical catalyst, or activation using thermal energy, and n is 1, 2, or 3. A cycloaddition reaction is also a reaction of two components in which [4n]π electrons are involved, there is photochemical activation, and n is 1, 2, or 3. Desirably, [4n+2]π electrons are involved in bond formation, and n=1. Representative cycloaddition reactions include the reaction of an alkene with a 1,3-diene (Diels-Alder reaction), the reaction of an alkene with an α,β-unsaturated carbonyl (hetero Diels-Alder reaction), and the reaction of an alkyne with an azide (Hüisgen cycloaddition).

The term "cycloalkyl," as used herein, represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this disclosure can be optionally substituted with: (1) acyl (e.g., carboxyaldehyde); (2) alkyl (e.g., alkoxyalkyl, alkylsulfinylalkyl, aminoalkyl, azidoalkyl, (carboxyaldehyde)alkyl, haloalkyl (e.g., perfluoroalkyl), hydroxyalkyl, nitroalkyl, or thioalkoxyalkyl); (3) alkoxy (e.g., perfluoroalkoxy); (4) alkylsulfinyl; (5) aryl; (6) amino; (7) alkaryl; (8) azido; (9) cycloalkyl; (10) alkcycloalkyl; (11) halo; (12) heterocyclyl (e.g., heteroaryl); (13) (heterocyclyl)oxy; (14) hydroxy; (15) nitro; (16) thioalkoxy; (17) —(CH$_2$)$_q$CO$_2$R$^A$, where q is an integer from zero to four, and R$^A$ is selected from the group consisting of (a) alkyl, (b) aryl, (c) hydrogen, and (d) alkaryl; (18) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) alkaryl; (19) —(CH$_2$)$_q$SO$_2$R$^D$, where q is an integer from zero to four and where R$^D$ is selected from the group consisting of (a) alkyl, (b) aryl, and (c) alkaryl; (20) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) alkaryl; (21) thiol; (22) aryloxy; (23) cycloalkoxy; (24) arylalkoxy; (25) alkheterocyclyl (e.g., alkheteroaryl); (26) oxo; (27) silyl; (28) cyano; (29) —S(O)R$^H$ where R$^H$ is selected from the group consisting of (a) hydrogen, (b) alkyl, (c) aryl, and (d) alkaryl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group.

The term "electrophile" or "electrophilic group," as used herein, represents a functional group that is attracted to electron rich centers and is capable of accepting pairs of electrons from one or more nucleophiles so as to form one or more covalent bonds. Electrophiles include, but are not limited to, cations; polarized neutral molecules; nitrenes; nitrene precursors such as azides; carbenes; carbene precursors; activated silicon centers; activated carbonyls; alkyl halides; alkyl pseudohalides; epoxides; electron-deficient aryls; activated phosphorus centers; and activated sulfur centers. Typically encountered electrophiles include cations such as H$^+$ and NO$^+$, polarized neutral molecules, such as HCl, alkyl halides, acyl halides, carbonyl containing compounds, such as aldehydes, and atoms which are connected to good leaving groups, such as mesylates, triflates, and tosylates.

The term "endosomal escape moiety," as used herein, represents a moiety which enhances the release of endosomal contents or allows for the escape of a molecule from an internal cellular compartment such as an endosome.

The term "halo," as used herein, represents a halogen selected from bromine, chlorine, iodine, and fluorine.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. In one embodiment, the heteroaryl is substituted with 1, 2, 3, or 4 substituents groups as defined for a heterocyclyl group.

The term "heterocyclyl," as used herein, represents a 5-, 6- or 7-membered ring, unless otherwise specified, containing one, two, three, or four heteroatoms independently selected from the group comprising nitrogen, oxygen, and sulfur. The 5-membered ring has zero to two double bonds, and the 6- and 7-membered rings have zero to three double bonds. Certain heterocyclyl groups include from 2 to 9 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3,4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7 H-purinyl); 1,2,3,6-tetrahydro-2,6-dioxo-1 H-purinyl (e.g., 1,2,3,6-tetrahydro-3,7-dimethyl-2,6-dioxo-1 H-purinyl); 2-oxobenz[c,d]indolyl; 1,1-dioxo-2H-naphth[1,8-c,d]isothiazolyl; and 1,8-naphthylenedicarboxamido. Heterocyclic groups also include groups of the formula

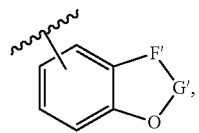

where
F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four or five substituents independently selected from the group consisting of: (1) acyl (e.g., carboxyaldehyde); (2) alkyl (e.g., alkoxyalkyl, alkylsulfinylalkyl, aminoalkyl, azidoalkyl, (carboxyaldehyde) alkyl, haloalkyl (e.g., perfluoroalkyl), hydroxyalkyl, nitroalkyl, or thioalkoxyalkyl); (3) alkoxy (e.g., perfluoroalkoxy); (4) alkylsulfinyl; (5) aryl; (6) amino; (7) alkaryl; (8) azido; (9) cycloalkyl; (10) alkcycloalkyl; (11) halo; (12) heterocyclyl (e.g., heteroaryl); (13) (heterocyclyl)oxy; (14) hydroxy; (15) nitro; (16) thioalkoxy; (17) —(CH$_2$)$_q$CO$_2$R$^A$, where q is an integer from zero to four, and R$^A$ is selected from the group consisting of (a) alkyl, (b) aryl, (c) hydrogen, and (d) alkaryl; (18) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) alkaryl; (19) —(CH$_2$)$_q$SO$_2$R$^D$, where q is an integer from zero to four and where R$^D$ is selected from the group consisting of (a) alkyl, (b) aryl, and (c) alkaryl; (20) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) alkaryl; (21) thiol; (22) aryloxy; (23) cycloalkoxy; (24) arylalkoxy; (25) alkheterocyclyl (e.g., alkheteroaryl); (26) oxo; and (27) (heterocyclyl)imino; (28) silyl; (29) cyano; and (30) —S(O)R$^H$ where R$^H$ is selected from the group consisting of (a) hydrogen, (b) alkyl, (c) aryl, and (d) alkaryl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group. In addition, when a heterocyclyl group is present in a bioreversible group of the disclosure it may be substituted with an ester, thioester, or disulfide group that is bound to a conjugating moiety, a hydrophilic functional group, or an auxiliary moiety as defined herein.

The term "hydrophilic functional group," as used herein, represents a moiety that confers an affinity to water and increase the solubility of an alkyl moiety in water. Hydrophilic functional groups can be ionic or non-ionic and include moieties that are positively charged, negatively charged, and/or can engage in hydrogen-bonding interactions. Exemplary hydrophilic functional groups include hydroxy, amino, carboxyl, carbonyl, thiol, phosphates (e.g., a mono-, di-, or tri-phosphate), polyalkylene oxides (e.g., polyethylene glycols), and heterocyclyls.

The term "hydroxyl," as used herein, represents an —OH group.

The term "hydroxy," as used herein, indicates the presence of a hydroxyl group.

The term "imine," as used herein, represents a group having a double bond between carbon and nitrogen, which can be represented as "C=N." In a particular embodiment, where a proton is α to the imine functional group, the imine may also be in the form of the tautomeric enamine. A type of imine bond is the hydrazone bond, where the nitrogen of the imine bond is covalently attached to a trivalent nitrogen (e.g., C=N—N(R)$_2$). In some embodiments, each R can be, independently, H, OH, optionally substituted C$_{1-6}$ alkoxy, or optionally substituted C$_{1-6}$ alkyl.

The term "nitrene," as used herein, represents a monovalent nitrogen species having six valence electrons and the structure =N: or —NR$^A$: where R$^A$ is selected from optionally substituted C$_{1-12}$ alkyl, optionally substituted C$_{6-12}$ aryl, optionally substituted C$_{1-12}$ alk C$_{6-12}$ aryl, or optionally substituted carbonyl; and N is a nitrogen with four valence electrons, at least two of which are paired. The two remaining electrons may be paired (i.e., singlet nitrene) or unpaired (i.e., triplet nitrene).

The term "nitro," as used herein, represents an —NO$_2$ group.

A "non-naturally occurring amino acid" is an amino acid not naturally produced or found in a mammal.

By "nonpolar σ bond" is meant a covalent bond between two elements having electronegativity values, as measured according to the Pauling scale, that differ by less than or equal to 1.0 units. Non-limiting examples of nonpolar σ bonds include C—C, C—H, Si—H, Si—C, C—Cl, C—Br, C—I, C—B, and C—Sn bonds.

The term "nucleobase," as used herein, represents a nitrogen-containing heterocyclic ring found at the 1' position of the sugar moiety of a nucleotide or nucleoside. Nucleobases can be unmodified or modified. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; those disclosed in *The Concise Encyclopedia Of Polymer Science And Engineering*, pages 858-859, Kroschwitz, J. I., ed. John Wiley & Sons, 1990; those disclosed by Englisch et al., *Angewandte Chemie, International Edition*, 1991, 30, 613; and those disclosed by Sanghvi, Y. S., Chapter 15, *Antisense Research and Applications*, pages 289 302, (Crooke et al., ed., CRC Press, 1993). Certain nucleobases are particularly useful for increasing the binding affinity of the polymeric compounds of the disclosure, including 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,594,121; 5,596,091; 5,614,617; and 5,681,941. For the purposes of this disclosure, "modified nucleobases," as used herein, further represents nucleobases, natural or nonnatural, which comprise one or more protecting groups as described herein.

The terms "nucleophile" or "nucleophilic functional group," as used herein, represent an optionally substituted functional group that engages in the formation of a covalent bond by donating electrons from electron pairs or π bonds. Nucleophiles may be selected from alkenes, alkynes, aryl, heteroaryl, hydrazine groups, hydroxy groups, phenoxy groups, amino groups, alkylamino groups, anilido groups, thio groups, and thiophenoxy groups.

The term a "nucleoside," as used herein, represents a nucleobase-sugar combination. The nucleobase portion of the nucleoside is normally a heterocyclic base. The term "nucleotide," as used herein, refers to a nucleoside that further includes an internucleotide bridging group or a terminal nucleotide group, such as a phosphate group, covalently linked to the sugar portion of the nucleoside. For those nucleosides that include a pentofuranosyl sugar, the internucleotide bridging group or terminal group, e.g., phosphate group, can be linked to either the 2', 3' or 5' hydroxyl moiety of the sugar. The sugar may or may not be a naturally occurring sugar, e.g., ribose or deoxyribose, and it may be a modified form of a naturally occurring sugar, e.g., 2' modified ribose. Exemplary modified sugars include 2-position sugar modifications, in which the 2-OH is replaced by a group such as an H, OR, R, halo (e.g., F), SH, SR, $NH_2$, NHR, $NR_2$, or CN, wherein R is an alkyl moiety. Modified sugars also include, e.g., non-ribose sugars, such as mannose, arabinose, glucopyranose, galactopyranose, 4-thioribose, and other sugars, heterocycles, or carbocycles. Nucleotides also include locked nucleic acids (LNA), peptide nucleic acids, glycerol nucleic acids, morpholino nucleic acids, and threose nucleic acids.

In other embodiments, the natural sugar phosphorodiester backbone can be replaced with a protein nucleotide (PNA) backbone having repeating N-(2-aminoethyl)-glycine units linked by peptide bonds. Other types of modifications for polynucleotides designed to be more resistant to nuclease degradation are described U.S. Pat. Nos. 6,900,540 and 6,900,301, incorporated herein by reference.

The term "polynucleotide" as used herein, represents two or more nucleotides and/or nucleosides covalently bound together by an internucleotide bridging group. Polynucleotides may be linear or circular. Moreover, for the purposes of this disclosure, the term "polynucleotide" is in reference to both oligonucleotides and longer sequences, and to mixtures of nucleotides, e.g., mixtures of DNA and RNA or mixtures of RNA and 2' modified RNA. The term "polynucleotide" encompasses polynucleotides which are comprised of one or more strands, unless stated otherwise.

The term "internucleotide bridging group," as used herein, represents a group which covalently links nucleotides and/or nucleosides together. A "terminal nucleotide" group is located at the 5', 3', or 2' end of a nucleotide. A terminal nucleotide group may or may not be capable of being connected to other nucleosides or nucleotides. Exemplary internucleotide bridging groups and terminal nucleotide groups include phosphate, thiophosphate, phosphonate (e.g., methyl phosphonate), phosphoramidate, boranophosphate, amide, methylene methylimino, formacetal, thioformacetal, sulfonyl, guanidine, and methylthiourea. Others are known in the art, see, e.g., Current Medicinal Chemistry, 2001, Vol. 8, No. 10, 1157. It will be understood that an internucleotide bridging group is bound to two nucleosides, and a terminal nucleotide group is bound to a single nucleoside, e.g., at the 3' or 5' end.

The term "oxo," as used herein, represents =O.

The term "peptide," as used herein, represents two to about 50 amino acid residues linked by peptide bonds. The term "polypeptide," as used herein, represents chains of 50 or more amino acids linked by peptide bonds. Moreover, for purposes of this disclosure, the term "polypeptide" and the term "protein" are used interchangeably herein in all contexts, unless provided for otherwise, e.g., naturally occurring or engineered proteins. A variety of polypeptides may be used within the scope of the methods and compositions provided herein. In a certain embodiment, polypeptides include antibodies or fragments of antibodies containing an antigen-binding site. Polypeptides made synthetically may include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_n COOH$ wherein n is 2-6, neutral nonpolar amino acids, such as sarcosine, t-butyl alanine, t-butyl glycine, N-methyl isoleucine, and norleucine.

The term "Ph," as used herein, represents phenyl.

The terms "photolytic activation" or "photolysis," as used herein, represent the promotion or initiation of a chemical reaction by irradiation of the reaction with light. The wavelengths of light suitable for photolytic activation range between 200-500 nm and include wavelengths that range from 200-260 nm and 300-460 nm. Other useful ranges include 200-230 nm, 200-250 nm, 200-275 nm, 200-300 nm, 200-330 nm, 200-350 nm, 200-375 nm, 200-400 nm, 200-430 nm, 200-450 nm, 200-475 nm, 300-330 nm, 300-350 nm, 300-375 nm, 300-400 nm, 300-430 nm, 300-450 nm, 300-475 nm, and 300-500 nm.

The term "protecting group," as used herein, represents a group intended to protect a functional group (e.g., a hydroxyl, an amino, or a carbonyl) from participating in one or more undesirable reactions during chemical synthesis (e.g., polynucleotide synthesis). The term "O-protecting group," as used herein, represents a group intended to protect an oxygen containing (e.g., phenol, hydroxyl or carbonyl) group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," $3^{rd}$ Edition (John Wiley & Sons, New York, 1999), which is incorporated herein by reference. Exemplary O- and N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy] ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "subject," as used herein, represents a human or non-human animal (e.g., a mammal).

The term "targeting moiety," as used herein, represents any moiety that specifically binds or reactively associates or complexes with a receptor or other receptive moiety associated with a given target cell population.

The term "therapeutically effective dose," as used herein, represents the quantity of an siRNA, or polynucleotide according to the disclosure necessary to ameliorate, treat, or at least partially arrest the symptoms of a disease or disorder (e.g., to inhibit cellular proliferation). Amounts effective for this use will, of course, depend on the severity of the disease and the weight and general state of the subject. Typically, dosages used in vitro may provide useful guidance in the amounts useful for in vivo administration of the pharmaceutical composition, and animal models may be used to determine effective dosages for treatment of particular disorders.

The term "thiol," as used herein, represents an —SH group.

The term "disorder," as used herein, is intended to be generally synonymous, and is used interchangeably with, the terms "disease", "syndrome", and "condition" (as in a medical condition), in that all reflect an abnormal condition presented by a subject, or one of its parts, that impairs normal functioning, and is typically manifested by distinguishing signs and symptoms.

The term "treating" as used in reference to a disorder in a subject, is intended to refer to reducing at least one symptom of the disorder by administrating a therapeutic (e.g., a nucleic acid construct of the disclosure) to the subject.

As used herein and in the appended claims, the singular forms "a," "and," and "the" include plural referents unless the context clearly dictates otherwise. Thus, for example, reference to "a PTD" includes a plurality of such PTDs and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure. The publications cited within this disclosure are incorporated in-full for all that they disclose. But, for purposes of this disclosure, any term which is presented in the publications or in the art which is identical to any term expressly defined in this disclosure, the term's definition presented in this disclosure will control in all respects.

BRIEF DESCRIPTION OF THE DRAWINGS

FIG. 3 shows the quantitative conversion of a polynucleotide construct including tBu-SATE bioreversible groups to wild-type siRNA. The conversion is contrasted with a construct that includes a phosphotriester that does not include a cleavable functional group.

FIG. 8 shows that duplexed polynucleotide constructs of the disclosure can be quantitatively measured using silver staining in a 10% non-denaturing gel (top panel); or by using SDS-PAGE gels and ethidium bromide staining (bottom panel).

FIGS. 9-10 presents summaries of hybridization studies using polynucleotide constructs of the disclosure having various numbers of bioreversible groups located at various sites on the passenger and guide strands.

FIG. 11 shows a process for purifying polynucleotide constructs of the disclosure.

DETAILED DESCRIPTION

Figure 1:
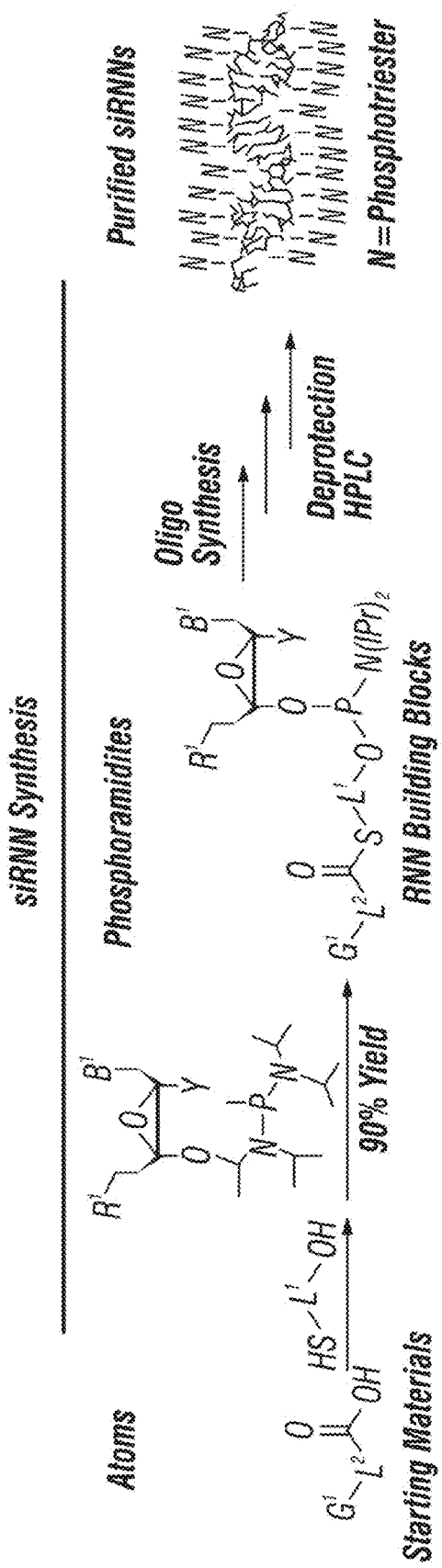
FIG. 1 presents a synthetic scheme for the preparation and purification of nucleic acid constructs of the disclosure.
Figure 1:
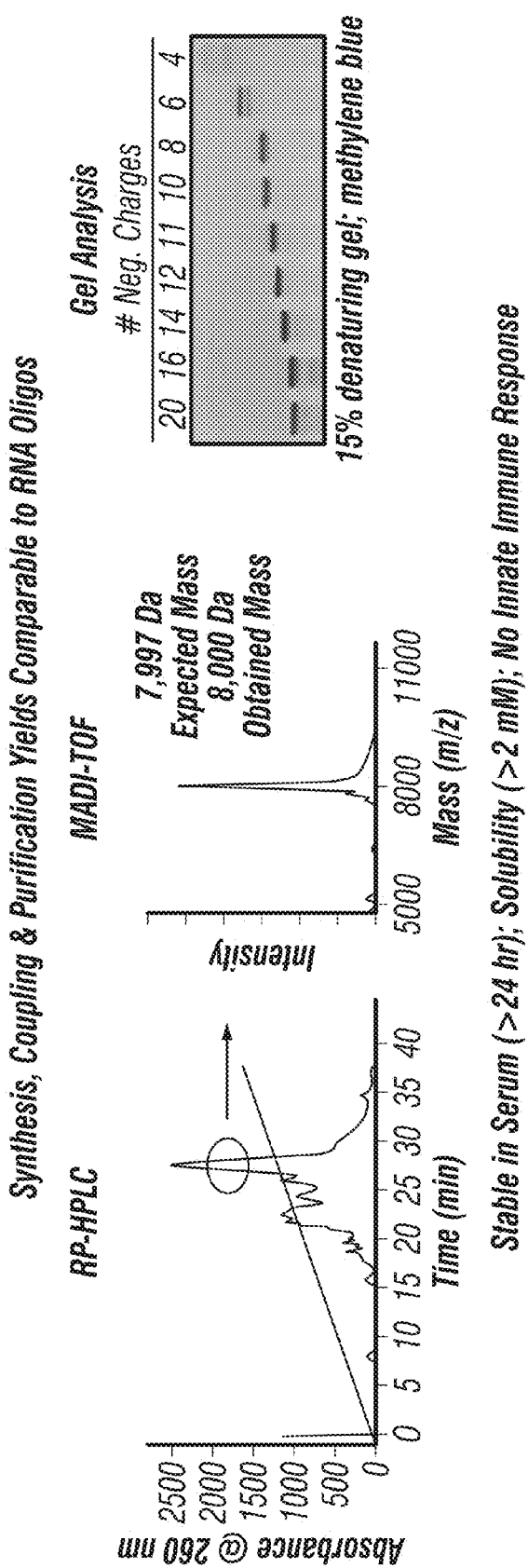

The ability to deliver certain bioactive agents to the interior of cells is problematic due to the selective permeability of the cell plasma membrane. The plasma membrane of the cell forms a barrier that restricts the intracellular uptake of molecules to those which are sufficiently non-polar and smaller than approximately 500 daltons in size. Previous efforts to enhance the cellular internalization of proteins have focused on fusing proteins with receptor ligands (Ng et al., *Proc. Natl. Acad. Sci. USA*, 99:10706-11, 2002) or by packaging them into caged liposomal carriers (Abu-Amer et al., *J. Biol. Chem.* 276:30499-503, 2001). However, these techniques can result in poor cellular uptake and intracellular sequestration into the endocytic pathway. Due to their anionic charge and large size of about 14,000 Daltons, delivery of siRNA is a formidable challenge in mammals, including humans. However, cationically charged peptides and proteins have led to advancements in polynucleotide delivery. For example, linking a peptide transduction domains (PTDs) to a nucleic acid has provided some advancement in polynucleotide delivery. However, even in these instances the anionic and cationic charges of the siRNA and PTD, respectively, often neutralize each other, thereby significantly reducing the uptake of these nucleic acid constructs.

The disclosure provides nucleic acid constructs comprising one or more bioreversible groups. The disclosure demonstrates that relatively large moieties, e.g., a peptide, a polypeptide, a carbohydrate, a neutral organic polymer, a positively charged polymer, a therapeutic agent, a targeting moiety, an endosomal escape moiety, or combination thereof, may be linked to bioreversible groups connected to internucleotide bridging groups, without affecting the ability of the bioreversible group to be cleaved intracellularly. The disclosure also provides for nucleic acid constructs comprising bioreversible groups that have hydrophobic or hydrophilic functional groups, and/or conjugating moieties, wherein these conjugating moieties allow for attachment of a peptide, a polypeptide, a small molecule, a carbohydrate, a neutral organic polymer, a positively charged polymer, a therapeutic agent, a targeting moiety, an endosomal escape moiety, or any combination thereof to an internucleotide bridging group or a terminal nucleotide group. The disclosure further provides for a nucleotide-based nucleic acid construct that comprises one or more bioreversible groups comprising one or more hydrophobic or hydrophilic functional groups, and/or one or more conjugating moieties, wherein the conjugating moieties allow for the attachment of an auxiliary moiety, e.g., a peptide, a polypeptide, a small molecule, a carbohydrate, a neutral organic polymer, a positively charged polymer, a therapeutic agent, a targeting moiety, an endosomal escape moiety, or any combination thereof, to the nucleotide. In a certain embodiment, the nucleic acid constructs disclosed herein comprise a certain number of bioreversible groups so as to reduce the overall negative charge of the constructs, to allow for or facilitate the uptake of the constructs by a cell. The nucleic acid constructs described herein can allow for or facilitate the intracellular transport of a polynucleotide itself or a polynucleotide linked to an attached auxiliary moiety, e.g., a small molecule, peptide, polypeptide, carbohydrate, neutral organic polymer, positively charged polymer, therapeutic agent, targeting moiety, endosomal escape moiety, or combination thereof. The action of intracellular enzymes (e.g., intracellular thioesterases) or exposure to the intracellular environment can result in the cleavage of the auxiliary moiety from the polynucleotide, thus allowing release of the auxiliary moiety as well as unmasking of the polynucleotide. The unmasked polynucleotide can then, e.g., initiate an antisense or RNAi-mediated response. Further, the nucleic acid constructs of the disclosure also allow for or facilitate the intracellular delivery of a polynucleotide or a polynucleotide linked to an attached auxiliary moiety, e.g., a small molecule, peptide, polypeptide, carbohydrate, neutral organic polymer, positively charged polymer, therapeutic agent, targeting moiety, endosomal escape moiety, or combination thereof, without the need for carriers, such as liposomes, or cationic lipids. Each of the features is further described herein.

The disclosure provides methods and compositions to facilitate and improve the cellular uptake of nucleic acid molecules by protecting/neutralizing the charge associated with anionically charged polynucleotides, and optionally adding further functionality to the molecule, e.g., cationic peptides, targeting moiety, and/or endosomal escape moiety. In a particular embodiment, the compositions of the disclosure promote uptake of a nucleic acid by generating nucleic acid constructs that have a cationic charge.

The disclosure provides compositions and methods for the delivery of sequence specific polynucleotides useful for selectively treating human disorders and for promoting research. The compositions and methods of the disclosure effectively deliver polynucleotides, including siRNAs, RNA, and DNA to subjects and to cells, without the drawbacks of current nucleic acid delivery methods. The disclosure provides compositions and methods which overcome size and charge limitations that make RNAi constructs difficult to deliver into cells or make the constructs undeliverable. By reversibly neutralizing the anionic charge of nucleic acids (e.g., dsRNA), a nucleic acid construct comprising a phosphotriester and/or phosphothioate bioreversible protecting group according to the disclosure can deliver nucleic acids into a cell in vitro and in vivo.

The disclosure provides nucleic acid constructs comprising a charge neutralizing moiety (e.g., a phosphotriester and/or phosphothioate protecting group). The construct can further include auxiliary moieties useful in cellular transfection and cellular modulation. Such auxiliary moieties can include a small molecule, peptide, a polypeptide, a carbohydrate, a neutral organic polymer, a positively charged polymer, a therapeutic agent, a targeting moiety, an endosomal escape moiety, or any combination thereof.

As demonstrated herein, the addition of one or more removable (e.g., reversibly attached) charge neutralizing moieties to a nucleic acid can effectively facilitate cell transfection. Any nucleic acid, regardless of sequence composition, can be modified. Accordingly, the disclosure is not limited to any particular sequence (i.e., any particular siRNA, dsRNA, DNA or the like).

The disclosure provides nucleic acid constructs having, in some embodiments, one or more bioreversible moieties that contribute to chemical and biophysical properties that enhance cellular membrane penetration and resistance to exo- and endonuclease degradation. The disclosure further provides reagents for the synthesis of the nucleic acid constructs disclosed herein, e.g., phosphoramidite reagents. Moreover, these bioreversible groups are stable during the synthetic processes.

In cells, the bioreversible moieties can be removed by the action of enzymes (e.g., endogenous carboxyesterases and thio-esterases) or by exposure to the intracellular conditions (e.g., pH and an oxidizing or reducing environment) or reactants (e.g., glutathione or other free thiol) to yield biologically active polynucleotide compounds that are capable of hybridizing to and/or having an affinity for specific endogenous nucleic acids.

The bioreversible moieties can be used with antisense polynucleotides of synthetic DNA or RNA or mixed molecules of complementary sequences to a target sequence belonging to a gene or to an mRNA whose expression they are specifically designed to block or down-regulate. These inhibitory polynucleotides may be directed against a target mRNA sequence or, alternatively against a target DNA sequence, and hybridize to the nucleic acid to which they are complementary thereby inhibiting transcription or translation. Accordingly, the nucleic acid constructs disclosed herein can effectively block or down-regulate gene expression.

The nucleic acid constructs of the disclosure may also be directed against certain bicatenary DNA regions (homopurine/homopyrimidine sequences or sequences rich in purines/pyrimidines) and thus form triple helices. The formation of a triple helix, at a particular sequence, can block the interaction of protein factors which regulate or otherwise control gene expression and/or may facilitate irreversible damage to be introduced to a specific nucleic acid site if the resulting polynucleotide is made to possess a reactive functional group.

The disclosure provides for nucleic acid constructs which are comprised of polynucleotides ("polynucleotide constructs") having one or more auxiliary moieties attached to an internucleotide bridging group or terminal nucleotide group. Examples of such auxiliary moieties include a small molecule, a conjugating moiety, a hydrophilic functional group, a peptide, a polypeptide, a carbohydrate, a neutral organic polymer, a positively charged polymer, a therapeutic agent, a targeting moiety, an endosomal escape moiety, and any combination thereof. Such auxiliary moieties can be attached to the polynucleotide by a bioreversible group, so that the auxiliary moiety is released from the polynucleotide when taken up by a cell. The bioreversible group may also be able to undergo a separate reaction, e.g., intramolecularly, to leave an unmodified internucleotide bridging group or terminal nucleotide group. While various sugars and backbones can be employed, as described in the definition of nucleotide provided herein, the polynucleotide will typically employ a ribose, deoxyribose, or LNA sugar and phosphate or thiophosphate internucleotide bridging groups. Mixtures of these sugars and bridging groups in a single polynucleotide are also contemplated.

The polynucleotides constructs described herein feature bioreversible groups that can be selectively cleaved intracellularly (e.g., by exposure to the passive environment, action of enzymes, or other reactants) thereby facilitating the intracellular delivery of polynucleotides to cells. Exemplary bioreversible groups include disulfide linkages, esters, and thioesters.

For example, the polynucleotide constructs described herein can include moieties (e.g., a thioester functional group) that can be cleaved by intracellular thioesterases. Upon entry into a cell, these enzymes can selectively cleave thioester groups (including moieties such as formula (I) described herein) in order to unmask the nucleic acid. Thioester groups such as formula (I) can also provide a useful handle by which to functionalize the nucleic acid with groups such as PTDs and other conjugates, or with groups that will modify the physicochemical properties of the nucleic acid (e.g., hydrophilic groups such as hydroxy (—OH) groups). The strategy can be readily generalized to a number of structurally and functionally diverse nucleic acids in order to allow for targeted cellular delivery without the use of separate delivery agents.

The polynucleotide constructs described herein can include, e.g., 1-40 independent bioreversible groups. For example, the polynucleotide constructs disclosed herein can include between 2-30, 2-25, 2-20, 5-15, 5-10, or 2-5 independent bioreversible groups. In a particular embodiment, no more than 75% of the constituent nucleotides include a bioreversible group (e.g., no more than 50%, 55%, 60%, 65%, 70%, or 75% include a bioreversible group). In another embodiment, up to 90% can have a bioreversible group. In yet another embodiment, no more than half of the bioreversible groups will include hydrophobic termini, e.g., alkyl groups. The polynucleotide constructs disclosed herein can feature any combination of bioreversible groups, e.g., that include a conjugating moiety, a hydrophilic functional group, a peptide, a polypeptide, a small molecule, a carbohydrate, a neutral organic polymer, a positively charged polymer, a therapeutic agent, a targeting moiety, an endosomal escape moiety, or any combination thereof. The polynucleotide construct will generally be up to 150 nucleotides in length. Exemplary sizes are 10-100, 10-75, 10-50, or 10-25 nucleotides in length.

In a certain embodiment, the polynucleotide construct is selected from the group comprising:
(a) a polynucleotide comprising a component (i) selected from a peptide, a polypeptide, a carbohydrate, a neutral organic polymer, a positively charged polymer, a therapeutic agent, a targeting moiety, an endosomal escape moiety, and any combination thereof, wherein component (i) is linked to the polynucleotide through a bioreversible group attached to an internucleotide bridging group;
(b) a polynucleotide comprising at least one component (i) selected from a peptide, a polypeptide, a carbohydrate, a neutral organic polymer, a positively charged polymer, a therapeutic agent, a targeting moiety, an endosomal escape moiety, and any combination thereof, and at least one second component (ii) a bioreversible group which comprises a hydrophilic functional group, a bioreversible group which comprises a conjugating moiety, or a bioreversible group which comprises a conjugating moiety and a hydrophilic group, wherein component (i) is linked to the polynucleotide through a bioreversible group attached to an internucleotide bridging group, wherein the conjugating moiety is a functional group which can form one or more covalent bonds to a peptide, a polypeptide, a carbohydrate, a neutral organic polymer, a positively charged polymer, a therapeutic agent, a targeting moiety, an endosomal escape moiety, and any combination thereof, and wherein the conjugating moiety or hydrophilic functional group may further comprise a protecting group; and
(c) a polynucleotide comprising one or more bioreversible groups attached to an internucleotide bridging group or terminal nucleotide group selected from the group consisting of:

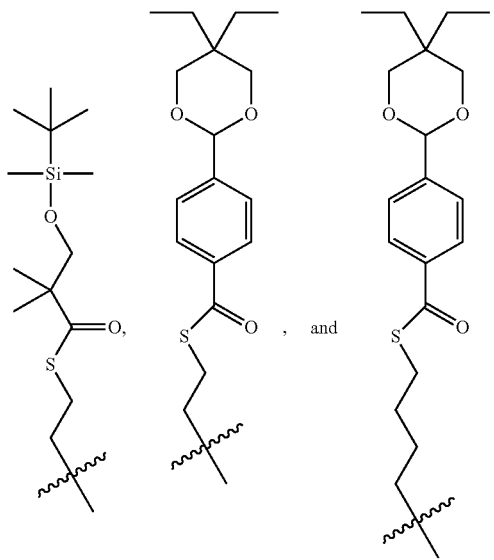

In a particular embodiment, the locations of bioreversible groups within a polynucleotide construct are selected so as to improve the stability of the resulting construct (e.g., to minimize steric and/or electronic repulsion). In particular, for double stranded polynucleotides, the location of the bioreversible groups will be such that a stable double-stranded molecule is formed.

In another embodiment, the nature of each bioreversible group can be selected so as to generate favorable solubility and delivery properties. Such variations can include modulating the linker length, e.g., between the internucleotide bridging group or terminal nucleotide group and the cleavable moiety and/or between the cleavable moiety and any conjugating moiety, hydrophilic functional group, or auxiliary moiety. Reductions in solubility caused by hydrophobic bioreversible groups can be offset, in part, by the use of one or more hydrophilic bioreversible groups elsewhere in the polynucleotide. In a particular embodiment, the sugar on the 3' end of an internucleotide bridging group having a bioreversible group does not include a 2' OH group, e.g., includes a 2' F or OMe group instead.

For example, some of the polynucleotide constructs described herein can have a structure according to Formula I,

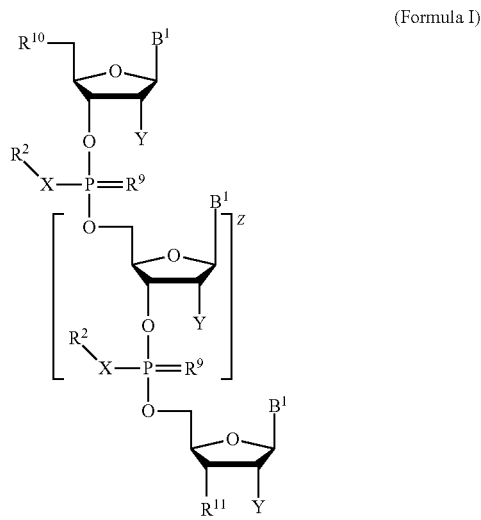

(Formula I)

wherein,
Z is a number from 0 to 150;
each $B^1$ is individually a nucleobase;
each X is individually selected from O, S and $NR^5$;
each Y is individually selected from halo, optionally substituted $C_{1-6}$ alkoxy, or a protected hydroxyl group;
each $R^2$ is individually absent, a hydrogen, or a bioreversible group that comprises a hydrophilic functional group, a conjugating moiety, a small molecule, a peptide, a polypeptide, a carbohydrate, a neutral organic polymer, a positively charged polymer, a therapeutic agent, a targeting moiety, an endosomal escape moiety, or combination thereof linked to the bioreversible group by one or more covalent bonds, wherein the conjugating moiety or hydrophilic functional group is optionally protected with a protecting group;
each $R^5$ is individually selected from H, an optionally substituted $C_{1-6}$ alkyl, S-pivaloyl thioethanol, hydroxyl, an optionally substituted $C_{1-6}$ alkoxy, an optionally substituted $C_{3-8}$ cycloalkyl, an optionally substituted $C_{6-12}$ aryl, and an optionally substituted $C_{2-9}$ heterocyclyl;

each $R^9$ is individually either an O or S;

$R^{10}$ is selected from H, hydroxyl, optionally substituted $C_{1-6}$ alkoxy, a protected hydroxyl group, a monophosphate, a disphosphate, a triphosphate, a tetraphosphate, a pentaphosphate, a 5' cap, phosphothiol, an optionally substituted $C_{1-6}$ alkyl, an amino containing group, a biotin containing group, a digoxigenin containing group, a cholesterol containing group, a dye containing group, a quencher containing group, a peptide, a polypeptide, a carbohydrate, a neutral organic polymer, a positively charged polymer, a therapeutic agent, a targeting moiety, an endosomal escape moiety, and any combination thereof; and $R^{11}$ is selected from H, hydroxyl, optionally substituted $C_{1-6}$ alkoxy, a protected hydroxyl group, a monophosphate, a disphosphate, a triphosphate, a tetraphosphate, a pentaphosphate, an optionally substituted $C_{1-6}$ alkyl, an amino containing group, a biotin containing group, a digoxigenin containing group, a cholesterol containing group, a dye containing group, a quencher containing group, a phosphothiol, a peptide, a polypeptide, a carbohydrate, a neutral organic polymer, a positively charged polymer, a therapeutic agent, a targeting moiety, an endosomal escape moiety, and any combination thereof.

Exemplary embodiments of Formula (I) include those in which X and $R^9$ are both O. In an alternate embodiment, polynucleotide constructs disclosed herein largely comprise the structure of formula (I) but the depicted internucleotide bridging group of formula (I) is replaced with another internucleotide bridging group (e.g., modified polynucleotide backbones) described herein. In an alternate embodiment, polynucleotide constructs disclosed herein largely comprise the structure of formula (I) but the depicted group $R^{10}$ and/or $R^{11}$ of formula (I) is replaced with a terminal nucleotide group having a bioreversible group $R^2$. Polynucleotide constructs disclosed herein may have modified polynucleotide backbones. Examples of modified polynucleotide backbones include, for example, phosphorothioates, chiral phosphorothioates, phosphorodithioates, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkyl-phosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Representative United States patents that teach the preparation of the above phosphorus-containing linkages include U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference. Nucleic acid constructs disclosed herein having modified polynucleotide backbones that do not include a phosphorus atom therein may have backbones that are formed by short chain alkyl or cycloalkyl internucleotide bridging groups, mixed heteroatom and alkyl or cycloalkyl internucleotide bridging groups, or one or more short chain heteroatomic or heterocyclic internucleotide bridging groups. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above polynucleotides include U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In any of the formulas described herein, $R^2$ can be described by the following Formula V,

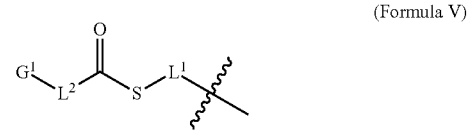

(Formula V)

wherein, $G^1$ is the conjugating moiety, the hydrophilic functional group, the small molecule, the peptide, the polypeptide, the carbohydrate, the neutral organic polymer, the positively charged polymer, the therapeutic agent, the targeting moiety, the endosomal escape moiety, or combination thereof;

$L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and $L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S. For any of the groups of Formula V provided herein, the thioester (—C(O)S—) may be replaced with an ester (—C(O)O—) or a disulfide (—S—S—).

Exemplary $R^2$ groups are provided in Table 1.

TABLE 1

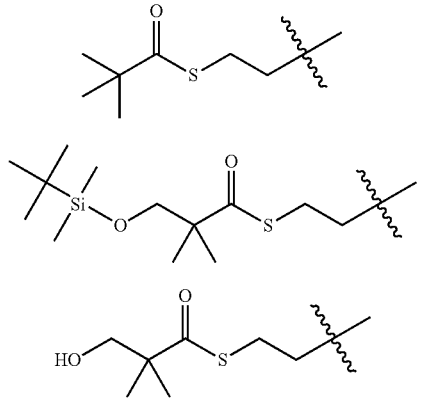

TABLE 1-continued
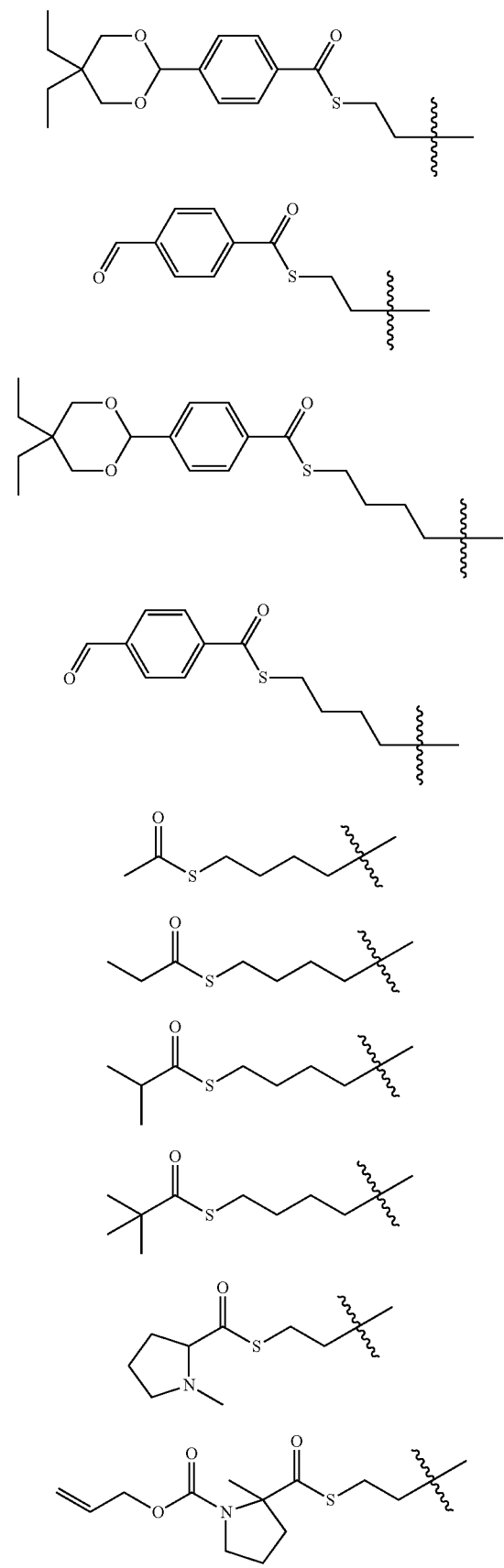
TABLE 1-continued
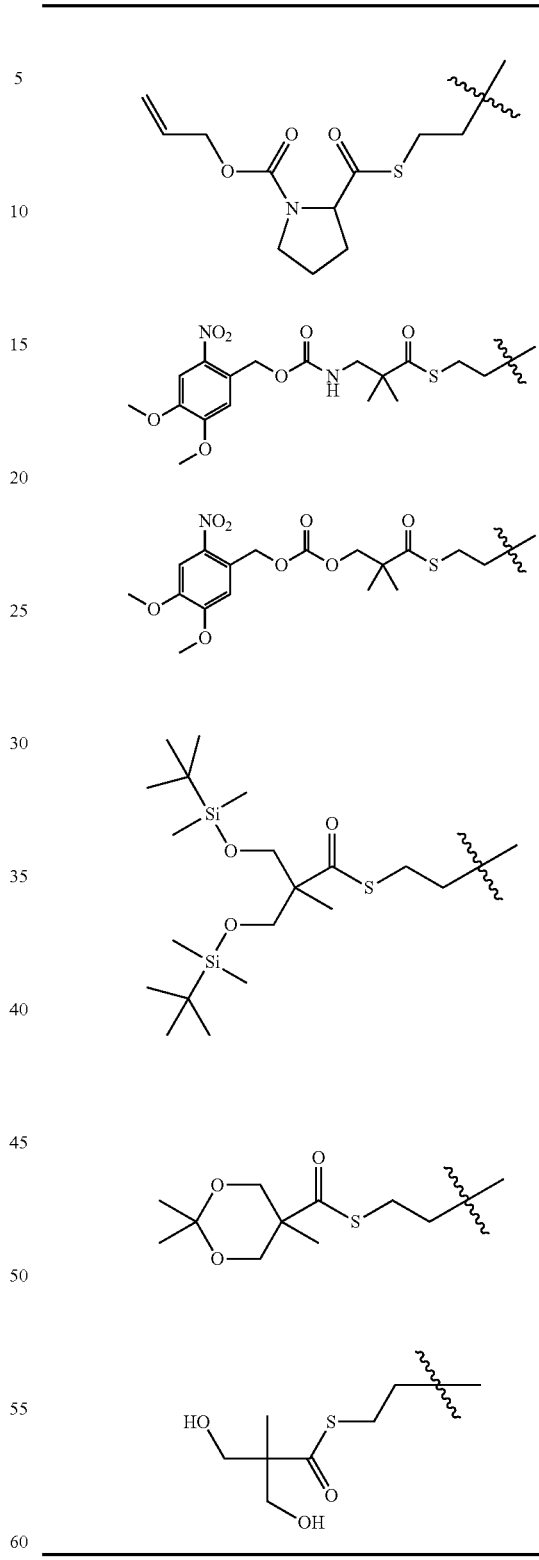
As it will be appreciated, certain of the bioreversible groups of Table 1 include a protected amine group, hydroxyl, heterocyclyl, or aldehyde group. The exemplified protecting groups may be replaced with other protecting groups as described herein.

Another bioreversible group is of the form:

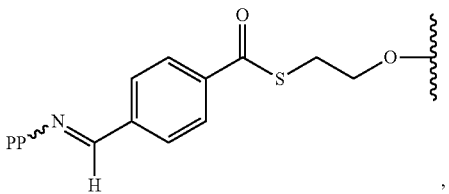

wherein, PP is a small molecule, a peptide, a polypeptide, a carbohydrate, a neutral organic polymer, a positively charged polymer, a therapeutic agent, a targeting moiety, a endosomal escape moiety, or any combination thereof.

In other embodiments, $L^1$ is

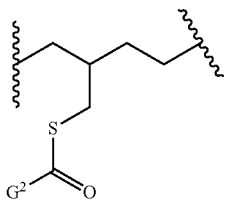

wherein $G^2$ is selected from the same substituents as $G^1$.

In a further embodiment, the nucleic acid constructs of the disclosure comprise one or more bioreversible groups known in the art, e.g., as described in International Publication Nos. WO 98/07734, 96/07392, 2008/008476, 2010/036905, 2011/005761, and 2010/039546, and U.S. Pat. Nos. 6,399,589 and 6,124,445.

In a particular embodiment, a polynucleotide construct of the disclosure comprises a structure according to Formula IV:

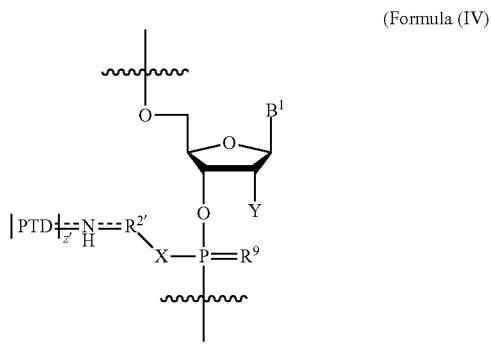

(Formula (IV))

wherein,
PTD is a peptide transduction domain;
$R^{2'}$ is the residue of the bioreversible group bound to the PTD;
z' is a number from 1 to 10, wherein, when z' is greater than 1, the PTDs are linked together through linker groups, such as poly($C_{1-4}$ alkyleneoxide) groups having 1-10 repeating units.

Polynucleotide constructs of the disclosure may be single stranded or double stranded. When double stranded, one or both strands may include one or more bioreversible groups. When the polynucleotide acts as siRNA, the passenger strand may include a group that is irreversibly bound to an internucleotide bridging group, e.g., an alkyl phosphotriester. Typically, such a group is located after the first or second nucleotide from the 3' end. The irreversible group prevents the passenger strand from acting as a guide strand and thereby prevents or reduces possible off-target effects.

The disclosure further provides methods for manufacturing the polynucleotide constructs of the disclosure. Methods for the preparation of nucleotides and polynucleotides are known in the art. For example, the practice of phosphoramidite chemistry to prepare polynucleotides is known from the published work of Caruthers and Beaucage and others. See, e.g., U.S. Pat. Nos. 4,458,066; 4,500,707; 5,132,418; 4,415,732; 4,668,777; 4,973,679; 5,278,302; 5,153,319; 5,218,103; 5,268,464; 5,000,307; 5,319,079; 4,659,774; 4,672,110; 4,517,338; 4,725,677; and RE34,069, each of which is herein incorporated by reference, describe methods of polynucleotide synthesis. Additionally, the practice of phosphoramidite chemistry has been systematically reviewed by Beaucage et al., *Tetrahedron*, 48: 2223-2311, 1992; and Beaucage et al., *Tetrahedron*, 49:6123-6194, 1993, as well as references referred to therein, all of which are herein incorporated by reference.

Nucleic acid synthesizers are commercially available, and their use is generally understood by persons of ordinary skill in the art as being effective in generating nearly any polynucleotide of reasonable length which may be desired.

In practicing phosphoramidite chemistry, useful 5'OH sugar blocking groups are trityl, monomethoxytrityl, dimethoxytrityl and trimethoxytrityl, especially dimethoxytrityl (DMTr). In practicing phosphoramidite chemistry, useful phosphite activating groups are dialkyl substituted nitrogen groups and nitrogen heterocycles. One approach includes the use of the di-isopropylamino activating group.

Polynucleotides can be synthesized by a Mermade-6 solid phase automated polynucleotide synthesizer or any commonly available automated polynucleotide synthesizer. Triester, phosphoramidite, or hydrogen phosphonate coupling chemistries (described in, for example, M. Caruthers, *Oligonucleotides: Antisense Inhibitors of Gene Expression*, pp. 7-24, J. S. Cohen, ed. (CRC Press, Inc. Boca Raton, Fla., 1989); *Oligonucleotide synthesis, a practical approach*, Ed. M. J. Gait, IRL Press, 1984; and *Oligonucleotides and Analogues, A Practical Approach*, Ed. F. Eckstein, IRL Press, 1991) are employed by these synthesizers to provide the desired polynucleotides. The Beaucage reagent, as described in, for example, *Journal of American Chemical Society*, 112:1253-1255, 1990, or elemental sulfur, as described in Beaucage et al., *Tetrahedron Letters* 22:1859-1862, 1981, is used with phosphoramidite or hydrogen phosphonate chemistries to provide substituted phosphorothioate polynucleotides.

For example, the reagents comprising the protecting groups recited herein can be used in numerous applications where protection is desired. Such applications include, but are not limited to, both solid phase and solution phase, polynucleotide synthesis and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. For use with phosphoramidite chemistry, various phosphoramidite reagents are commercially available, including 2'-deoxy phosphoramidites, 2'-O-methyl phosphoramidites and 2'-O-hydroxyl phosphoramidites. Any other means for such synthesis may also be employed. The actual synthesis of the polynucleotides is well within the talents of those skilled in the art. It is also well known to use similar techniques to prepare other polynucleotides such as the phosphorothioates, methyl phosphonates and alkylated derivatives. It is also well known to use similar techniques and commercially available modified phosphoramidites and controlled-pore glass (CPG) products such as biotin, Cy3, fluorescein, acridine or psoralen-modified phosphoramidites and/or CPG (available from Glen Research, Sterling Va.) to synthesize fluorescently labeled, biotinylated or other conjugated polynucleotides.

In a particular embodiment, a method of manufacturing a polynucleotide construct of the disclosure, comprises
(1) de-blocking a first nucleoside or nucleotide which comprises a O-protecting group, such as a (4,4'-dimethoxytrityl) group (DMT), at the 5' position, by removing the O-protecting group under acidic conditions in an aprotic solvent system to afford a free hydroxyl, wherein the first nucleoside or nucleotide may be fixed to a solid support at the 3' position, or alternatively the 3' position is protected with an O-protecting group that is resistant to acids and the first nucleoside or nucleotide is in solution;
(2) coupling the de-blocked first nucleoside or nucleotide with either an activated nucleotide construct disclosed herein or an activated nucleotide known in the art comprising a phosphoramidite at the 3' position in the presence of a catalyst, such as an acidic azole, to a solvent system;
(3) oxidizing the coupled nucleotides with an oxidizing agent in a solvent system comprising a protic solvent and a weak base;
(4) de-blocking the coupled nucleotides by removing an O-protecting group, such as a DMT group, at the 5' position under acidic conditions in an aprotic solvent system; and
repeating steps (2)-(4) from 1 to 149 times, wherein the resulting polynucleotide construct comprises one or more nucleotide constructs of the disclosure.

In a further embodiment, the first nucleoside or nucleotide of step (1) is attached to a solid support. In yet a further embodiment, the resulting synthesized polynucleotide construct is cleaved from the solid support after the last de-blocking step, if the first nucleoside or nucleotide of step (1) is attached to a solid support. In an alternate embodiment, the first nucleoside or nucleotide of step (1) is not attached to a solid support.

In another embodiment, a method of manufacturing the polynucleotide constructs herein can be carried out using a computer controlled instrument. In an alternate embodiment, a method of manufacturing the polynucleotide constructs herein can be carried out without using a computer controlled instrument.

In yet another embodiment, a method of manufacturing a polynucleotide construct, comprises the use of one or more nucleotide constructs having Formula I(a):

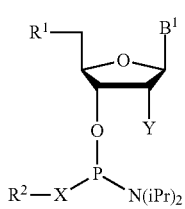

(Formula I(a))

wherein,
$B^1$ is a nucleobase;
X is O or S;
Y is a halo, optionally substituted $C_{1-6}$ alkoxy, or a protected hydroxyl group;
$R^1$ is a 4,4'-dimethoxytrityl group (DMT) protected hydroxyl group; and
$R^2$ is a bioreversible group, as described herein or exemplified in Table 1.

In a further embodiment, a method of manufacturing a polynucleotide construct, comprises the use of one or more nucleotide constructs having Formula I(a):

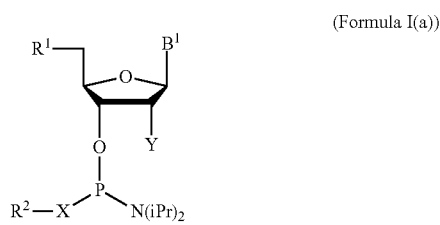

(Formula I(a))

wherein,
$B^1$ is a nucleobase;
X is O;
Y is a halo, optionally substituted $C_{1-6}$ alkoxy, or a protected hydroxyl group;
$R^1$ is a 4,4'-dimethoxytrityl group (DMT) protected hydroxyl group; and
$R^2$ is a bioreversible group selected from:

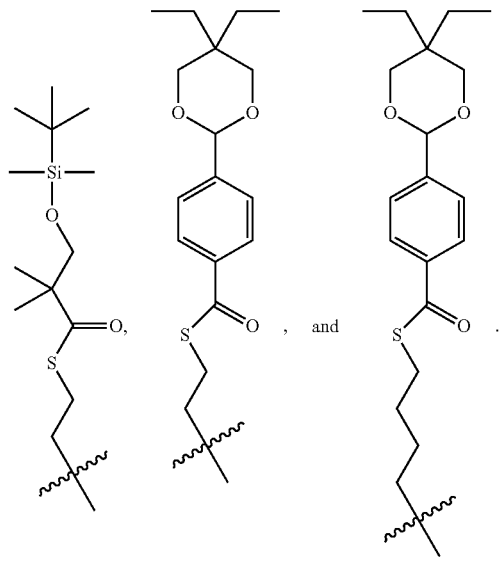 [SMILES: *CCSC(=O)C(C)(C)CO[Si](C)(C)C(C)(C)C ; *CCSC(=O)c1ccc(C2OCC(CC)(CC)CO2)cc1 ; "and" ; *CCCCSC(=O)c1ccc(C2OCC(CC)(CC)CO2)cc1]

The disclosure further provides methods to process a polynucleotide construct synthesized by using a method of manufacture disclosed herein. For example, post synthesis of the polynucleotide construct, if a nucleobase comprises one or more protecting groups, then the protecting groups are removed; and/or for any bioreversible groups which comprise a hydrophilic functional group or conjugating moiety that is protected by a protecting group, then the protecting group is removed.

Additionally, post synthesis of the polynucleotide construct, a small molecule, a peptide, a polypeptide, a carbohydrate, a neutral organic polymer, a positively charged polymer, a therapeutic agent, a targeting moiety, and/or an endosomal escape moiety can be linked to one or more conjugating moieties of one or more bioreversible groups.

The disclosure further provides for nucleic acid constructs which are comprised of a single nucleotide ("nucleotide construct").

The disclosure features a nucleotide construct that has a structure according to Formula (I):

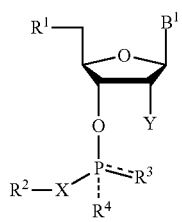

(Formula (I))

wherein,
B$^1$ is a nucleobase;
X is an O, S, or NR$^5$;
Y is a halo, optionally substituted C$_{1-6}$ alkoxy, or a protected hydroxyl group;
R$^1$ is hydroxyl, optionally substituted C$_{1-6}$ alkoxy, a protected hydroxyl group, a monophosphate, a disphosphate, a triphosphate a tetraphosphate, or a pentaphosphate;
R$^2$ is a bioreversible group that comprises a hydrophilic functional group, a conjugating moiety, or a hydrophilic functional group and a conjugating moiety, wherein the conjugating moiety and/or the hydrophilic functional group is optionally protected with a protecting group;
R$^3$ is an O, S, or an optionally substituted amino;
R$^4$ is an H, hydroxyl, optionally substituted C$_{1-6}$ alkoxy, a protected hydroxyl group, a monophosphate, a disphosphate, a triphosphate, a tetraphosphate, a pentaphosphate, or absent when R$^3$ is an optionally substituted amino; and
R$^5$ is H, an optionally substituted C$_{1-6}$ alkyl, S-pivaloyl thioethanol, a hydroxyl, an optionally substituted C$_{1-6}$ alkoxy, an optionally substituted C$_{3-8}$ cycloalkyl, an optionally substituted C$_{6-12}$ aryl, or an optionally substituted C$_{2-9}$ heterocyclyl.

In another embodiment, a nucleotide construct has a structure according to Formula I(a):

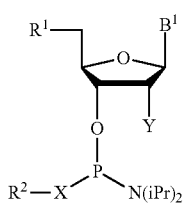

(Formula I(a))

wherein,
B$^1$ is a nucleobase;
X is O;
Y is a halo, optionally substituted C$_{1-6}$ alkoxy, or a protected hydroxyl group;

R$^1$ is a 4,4'-dimethoxytrityl group (DMT) protected hydroxyl group; and
R$^2$ is a bioreversible group as described herein, e.g., as exemplified in Table 1.

In yet another embodiment, a nucleotide construct has a structure according to Formula I(a):

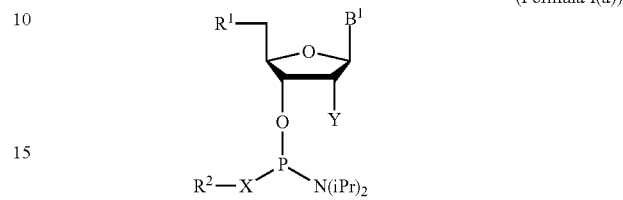

(Formula I(a))

wherein,
B$^1$ is a nucleobase;
X is O;
Y is a halo, optionally substituted C$_{1-6}$ alkoxy, or a protected hydroxyl group;
R$^1$ is a 4,4'-dimethoxytrityl group (DMT) protected hydroxyl group; and
R$^2$ is a bioreversible group selected from:

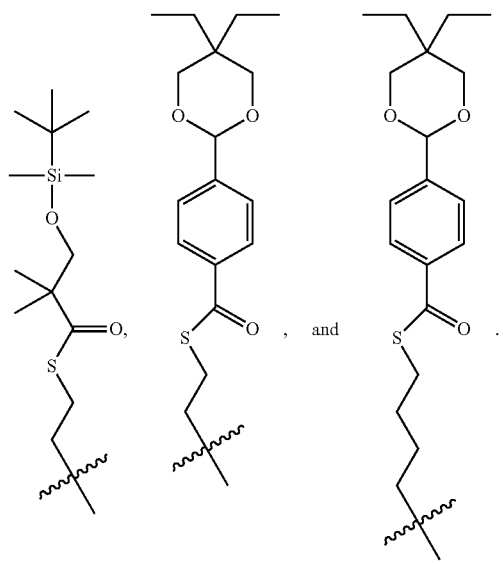 [SMILES: *CCSC(=O)C(C)(C)CO[Si](C)(C)C(C)(C)C ; *CCSC(=O)c1ccc(C2OCC(CC)(CC)CO2)cc1 ; "and" ; *CCCCSC(=O)c1ccc(C2OCC(CC)(CC)CO2)cc1]

As it will be appreciated, these bioreversible groups include a protected hydroxyl group or a protected aldehyde group. The exemplified protecting groups may be replaced with other hydroxyl or carbonyl protecting groups as described herein.

The disclosure additionally provides for deprotecting a conjugating moiety of a nucleic acid construct, such as a nucleotide construct, which comprises a protected conjugating moiety. For example, a hydroxy-based conjugating moiety which is protected as a silyl ether may be deprotected to a hydroxyl group by the addition of acids or fluorides; and a carbonyl-based conjugating moiety which is protected as a 1,3-dioxane or 1,3-dioxolane can be deprotected to a form an aldehyde or ketone by the addition of catalytic amounts of an acid, such as catalytic amounts of toluenesulfonic acid.

The disclosure further provides for a nucleotide construct comprising an auxiliary moiety selected from a small molecule, peptide, polypeptide, carbohydrate, neutral organic polymer, positively charged polymer, therapeutic agent, targeting moiety, endosomal escape moiety, or any combination thereof, wherein the auxiliary moiety is linked to the bioreversible group by one or more covalent bonds. In a particular embodiment, the auxiliary moiety can be attached to the bioreversible group through forming one or more covalent bonds to a conjugating moiety found on a bioreversible group.

In a particular embodiment, a nucleotide construct comprises a structure according to Formula I(b):

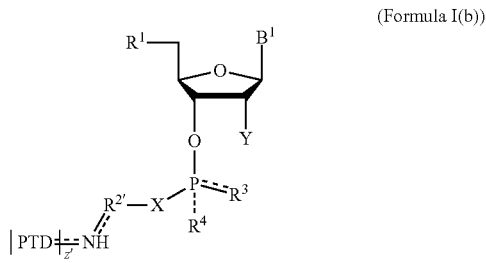

(Formula I(b))

wherein,
PTD is a peptide transduction domain;
z' is a number from 1 to 10, wherein, when z' is greater than 1, the PTDs can be linked together through linking groups, such as poly($C_{1-4}$ alkyleneoxide) groups having 1-10 repeating units;
$B^1$ is a nucleobase;
X is an O, S, or $NR^5$;
Y is a halo, optionally substituted $C_{1-6}$ alkoxy, or a protected hydroxyl group;
$R^1$ is hydroxyl, optionally substituted $C_{1-6}$ alkoxy, a protected hydroxyl group, a monophosphate, a disphosphate, a triphosphate, a tetraphosphate, or a pentaphosphate;
$R^{2'}$ is a residue of a bioreversible group that has formed one or more covalent bonds to auxiliary moiety $|PTD|_{z'}$;
$R^3$ is an O, S, or an optionally substituted amino;
$R^4$ is an H, hydroxyl, optionally substituted $C_{1-6}$ alkoxy, a protected hydroxyl group, a monophosphate, a disphosphate, a triphosphate, a tetraphosphate, a pentaphosphate, or absent when $R^3$ is an optionally substituted amino; and
$R^5$ is H, an optionally substituted $C_{1-6}$ alkyl, S-pivaloyl thioethanol, a hydroxyl, an optionally substituted $C_{1-6}$ alkoxy, an optionally substituted $C_{3-8}$ cycloalkyl, an optionally substituted $C_{6-12}$ aryl, or an optionally substituted $C_{2-9}$ heterocyclyl.

Nucleic acid constructs of the disclosure may include various conjugating moieties. The conjugating moieties can in turn be used to attach various other auxiliary moieties, e.g., a small molecule, a peptide, a polypeptide, a carbohydrate, a neutral organic polymer, a positively charged polymer, a therapeutic agent, a targeting moiety, an endosomal escape moiety, or combination thereof, to the nucleic acid construct. In a certain embodiment, more than one type of conjugating moiety is present in a nucleic acid construct, thereby allowing the selective and/or sequential coupling of auxiliary moieties to the nucleic acid construct. The location of attachment in a polynucleotide construct is determined by the use of the appropriate nucleotide construct in the synthesis of the polymer. A nucleic acid construct comprising one more conjugating moieties will react, under appropriate conditions, with one or more corresponding conjugating moieties on auxiliary moieties. The auxiliary moiety may intrinsically possess the conjugating moiety, e.g., terminal or lysine amine groups and thiol groups in peptides or polypeptides, or it may be modified to include a small linking group to introduce the conjugating moiety. Introduction of such linking groups is well known in the art. It will be understood that an auxiliary moiety attached to a nucleic acid construct of the disclosure includes any necessary linking group.

Diverse bond-forming methods can be used to conjugate the auxiliary moiety to the nucleic acid constructs described herein. Exemplary reactions include: Huisgen cycloaddition between an azide and an alkyne to form a triazol; the Diels-Alder reaction between a dienophile and a diene/hetero-diene; bond formation via other pericyclic reactions such as the ene reaction; amide or thioamide bond formation; sulfonamide bond formation; alcohol or phenol alkylation (e.g., with diazo compounds), condensation reactions to form oxime or hydrazone bonds, conjugate addition reactions by nucleophiles (e.g., amines and thiols), disulfide bond formation, and nucleophilic substitution at a carboxylic functionality (e.g., by an amine, thiol, or hydroxyl nucleophile). Other exemplary methods of bond formation are described herein and known in the art.

Nucleophiles and electrophiles can engage in bond forming reactions selected from, without limitation, insertion by an electrophile into a C—H bond, insertion by an electrophile into an O—H bond, insertion by an electrophile into an N—H bond, addition of the electrophile across an alkene, addition of the electrophile across an alkyne, addition to electrophilic carbonyl centers, substitution at electrophilic carbonyl centers, addition to ketenes, nucleophilic addition to isocyanates, nucleophilic addition to isothiocyanates, nucleophilic substitution at activated silicon centers, nucleophilic displacement of an alkyl halide, nucleophilic displacement at an alkyl pseudohalide, nucleophilic addition/elimination at an activated carbonyl, 1,4-conjugate addition of a nucleophile to an α,β-unsaturated carbonyl, nucleophilic ring opening of an epoxide, nucleophilic aromatic substitution of an electron deficient aromatic compound, a nucleophilic addition to activated phosphorus centers, nucleophilic substitution at activated phosphorous centers, nucleophilic addition to activated sulfur centers, and nucleophilic substitution at activated sulfur centers.

A nucleophilic conjugating moiety may be selected from optionally substituted alkenes, optionally substituted alkynes, optionally substituted aryl, optionally substituted heterocyclyl, hydroxyl groups, amino groups, alkylamino groups, anilido groups, and thio groups.

An electrophilic conjugating moiety may be selected from nitrenes, nitrene precursors such as azides, carbenes, carbene precursors, activated silicon centers, activated carbonyls, anhydrides, isocyanates, thioisocyanates, succinimidyl esters, sulfosuccinimidyl esters, maleimides, alkyl halides, alkyl pseudohalides, epoxides, episulfides, aziridines, electron-deficient aryls, activated phosphorus centers, and activated sulfur centers.

For example, conjugation can occur via a condensation reaction to form a linkage that is a hydrazone bond.

Conjugation via the formation of an amide bond can be mediated by activation of a carboxyl-based conjugating moiety and subsequent reaction with a primary amine-based conjugating moiety. Activating agents can be various carbodiimides like: EDC (1-Ethyl-3-(3-dimethylaminopropyl) carbodiimide hydrochloride), EDAC (1-ethyl-3(3-dimethylaminopropyl)carbodiimide hydrochloride), DCC (dicyclohexyl carbodiimide), CMC (1-Cyclohexyl-3-(2-morpholinoethyl) carbodiimide), DIC (diisopropyl carbodiimide) or Woodward's reagent K (N-ethyl-3-phenylisoxazolium-3'-sulfonate). Reaction of an activated NHS-Ester-based conjugating moiety with a primary amine-based conjugating moiety also results in formation of an amide bond.

The nucleic acid construct may comprise a carbonyl-based conjugating moiety. Conjugation via the formation of a secondary amine can be achieved by reacting an amine-based conjugating moiety with an aldehyde-based conjugating moiety, followed by reducing with a hydride donor like sodium cyanoborohydride. Aldehyde-based conjugating moieties can be introduced for instance by oxidation of sugar moieties or by reaction with SFB (succinimidyl-p-formyl benzoate) or SFPA (succinimidyl-p-formylphenoxyacetate).

Ether formation can also be used to conjugate auxiliary moieties to the nucleic acid constructs of the disclosure. Conjugation via ether linkages can be mediated by reaction of an epoxide-based conjugating moiety with a hydroxy-based conjugating moiety.

Thiols can also be used as conjugating moieties. For example, conjugation via the formation of disulfide bonds can be accomplished by pyridyldisulfide mediated thiol-disulfide exchange. Introduction of sulfhydryl-based conjugating moieties is mediated for instance by Traut's Reagent (2-iminothiolane) SATA (N-succinimidyl S-acetylthioacetate, SATP (succinimidyl acetylthiopropionate), SPDP (N-succinimidyl 3-(2-pyridyldithio)propionate, SMPT (succinimidyloxycarbonyl-α-methyl-α-(2-pyridyldithio)toluene), N-acetylhomocysteinethiolactone, SAMSA (S-acetylmercaptosuccinic anhydride), AMBH (2-Acedamido-4-mercaptobuturic acid hydrazide), and cystamine (2,2'-dithiobis(ethylamine).

Conjugation via the formation of thioether linkages can be performed by reacting a sulfhydryl based conjugating moieties with maleimide- or iodoacetyl-based conjugating moieties or by reacting with epoxide-based conjugating moieties. Maleimide-based conjugating moieties can be introduced by SMCC (succinimidyl-4-(N-maleimidomethyl)cyclohexane-1-carboxylate), sulfo-SMCC (sulfosuccinimidyl 4-(N-maleidomethyl)-cyclohexane-1-carboxylate), MBS (m-Maleimidobenzoyl-N-hydroxysuccinimide ester), sulfo-MBS (m-Maleimidobenzoyl-N-sulfohydroxysuccinimide ester), SMPB (Succinimidyl-4-(p-maleidophenyl)butyrate), sulfo-SMPB (sulfosuccinimidyl 4-(p-maleimidophenyl)butyrate), GMBS (N-α-maleimidobuturyl-oxysuccinimide ester), sulfo GMBS (N-α-maleimidobuturyl-oxysulfosuccinimide ester).

Thiol-based conjugating moieties can also react with iodoacetyl-based conjugating moieties. Iodoacetyl-based conjugating moieties can be inserted with SIAB (N-succinimidyl(4-iodoacetyl)aminobenzoate, sulfo SIAB (sulfo-succinimidyl(4-iodoacetyl)-aminobenzoate), SIAX (succinimidyl6-[(iodoacetyl-amino]hexanoate), SIAXX (succinimidyl6-[6-(((iodoacetyl)amino)-hexanoyl)amino] hexanoate), SIAC (succinimidyl 4-(((iodoacetyl)amino) methyl)-cyclohexane-1-carboxylate), SIACX (succinimidyl 6-((((4-(iodoacetyl)amino)methyl)-cyclohexane-1-carbonyl)amino) hexanoate), and NPIA (p-nitrophenyl iodoacetate).

Conjugation via the formation of a carbamate linkage can be performed by reaction of a hydroxy-based conjugating moiety with CDI (N,N'-carbonyldiimidazole) or DSC (N,N'-disuccinimidyl carbonate) or N-hydroxysuccinimidylchloroformate and subsequent reaction with an amine-based conjugating moiety.

Alternatively, the conjugating moiety can employ photolytic or thermolytic activation in order to form the desired covalent bond. Conjugating moieties that include azide functionality are one example. Thus, conjugation can also be achieved by the introduction of a photoreactive conjugating moiety. Photoreactive conjugating moieties are aryl azides, halogenated aryl azides, benzophenones certain diazo compounds and diazirine derivatives. They react with amine-based conjugating moieties or with conjugating moieties that have activated hydrogen bonds.

The azide-based conjugating moieties are UV labile and, upon photolysis, can lead to the formation of nitrene electrophiles that can react with nucleophilic conjugating moieties such as aryl-based conjugating moieties or alkenyl-based conjugating moieties. Alternatively, the heating of these azide compounds can also result in nitrene formation.

Cycloaddition reactions can be used to form the desired covalent bond. Representative cycloaddition reactions include, but are not limited to, the reaction of an alkene-based conjugating moiety with a 1,3-diene-based conjugating moiety (Diels-Alder reaction), the reaction of an alkene-based conjugating moiety with an α,β-unsaturated carbonyl-based conjugating moiety (hetero Diels-Alder reaction), and the reaction of an alkyne-based conjugating moiety with an azide-based conjugating moiety (Hüisgen cycloaddition). Selected, non-limiting examples of conjugating moieties that comprise reactants for cycloaddition reactions are: alkenes, alkynes, 1,3-dienes, α,β-unsaturated carbonyls, and azides. For example, the Huisgen cycloaddition between azides and alkynes has been used for the functionalization of diverse biological entities.

Conjugating moieties also include, but are not limited to, reactants for hydrosilylation, Stille coupling, Suzuki coupling, Sonogashira coupling, Hiyama coupling, and the Heck reactions. Conjugation moieties for these reactions include hydridosilanes, alkenes, and alkynes.

Various auxiliary moieties can be conjugated to the nucleic acid constructs of the disclosure (e.g., siRNA), and the auxiliary moieties can have any number of biological or chemical effects. Biological effects include, but are not limited to, inducing intracellularization, binding to a cell surface, targeting a specific cells type, allowing endosomal escape, altering the half-life of the polynucleotide in vivo, and providing a therapeutic effect. Chemical effects include, but are not limited to, changing the solubility, charge, size, and reactivity.

Small molecule-based auxiliary moieties (e.g., organic compounds having molecular weights of ~1000 Da or less) can be conjugated to nucleic acid constructs of the disclosure. Examples of such small molecules include, but are not limited to, substituted or unsubstituted alkanes, alkenes, or alkynes, e.g., hydroxy-substituted, $NH_2$-substituted, mono-, di-, or trialkyl amino substituted, guanidino substituted, heterocyclyl substituted, and protected version thereof. Other small molecules include steroids (e.g., cholesterol), other lipids, bile, and amino acids. A small molecule may be added to a polynucleotide to provide neutral or positive charge or to alter the hydrophilicity or hydrophobicity of the polynucleotide.

A peptide or polypeptide (including a fusion polypeptide) refers to a polymer in which the monomers are amino acid residues which are joined together through amide bonds. When the amino acids are alpha-amino acids, either the L-optical isomer or the D-optical isomer can be used. A peptide or polypeptide encompasses an amino acid sequence and includes modified sequences such as glycoproteins, retro-inverso polypeptides, D-amino acid and the like. A peptide or polypeptide includes naturally occurring proteins, as well as those which are recombinantly or synthetically synthesized. A polypeptide (and less commonly a peptide) may comprise more than one domain have a function that can be attributed to the particular fragment or portion of a polypeptide. A domain, for example, includes a portion of a peptide or polypeptide which exhibits at least one useful epitope or functional domain. Two or more domains may be functionally linked such that each domain retains its function yet comprises a single peptide or polypeptide (e.g., a fusion polypeptide). For example, a functional fragment of a PTD includes a fragment which retains transduction activity. Biologically functional fragments, for example, can vary in size from a fragment as small as an epitope capable of binding an antibody molecule, to a large polypeptide capable of participating in the characteristic induction or programming of phenotypic changes within a cell.

In some embodiments, retro-inverso peptides or polypeptides are used. "Retro-inverso" means an amino-carboxy inversion as well as enantiomeric change in one or more amino acids (i.e., levorotatory (L) to dextrorotatory (D)). A peptide or polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be devised as described by Brugidou et al. (*Biochem. Biophys. Res. Comm.* 214(2): 685-693, 1995) and Chorev et al. (*Trends Biotechnol.* 13(10): 438-445, 1995). The overall structural features of a retro-inverso peptide or polypeptide are similar to those of the parent L-polypeptide. The two molecules, however, are roughly mirror images because they share inherently chiral secondary structure elements. Main-chain peptidomimetics based on peptide-bond reversal and inversion of chirality represent important structural alterations for peptides and proteins, and are highly significant for biotechnology. Antigenicity and immunogenicity can be achieved by metabolically stable antigens such as all-D- and retro-inverso-isomers of natural antigenic peptides and polypeptide. Several PTD-derived peptidomimetics are provided herein.

Polypeptides and fragments can have the same or substantially the same amino acid sequence as the naturally derived polypeptide or domain. "Substantially identical" means that an amino acid sequence is largely, but not entirely, the same, but retains a functional activity of the sequence to which it is related. An example of a functional activity is that the fragment is capable of transduction, or capable of binding to an RNA. For example, fragments of full length TAT are described herein that have transduction activity. In general two peptides, polypeptides or domains are "substantially identical" if their sequences are at least 85%, 90%, 95%, 98% or 99% identical, or if there are conservative variations in the sequence. A computer program, such as the BLAST program (Altschul et al., 1990) can be used to compare sequence identity.

A peptide or polypeptide of the disclosure can be composed of amino acids joined to each other by peptide bonds or modified peptide bonds, i.e., peptide isosteres, and may contain amino acids other than the 20 gene-encoded amino acids. The peptides or polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a peptide or polypeptide, including the backbone, the amino acid side-chains and the amino or carboxyl termini. It will be appreciated that the same type of modification may be present in the same or varying degrees at several sites in a given peptide or polypeptide. Also, a given peptide or polypeptide may contain many types of modifications. A peptide or polypeptide may be branched, for example, as a result of ubiquitination, and they may be cyclic, with or without branching. Cyclic, branched, and branched cyclic peptides and polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, 2nd Ed., T. E. Creighton, W. H. Freeman and Company, New York (1993); *Posttranslational Covalent Modification of Proteins*, B. C. Johnson, Ed., Academic Press, New York, pgs. 1-12 (1983); Seifter et al., *Meth Enzymol* 182:626-646 (1990); Rattan et al., Ann N.Y. Acad Sci 663:48-62 (1992)).

A peptide or polypeptide domain or a fusion polypeptide of the disclosure can be synthesized by commonly used methods such as those that include t-BOC or FMOC protection of alpha-amino groups. Both methods involve stepwise synthesis in which a single amino acid is added at each step starting from the C-terminus of the peptide or polypeptide (See, Coligan, et al., Current Protocols in Immunology, Wiley Interscience, 1991, Unit 9). Polypeptides and peptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly (styrene-divinylbenzene) containing 0.1-1.0 mMol amines/g polymer. On completion of chemical synthesis, the peptides or polypeptides can be deprotected and cleaved from the polymer by treatment with liquid HF-10% anisole for about ¼-1 hours at 0° C. After evaporation of the reagents, the peptides or polypeptides are extracted from the polymer with a 1% acetic acid solution, which is then lyophilized to yield the crude material. The peptides or polypeptides can be purified by such techniques as gel filtration on Sephadex G-15 using 5% acetic acid as a solvent. Lyophilization of appropriate fractions of the column eluate yield homogeneous peptide or polypeptide, which can then be characterized by standard techniques such as amino acid analysis, thin layer chromatography, high performance liquid chromatography, ultraviolet absorption spectroscopy, molar rotation, or measuring solubility. If desired, the peptides or polypeptides can be quantified by the solid phase Edman degradation.

Carbohydrate-based auxiliary moieties that can be attached to the nucleic acid constructs of the disclosure include monosaccharides, disaccharides, and polysaccharides. Examples include allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate gulose glyceraldehyde, L-glycero-D-mannos-heprose, glycerol, glycerone, gulose idose, lyxose, mannosamine, mannose, mannose-6-phosphate,psicose, quinovose, quinovosamine, rhamnitol, rhamnosamine, rhamnose, ribose, ribulose, sedoheptulose, sorbose, tagatose, talose, tararic acid, threose, xylose and xylulose. A monosaccharide can be in D- or L-configuration. A monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), a imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, such as galactosamine, glucosamine, mannosamine, fucosmine, quinavosamine, neuraminic acid, muramic acid, lactosediamine, acosamine, bacillosamine, daunosamine, desosamine, forosamine, garosamine, kanosamine, kanosamine, mycaminose, myosamine, persosamine, pneumosamine, purpurosamine, rhodosmine. It is understood that the monosaccharide and the like can be further substituted. Di- and polysaccharides include abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose diginose, digitalose, digitoxose, evalose, evemitrose, fructooligosaccharide, galto-oligosaccharide, gentianose, genitiobiose, glucan, gluicogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, migerose, nojirimycon, noviose, oleandrose, panose, paratose, planteose, primeverose, raffinose, rhodone, rutinose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trahalosamine, turanose, tyvelose, xylobiose, umbelliferose and the like.

The nucleic acid constructs described herein can also comprise covalently attached neutral or charged (e.g., cationic) polymer-based auxiliary moieties. Examples of positively charged polymers include poly(ethylene imine) (PEI), spermine, spermidine, and poly(amidoamine) (PAMAM). Neutral polymers include poly($C_{1-4}$alkylene oxide), e.g., poly(ethylene glycol) and poly(propylene glycol) and copolymers thereof, e.g., di- and triblock copolymers. Other examples of polymers include esterified poly(acrylic acid), esterified poly(glutamic acid), esterified poly(aspartic acid), poly(vinyl alcohol), poly(ethylene-co-vinyl alcohol), poly (N-vinyl pyrrolidone), poly(acrylic acid), poly(ethyloxazoline), poly(alkylacrylates), poly(acrylamide), poly(N-alkylacrylamides), poly(N-acryloylmorpholine), poly(lactic acid), poly(glycolic acid), poly(dioxanone), poly(caprolactone), styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyurethane, poly(2-ethylacrylic acid), N-isopropylacrylamide polymers, polyphosphazine and poly(N,N-dialkylacrylamides). Exemplary polymer auxiliary moieties may have molecular weights of less than 100, 300, 500, 1000, or 5000. Other polymers are known in the art.

Therapeutic agents, which include diagnostic/imaging agents, can be covalently attached as auxiliary moieties to the nucleic acid constructs of the disclosure or can be administered as a co-therapy as described herein. They can be naturally occurring compounds, synthetic organic compounds, or inorganic compounds. Exemplary therapeutic agents include, but are not limited to, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, antibodies, neurotransmitters, psychoactive drugs, and combinations thereof. Additional examples of therapeutic agents include, but are not limited to, cell cycle control agents; agents which inhibit cyclin protein production; cytokines, including, but not limited to, Interleukins 1 through 13 and tumor necrosis factors; anticoagulants, anti-platelet agents; TNF receptor domains and the like. Typically the therapeutic agent is neutral or positively charged. In certain instances, where the therapeutic agent is negatively charged, an additional charge neutralization moiety (e.g., a cationic peptide) can be used.

A therapeutic moiety can be linked as an auxiliary moiety to a nucleic acid construct disclosed herein to allow for diagnostic assay/imaging. Examples of such moieties include, but are not limited to, detectable labels, such as an isotope, a radioimaging agent, a marker, a tracer, a fluorescent label (e.g., rhodamine), and a reporter molecule (e.g., biotin).

Exemplary diagnostic agents include, but are not limited to, imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include, but are not limited to, gadolinium chelates, as well as iron, magnesium, manganese, copper, and chromium chelates. Examples of materials useful for CAT and X-rays include, but are not limited to, iodine based materials.

Examples of radioimaging agents emitting radiation (detectable radio-labels) that may be suitable are exemplified by indium-111, technitium-99, or low dose iodine-131. Detectable labels, or markers, for use in conjunction with or attached to the nucleic acid constructs of the disclosure as auxiliary moieties may be a radiolabel, a fluorescent label, a nuclear magnetic resonance active label, a luminescent label, a chromophore label, a positron emitting isotope for PET scanner, a chemiluminescence label, or an enzymatic label. Fluorescent labels include, but are not limited to, green fluorescent protein (GFP), fluorescein, and rhodamine. The label may be for example a medical isotope, such as for example and without limitation, technetium-99, iodine-123 and -131, thallium-201, gallium-67, fluorine-18, indium-111, etc.

Other therapeutic agents known in the art can likewise be used in conjunction with, or attached to the nucleic acid constructs of the disclosure as auxiliary moieties.

The disclosure provides for one or more targeting moieties which can be attached to a nucleic acid construct disclosed herein as an auxiliary moiety, for example as a targeting auxiliary moiety. A targeting moiety is selected based on its ability to target constructs of the disclosure to a desired or selected cell population that expresses the corresponding binding partner (e.g., either the corresponding receptor or ligand) for the selected targeting moiety. For example, a construct of the disclosure could be targeted to cells expressing epidermal growth factor receptor (EGFR) by selected epidermal growth factor (EGF) as the targeting moiety.

In one embodiment, the targeting moiety is a receptor binding domain. In another embodiment, the targeting moiety is or specifically binds to a protein selected from the group comprising insulin, insulin-like growth factor receptor 1 (IGF1R), IGF2R, insulin-like growth factor (IGF; e.g., IGF 1 or 2), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-$\alpha$), TNF-$\beta$, folate receptor (FOLR), folate, transferring, transferrin receptor (TfR), mesothelin, Fc receptor, c-kit receptor, c-kit, an integrin (e.g., an $\alpha$4 integrin or a $\beta$-1 integrin), P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), IL-1ra, IL-2, IL-3, IL-4, IL-6, IL-7, IL-8, CTLA-4, MART-1, gp100, MAGE-1, ephrin (Eph) receptor, mucosal addressin cell adhesion molecule 1 (MAdCAM-1), carcinoembryonic antigen (CEA), Lewis$^Y$, MUC-1, epithelial cell adhesion molecule (EpCAM), cancer antigen 125 (CA125), prostate specific membrane antigen (PSMA), TAG-72 antigen, and fragments thereof. In a further embodiment, the targeting moiety is erythroblastic leukemia viral oncogene homolog (ErbB) receptor (e.g., ErbB1 receptor; ErbB2 receptor; ErbB3 receptor; and ErbB4 receptor).

The targeting moiety can also be selected from bombesin, gastrin, gastrin-releasing peptide, tumor growth factors (TGF), such as TGF-$\alpha$ and TGF-$\beta$, and vaccinia virus growth factor (VVGF). Non-peptidyl ligands can also be used as the targeting moiety and may include, for example, steroids, carbohydrates, vitamins, and lectins. The targeting moiety may also be selected from a peptide or polypeptide, such as somatostatin (e.g., a somatostatin having the core sequence cyclo[Cys-Phe-D-Trp-Lys-Thr-Cys], and in which, for example, the C-terminus of the somatostatin analog is: Thr-NH$_2$), a somatostatin analog (e.g., octreotide and lanreotide), bombesin, a bombesin analog, or an antibody, such as a monoclonal antibody.

Other peptides or polypeptides for use as a targeting auxiliary moiety in nucleic acid constructs of the disclosure can be selected from KiSS peptides and analogs, urotensin II peptides and analogs, GnRH I and II peptides and analogs, depreotide, vapreotide, vasoactive intestinal peptide (VIP), cholecystokinin (CCK), RGD-containing peptides, melanocyte-stimulating hormone (MSH) peptide, neurotensin, calcitonin, peptides from complementarity determining regions of an antitumor antibody, glutathione, YIGSR (leukocyte-avid peptides, e.g., P483H, which contains the heparin-binding region of platelet factor-4 (PF-4) and a lysine-rich sequence), atrial natriuretic peptide (ANP), $\beta$-amyloid peptides, delta-opioid antagonists (such as ITIPP(psi)), annexin-V, endothelin, leukotriene B4 (LTB4), chemotactic peptides (e.g., N-formyl-methionyl-leucyl-phenylalanine-lysine (fM-LFK)), GP IIb/IIIa receptor antagonists (e.g., DMP444), human neutrophil elastase inhibitor (EPI-HNE-2 and EPI-HNE-4), plasmin inhibitor, antimicrobial peptides, apticide (P280 and P274), thrombospondin receptor (including analogs such as TP-1300), bitistatin, pituitary adenylyl cyclase type I receptor (PAC1), fibrin $\alpha$-chain, peptides derived from phage display libraries, and conservative substitutions thereof.

Immunoreactive ligands for use as a targeting moiety in nucleic acid constructs of the disclosure include an antigen-recognizing immunoglobulin (also referred to as "antibody"), or antigen-recognizing fragment thereof. As used herein, "immunoglobulin" refers to any recognized class or subclass of immunoglobulins such as IgG, IgA, IgM, IgD, or IgE. Typical are those immunoglobulins which fall within the IgG class of immunoglobulins. The immunoglobulin can be derived from any species. Typically, however, the immunoglobulin is of human, murine, or rabbit origin. In addition, the immunoglobulin may be polyclonal or monoclonal, but is typically monoclonal.

Targeting moieties of the disclosure may include an antigen-recognizing immunoglobulin fragment. Such immunoglobulin fragments may include, for example, the Fab', F(ab')$_2$, F$_v$ or Fab fragments, single-domain antibody, ScFv, or other antigen-recognizing immunoglobulin fragments. Fc fragments may also be employed as targeting moieties. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, J. Immunology, 131, 2895, 1983; Lamoyi et al., J. Immunological Methods, 56, 235, 1983.

Targeting moieties of the disclosure include those targeting moieties which are known in the art but have not been provided as a particular example in this disclosure.

The disclosure provides for one or more endosomal escape moieties which can be attached to a nucleic acid construct disclosed herein as an auxiliary moiety, for example as an endosomal escape auxiliary moiety. Exemplary endosomal escape moieties include chemotherapeutics (e.g., quinolones such as chloroquine); fusogenic lipids (e.g., dioleoylphosphatidyl-ethanolamine (DOPE)); and polymers such as polyethylenimine (PEI); poly(beta-amino ester)s; peptides or polypeptides such as polyarginines (e.g., octaarginine) and polylysines (e.g., octalysine); proton sponges, viral capsids, and peptide transduction domains as described herein. For example, fusogenic peptides can be derived from the M2 protein of influenza A viruses; peptide analogs of the influenza virus hemagglutinin; the HEF protein of the influenza C virus; the transmembrane glycoprotein of filoviruses; the transmembrane glycoprotein of the rabies virus; the transmembrane glycoprotein (G) of the vesicular stomatitis virus; the fusion protein of the Sendai virus; the transmembrane glycoprotein of the Semliki forest virus; the fusion protein of the human respiratory syncytial virus (RSV); the fusion protein of the measles virus; the fusion protein of the Newcastle disease virus; the fusion protein of the visna virus; the fusion protein of murine leukemia virus; the fusion protein of the HTL virus; and the fusion protein of the simian immunodeficiency virus (SIV). Other moieties that can be employed to facilitate endosomal escape are described in Dominska et al., *Journal of Cell Science*, 123(8): 1183-1189, 2010.

The disclosure provides for one or more delivery domain moieties which can be attached to a nucleic acid construct disclosed herein as an auxiliary moiety, for example as an delivery domain auxiliary moiety. A delivery domain is a moiety that induces transport of a polynucleotide of the disclosure into a cell, by any mechanism. Typically, nucleic acid constructs of the disclosure will be internalized by macropinocytosis, phagocytosis, or endocytosis (e.g., clathrin-mediated endocytosis, caveolae-mediated endocytosis, and lipid-raft dependent endocytosis), see, e.g., *Chem. Soc. Rev.*, 2011, 40, 233-245. Delivery domains may include peptides or polypeptides (e.g., peptide transduction domains), carbohydrates (hyaluronic acid), and positively charged polymers (poly(ethylene imine), as described herein.

Cellular delivery can be accomplished by macromolecule fusion of "cargo" biological agents (in this case the polynucleotide) to a cationic Peptide Transduction Domain (PTD; also termed Cell Penetrating Peptide (CPP)) such as TAT or (Args) (Snyder and Dowdy, 2005, *Expert Opin. Drug Deliv.* 2, 43-51). PTDs can be used to deliver a wide variety of macromolecular cargo, including the polynucleotides described herein (Schwarze et al., 1999, *Science* 285, 1569-1572; Eguchi et al., 2001, *J. Biol. Chem.* 276, 26204-26210; and Koppelhus et al., 2002, *Antisense Nucleic Acid Drug Dev.* 12, 51-63). Cationic PTDs enter cells by macropinocytosis, a specialized form of fluid phase uptake that all cells perform.

Biophysical studies on model vesicles suggest that cargo escape from macropinosome vesicles into the cytoplasm, thus requiring a pH decrease (Magzoub et al., 2005, *Biochemistry* 44, 14890-14897). The cationic charge of the PTDs is essential for the molecules to traverse the cell membrane. Not surprisingly, conjugation of cationic PTDs (6-8 positive charges) to anionic siRNAs (~40 negative charges) results in charge neutralization and inactivation of the PTD with no siRNA entering the cells (Turner et al., *Blood Cells Mol. Dis.*, 38(1): 1-7, 2007). However, chemical conjugation of cationic PTDs to a nucleic acid construct described herein (e.g., anionic RNA or DNA) still results in the nucleic acid construct being able to be taken up by cells, and therefore the novel and nonobvious nucleic acid constructs disclosed herein do not suffer from any charge neutralization deleterious artifacts seen with other similar methods. Further, cleavage of these PTDs intracellularly allows the polynucleotide to be irreversibly delivered to the targeted cell.

The discovery of several proteins which could efficiently pass through the plasma membrane of eukaryotic cells has led to the identification of a class of proteins from which peptide transduction domains have been derived. The best characterized of these proteins are the *Drosophila homeoprotein antennapedia* transcription protein (AntHD) (Joliot et al., *New Biol.* 3:1121-34, 1991; Joliot et al., *Proc. Natl. Acad. Sci. USA*, 88:1864-8, 1991; Le Roux et al., *Proc. Natl. Acad. Sci. USA*, 90:9120-4, 1993), the herpes simplex virus structural protein VP22 (Elliott and O'Hare, *Cell* 88:223-33, 1997), the HIV-1 transcriptional activator TAT protein (Green and Loewenstein, *Cell* 55:1179-1188, 1988; Frankel and Pabo, *Cell* 55:1189-1193, 1988), and more recently the cationic N-terminal domain of prion proteins. Exemplary PTD sequences are provided in Table 2. The disclosure further provides for one or more of the PTDs listed in Table 2 or other PTDs known in the art (see, e.g., Joliot et al., *Nature Cell Biology*, 6(3):189-196, 2004) to be conjugated to the nucleic acid constructs disclosed herein as auxiliary moieties. Strategies for conjugation include the use of a bifunctional linker that includes a functional group that can be cleaved by the action of an intracellular enzyme.

TABLE 2

| PDP | Sequence | SEQ ID NO. |
|---|---|---|
| TAT | RKKRRQRRR | SEQ ID NO.: 1 |
| Penetratin | RQIKIWFQNRRMKWKK | SEQ ID NO.: 2 |
| Buforin II | TRSSRAGLQFPVGRVHRLLRK | SEQ ID NO.: 3 |
| Transportan | GWTLNSAGYLLGKINKALAAL AKKIL | SEQ ID NO.: 4 |
| MAP (model amphipathic peptide) | KLALKLALKALKAALKLA | SEQ ID NO.: 5 |
| K-FGF | AAVALLPAVLLALLAP | SEQ ID NO.: 6 |
| Ku70 | VPMLK-PMLKE | SEQ ID NO.: 7 |
| Prion | MANLGYWLLALFVTMWTDVGL CKKRPKP | SEQ ID NO.: 8 |
| pVEC | LLIILRRRIRKQAHAHSK | SEQ ID NO.: 9 |
| Pep-1 | KETWWETWWTEWSQPKKKRKV | SEQ ID NO.: 10 |
| SynB1 | RGGRLSYSRRRFSTSTGR | SEQ ID NO.: 11 |
| Pep-7 (phage display) | SDLWEMMMVSLACQY | SEQ ID NO.: 12 |
| HN-1 (phage display) | TSPLNIHNGQKL | SEQ ID NO.: 13 |

Exemplary auxiliary moieties, which comprise TAT peptides that can be conjugated to any of the nucleic acid constructs described herein are provided in Table 3.

TABLE 3

| Sequence (N' to C') |
|---|
| PEG-(PTD) |
| GG-(PTD)-PEG-(PTD) |
| PEG-(PTD)-PEG-(PTD) |
| GG-(PTD)-PEG-PEG-PEG-(PTD) |
| PEG-(PTD)-PEG-PEG-PEG-(PTD) |
| GG-(PTD)-PEG-(PTD)-PEG-(PTD) |
| GG-(PTD)-PEG-PEG-PEG-(PTD)-PEG-PEG-PEG-(PTD) |

PEG = a poly(ethyleneglycol) linker having six repeat units

In a particular embodiment, the auxiliary moieties described in Table 3 include a covalent bond to Z' at the N' terminus, where Z' is the residue of conjugation of 6-hydrazinonicotinic acid or an amino group of a polypeptide $R^Z$ to an aldehyde.

Thus, PTDs that can be conjugated to a nucleic acid construct of the disclosure include, but are not limited to, AntHD, TAT, VP22, cationic prion protein domains, and functional fragments thereof. Not only can these peptides pass through the plasma membrane, but the attachment of other peptide or polypeptides, such as the enzyme β-galactosidase, are sufficient to stimulate the cellular uptake of these complexes. Such chimeric proteins are present in a biologically active form within the cytoplasm and nucleus. Characterization of this process has shown that the uptake of these fusion polypeptides is rapid, often occurring within minutes, in a receptor independent fashion. Moreover, the transduction of these proteins does not appear to be affected by cell type, and these proteins can efficiently transduce ~100% of cells in culture with no apparent toxicity (Nagahara et al., *Nat. Med.* 4:1449-52, 1998). In addition to full-length proteins, peptide transduction domains have also been used successfully to induce the intracellular uptake of DNA (Abu-Amer, supra), antisense polynucleotides (Astriab-Fisher et al., *Pharm. Res,* 19:744-54, 2002), small molecules (Polyakov et al., *Bioconjug. Chem.* 11:762-71, 2000) and even inorganic 40 nm iron particles (Dodd et al., *J. Immunol. Methods* 256:89-105, 2001; Wunderbaldinger et al., *Bioconjug. Chem.* 13:264-8, 2002; Lewin et al., *Nat. Biotechnol.* 18:410-4, 2000; Josephson et al., *Bioconjug., Chem.* 10:186-91, 1999) suggesting that there is considerable flexibility in particle size in this process.

In a particular embodiment, the disclosure therefore provides methods and compositions that combine the use of PTDs, such as TAT and poly-Arg, with a nucleic acid construct disclosed herein to facilitate the targeted uptake of the construct into and/or release within targeted cells. Nucleic acid constructs disclosed herein therefore provide methods whereby a therapeutic or diagnostic agent which is linked as an auxiliary moiety can be targeted to be delivered in certain cells by the nucleic acid constructs further comprising one or more PTDs linked as auxiliary moieties.

The nucleic acid construct of the disclosure can be an siRNA or other inhibitory nucleic acid sequence that itself provides a therapeutic or diagnostic benefit. However, in some instances it may be desirable to attach additional auxiliary moieties as therapeutics or to promote uptake. In the case of PTDs, the PTDs serve as additional charge modifying moieties to promote uptake of the nucleic acid construct by neutralizing the charge on the nucleic acid construct or typically providing a slight net cationic charge to the nucleic acid construct. It will be further understood, that the nucleic acid construct may include other auxiliary moieties such as, but not limited to, targeting moieties, biologically active molecules, therapeutics, small molecules (e.g., cytotoxics), and the like. In such instances the nucleic acid construct having such auxiliary moieties may be neutrally charged or cationically charged depending upon the auxillary moieties size and charge. In instances where the auxiliary moieties are anionically charged the addition of cationically charged peptides (e.g., PTDs) can further neutralize the charge or improve the net cationic charge of the construct.

In general, the delivery domain that is linked to a nucleic acid construct disclosed herein can be nearly any synthetic or naturally-occurring amino acid sequence which assists in the intracellular delivery of a nucleic construct disclosed herein into targeted cells. For example, transfection can be achieved in accordance with the disclosure by use of a peptide transduction domain, such as an HIV TAT protein or fragment thereof, that is covalently linked to a conjugating moiety of a nucleic acid construct of the disclosure. Alternatively, the peptide transduction domain can comprise the Antennapedia homeodomain or the HSV VP22 sequence, the N-terminal fragment of a prion protein or suitable transducing fragments thereof such as those known in the art.

The type and size of the PTD will be guided by several parameters including the extent of transfection desired. Typically the PTD will be capable of transfecting at least about 20%, 25%, 50%, 75%, 80% or 90%, 95%, 98% and up to, and including, about 100% of the cells. Transfection efficiency, typically expressed as the percentage of transfected cells, can be determined by several conventional methods.

PTDs will manifest cell entry and exit rates (sometimes referred to as $k_1$ and $k_2$, respectively) that favor at least picomolar amounts of a nucleic acid construct disclosed herein into a targeted cell. The entry and exit rates of the PTD and any cargo can be readily determined or at least approximated by standard kinetic analysis using detectably-labeled fusion molecules. Typically, the ratio of the entry rate to the exit rate will be in the range of between about 5 to about 100 up to about 1000.

In one embodiment, a PTD useful in the methods and compositions of the disclosure comprises a peptide or polypeptide featuring substantial alpha-helicity. It has been discovered that transfection is optimized when the PTD exhibits significant alpha-helicity. In another embodiment, the PTD comprises a sequence containing basic amino acid residues that are substantially aligned along at least one face of the peptide or polypeptide. A PTD domain useful in the disclosure may be a naturally occurring peptide or polypeptide or a synthetic peptide or polypeptide.

In another embodiment, the PTD comprises an amino acid sequence comprising a strong alpha helical structure with arginine (Arg) residues down the helical cylinder.

In yet another embodiment, the PTD domain comprises a peptide represented by the following general formula: $B_{P1}$-$X_{P1}$-$X_{P2}$-$X_{P3}$-$B_{P2}$-$X_{P4}$-$X_{P5}$-$B_{P3}$ (SEQ ID NO: 14) wherein $B_{P1}$, $B_{P2}$, and $B_{P3}$ are each independently a basic amino acid, the same or different; and $X_{P1}$, $X_{P2}$, $X_{P3}$, $X_{P4}$, and $X_{P5}$ are each independently an alpha-helix enhancing amino acid, the same or different.

In another embodiment, the PTD domain is represented by the following general formula: $B_{P1}$-$X_{P1}$-$X_{P2}$-$B_{P2}$-$B_{P3}$-$X_{P3}$-$X_{P4}$-$B_{P4}$ (SEQ ID NO:15) wherein $B_{P1}$, $B_{P2}$, $B_{P3}$, and $B_{P4}$ are each independently a basic amino acid, the same or different; and $X_{P1}$, $X_{P2}$, $X_{P3}$, and $X_{P4}$ are each independently an alpha-helix enhancing amino acid the same or different.

Additionally, PTD domains comprise basic residues, e.g., lysine (Lys) or arginine (Arg), and further can include at least one proline (Pro) residue sufficient to introduce "kinks" into the domain. Examples of such domains include the transduction domains of prions. For example, such a peptide comprises KKRPKPG (SEQ ID NO: 16).

In one embodiment, the domain is a peptide represented by the following sequence: $X_P$-$X_P$-R-$X_P$-(P/$X_P$)-($B_P$/$X_P$)-$B_P$-(P/$X_P$)-$X_P$-$B_P$-($B_P$/$X_P$) (SEQ ID NO: 17), wherein X is any alpha helical promoting residue such as alanine; P/$X_P$ is either proline or $X_P$ as previously defined; $B_P$ is a basic amino acid residue, e.g., arginine (Arg) or lysine (Lys); R is arginine (Arg) and $B_P$/$X_P$ is either $B_P$ or $X_P$ as defined above.

In another embodiment the PTD is cationic and consists of between 7 and 10 amino acids and has the formula $KX_{P1}RX_{P2}X_{P1}$ (SEQ ID NO:18), wherein $X_{P1}$ is R or K and $X_{P2}$ is any amino acid. An example of such a peptide comprises RKKRRQRRR (SEQ ID NO:1). In another example, the PTD is a cationic peptide sequence having 5-10 arginine (and/or lysine) residues over 5-15 amino acids.

Additional delivery domains in accord with this disclosure include a TAT fragment that comprises at least amino acids 49 to 56 of TAT up to about the full-length TAT sequence (see, e.g., SEQ ID NO:1). A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment that impede alpha helix formation or stability. In a more specific embodiment, the TAT fragment will include at least one amino acid substitution with an alpha-helix enhancing amino acid. Typically the TAT fragment will be made by standard peptide synthesis techniques although recombinant DNA approaches may be used in some cases. In one embodiment, the substitution is selected so that at least two basic amino acid residues in the TAT fragment are substantially aligned along at least one face of that TAT fragment. In a more specific embodiment, the substitution is chosen so that at least two basic amino acid residues in the TAT 49-56 sequence are substantially aligned along at least one face of that sequence.

Additional transduction proteins (PTDs) that can be used in the compositions and methods of the disclosure include the TAT fragment in which the TAT 49-56 sequence has been modified so that at least two basic amino acids in the sequence are substantially aligned along at least one face of the TAT fragment. Illustrative TAT fragments include at least one specified amino acid substitution in at least amino acids 49-56 of TAT which substitution aligns the basic amino acid residues of the 49-56 sequence along at least one face of the segment and typically the TAT 49-56 sequence.

Also included are chimeric PTD domains. Such chimeric PTDs include parts of at least two different transducing proteins. For example, chimeric PTDs can be formed by fusing two different TAT fragments, e.g., one from HIV-1 and the other from HIV-2 or one from a prion protein and one from HIV.

A PTD can be linked as an auxiliary moiety to a nucleic acid construct of disclosure using phosphoramidate or phosphotriester linkers at an internucleotide bridging group or at the 3' or 5' ends. For example, a siRNA construct comprising a 3'-amino group with a 3-carbon linker may be utilized for linking the siRNA construct to a PTD. The siRNA construct may be conjugated to the PTD via a heterobifunctional cross linker.

The PTD can be attached as an auxiliary moiety to a nucleic acid construct via a bioreversible group, whereby the bioreversible group can be cleaved intracellularly, e.g., by an intracellular enzyme (e.g., a thioesterase) and thereby release the polynucleotide.

For example, in addition to the PTD being conjugated between the 5' and 3' ends, a PTD can be conjugated directly to a polynucleotide (e.g., an RNA or DNA) comprising a nucleic acid construct disclosed herein, at the 5' and/or 3' end via a free thiol group. For example, a PTD can be linked to the polynucleotide by a biologically sensitive and reversible manner, such as a disulfide linkage or a functional group that can be cleaved by the action of an intracellular enzyme (e.g., a thioester). This approach can be applied to any polynucleotide length and will allow for delivery of the polynucleotide (e.g., siRNA) into cells. The polynucleotide can also include, for example, one or more delivery domains and/or a protecting group that contains a basic group. Once inside the cell the polynucleotide reverts to an unprotected polynucleotide based on the intracellular conditions, e.g., reducing environment, by hydrolysis or other enzymatic activity (e.g., thioesterase activity).

Peptide linkers that can be used in the constructs and methods of the disclosure will typically comprise up to about 20 or 30 amino acids, commonly up to about 10 or 15 amino acids, and still more often from about 1 to 5 amino acids. The linker sequence is generally flexible so as not to hold the fusion molecule in a single rigid conformation. The linker sequence can be used, e.g., to space the PTD domain from the nucleic acid. For example, the peptide linker sequence can be positioned between the peptide transduction domain and the nucleic acid domain, e.g., to provide molecular flexibility. The length of the linker moiety is chosen to optimize the biological activity of the peptide or polypeptide comprising, for example, a PTD domain fusion construct and can be determined empirically without undue experimentation. Examples of linker moieties are -Gly-Gly-, GGGGS (SEQ ID NO: 19), (GGGGS)$_N$(SEQ ID NO:20), GKSSGSGSESKS (SEQ ID NO:21), GSTSGSGKSSEGKG (SEQ ID NO:22), GSTSGSGKSSEGSGSTKG (SEQ ID NO:23), GSTSGSGKPGSGEGSTKG (SEQ ID NO:24), or EGKSSGSGSESKEF (SEQ ID NO:25). Peptide or polypeptide linking moieties are described, for example, in Huston et al., *Proc. Nat'l Acad. Sci.* 85:5879, 1988; Whitlow et al., *Protein Engineering* 6:989, 1993; and Newton et al., *Biochemistry* 35:545, 1996. Other suitable peptide or polypeptide linkers are those described in U.S. Pat. Nos. 4,751, 180 and 4,935,233, which are hereby incorporated by reference.

Delivery of a nucleic acid construct of the disclosure can be achieved by contacting a cell with the construct using a variety of methods known to those of skill in the art. In a particular embodiment, a nucleic acid construct of the disclosure is formulated with various carriers, dispersion agents and the like, as are described more fully elsewhere herein.

A pharmaceutical composition according to the disclosure can be prepared to include a nucleic acid construct disclosed herein, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, and The National Formulary, 30th ed., the contents of which are hereby incorporated by reference. The pH and exact concentration of the various components of the pharmaceutical composition are adjusted according to routine skills in the art. See Goodman and Gilman's, The Pharmacological Basis for Therapeutics.

The pharmaceutical compositions according to the disclosure may be administered locally or systemically. The therapeutically effective amounts will vary according to factors, such as the degree of infection in a subject, the age, sex, and weight of the individual. Dosage regimes can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, intraorbital, and the like), oral administration, ophthalmic application, inhalation, transdermal application, topical application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit. The tablets, troches, pills, capsules, and the like can also contain the following: a binder, such as gum tragacanth, *acacia*, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a pharmaceutically acceptable carrier is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve. The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

For topical formulations, the base composition can be prepared with any solvent system, such as those Generally Regarded as Safe (GRAS) by the U.S. Food & Drug Administration (FDA). GRAS solvent systems include many short chain hydrocarbons, such as butane, propane, n-butane, or a mixture thereof, as the delivery vehicle, which are approved by the FDA for topical use. The topical compositions can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The compounds may also be administered in liposomal formulations that allow compounds to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. Nos. 4,877,805, 4,980,378, 5,082,866, 6,118,020 and EP Publication No. 0586106A1. Suitable vehicles of the disclosure may also include mineral oil, petrolatum, polydecene, stearic acid, isopropyl myristate, polyoxyl 40 stearate, stearyl alcohol, or vegetable oil.

Topical compositions can be provided in any useful form. For example, the compositions of the disclosure may be formulated as solutions, emulsions (including microemulsions), suspensions, creams, foams, lotions, gels, powders, balm, or other typical solid, semi-solid, or liquid compositions used for application to the skin or other tissues where the compositions may be used. Such compositions may contain other ingredients typically used in such products, such as colorants, fragrances, thickeners, antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetration enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

In some formulations, the composition is formulated for ocular application. For example, a pharmaceutical formulation for ocular application can include a polynucleotide construct as described herein in an amount that is, e.g., up to 99% by weight mixed with a physiologically acceptable ophthalmic carrier medium such as water, buffer, saline, glycine, hyaluronic acid, mannitol, and the like. For ophthalmic delivery, a polynucleotide construct as described herein may be combined with ophthalmologically acceptable preservatives, co-solvents, surfactants, viscosity enhancers, penetration enhancers, buffers, sodium chloride, or water to form an aqueous, sterile ophthalmic suspension or solution. Ophthalmic solution formulations may be prepared by dissolving the polynucleotide construct in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the disclosure to improve the retention of the compound.

Topical compositions can be delivered to the surface of the eye, e.g., one to four times per day, or on an extended delivery schedule such as daily, weekly, bi-weekly, monthly, or longer, according to the routine discretion of a skilled clinician. The pH of the formulation can range from about pH 4-9, or about pH 4.5 to pH 7.4.

For nucleic acid constructs of the disclosure, suitable pharmaceutically acceptable salts include (i) salts formed with cations such as sodium, potassium, ammonium, magnesium, calcium, polyamines such as spermine and spermidine, etc.; (ii) acid addition salts formed with inorganic acids, for example hydrochloric acid, hydrobromic acid, sulfuric acid, phosphoric acid, nitric acid and the like; (iii) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (iv) salts formed from elemental anions such as chlorine, bromine, and iodine.

While the nucleic acid constructs described herein may not require the use of a carrier for delivery to the target cell, the use of carriers may be advantageous in some embodiments. Thus, for delivery to the target cell, the nucleic acid construct of the disclosure can non-covalently bind a carrier to form a complex. The carrier can be used to alter biodistribution after delivery, to enhance uptake, to increase half-life or stability of the polynucleotide (e.g., improve nuclease resistance), and/or to increase targeting to a particular cell or tissue type.

Exemplary carriers include a condensing agent (e.g., an agent capable of attracting or binding a nucleic acid through ionic or electrostatic interactions); a fusogenic agent (e.g., an agent capable of fusing and/or being transported through a cell membrane); a protein to target a particular cell or tissue type (e.g., thyrotropin, melanotropin, lectin, glycoprotein, surfactant protein A, or any other protein); a lipid; a lipopolysaccharide; a lipid micelle or a liposome (e.g., formed from phospholipids, such as phosphotidylcholine, fatty acids, glycolipids, ceramides, glycerides, cholesterols, or any combination thereof); a nanoparticle (e.g., silica, lipid, carbohydrate, or other pharmaceutically-acceptable polymer nanoparticle); a polyplex formed from cationic polymers and an anionic agent (e.g., a CRO), where exemplary cationic polymers include polyamines (e.g., polylysine, polyarginine, polyamidoamine, and polyethylene imine); cholesterol; a dendrimer (e.g., a polyamidoamine (PAMAM) dendrimer); a serum protein (e.g., human serum albumin (HSA) or low-density lipoprotein (LDL)); a carbohydrate (e.g., dextran, pullulan, chitin, chitosan, inulin, cyclodextrin, or hyaluronic acid); a lipid; a synthetic polymer, (e.g., polylysine (PLL), polyethylenimine, poly-L-aspartic acid, poly-L-glutamic acid, styrene-maleic acid anhydride copolymer, poly(L-lactide-co-glycolic) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymer, pseudopeptide-polyamine, peptidomimetic polyamine, or polyamine); a cationic moiety (e.g., cationic lipid, cationic porphyrin, quaternary salt of a polyamine, or alpha helical peptide); a multivalent sugar (e.g., multivalent lactose, multivalent galactose, N-acetyl-galactosamine, N-acetyl-glucosamine, multivalent mannose, or multivalent fucose); a vitamin (e.g., vitamin A, vitamin E, vitamin K, vitamin B, folic acid, vitamin B12, riboflavin, biotin, or pyridoxal); a cofactor; or a drug to disrupt cellular cytoskeleton to increase uptake (e.g., taxon, vincristine, vinblastine, cytochalasin, nocodazole, japlakinolide, latrunculin A, phalloidin, swinholide A, indanocine, or myoservin).

Other therapeutic agents as described herein may be included in a pharmaceutical composition of the disclosure in combination with a nucleic acid construct of the disclosure.

The disclosure provides compositions and methods for delivering nucleic acid constructs disclosed herein (e.g., RNA, DNA, nucleic acids comprising modified bases, other anionic nucleic acids, and the like). The disclosure therefore provides methods and compositions useful for delivery of non-coding nucleic acid constructs that exert a regulating effect on gene or protein expression.

RNA interference (RNAi) is the process whereby messenger RNA (mRNA) is degraded by small interfering RNA (siRNA) derived from double-stranded RNA (dsRNA) containing an identical or very similar nucleotide sequence to that of a target gene to be silenced. This process prevents the production of a protein encoded by the targeted gene through post-transcriptional, pre-translational manipulation. Accordingly, silencing of dominant disease genes or other target genes can be accomplished.

In vivo RNAi proceeds by a process in which the dsRNA is cleaved into short interfering RNAs (siRNAs) by an enzyme called Dicer, a dsRNA endoribonuclease, (Bernstein et al., 2001; Hamilton & Baulcombe, 1999, Science 286: 950; Meister and Tuschl, 2004, Nature 431, 343-9), thus producing multiple molecules from the original single dsRNA. siRNAs are loaded into the multimeric RNAi Silencing Complex (RISC) resulting in both catalytic activation and mRNA target specificity (Hannon and Rossi, Nature 431, 371-378, 2004; Novina and Sharp, Nature 430, 161-164, 2004). During siRNA loading into RISC, the antisense or guide strand is separated from the siRNA and remains docked in Argonaute-2 (Ago2), the RISC catalytic subunit (Leuschner et al., EMBO Rep. 7, 314-320, 2006). mRNAs exported from the nucleus into the cytoplasm are thought to pass through activated RISCs prior to ribosomal arrival, thereby allowing for directed, post-transcriptional, pre-translational regulation of gene expression. In theory, each and every cellular mRNA can be regulated by induction of a selective RNAi response.

The ability of 21-23 bp siRNAs to efficiently induce an RNAi response in mammalian cells is now routine (Sontheimer, Nat. Rev. Mol. Cell. Biol. 6, 127-138, 2005). The $IC_{50}$ for siRNAs is in the 10-100 pM range, significantly below the best drugs with $IC_{50}$ values in the 1-10 nM range. Consequently, due to its exquisite selectivity, RNAi has become a corner-stone for directed manipulation of cellular phenotypes, mapping genetic pathways, discovering and validating therapeutic targets, and has significant therapeutic potential.

Aspects of RNAi include (1) dsRNA, rather than single-stranded antisense RNA, is the interfering agent; (2) the process is highly specific and is remarkably potent (only a few dsRNA molecules per cell are required for effective interference); (3) the interfering activity (and presumably the dsRNA) can cause interference in cells and tissues far removed from the site of introduction. However, effective delivery of dsRNA is difficult. For example, a 21 bp dsRNA with a molecular weight of 13,860 Daltons cannot traverse the cell membrane to enter the cytoplasm, due to (1) the size and (2) the extremely negative (acidic) charge of the RNA. The methods and compositions provided by the disclosure enable the delivery of nucleic acid constructs, such as dsRNA, into a cell through charge neutralization and improved uptake.

dsRNA comprising siRNA sequences that are complementary to a nucleotide sequence of the target gene can be prepared in any number of methods. Methods and techniques for identifying siRNA sequences are known in the art. The siRNA nucleotide sequence can be obtained from the siRNA Selection Program, Whitehead Institute for Biomedical Research, Massachusetts Institute of Technology, Cambridge, Mass. (currently available at http:[//]jura.wi.mit.edu/bioc/siRNAext/; note that brackets have been added to remove hyperlinks) after supplying the Accession Number or GI number from the National Center for Biotechnology Information website (available on the World Wide Web at ncbi.nlm.nih.gov). Alternatively, dsRNA containing appropriate siRNA sequences can be ascertained using the strategy of Miyagishi and Taira (2003). Commercially available RNAi designer algorithms also exist (http:[//]rnaidesigner.invitrogen.com/rnaiexpress/). Preparation of RNA to order is commercially available.

Nucleic acid constructs of the disclosure may also act as miRNA to induce cleavage of mRNA. Alternatively, nucleic acid constructs of the disclosure may act as antisense agents to bind to mRNA, either to induce cleavage by RNase or to sterically block translation.

Exemplary methods by which the nucleic acid constructs of the disclosure can be transported into a cell are described herein.

Various diseases and disorders can be treated using nucleic acid constructs of the disclosure. For example, growth of tumor cells can be inhibited, suppressed, or destroyed upon delivery of an anti-tumor siRNA. For example, an anti-tumor siRNA can be an siRNA targeted to a gene encoding a polypeptide that promotes angiogenesis. Various angiogenic proteins associated with tumor growth are known in the art. The nucleic acid constructs described herein can therefore be used in the treatment of diseases such as anti-proliferative disorders (e.g., cancer), virus infections, and genetic diseases. Other diseases that may be treated using polynucleotides on the disclosure are in ocular disorders such as age-related macular degeneration (e.g., as described in U.S. Pat. No. 7,879,813 and U.S. 2009/0012030) and topical disorders such as psoriasis.

The compositions containing an effective amount can be administered for prophylactic or therapeutic treatments. In prophylactic applications, compositions can be administered to a subject with a clinically determined predisposition or increased susceptibility to cancer, or any disease described herein. Compositions of the disclosure can be administered to the subject (e.g., a human) in an amount sufficient to delay, reduce, or prevent the onset of clinical disease. In therapeutic applications, compositions are administered to a subject (e.g., a human) already suffering from disease (e.g., cancer, such as leukemia or a myelodysplastic syndrome) in an amount sufficient to cure or at least partially arrest the symptoms of the condition and its complications.

Amounts effective for this use may depend on the severity of the disease or condition and the weight and general state of the subject, but generally range from about 0.05 µg to about 1000 µg (e.g., 0.5-100 µg) of an equivalent amount of the agent per dose per subject. Suitable regimes for initial administration and booster administrations are typified by an initial administration followed by repeated doses at one or more hourly, daily, weekly, or monthly intervals by a subsequent administration. The total effective amount of an agent present in the compositions of the disclosure can be administered to a mammal as a single dose, either as a bolus or by infusion over a relatively short period of time, or can be administered using a fractionated treatment protocol, in which multiple doses are administered over a more prolonged period of time (e.g., a dose every 4-6 hours, 8-12 hours 14-16 hours, 18-24 hours, every 2-4 days, every 1-2 weeks, and once a month). Alternatively, continuous intravenous infusions sufficient to maintain therapeutically effective concentrations in the blood are contemplated.

The therapeutically effective amount of one or more agents present within the compositions of the disclosure and used in the methods of this disclosure applied to mammals (e.g., humans) can be determined by the ordinarily-skilled artisan with consideration of individual differences in age, weight, and the condition of the mammal. Single or multiple administrations of the compositions of the disclosure including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

One or more nucleic acid constructs of the disclosure may be used in combination with either conventional methods of treatment or therapy or may be used separately from conventional methods of treatment or therapy.

When one or more nucleic acid constructs of the disclosure are administered in combination therapies with other agents, they may be administered sequentially or concurrently to an individual. Alternatively, pharmaceutical compositions according to the disclosure may be comprised of a combination of a nucleic acid construct of the disclosure in association with a pharmaceutically acceptable excipient, as described herein, and another therapeutic or prophylactic agent known in the art.

EXAMPLES

General Synthesis & Purification of RNN Oligonucleotides. In the following examples, nucleic acid constructs of the disclosure are referred to as RNNs, or ribonucleic neutrals. The polynucleotide constructs of the disclosure can be prepared according to the generalized and specific methods and schemes described herein. For example, carboxylic acid containing starting materials were condensed with thiol alcohols (e.g., see FIG. 1, top left panel) and then reacted with nucleoside phosphordiamidites to generate RNN nucleotide constructs (e.g., see FIG. 1, middle top panel). These RNN nucleotide constructs were then used in standard oligonucleotide synthesis protocols to form RNN polynucleotide constructs. These RNN polynucleotide constructs were then deprotected, HPLC purified (e.g., see FIG. 1, bottom left panel) and analyzed by MALDI-TOF mass spectrometry analysis (e.g., see FIG. 1, bottom middle panel). The migration rate of a 21 mer polynucleotide, which contains 20 phosphate groups, through a 15% denaturing PAGE gel (stained with methylene blue) was progressively retarded as more and more of the anionic phosphates were neutralized as phosphotriester groups (e.g., see FIG. 1, bottom right panel). Increasing the number of neutral phosphotriester groups on RNN polynucleotide construct resulted in slower migration, primarily due to loss of charge, until after addition of 16 phosphotriester groups, the RNN polynucleotide did not have enough remaining phosphodiester negative charges to enter the gel (e.g., see FIG. 1, bottom right panel).

Specific Syntheses & Purification of RNN Nucleic Acid Constructs. An exemplary synthesis of a nucleotide construct that can be used in the methods described herein is provided in Scheme 1.

Scheme 1

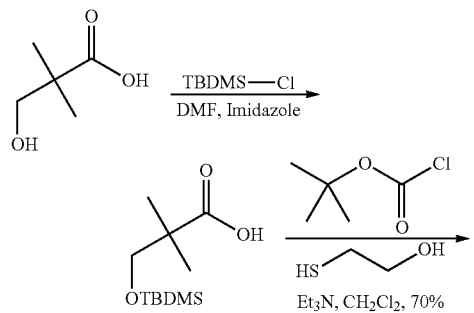

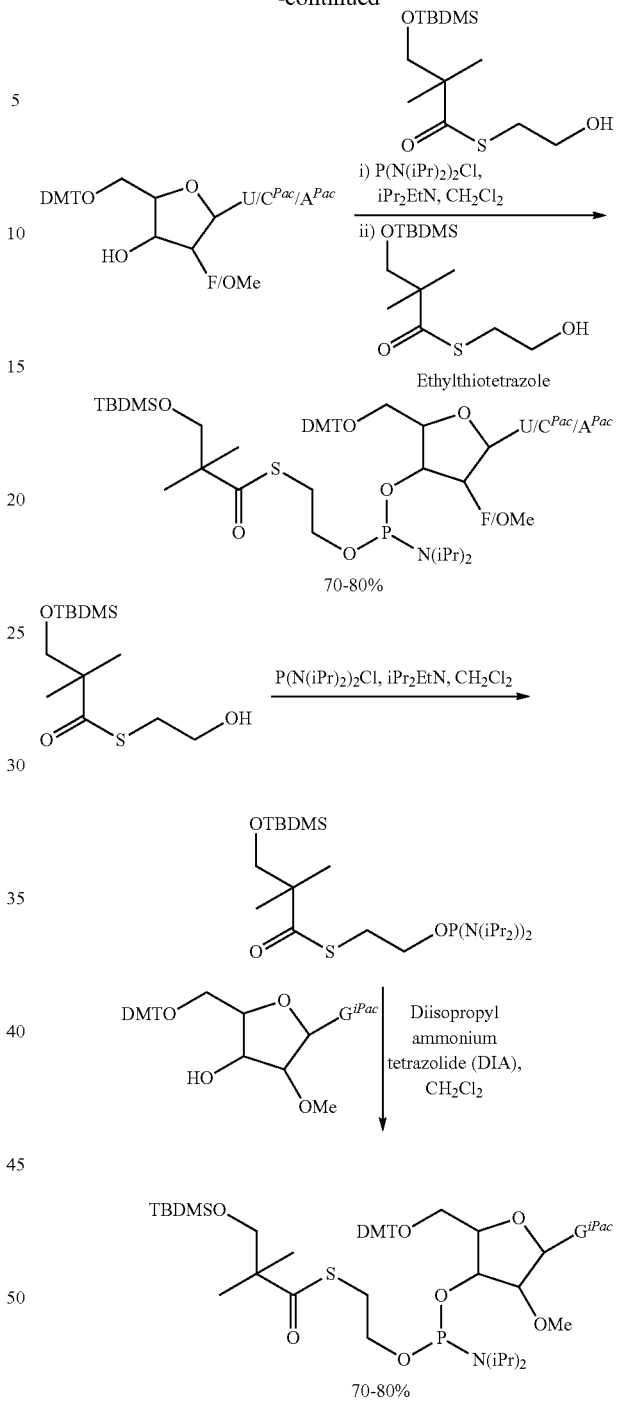

Scheme 1 shows two alternate routes for the preparation of a nucleotide construct that can be used to prepare the polynucleotide constructs described herein. One route employs the sequential treatment of a protected nucleoside with $P(N(iPr)_2)_2Cl$ followed by an S-acyl thioethanol (SATE) reagent. Alternatively, a protected nucleoside can be treated with the pre-formed thiophosphoramidite reagent.

The synthesis of aldehyde SATE and the analogous propyl and butyl (SATB) phosphoramidites can similarly proceed as outlined in Scheme 2.

Scheme 2
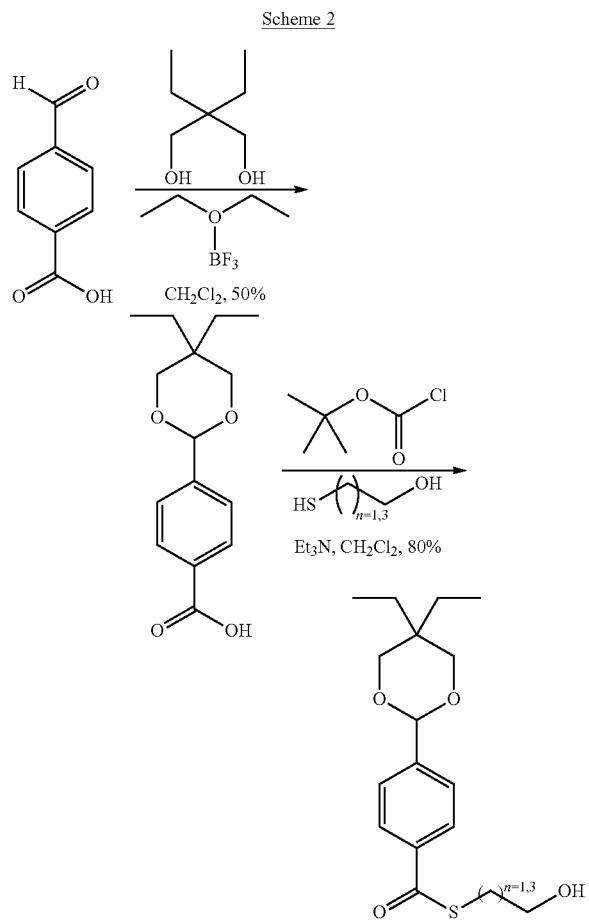
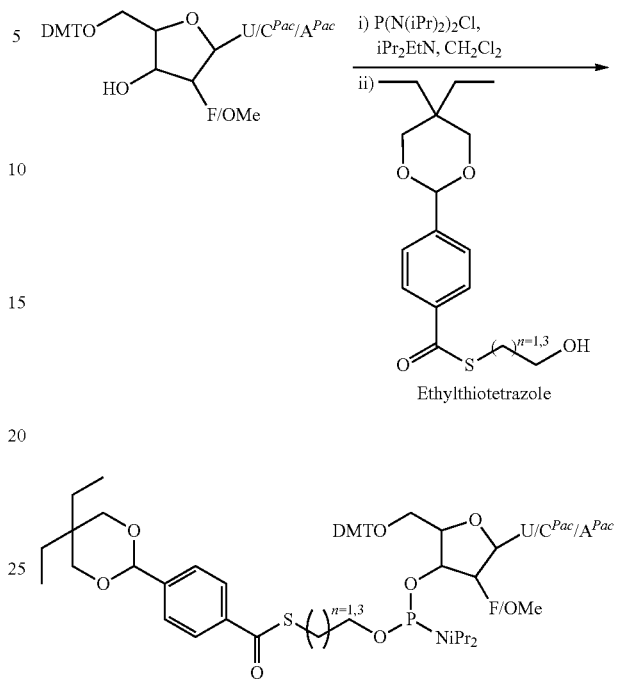
The phosphoramidites can then be used to prepare the corresponding triester group, which may or may not be bioreversible. Exemplary triester groups than have been prepared and studied are shown in Table 4, unless stated otherwise, all of the triester groups exemplified in Table 4 are bioreversible.
TABLE 4
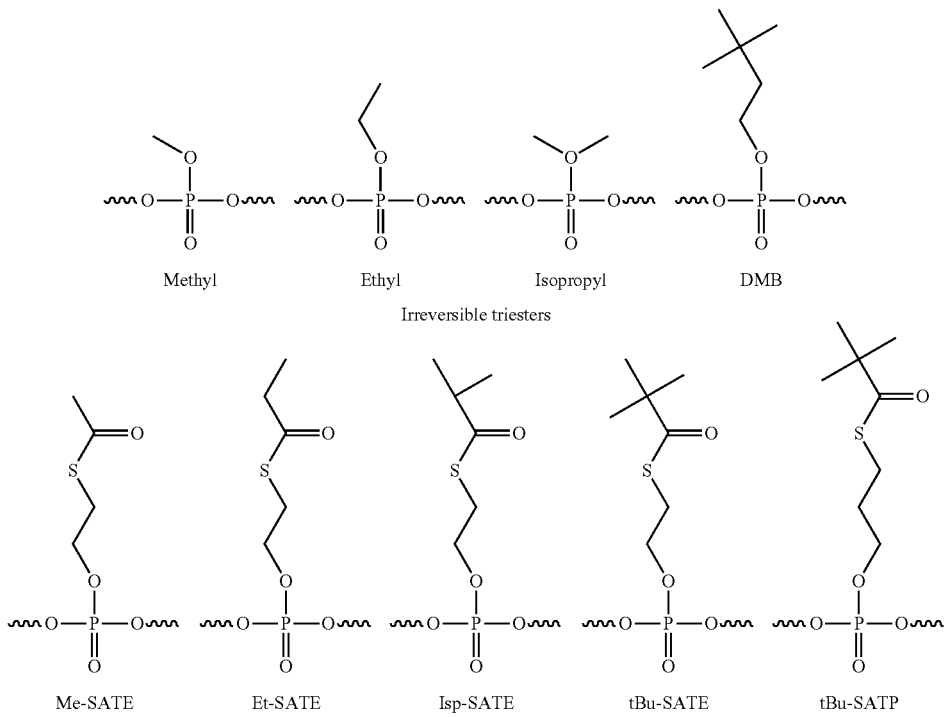

TABLE 4-continued
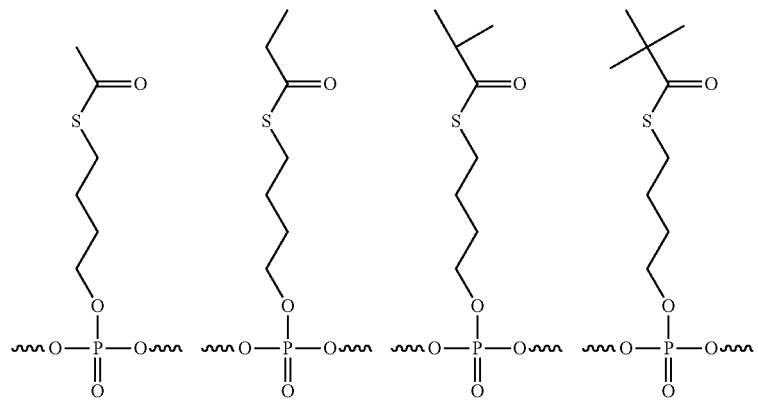
Me-SATB  Et-SATB  Isp-SATB  tBu-SATB
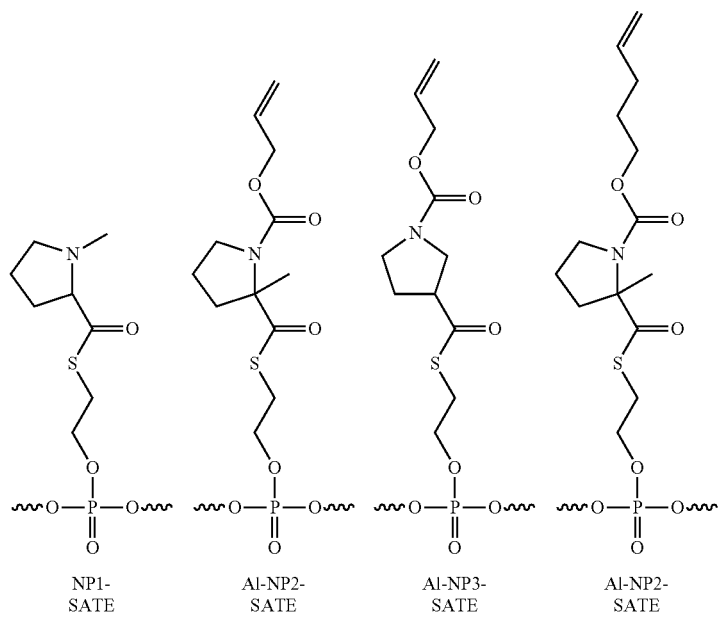
NP1-SATE  Al-NP2-SATE  Al-NP3-SATE  Al-NP2-SATE TABLE 4-continued

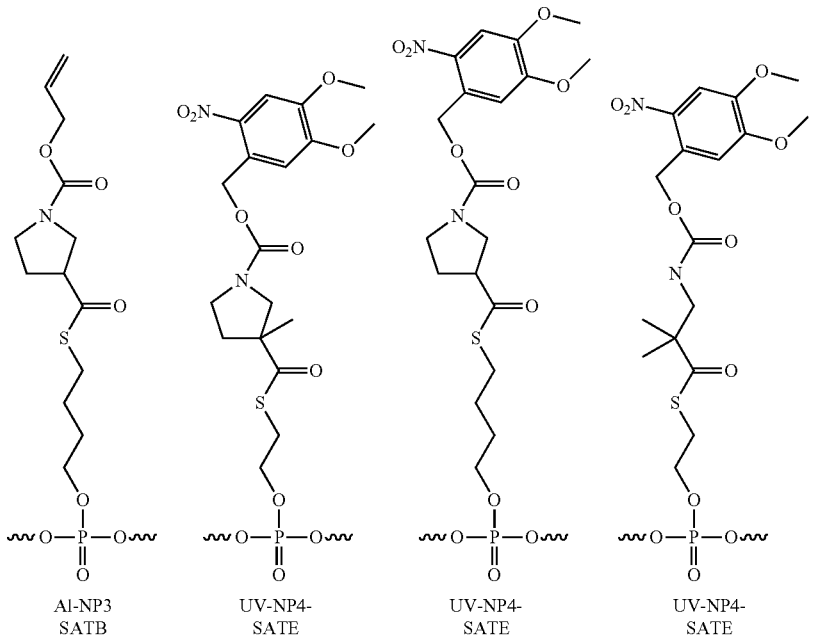

Al-NP3 SATB | UV-NP4-SATE | UV-NP4-SATE | UV-NP4-SATE

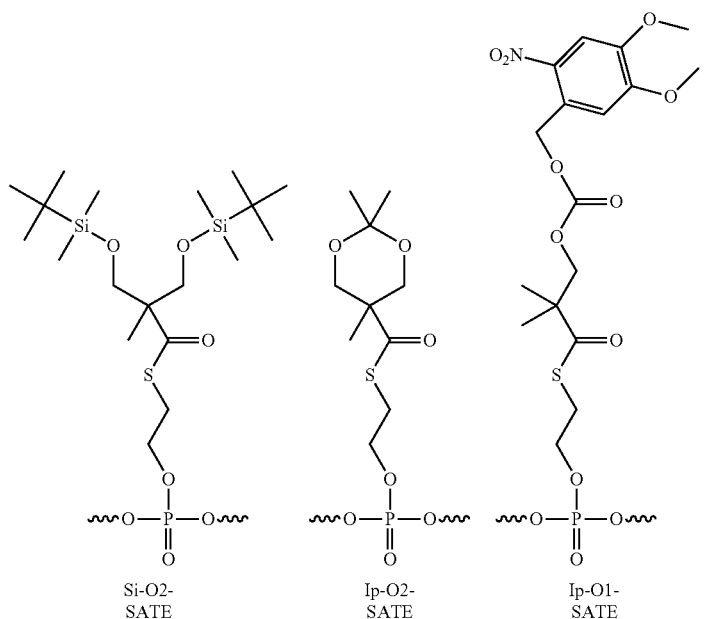

Si-O2-SATE | Ip-O2-SATE | Ip-O1-SATE

Moreover, for any bioreversible triester group in Table 4 which comprises one or more protecting groups, such as Si—O2-SATE, the disclosure also provides for these bioreversible triester groups to be in their de-protected form. For example, the phosphoramidite method disclosed herein can be used to prepare a protected nucleotide construct, which, following oligo synthesis and deprotection, can afford the desired polynucleotide construct. Exemplary nucleic acid constructs have been prepared that include the bioreversible thioesters shown in Scheme 3.

Scheme 3

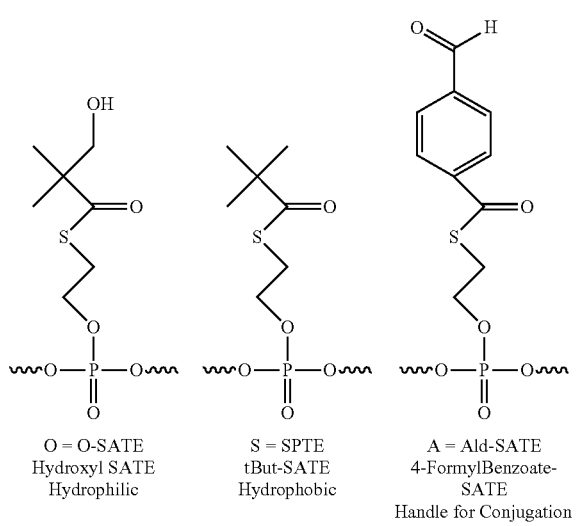

O = O-SATE
Hydroxyl SATE
Hydrophilic

S = SPTE
tBut-SATE
Hydrophobic

A = Ald-SATE
4-FormylBenzoate-SATE
Handle for Conjugation

The nucleic acid constructs prepared by this method can be characterized by a variety of analytical methods, e.g., HPLC, mass spectrometry, NMR, and gel analysis.

Still other exemplary nucleic acid constructs of the disclosure have been prepared according to the methods described herein, and are shown in FIGS. 2A-2L, along with analytical data verifying their synthesis.

Synthesis of TBSOSATE

Reaction 1:

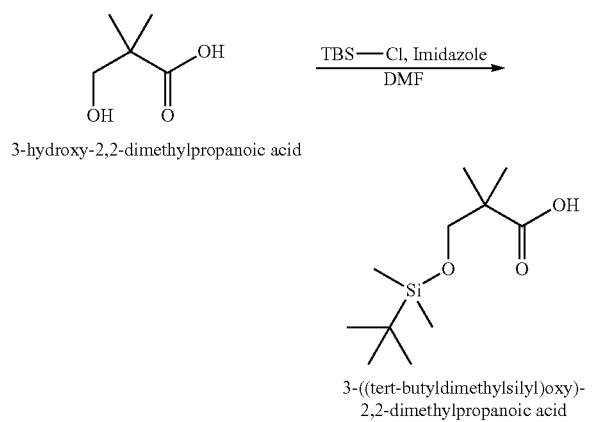

3-hydroxy-2,2-dimethylpropanoic acid 3-((tert-butyldimethylsilyl)oxy)-2,2-dimethylpropanoic acid 3-Hydroxy-2,2-dimethylpropanoic acid (5 g, 42.4 mmol) and imidazole (7.2 g, 106 mmol) were dissolved in dimethyl formamide (DMF) (10 ml). tert-Butyl dimethylsilyl chloride (TBS-Cl) (7.6 g, 51 mmol) in DMF (8 ml) was then slowly added to the solution over a period of 15 minutes. The resulting mixture was stirred for 12 hours, and the reaction was quenched by addition of water (10 ml). The resulting product was isolated by extraction with EtOAc/Water (250 ml: 250 ml). The ethyl acetate layer was washed with water (3×250 ml), and then the EtOAc was evaporated in vacuo to give a crude mixture. The crude mixture was dissolved in 1M NaOH (10 ml) and water (40 ml). After the insoluble impurities were removed by extracting with EtOAc, the water layer was neutralized with 1M HCl (40 ml). The resulting product was extracted with EtOAc (250 ml), washed with brine (2×200 ml), and dried over anhydrous Na$_2$SO$_4$. The solvent was evaporated in vacuo to afford 3-((tert-butyldimethylsilyl)oxy)-2,2-dimethylpropanoic acid (82% yield, 8 g), which was used in the next reaction without any further purification.

Reaction 2:

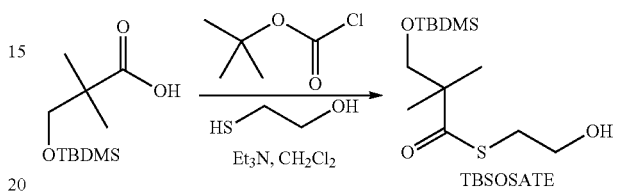

TBSOSATE

As 3-((tert-Butyldimethylsilyl)oxy)-2,2-dimethylpropanoic acid (4.2 g, 18 mmol) in dichloromethane (CH$_2$Cl$_2$) (120 ml) was cooled in a dry ice, isobutyl chloroformate (2.36 ml, 18 mmol) and triethyl amine (Et$_3$N) (2.5 ml, 18 mol) were added dropwise over a period of 10 minutes. The resulting mixture was stirred in a dry ice bath for 10 minutes, and then stirred for 30 minutes at ambient temperature. After which, Et$_3$N (2.5 ml) and β-mercapto ethanol (36 mmol; 2.5 ml) were added. The mixture was stirred at ambient temperature for 2.5 hours. After the reaction was quenched with a saturated NaHCO$_3$ solution (30 ml), the organic layer was isolated and dried over anhydrous Na$_2$SO$_4$. The solvent was evaporated in vacuo and the resulting crude mixture was then purified by silica gel column chromatography using (hexane:ethyl acetate) (0-30% gradient on Combi Flash Rf instrument) to give TBSOSATE (78% yield; 4 g). $^1$H NMR (400 MHz) δ 0.01 (s, 6H), 0.8 (s, 9H), 1.2 (s, 6H), 1.9 (s, 1H), 3.0 (t, 2H), 3.6 (s, 2H), 3.7 (m, 2H). ESI MS for C$_{13}$H$_{28}$O$_3$SSi Calc. 292.15 Obs. [M+H]$^+$ 293.17, [M+NH$_4$]$^+$ 310.16, [M+Na]$^+$ 315.17. The representative spectrum for TBSOSATE is presented in FIG. 2A.

Synthesis of TBSOSATE Phosphoramidite

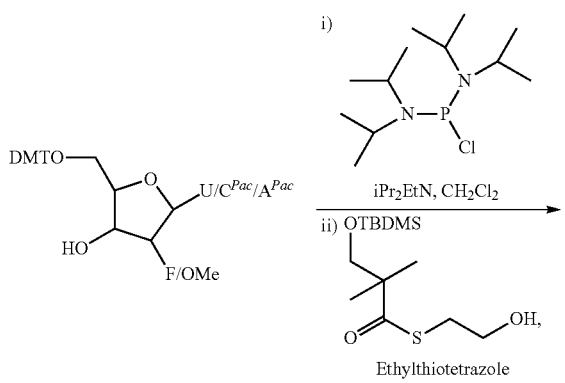

Ethylthiotetrazole

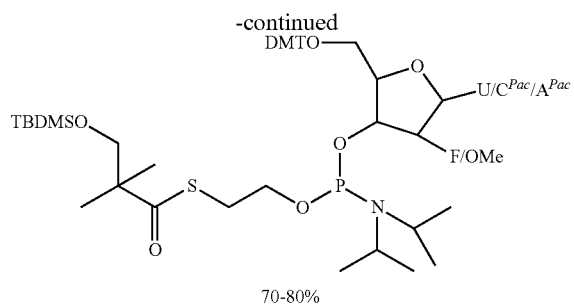

70-80%

Figure 2A:
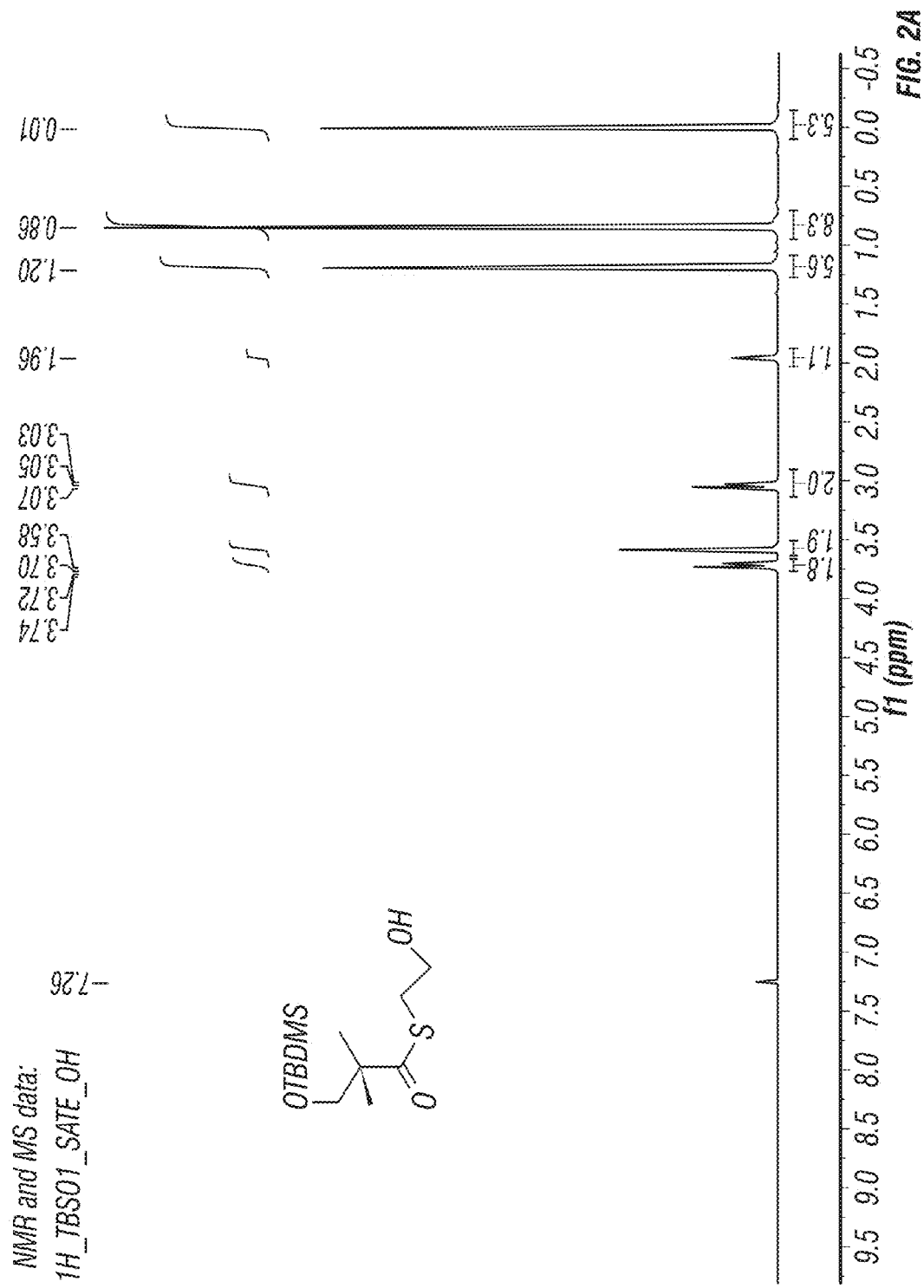
FIGS. 2A-2L provide structures and analytical data for chemically synthesized intermediates, and nucleotide constructs which can be employed in the manufacture of polynucleotide constructs of the disclosure.
Figure 2A:
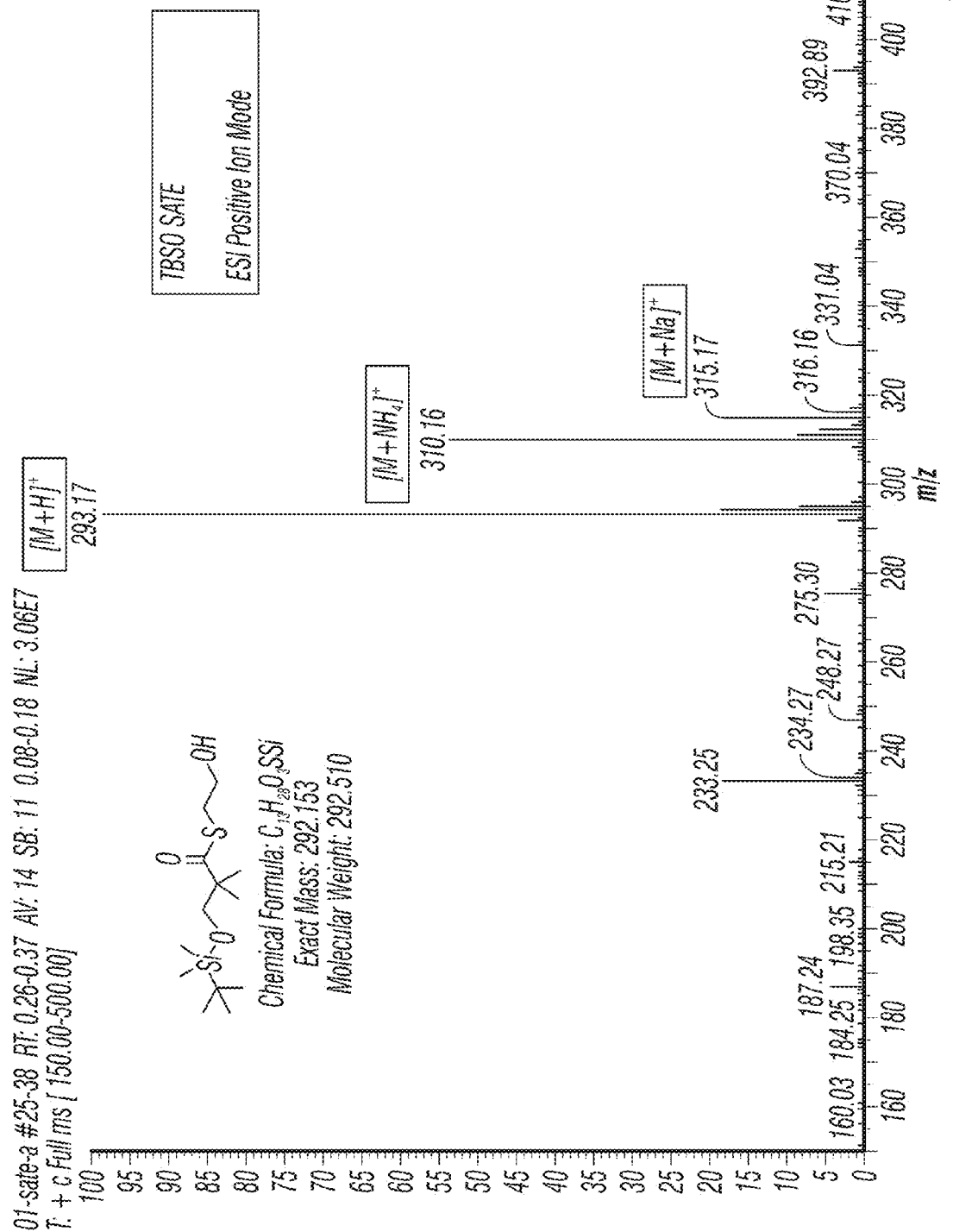
Figure 2B:
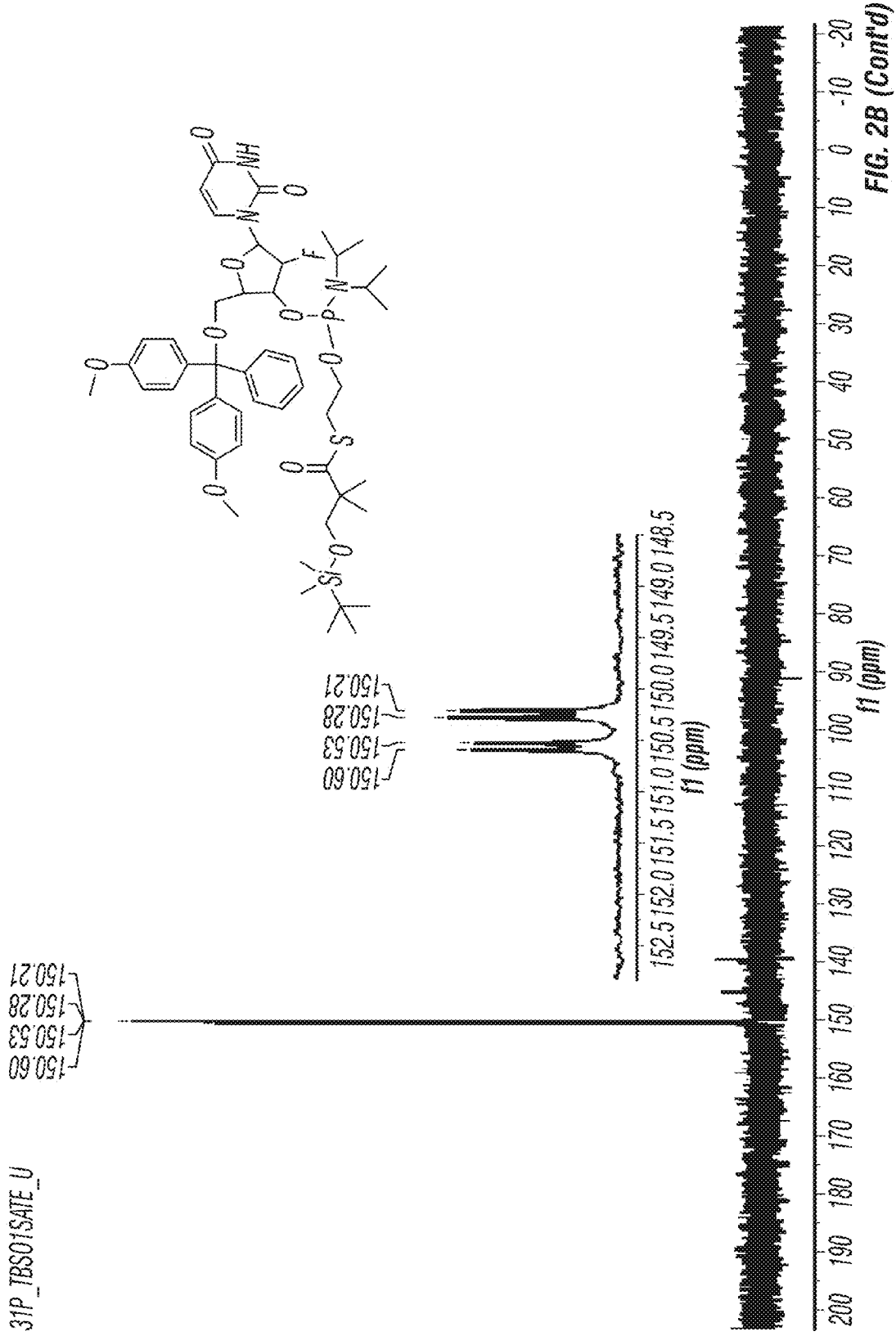
Figure 2C:
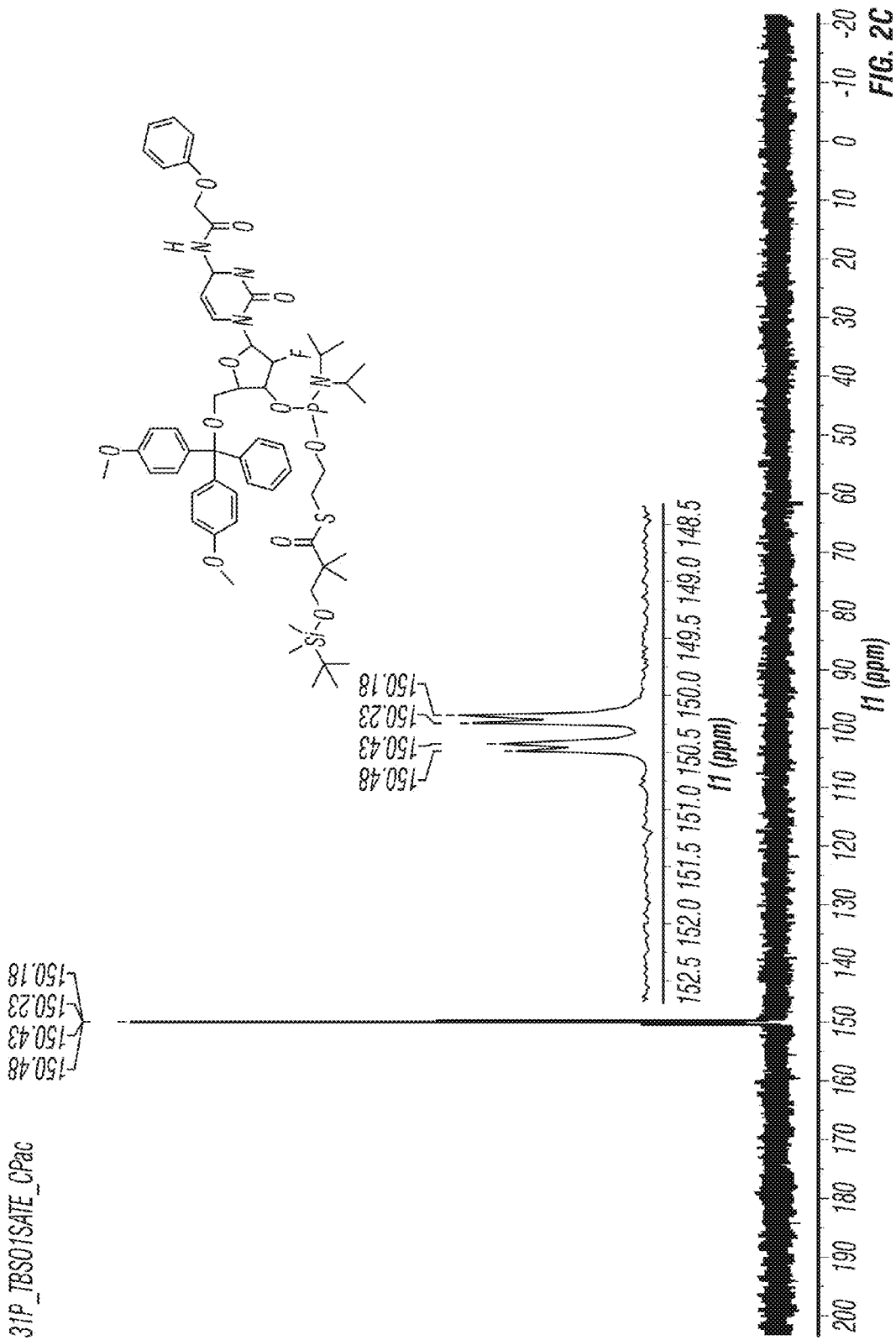
Figure 2C:
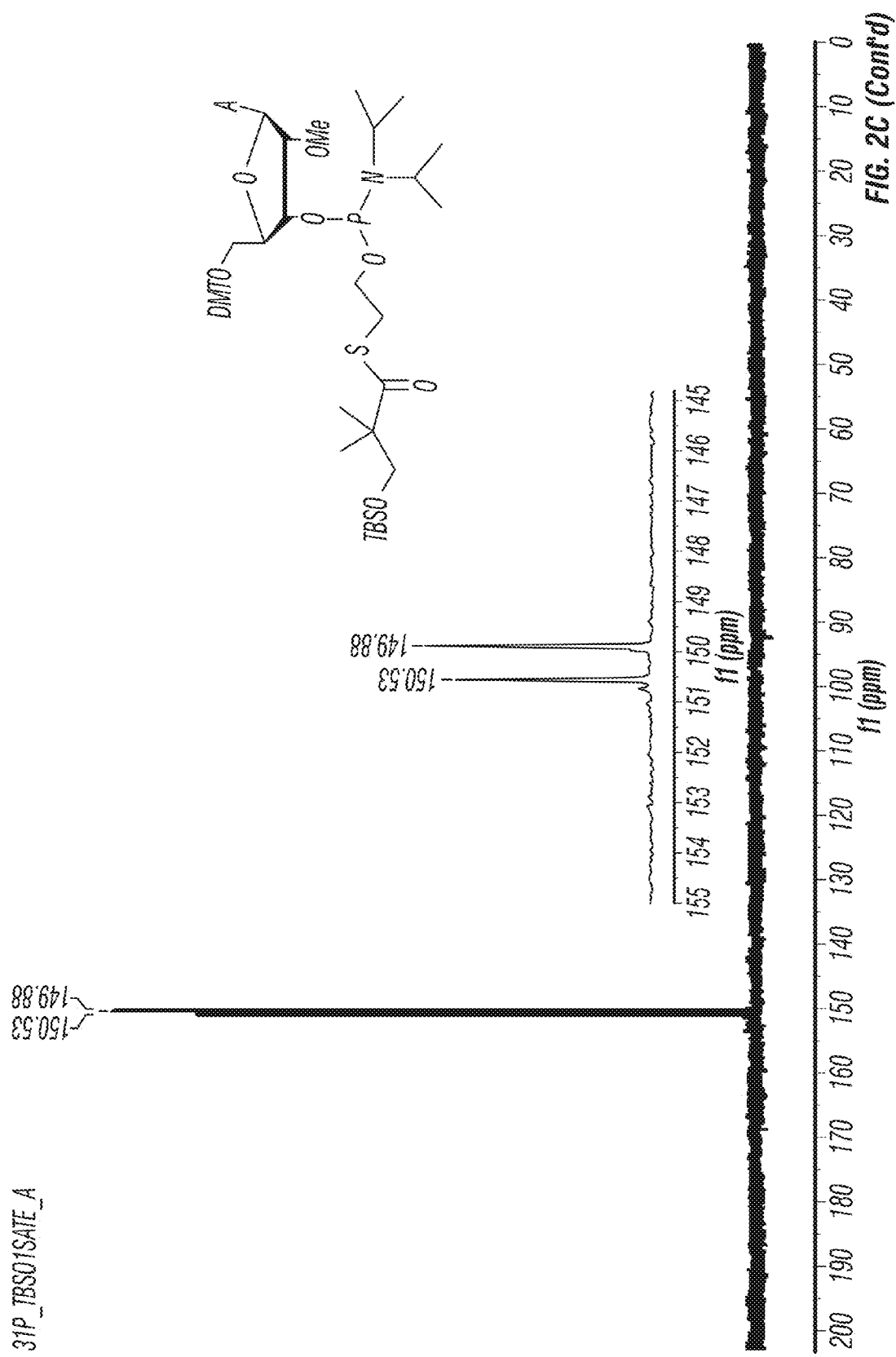
Figure 2D:
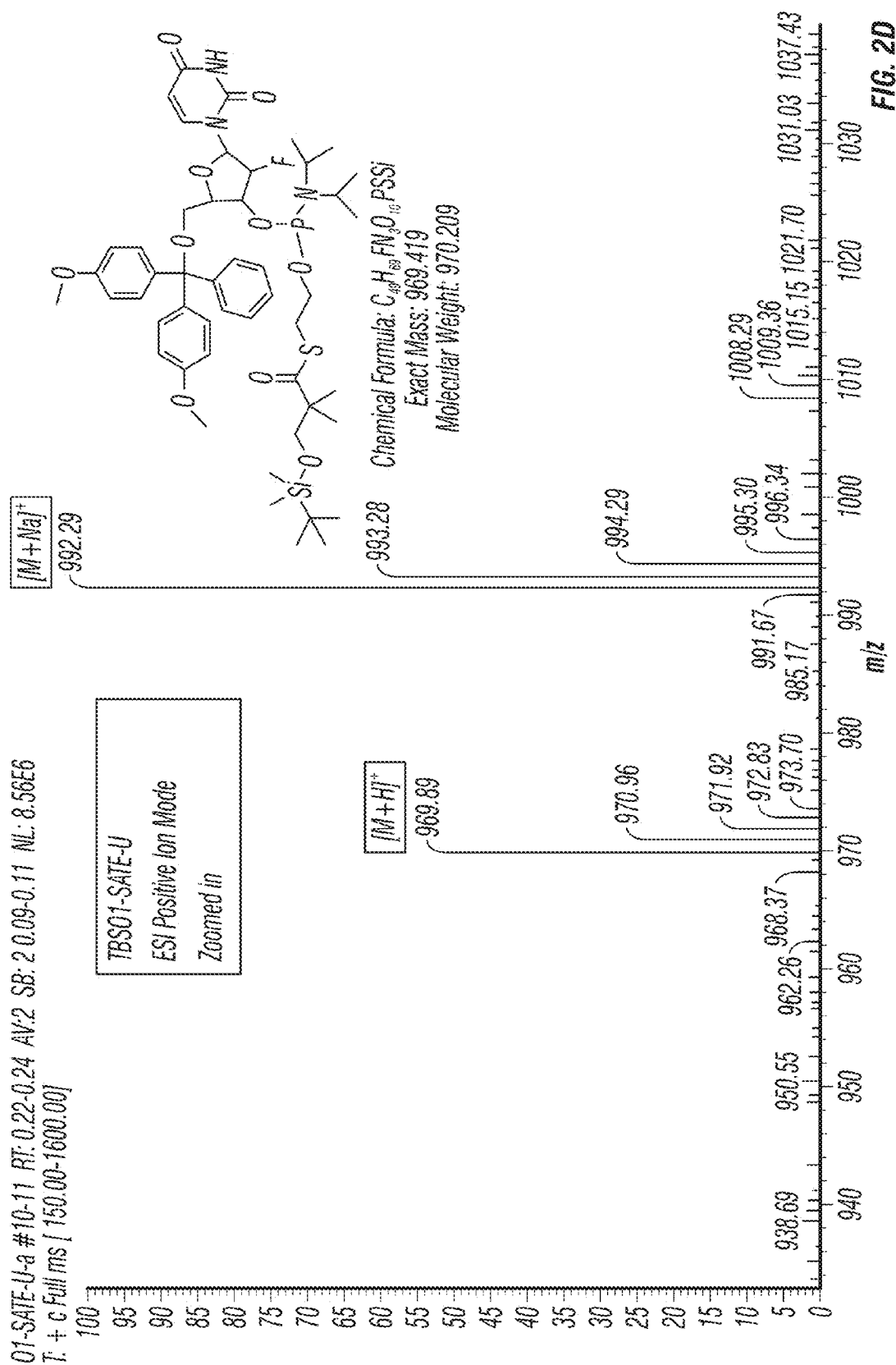
Figure 2D:
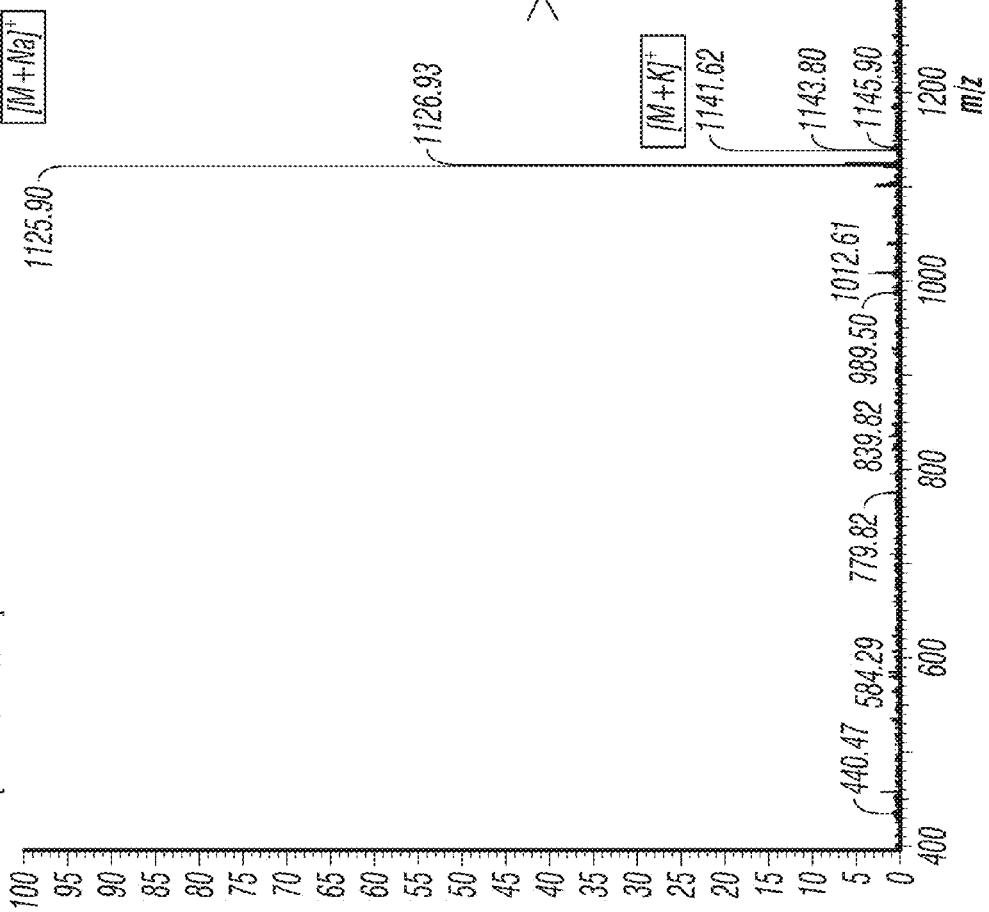

A solution of bis-(N,N-diisopropylamino)-chlorophosphine (1 g, 4 mmol) in dry $CH_2Cl_2$ (5 ml) was added dropwise to a magnetically stirred and chilled solution (−78° C.) of 5'-O-(4,4'-dimethoxytrityl)-2'-F-uridine (2 g, 3.64 mmol) and N,N-diisopropylethylamine (0.71 ml, 0.4 mmol) in dry $CH_2Cl_2$ (24 ml). The reaction mixture was allowed to warm to ambient temperature while stirring was maintained for 1-1.5 hours. After portion wise adding TBSOSATE (1 g, 4 mmol) in dry $CH_2Cl_2$ (5 ml), the reaction mixture was stirred for 10 minutes. Ethyl thiotetrazole (7.3 ml, 0.25M solution in acetonitrile, 1.82 mmol) was then added to the reaction mixture. The reaction mixture was stirred for 4-6 hours and then $CH_2Cl_2$ (60 ml) was added. The reaction mixture was washed with saturated aqueous sodium hydrogen carbonate (20 ml) and brine (2×20 ml) and then dried over anhydrous sodium sulfate. The solvent was evaporated in vacuo and the resulting crude residue was purified by flash silica gel column chromatography (on a combiflash Rf instrument using hexane:ethyl acetate (0.5% TEA) as the solvent). The fractions containing the products were collected, pooled together, and then evaporated to dryness. The resulting foamy residue was redissolved in benzene, frozen and lyophilized to afford TBSOSATE_U as a colorless powder (80% yield as a diastereomeric mixture; 2.8 g). ESI MS for $C_{49}H_{69}FN_3O_{10}PSSi$ calculated 969.42, observed $[M+H]^+$ 969.89, $[M+Na]^+$ 992.29. $^{31}P$ NMR (121 MHz, $CDCl_3$) δ 150.21 (d, $J_{P-F}$=7.9 Hz), 150.53 (d, $J_{P-F}$=8.5 Hz). Representative spectra for TBSOSATE U are shown in FIG. 2B and FIG. 2D.

Synthesis of TBOSATE $C^{Pac}$ Phosphoramidite

TBSOSATE $C^{Pac}$ phosphoramidite was synthesized by following the protocol for TBSOSATE U phosphoramidite disclosed herein, but substituting 5'-O-(4,4'-dimethoxytrityl)-2'-F—$C^{Pac}$ for 5'-O-(4,4'-dimethoxytrityl)-2'-F-uridine. TBSOSATE_$C^{Pac}$ was isolated in 70% yield. ESI MS for $C_{57}H_{76}FN_4O_{11}PSSi$ calculated 1102.47, observed $[M+Na]^+$ 1125.9, $[M+K]^+$ 1141.62. $^{31}P$ NMR (121 MHz, $CDCl_3$) δ 150.18 (d, $J_{P-F}$=8.4 Hz), 150.43 (d, $J_{P-F}$=8.7 Hz). Representative spectra for TBSOSATE_$C^{Pac}$ are shown in FIG. 2C and FIG. 2D.

Synthesis of TBOSATE $A^{Pac}$ Phosphoramidite

Figure 2E:
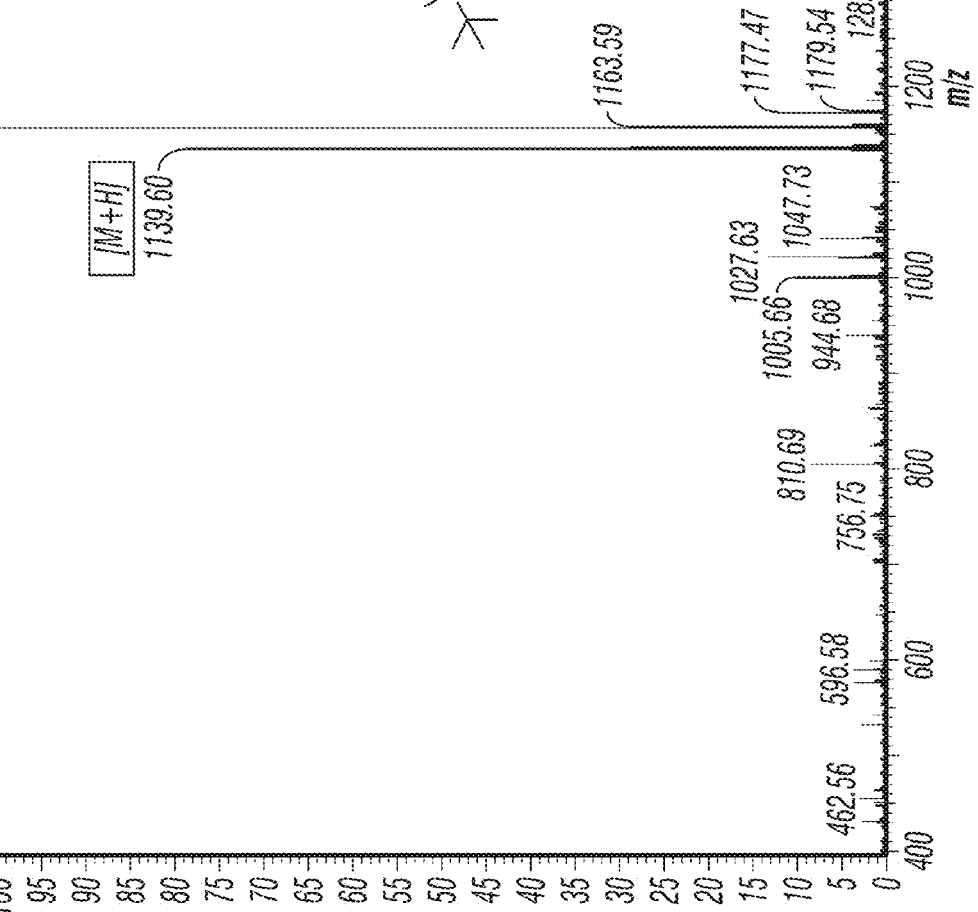
Figure 2E:
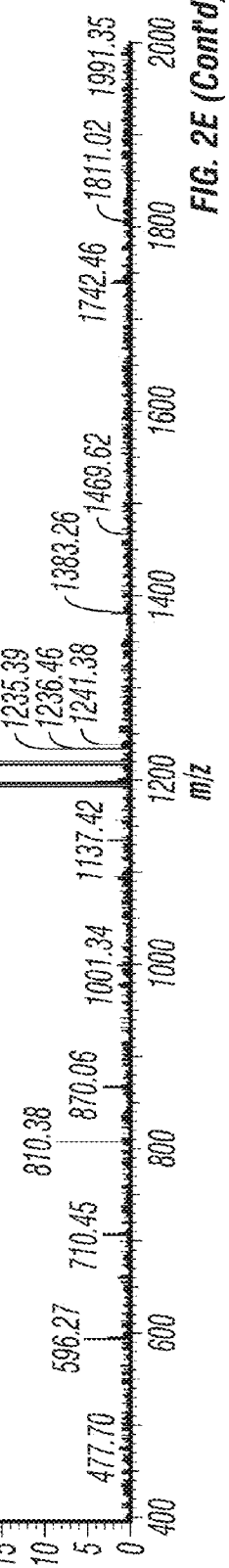

TBSOSATE $A^{Pac}$ phosphoramidite was synthesized by following the protocol for TBSOSATE U phosphoramidite disclosed herein, but substituting 5'-O-(4,4'-dimethoxytrityl)-2'-F-$A^{Pac}$ for 5'-O-(4,4'-dimethoxytrityl)-2'-F-uridine. TBSOSATE_$A^{Pac}$ was isolated in 70% yield. ESI MS for $C_{59}H_{79}N_6O_{11}PSSi$ calculated 1138.503, observed $[M+H]^+$ 1139.6, $[M+Na]^+$ 1161.65. $^{31}P$ NMR (121 MHz, $CDCl_3$) δ 149.88 & 150.53. Representative spectra for TBSOSATE_$A^{Pac}$ are shown in FIG. 2C and FIG. 2E.

Synthesis of TBSOSATE_$G^{iPac}$

Reaction 1:

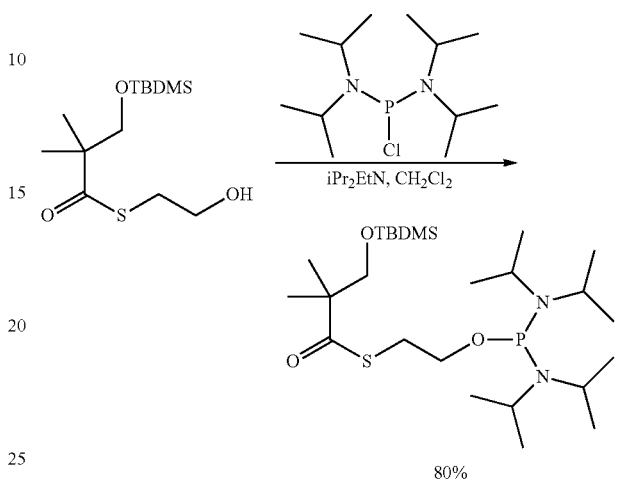

80%

A solution of bis-(N,N-diisopropylamino)-chlorophosphine (1.75 g, 6.6 mmol) in dry $CH_2Cl_2$ (5 ml) was added dropwise to a magnetically stirred chilled solution (−78° C.) of TBSOSATE (1.6 g, 5.5 mmol) and N,N-diisopropylethylamine (0.71 ml, 6.6 mmol) in dry $CH_2Cl_2$ (15 ml). The stirring was maintained at −78° C. for 1 hour. The solvent was evaporated in vacuo. Hexane (50 ml) was then added which resulted in a white precipitate of the byproduct diisopropylethyl hydrochloride. The precipitate was filtered under the atmosphere of Argon. The filtrate was evaporated in vacuo to give ~3 g of crude TBSOSATE tetraisopropyl phosphoramidite, which was used for the next reaction without any further purification. $^{31}P$ NMR (121 MHz, $CDCl_3$) δ125 ppm.

Reaction 2:

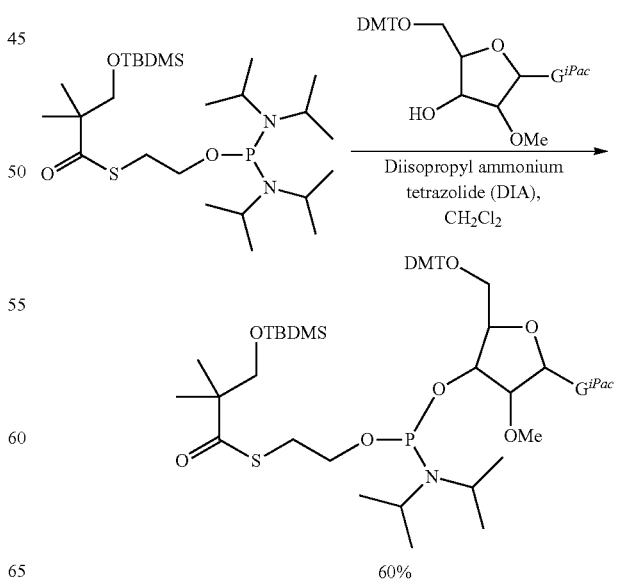

60%

To a solution of dimethoxytrityl-2'-OMe-isopropylphenoxyacetyl-guanosine (1 g, 1.3 mmol) and diisopropyl ammonium tetrazolide (0.22 g, 1.3 mmol) in dry $CH_2Cl_2$ (15 ml), TBSOSATE tetraisopropyl phosphoramidite (1.4 g, 2.6 mmol) was added. The mixture was stirred for 16 hours and then DCM (50 ml) and a saturated $NaHCO_3$ solution (20 ml) were added. The organic layer was separated and dried over anhydrous sodium sulfate. The solvent was evaporated in vacuo, and the resulting crude residue was purified by flash silica gel column chromatography (on a combiflash Rf instrument) using hexane:ethyl acetate (0.5% TEA) as the solvent (0-100%). The fractions containing the products were isolated, pooled together, and evaporated to dryness. The resulting foamy residue was redissolved in benzene, frozen and lyophilized which afforded a colorless powder (Yield 60% as a diastereomeric mixture; 0.75 g). ESI MS for $C_{62}H_{85}N_6O_{12}PSSi$ calculated 1196.54, observed $[M+H]^+$ 1197.33, $[M+Na]^+$ 1219.5. $^{31}P$ NMR (121 MHz, $CDCl_3$) δ 150.23 & 150.74. Representative spectra for TBSOSATE_$G^{iPac}$ are shown in FIG. 2B and FIG. 2E.

Synthesis of Acetal AldSATE

Reaction 1:

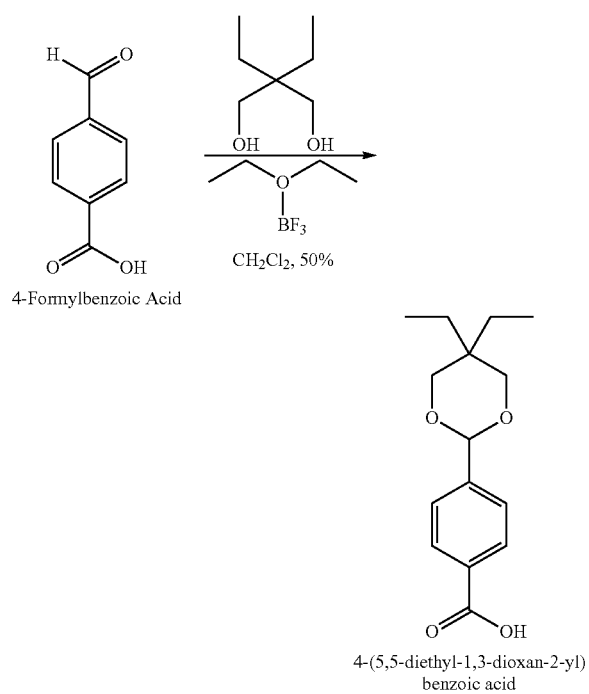

4-Formylbenzoic Acid 4-(5,5-diethyl-1,3-dioxan-2-yl) benzoic acid $BF_3 \cdot Et_2O$ (2.5 ml, 20 mmol) was added to 4-formyl benzoic acid (3 g, 20 mmol), 2,2-diethyl 1,3-propanediol (3.25 g, 26 mmol) in $CH_2Cl_2$ (30 ml). The reaction mixture was stirred at ambient temperature for 2 hours. The reaction was quenched by adding triethylamine (2.8 ml), and then the solvent was evaporated in vacuo. The resulting residue was redisolved in DCM (100 ml), washed with water (2×100 ml) and dried over anhydrous sodium sulfate. The solvent was evaporated in vacuo to afford 4-(5,5-diethyl-1,3-dioxan-2-yl)benzoic acid (3.5 g). The product was used for the next reaction without any further purification. ESI MS for C15H20O4 calculated 264.136, observed $[M+H]^+$ 265.1, $[M+Na]^+$ 287.1.

Reaction 2:

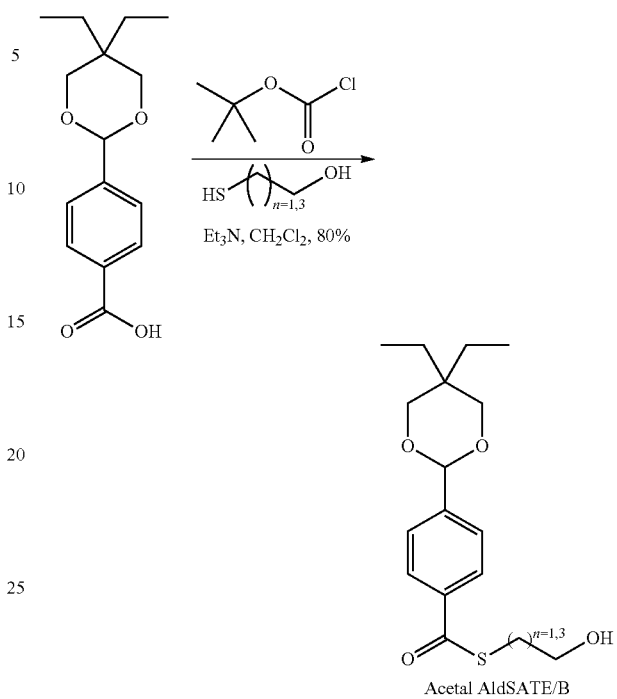

Acetal AldSATE/B

Figure 2F:
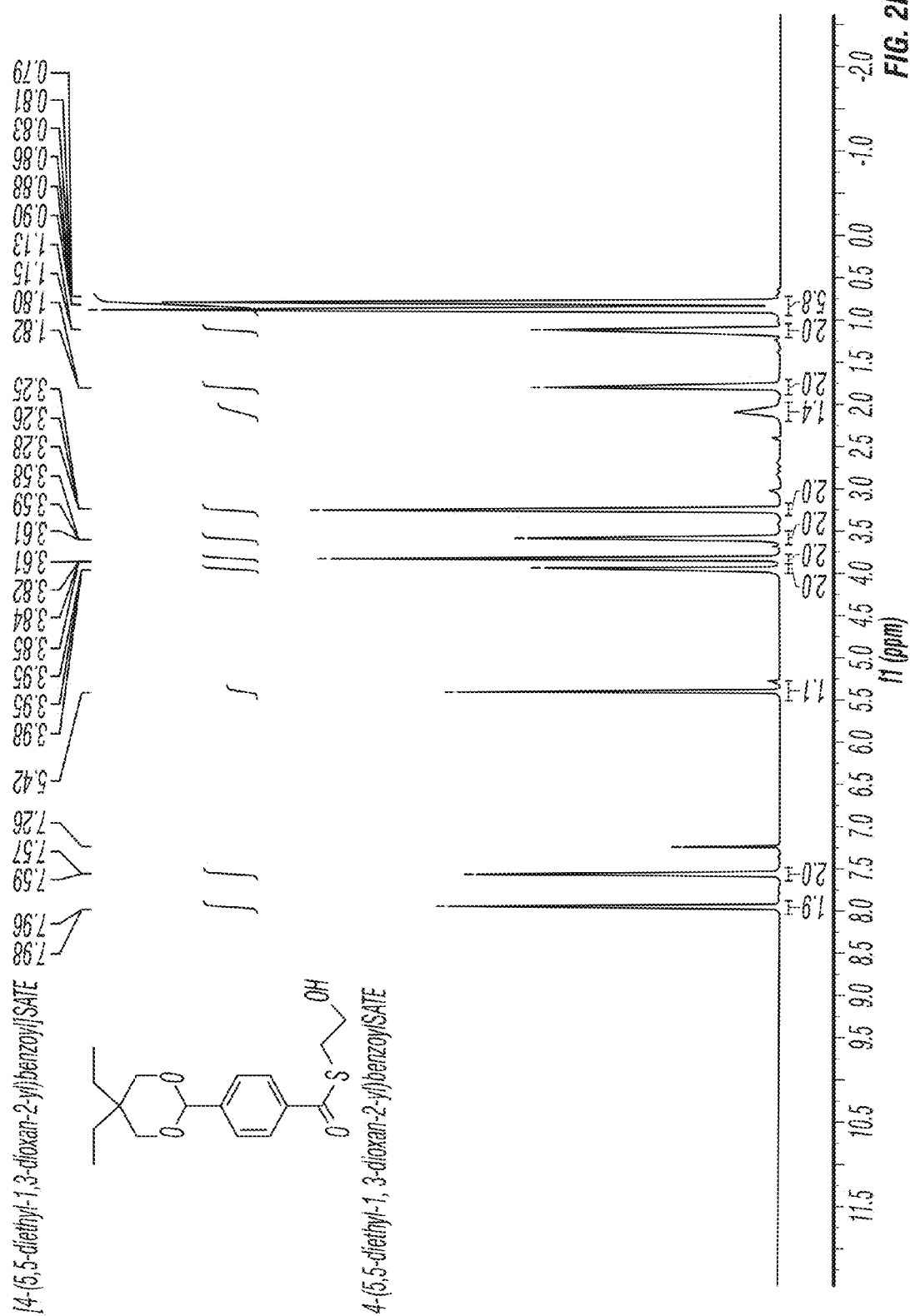
Figure 2F:
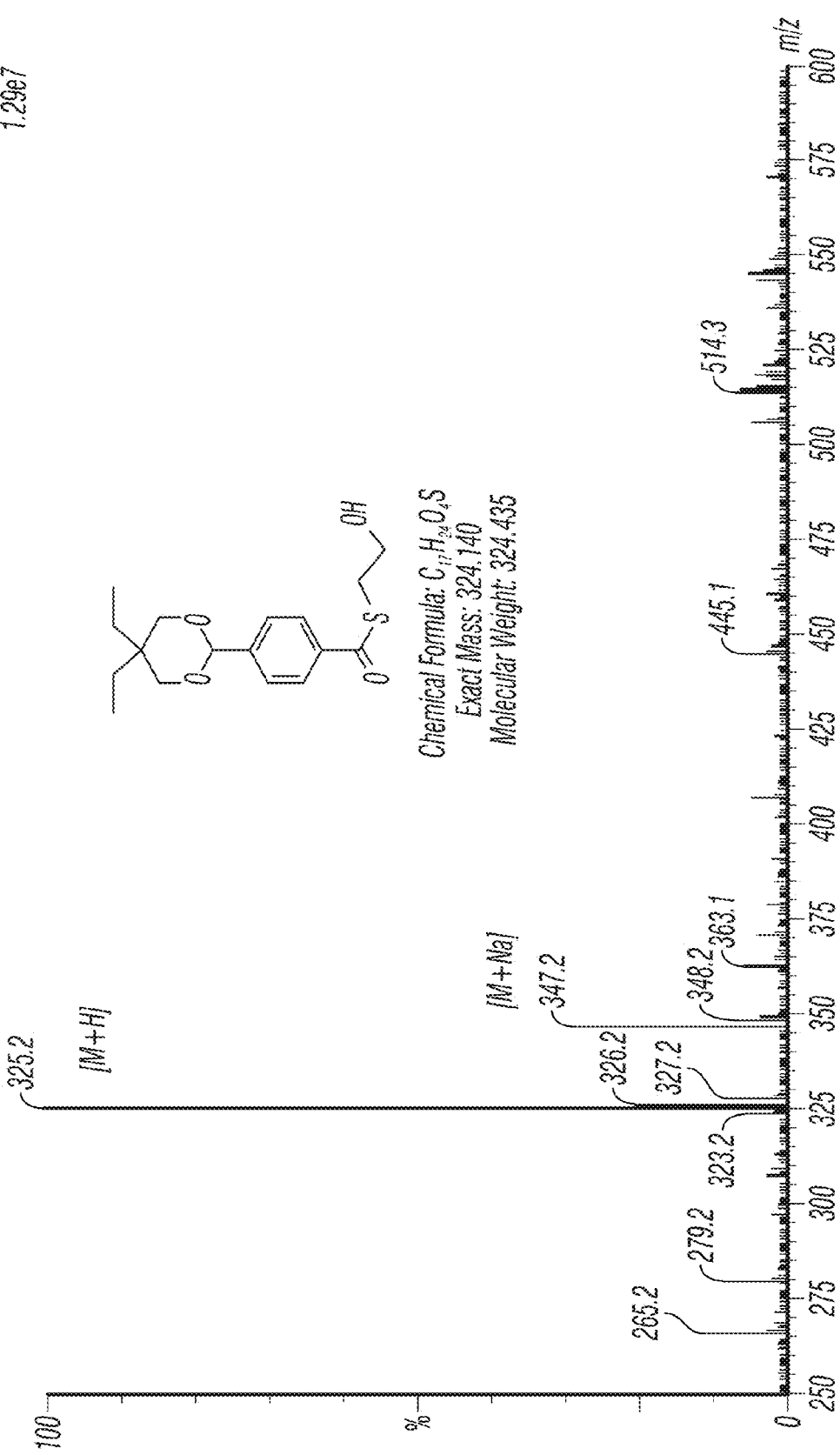

As 4-(5,5-diethyl-1,3-dioxan-2-yl)benzoic acid (3.4 g, 13.3 mmol) in dichloromethane ($CH_2Cl_2$) (120 ml) was cooled in a dry ice bath, isobutyl chloroformate (1.8 ml, 13.3 mmol) and triethyl amine ($Et_3N$) (1.85 ml, 13.3 mol) were added dropwise over a period of 10 minutes. The mixture was stirred in a dry ice bath for 10 minutes, and then stirred at ambient temperature for 30 minutes. $Et_3N$ (1.85 ml) and β-mercapto ethanol (26.6 mmol) (1.9 ml) were then added. The reaction mixture was stirred at ambient temperature for 2.5 hours. Product formation was verified by thin layer chromatography. After the reaction was quenched by adding a saturated $NaHCO_3$ solution (30 ml), the organic layer was separated and dried over anhydrous $Na_2SO_4$. The solvent was evaporated in vacuo, and the crude mixture was purified by silica gel column chromatography using hexane: ethyl acetate (0-30% gradient on Combi Flash Rf instrument) to afford Acetal AldSATE (80% yield; 3.4 g). $^1H$ NMR (400 MHz) δ 0.79-0.88 (m, 6H), 1.13 (m, 2H), 1.8 (t, 2H), 3.25 (t, 2H), 3.6 (t, 2H), 3.8 (m, 2H), 3.85 (m, 2H), 5.42 (s, 1H), 7.6 (d, 2H). ESI MS for $C_{17}H_{24}O_4S$ Calc. 324.14 Obs. $[M+H]^+$ 325.2, $[M+Na]^+$ 347.2. A representative spectrum for Acetal AldSATE is shown in FIG. 2F.

Synthesis of Acetal AldSATB

Figure 2G:
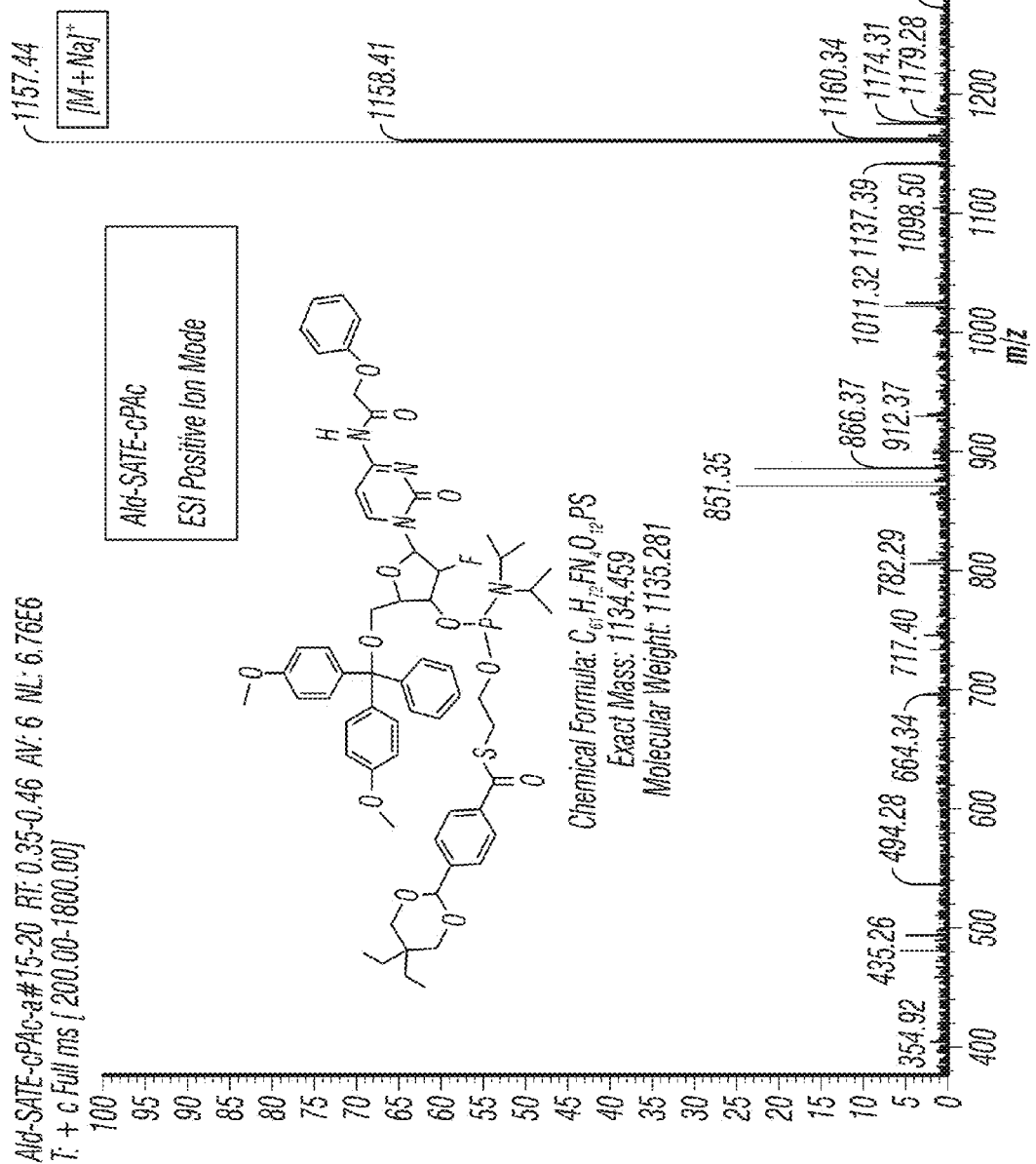
Figure 2H:
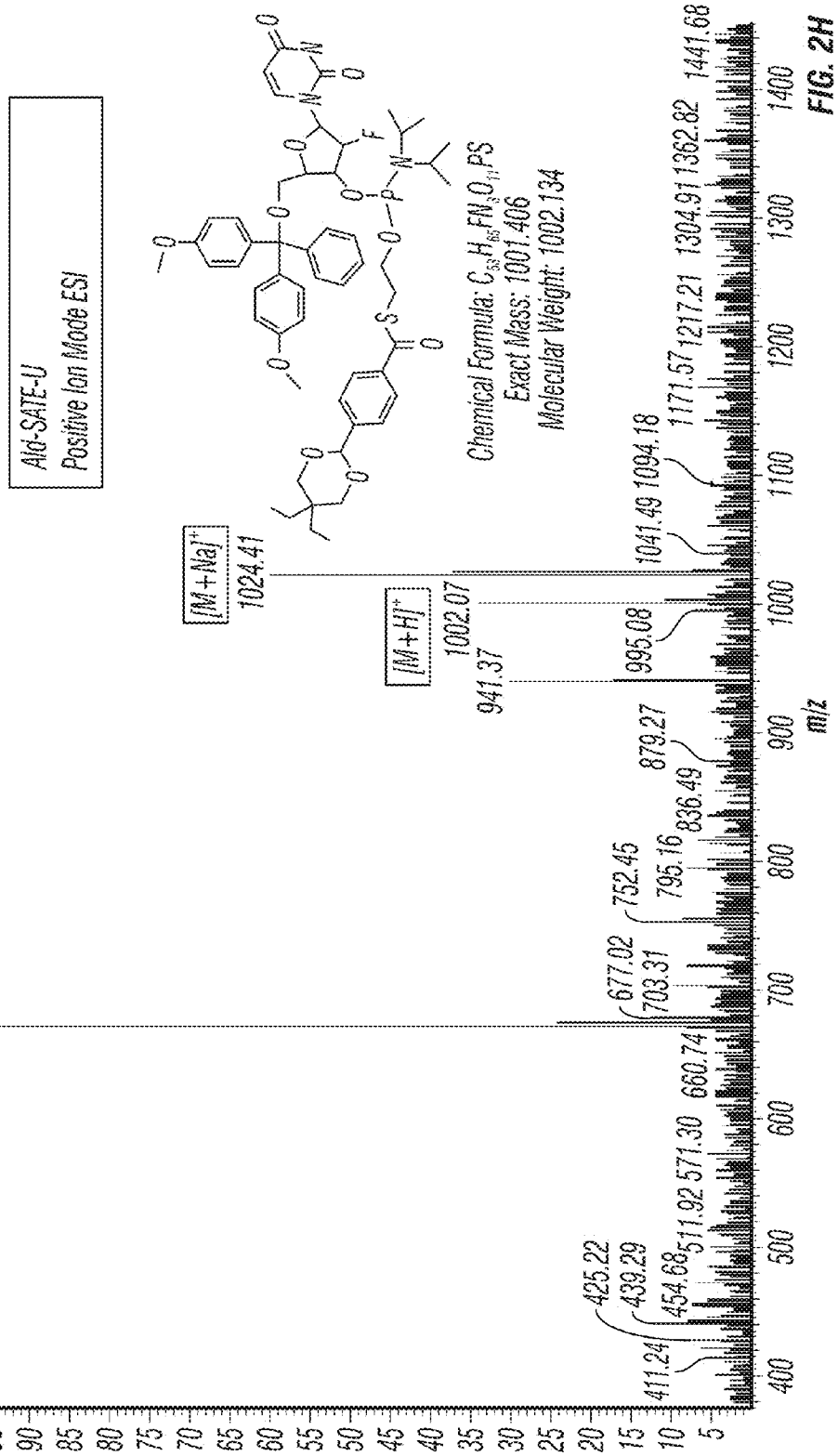
Figure 2H:
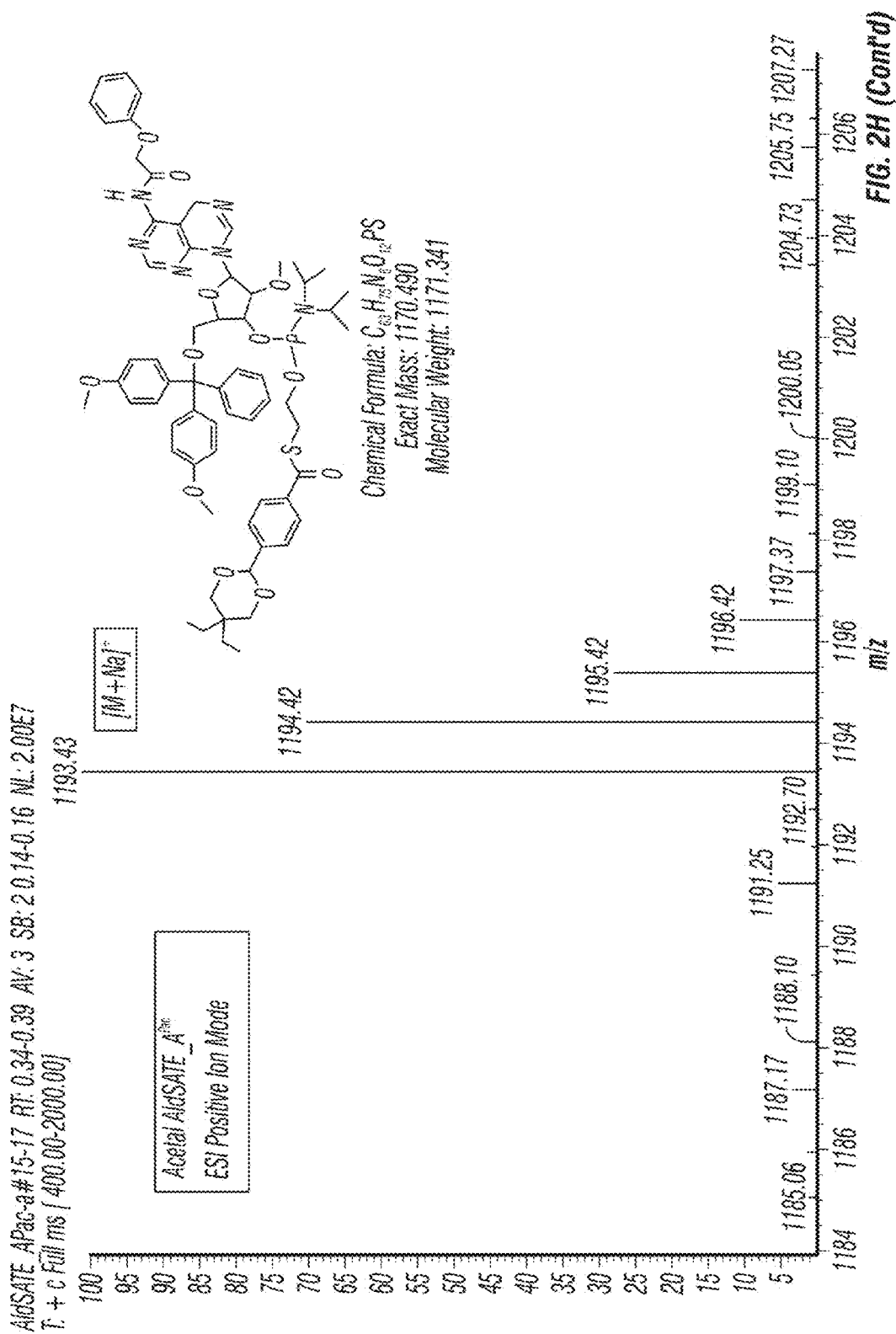
Figure 21:
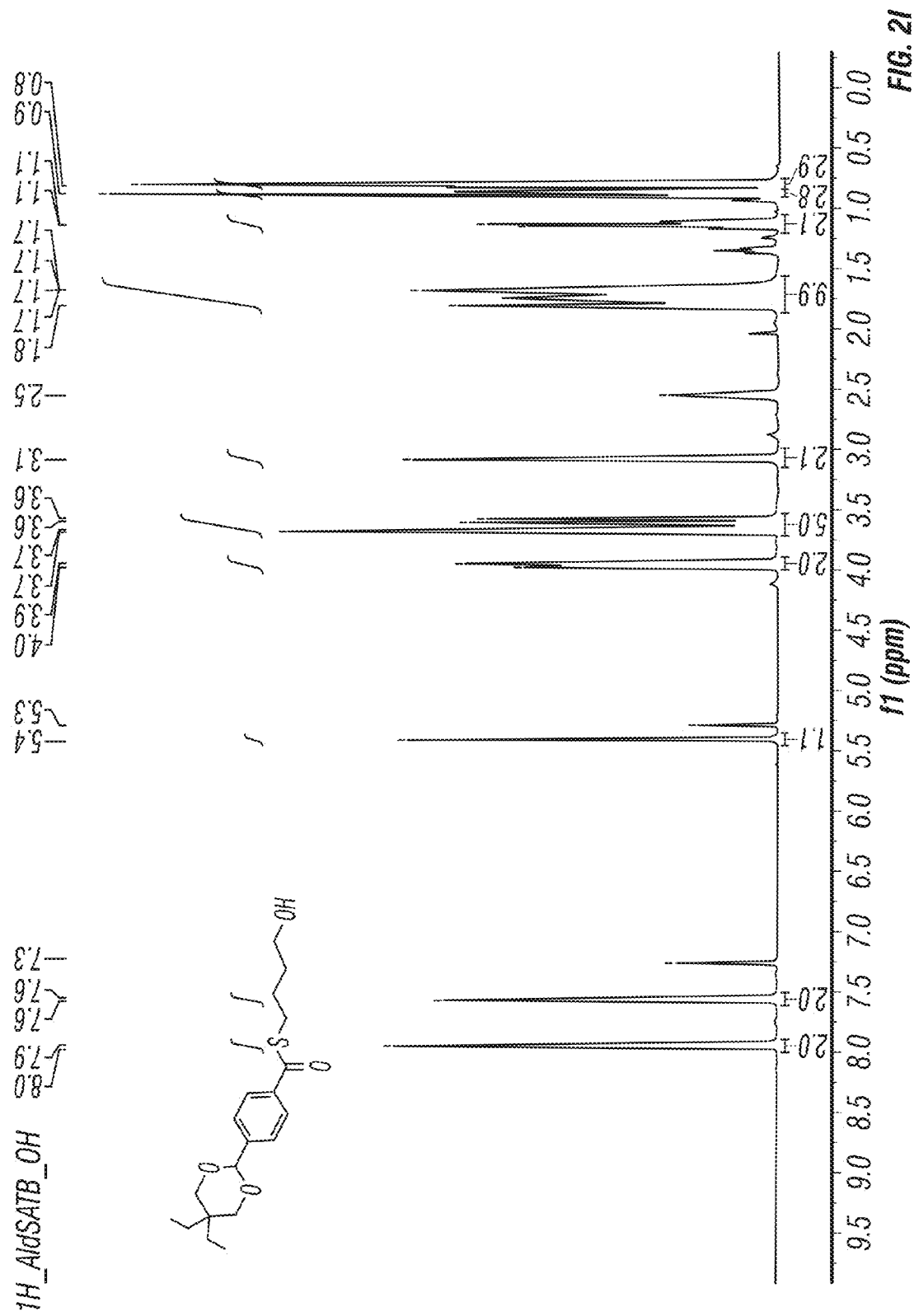
Figure 2I:
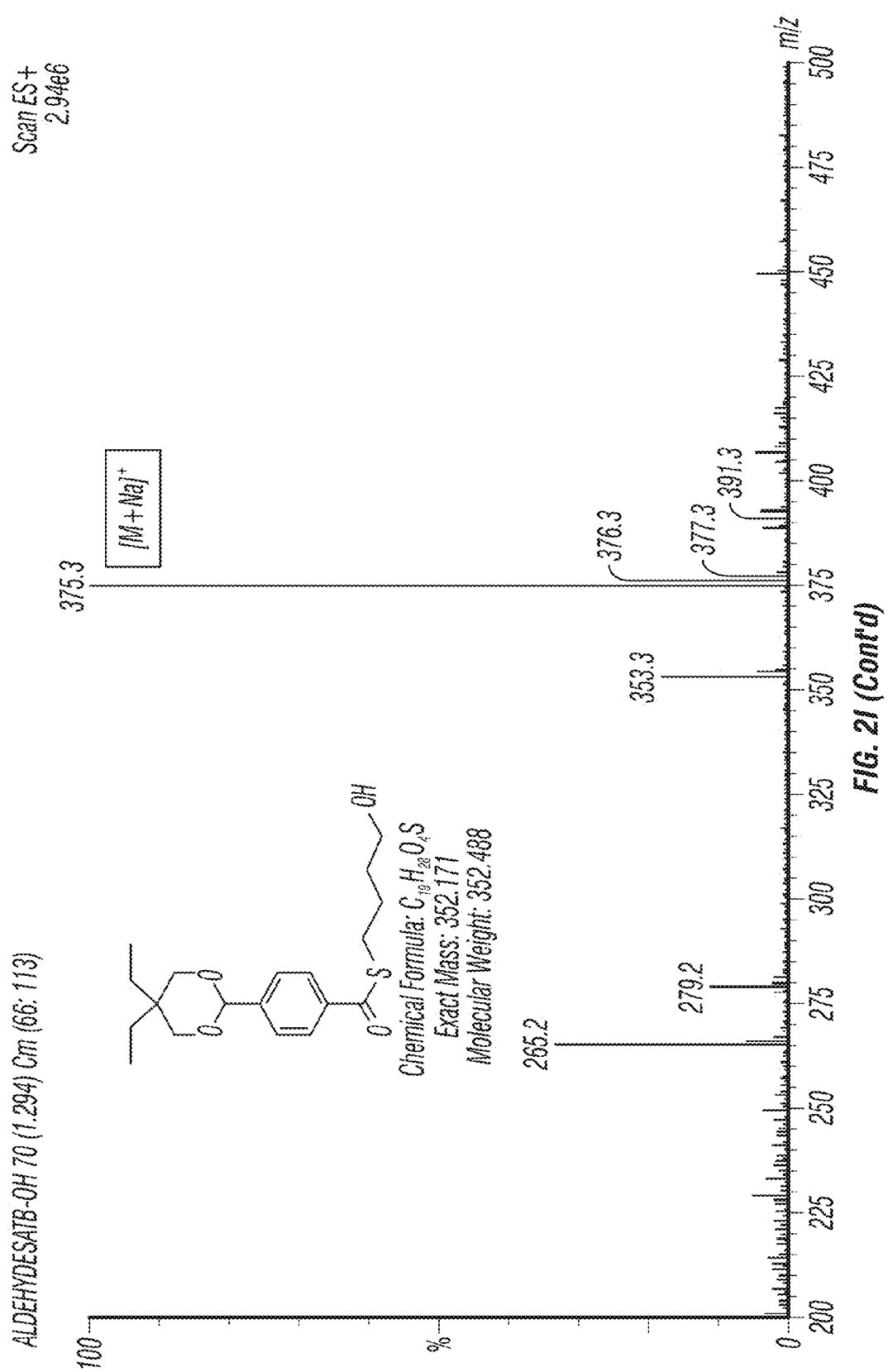

Acetal AldSATB was synthesized by following the protocol for Acetal AldSATE disclosed herein, but substituting 4-mercapto-butan-1-ol for β-mercapto ethanol. AldSATB was isolated in 80% yield. $^1H$ NMR (400 MHz) δ 0.8-1.0 (m, 6H), 1.1 (t, 2H), 1.7-1.8 (m, 10H), 3.1 (t, 2H), 3.6-3.7 (m, 5H), 3.9 (t, 2H), 5.4 (s, 1H), 7.6 (d, 2H), 7.9 (d, 2H). ESI MS for $C_{19}H_{28}O_4S$ Calc. 352.17 Obs. $[M+H]^+$ 353.3, $[M+Na]^+$ 375.3. A representative spectrum for AldSATB is shown in FIG. 2I.

Synthesis of Acetal AldSATE Phosphoramidite

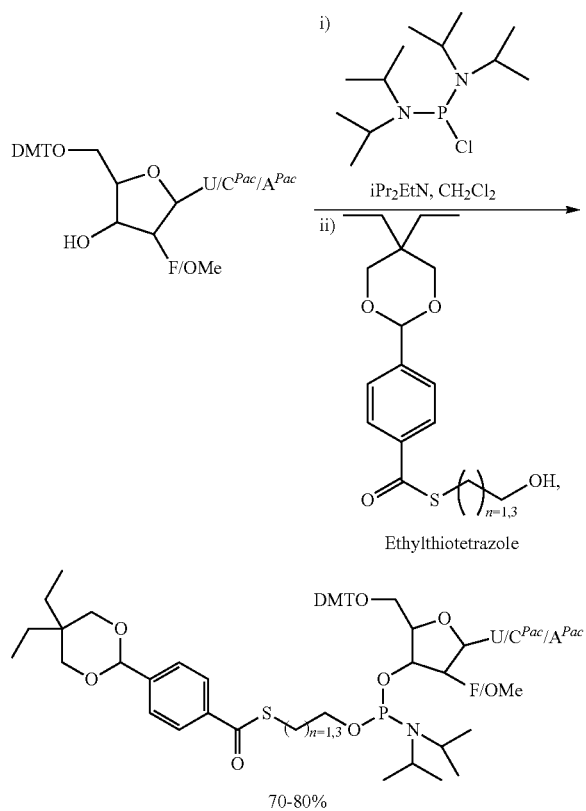

A solution of bis-(N,N-diisopropylamino)-chlorophosphine (1 g, 4 mmol) in dry $CH_2Cl_2$ (5 ml) was added dropwise to a magnetically stirred cooled solution (−78° C.) of 5'-O-(4,4'-Dimethoxytrityl)-2'-F-uridine (2 g, 3.64 mmol) and N,N-diisopropylethylamine (0.71 ml, 4 mmol) in dry $CH_2Cl_2$ (24 ml). The reaction mixture was allowed to warm to ambient temperature while stirring was maintained for 1-1.5 hours. After acetalAldSATE (1 g, 3.3 mmol) in dry $CH_2Cl_2$ (5 ml) was portion wise added to the reaction mixture, the mixture was stirred for 10 minutes, and then ethyl thiotetrazole (7.3 ml, 0.25M solution in acetonitrile, 1.82 mmol) was added. The reaction mixture was stirred for 4-6 hours, and then $CH_2Cl_2$ (60 ml) was added. The reaction mixture was washed with saturated aqueous sodium hydrogen carbonate (20 ml) and brine (2×20 ml) and then dried over anhydrous sodium sulfate. The solvent was evaporated in vacuo, and the resulting crude residue was purified by flash silica gel chromatography (on a combiflash Rf instrument using hexane:ethyl acetate (0.5% TEA) as the solvent). The fractions containing the products were isolated, pooled together, and evaporated to dryness. The resulting foamy residue was redissolved in benzene, frozen and lyophilized to afford acetal AldSATE_U phosphoramidite as a colorless powder (80% yield of a diastereomeric mixture; 2.9 g). ESI MS for $C_{53}H_{65}FN_3O_{11}PS$ calculated 1001.4, observed $[M+H]^+$ 1002.07, $[M+Na]^+$ 1024.41. $^{31}P$ NMR (121 MHz, $CDCl_3$) δ 150.27 (d, $J_{P-F}$=8.0 Hz), 150.63 (d, $J_{P-F}$=7.8 Hz). A representative spectrum for Acetal AldSATE_U is shown in FIG. 2H.

Synthesis of Acetal AldSATB_U Phosphoramidite

Figure 2J:
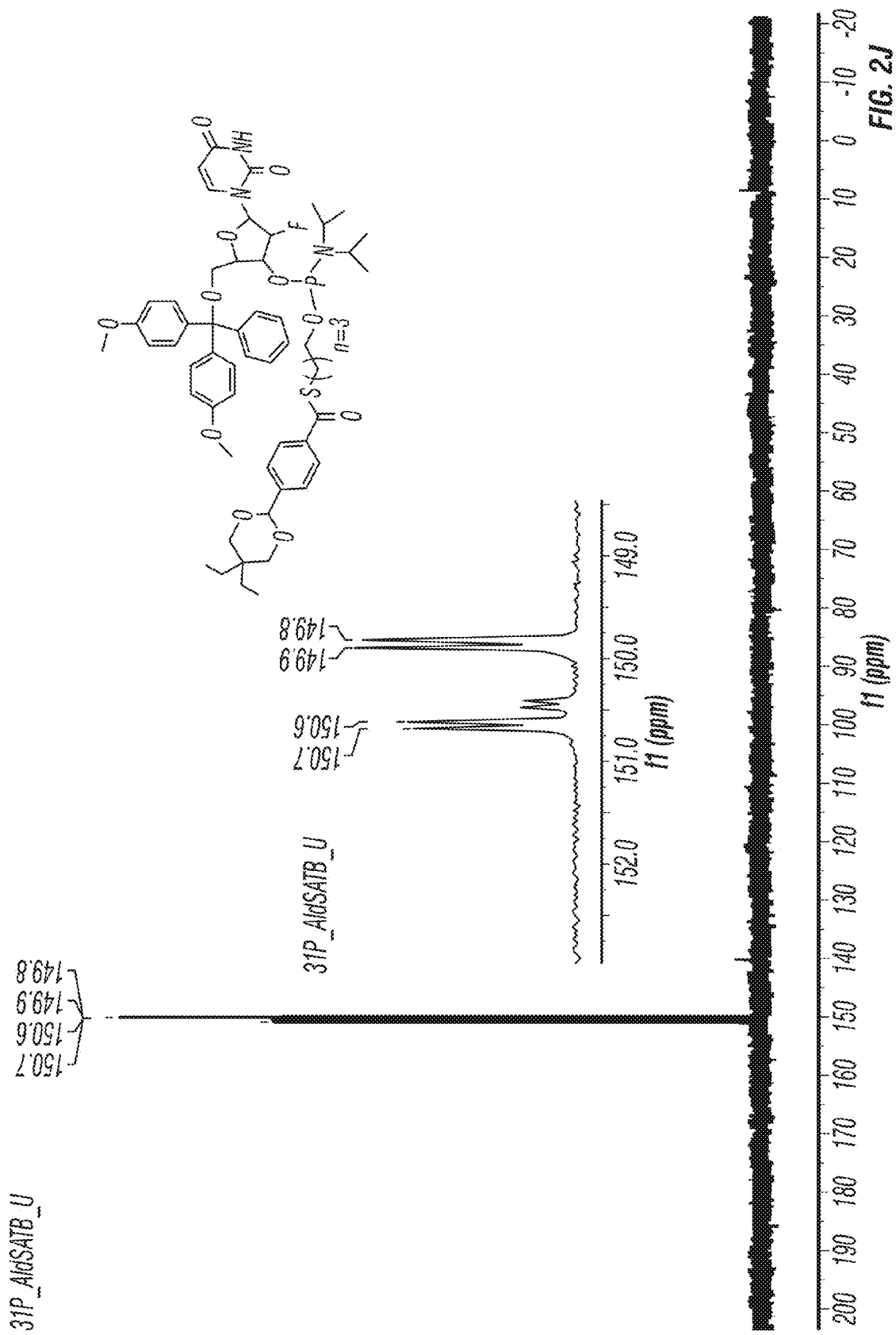
Figure 2J:
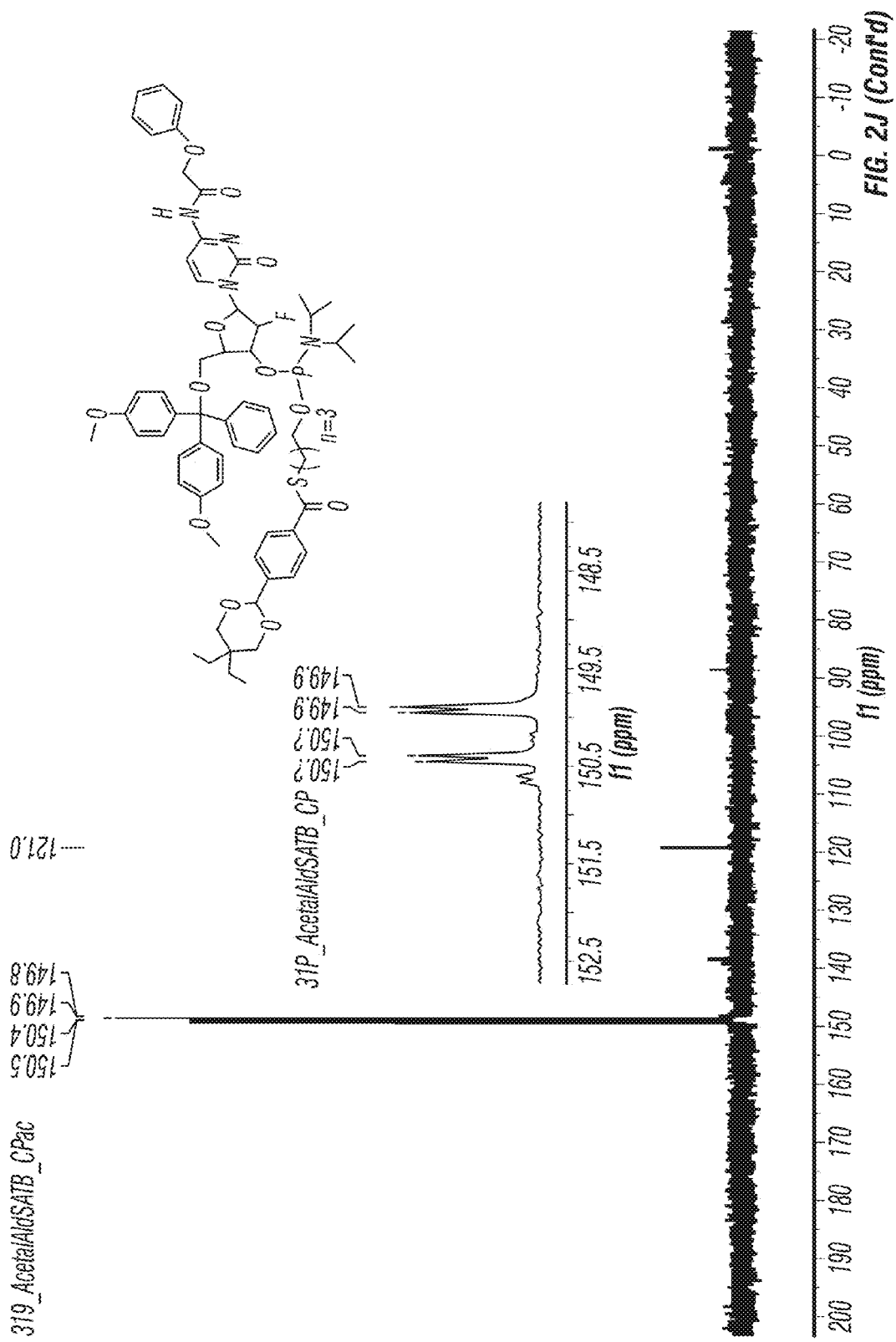
Figure 2K:
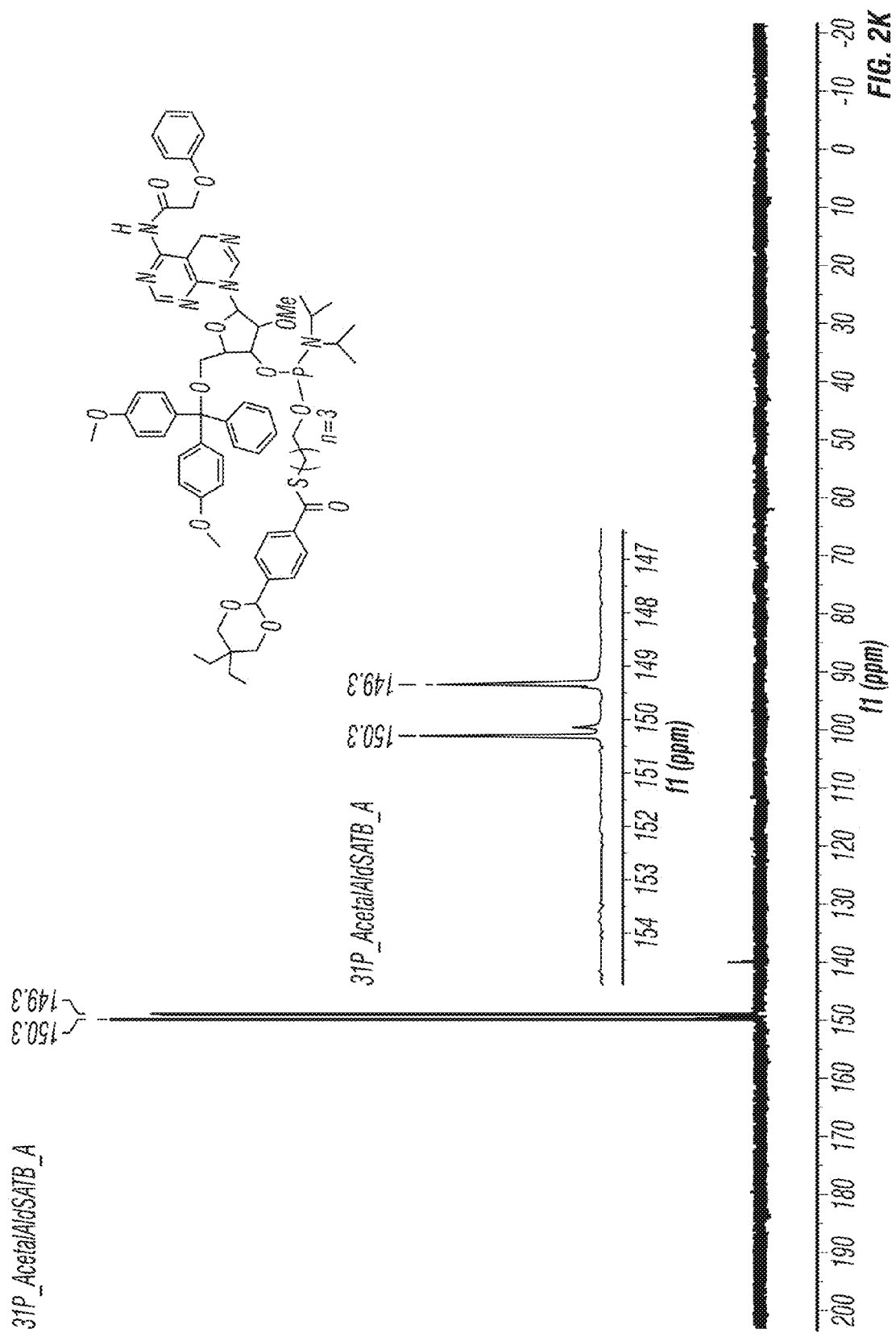
Figure 2K:
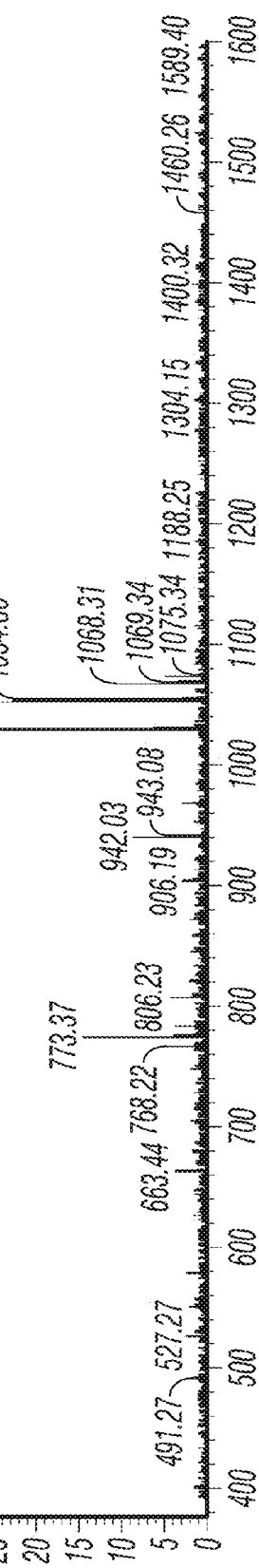

AcetalAldSATB_U phosphoramidite was synthesized by following the protocol for Acetal AldSATE_U phosphoramidite disclosed herein, but substituting acetalAldSATB for acetalAldSATE. AldSATB_U was isolated in 70% yield. ESI MS for $C_{55}H_{69}FN_3O_{11}PS$ calculated 1029.43, observed $[M+H]^+$ 1030.12, $[M+Na]^+$ 1052.35. $^{31}P$ NMR (121 MHz, $CDCl_3$) δ 150.27 (d, $J_{P-F}$=8.0 Hz), 150.63 (d, $J_{P-F}$=7.8 Hz). Representative spectra for AcetalAldSATB_U are shown in FIG. 2J and FIG. 2K.

Synthesis of Acetal AldSATE_$C^{Pac}$ Phosphoramidite

Acetal AldSATE_$C^{Pac}$ phosphoramidite was synthesized by following the protocol for Acetal AldSATE_U phosphoramidite disclosed herein, but substituting 5'-O-(4,4'-Dimethoxytrityl)-2'-F-$C^{Pac}$ for 5'-O-(4,4'-Dimethoxytrityl)-2'-F-uridine. Acetal AldSATE_$C^{Pac}$ phosphoramidite was isolated in 70% yield. ESI MS for $C_{61}H_{72}FN_4O_{12}PS$ calculated 1132.46, observed $[M+Na]^+$ 1157.44.

Figure 2L:
Figure 2L:
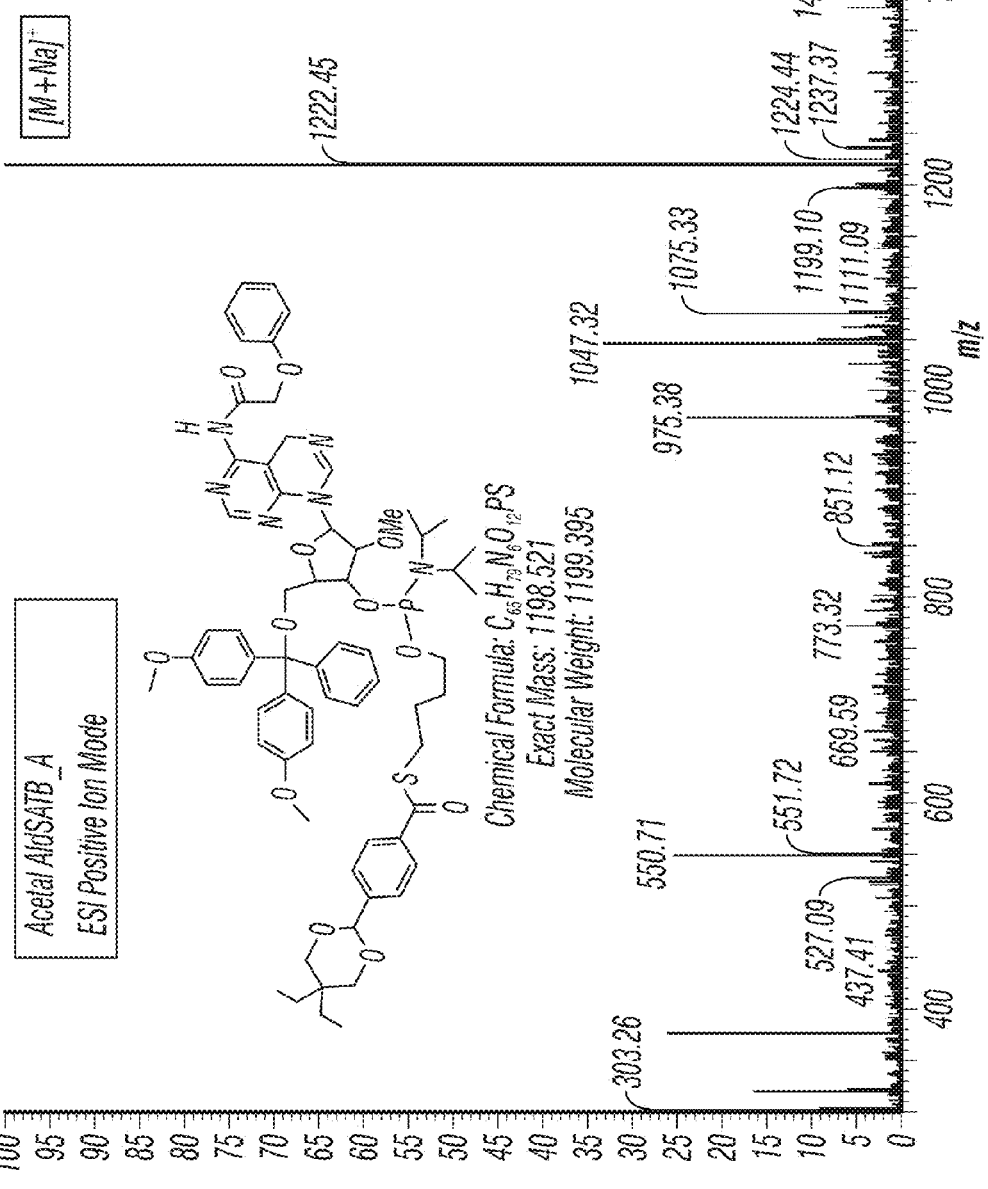

$^{31}P$ NMR (121 MHz, $CDCl_3$) δ 150.44 (d, $J_{P-F}$=8.1 Hz), 150.74 (d, $J_{P-F}$=8.5 Hz). Representative spectra for Acetal AldSATE_$C^{Pac}$ phosphoramidite are shown in FIG. 2G and FIG. 2L.

Synthesis of Acetal AldSATB_$C^{Pac}$ Phosphoramidite

Acetal AldSATB_$C^{Pac}$ phosphoramidite was synthesized by following the protocol for Acetal AldSATE_$C^{Pac}$ phosphoramidite disclosed herein, but substituting acetalAldSATB for acetalAldSATE. Acetal AldSATB_$C^{Pac}$ phosphoramidite was isolated in 70% yield. ESI MS for $C_{63}H_{76}FN_4O_{12}PS$ calculated 1162.49, observed $[M+Na]^+$ 1185.45. $^{31}P$ NMR (121 MHz, $CDCl_3$) δ 149.9 (d, $J_{P-F}$=8.2 Hz), 150.4 (d, $J_{P-F}$=8.3 Hz). A representative spectrum for AldSATB_$C^{Pac}$ phosphoramidite is shown in FIG. 2J.

Synthesis of Acetal AldSATE_$A^{Pac}$ Phosphoramidite

Acetal AldSATE_$A^{Pac}$ phosphoramidite was synthesized by following the protocol for Acetal AldSATE_U phosphoramidite disclosed herein, but substituting 5'-O-(4,4'-Dimethoxytrityl)-2'-F-$A^{Pac}$ for 5'-O-(4,4'-Dimethoxytrityl)-2'-F-uridine. Acetal AldSATE_$A^{Pac}$ phosphoramidite was isolated in 70% yield. ESI MS for $C_{63}H_{75}N_6O_{12}PS$ calculated 1170.49, observed $[M+Na]^+$ 1193.43. $^{31}P$ NMR (121 MHz, $CDCl_3$) δ 149.9 & 150.8. A representative spectrum for Acetal AldSATE_$A^{Pac}$ phosphoramidite is shown in FIG. 2H.

Synthesis of Acetal AldSATB_$A^{Pac}$ Phosphoramidite

Acetal AldSATB_$A^{Pac}$ phosphoramidite was synthesized by following the protocol for Acetal AldSATE_$A^{Pac}$ phosphoramidite disclosed herein, but substituting acetalAldSATB for acetalAldSATE. Acetal AldSATB_$A^{Pac}$ phosphoramidite was isolated in 70% yield. ESI MS for $C_{65}H_{79}N_6O_{12}PS$ calculated 1198.52, observed $[M+Na]^+$ 1221.43. $^{31}P$ NMR (121 MHz, $CDCl_3$) δ 149.3 & 150.3. Representative spectra for Acetal AldSATB_$A^{Pac}$ phosphoramidite are shown in FIG. 2K and FIG. 2L.

Quantitative Intracellular Conversion of Bioreversible Neutral Phosphotriesters to Negatively Charged Phosphodiesters. An exemplary polynucleotide and exemplary lipofection data are provided in FIG. 3. As shown in FIG. 3, a modified polynucleotide that includes the hydrolysable tBu-SATE bioreversible moiety (SEQ ID NO:26) was quantitatively cleaved to afford the siRNA (with 2' modifications). By contrast, a functionalized polynucleotide that included irreversible dimethylbutyl phosphotriester (DMB) groups was not cleaved to siRNA intracellularly.

Figure 4:
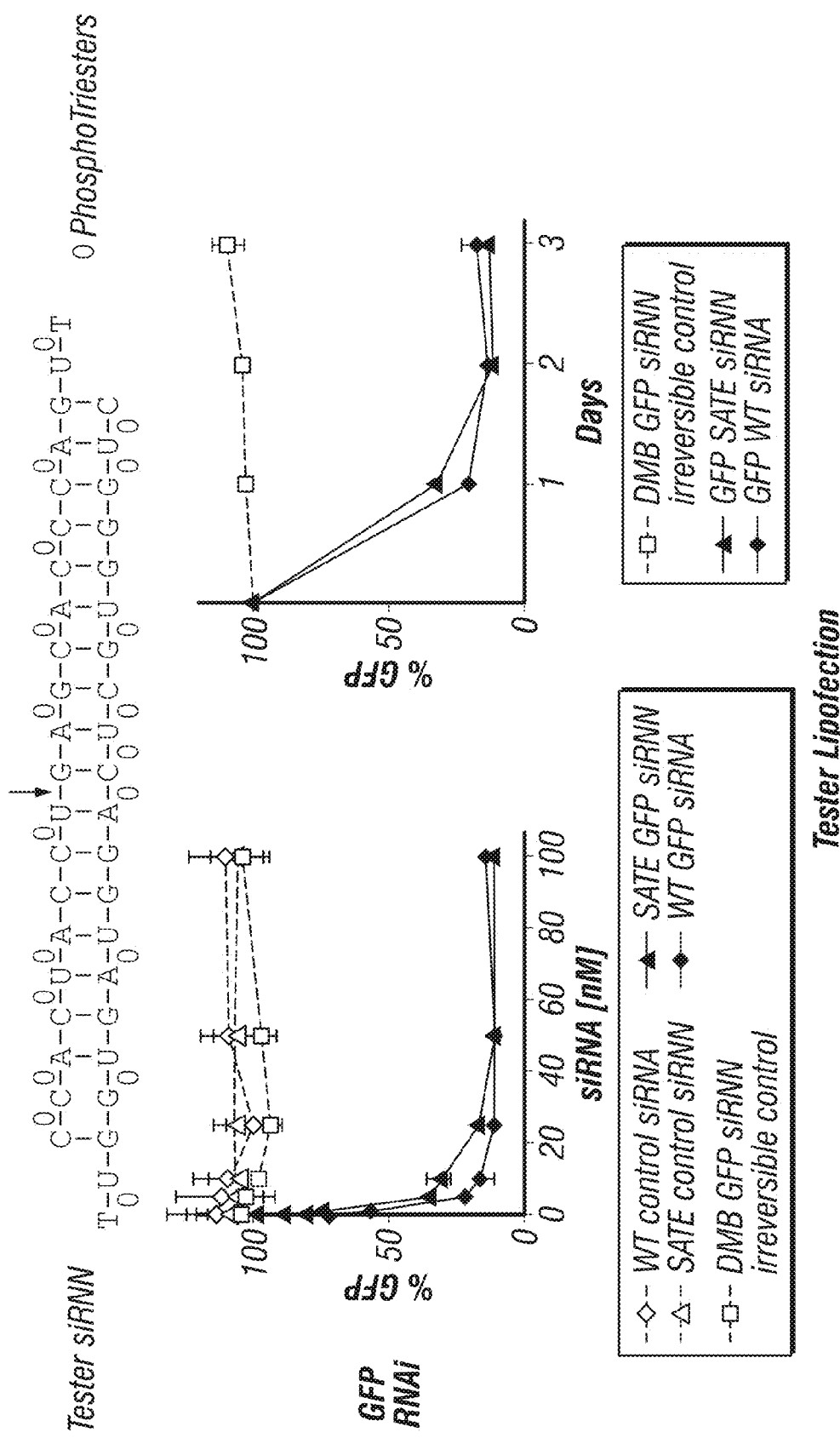
FIG. 4 shows that GFP expression can be silenced by using polynucleotide constructs of the disclosure and that the results are comparable to wild-type siRNA.
Figure 4:
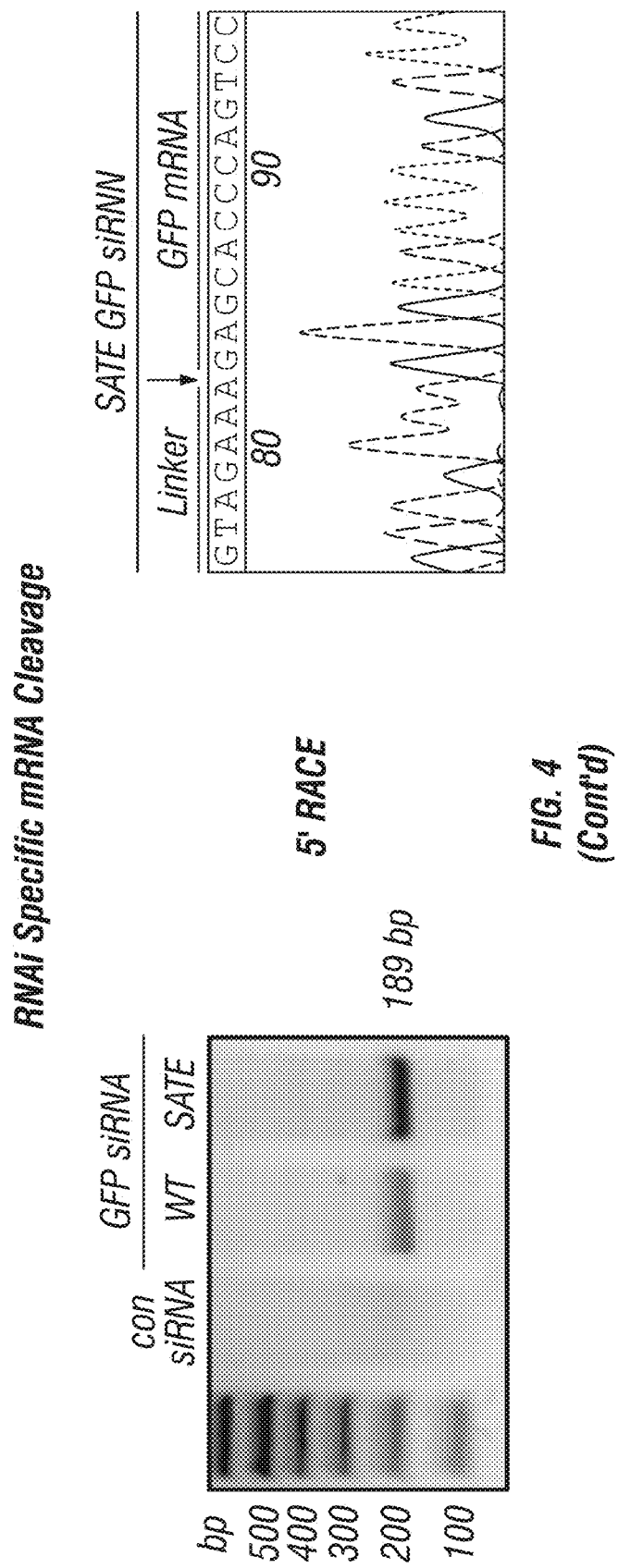

The induction of RNAi responses by phosphotriester containing oligonucleotides requires cleavage, decomposition and resolution of phosphotriesters into phosphodiester linkages for TRBP mediated loading into Ago2/RISC. Double stranded siRNN (phosphotriester groups are denoted as bubbles) targeting GFP mRNA was synthesized (see FIG. 3, top panel). The 5' end of the Guide (antisense) strand containing either bioreversible tBut-SATE or control irreversible DiMethylButyl (DMB) or control wild type phosphodiesters (see FIG. 3, bottom panel) was $^{32}$P-labeled. The siRNNs were transfected into cells. After co-immunoprecipitation using anti-Ago2, the cells lysates loaded and run on a 15% denaturing PAGE gel for 30 hours. As shown, there was quantitative intracellular conversion of tBut-SATE RNN oligonucleotide by thioesterases and co-migration with wild type phosphodiester oligonucleotide (see FIG. 3, middle panel). By contrast, only background levels of control $^{32}$P-labeled irreversible DMB RNN associated with Ago2 were detected, indicating that these constructs had not undergone intracellular cleavage. The data indicate that the SATE phosphotriester containing siRNNs were intracellularly converted into biologically active siRNAs, and loaded into Ago2.

siRNNs Induce GFP and Luciferase RNAi Responses In Vitro. siRNNs induced GFP RNAi responses in H1299 cells and silenced the expression of GFP (see FIG. 4). Double stranded siRNN (phosphotriester groups are denoted as blue bubbles) targeting GFP mRNA was synthesized (see FIG. 4, top panel). Wild type phosphodiester GFP siRNAs or non-targeting control siRNAs, and SATE phosphotriester siRNNs GFP or non-targeting control siRNNs were transfected into H1299 cells which constitutively express GFP. Dose and kinetic curves for RNAi inhibition of GFP expression were generated on day 2 for GFP expression by flow cytometry (see FIG. 4, middle left and right panel). 5' RACE studies for GFP expression from the transfected cells were performed by PCR amplification of GFP mRNA. While the correct 189 bp fragment was found from cells transfected with SATE phosphotriester siRNNs and siRNAs targeting GFP, this fragment was not found for non-targeting control siRNAs (see FIG. 4, bottom left panel). cDNA sequence analysis of 5' RACE cDNA fragment from bottom left panel shows the correct GFP mRNA cleavage for Ago2-mediated RNAi response (see FIG. 4, bottom right panel).

Figure 5:
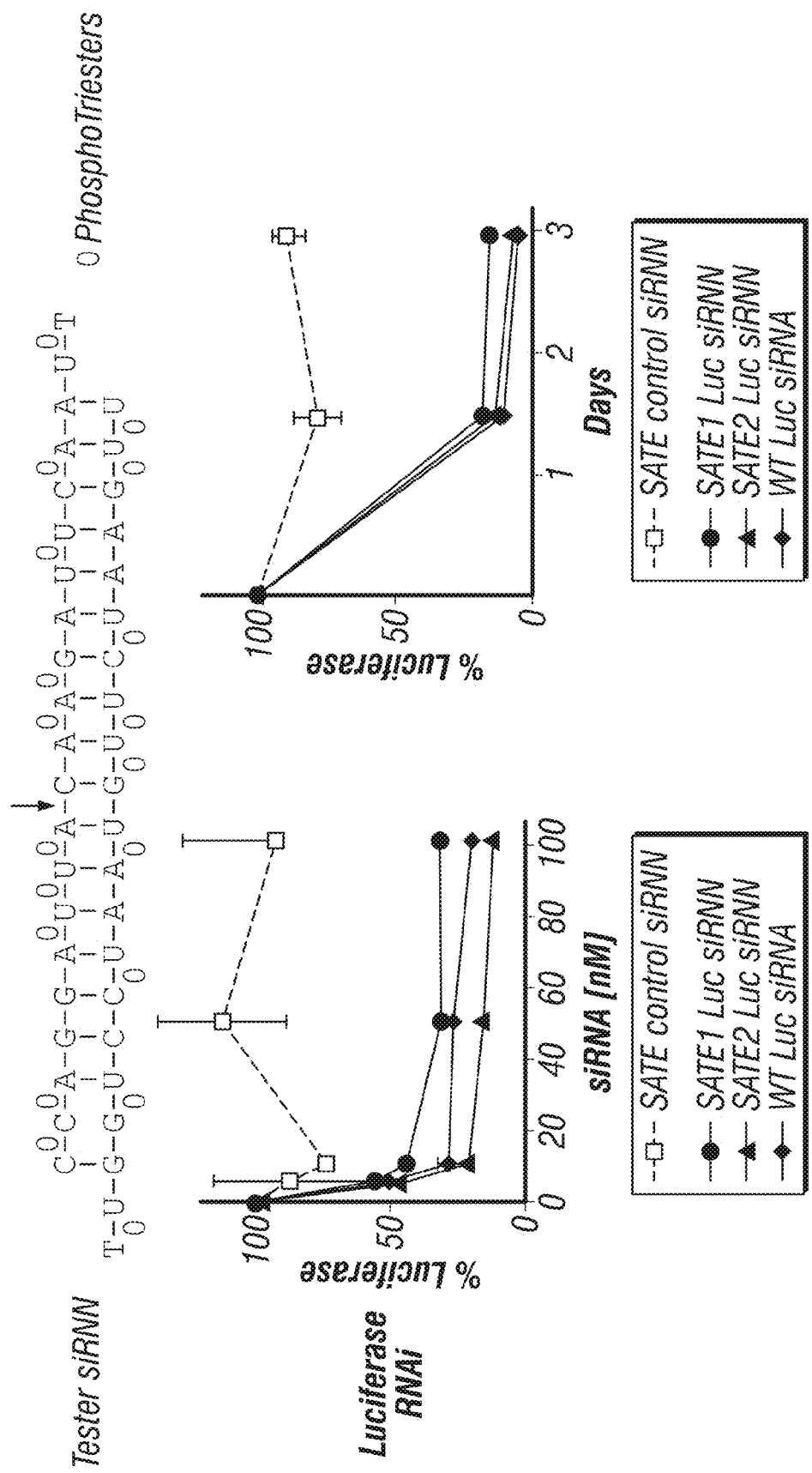
FIGS. 5-6 show that luciferase expression can be silenced using polynucleotide constructs of the disclosure, both in vitro (FIG. 5), and in vivo (FIG. 6).
Figure 5:
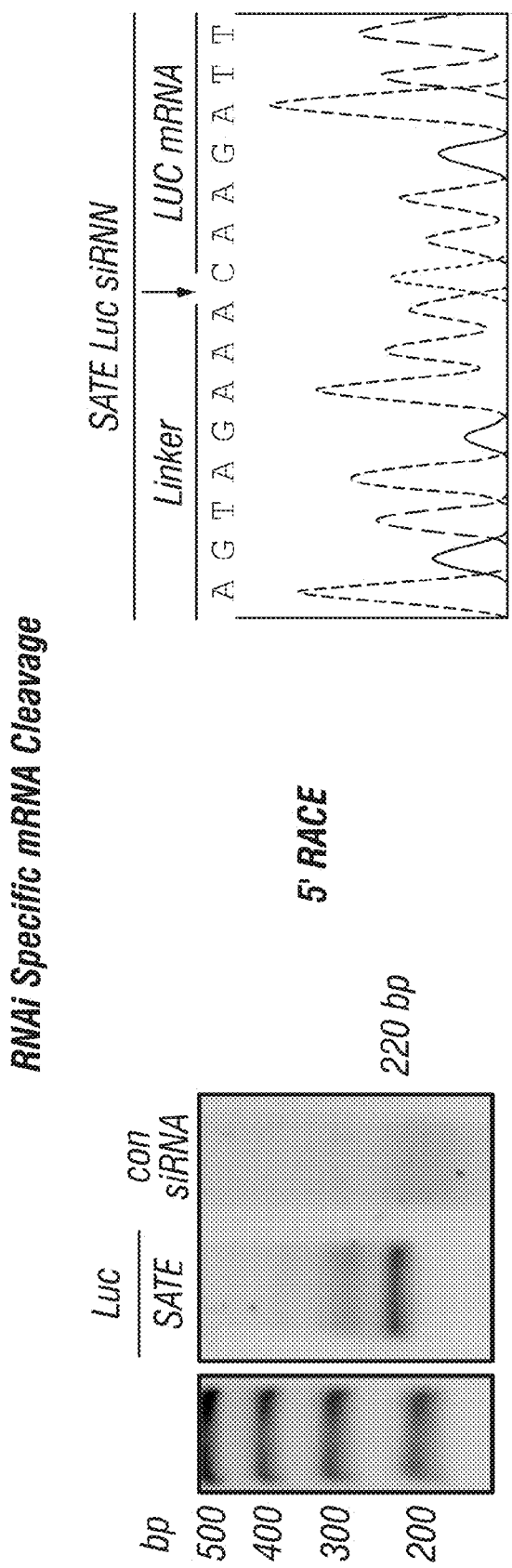
Figure 6:
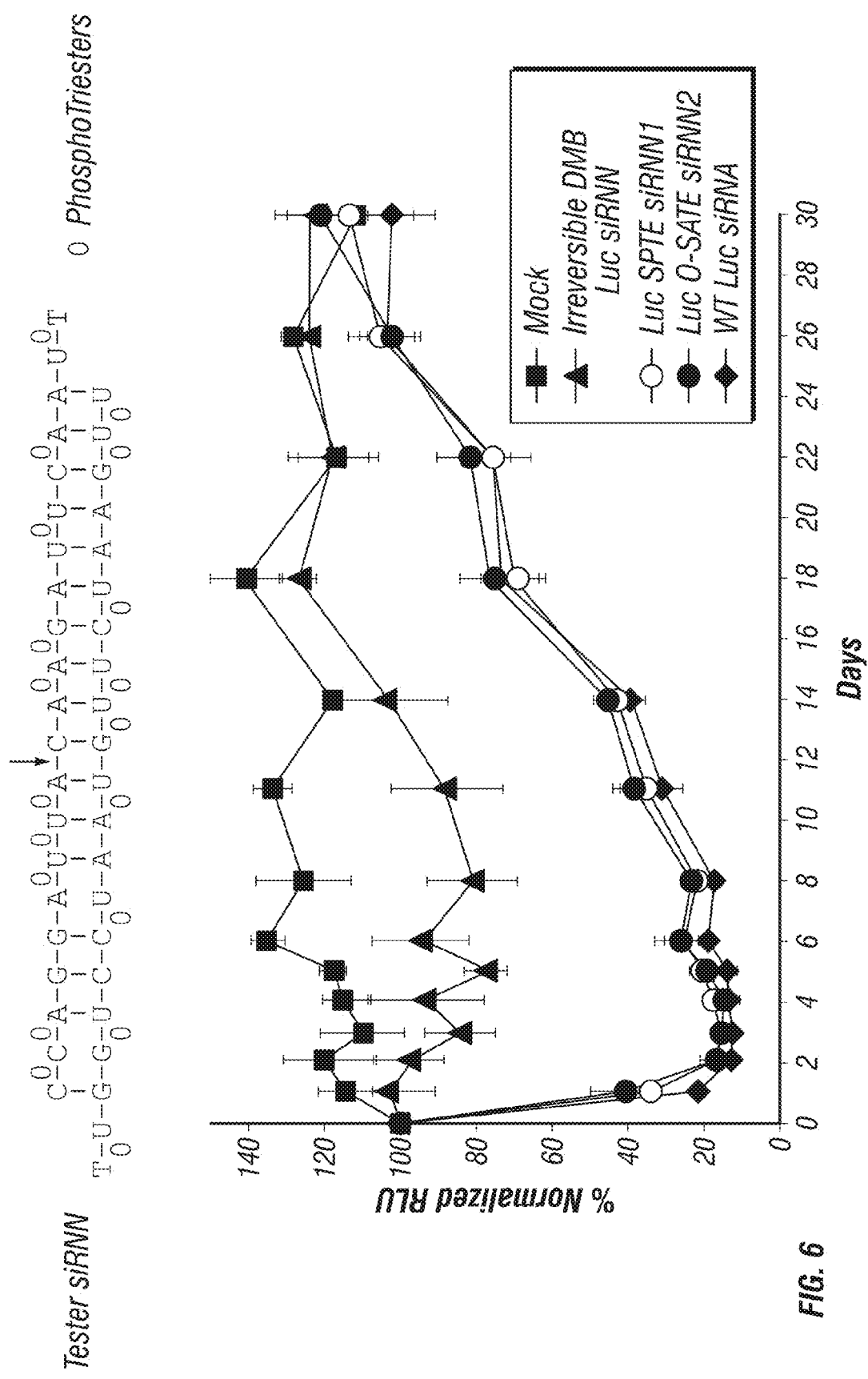
Figure 6:
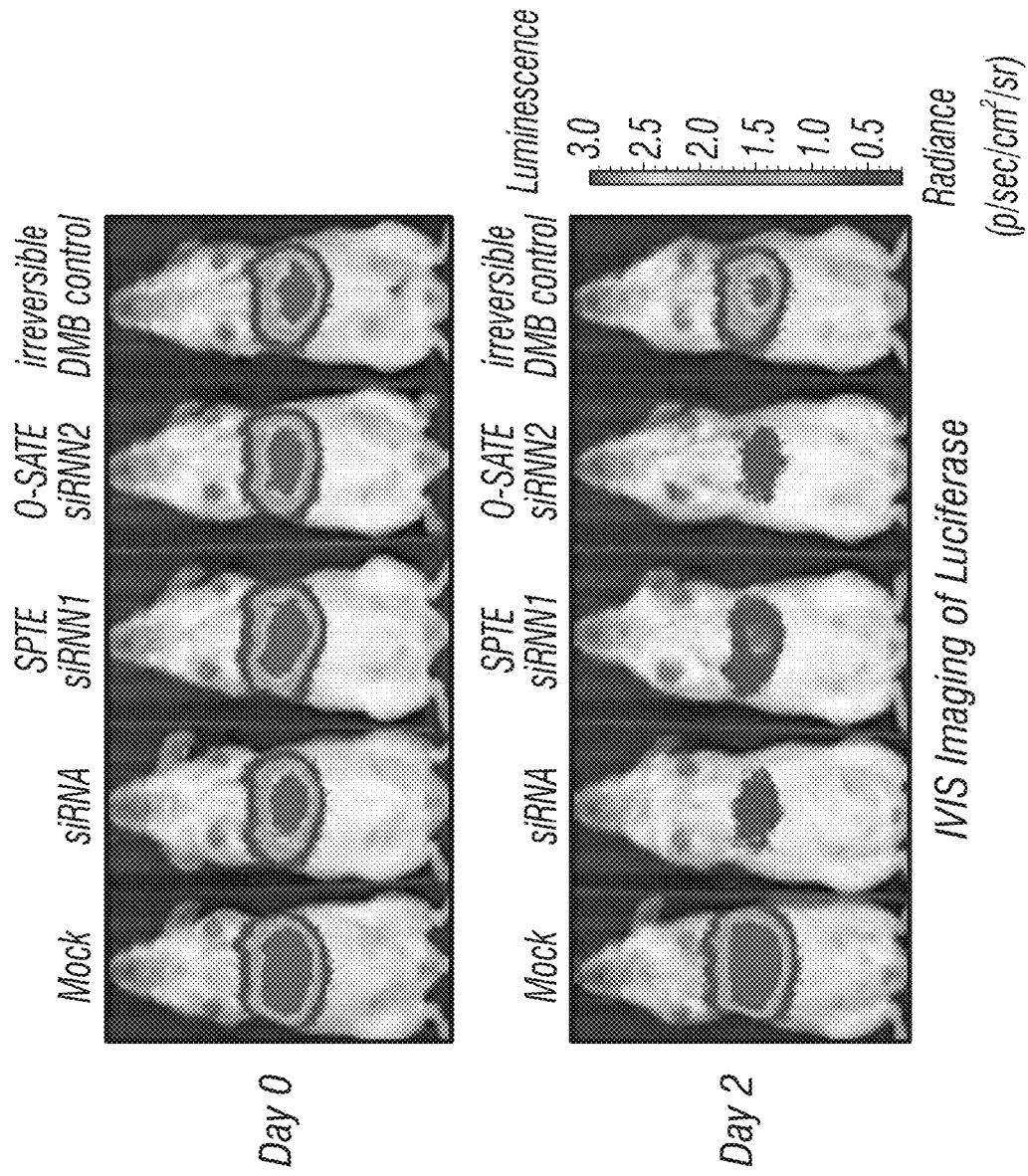
Figure 7:
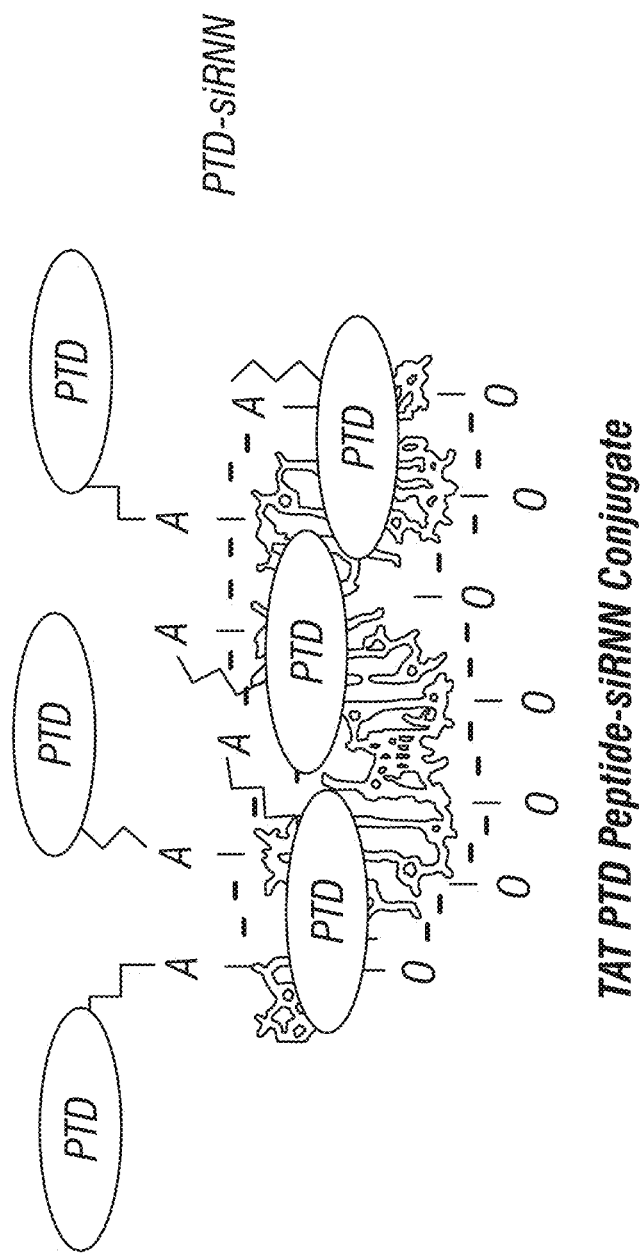
FIG. 7 presents an exemplary polynucleotide construct of the disclosure which includes six peptide transduction domains (PTDs) and shows that these polynucleotide constructs can lead to reduced GFP expression in cells.

Similar silencing experiments were carried out with H1299 cells which constitutively express Luciferase (see FIG. 5). Similar to the results with constitutive GFP expression, induction of RNAi responses were seen by transfecting the cells with siRNNs in contrast to the controls vectors (see FIG. 5).

siRNNs Induce Luciferase RNAi Responses In Vivo in Mouse Models Expressing Hepatic Luciferase. Double stranded siRNNs (phosphotriester groups are denoted as blue bubbles) targeting Luciferase mRNA were synthesized (see FIG. 7, top panel). Mice which selectively express hepatic (liver) Luciferase were randomly grouped (see FIG. 7, top left panel). Mock (PBS), Luciferase siRNA or tBut-SATE and O-SATE phosphotriester Luciferase siRNNs, or control irreversible DMB Luciferase siRNNs, were hydrodynamically delivered into the liver. Tail-vein hydrodynamic delivery temporarily (2-5 min) generated holes in the liver which allowed for siRNAs/siRNNs to diffuse through the holes and into the cytoplasm. The mice were then analyzed for Luciferase expression by IVIS in vivo imaging over the course of 30 days. Mice treated with wild type siRNAs, tBut-SATE siRNNs or O-SATE siRNNs targeting luciferase induced equivalent luciferase RNAi responses both in magnitude and duration, whereas the control irreversible DMB Luciferase siRNN failed to induce a RNAi response (see FIG. 7, right panel). These results demonstrate that bioreversible phosphotriester siRNNs are efficiently converted by intracellular thioesterases in vivo into active RNAi molecules.

Self-Delivery of TAT PTD-siRNNs. Experiments for self-delivery by siRNN conjugated with TAT PTD delivery peptides were performed (see FIG. 8, top panel). Dose curves of soluble and monomeric Self-Delivering siRNNs targeting the GFP reporter gene, control irreversible siRNN targeting the GFP reporter gene, and mock treated GFP cells were created. The curves were compared and analyzed by FACS histogram analysis using 0.22 nmoles (see FIG. 8, bottom left panel), and then normalized to the mock treated GFP cells (see FIG. 8, bottom right panel). For FIG. 8, P6(A6) denotes passenger strand with six Ald-SATEs; and G6(A6) denotes guide strand with six Ald-SATEs. The results demonstrate that treatment of GFP expressing cells with bioreversible TAT PTD-siRNN conjugates resulted in self-delivery and induction of RNAi responses, whereas treatment with control irreversible TAT PTD-siRNN conjugates failed to induce RNAi responses. These results demonstrate the ability of a siRNN to be self-delivered as a soluble, monomeric conjugate (not a nanoparticle) into cells, converted into an active charged phosphodiester RNAi molecule and induce RNAi responses.

Determination of dsRNN Formation with SDS-PAGE Analysis. In order to determine the maximal number of phosphotriester insertions tolerated for siRNN duplexing, passenger and guide strand ssRNN molecules containing varying numbers of phosphotriesters were annealed and analyzed by SDS-PAGE. Annealing was accomplished by heating passenger and guide strand mixtures to 65° C. for 5 minutes followed by cooling to ambient temperature for 15 minutes. Annealed dsRNN duplexes were analyzed by running on nondenaturing SDS-PAGE gels followed by either ethidium bromide staining (see FIG. 8, bottom panel) or silver staining (see FIG. 8, top panel). Percent dsRNN formation was determined for each dsRNN combination by densitometry of silver stained SDS-PAGE gels. In FIG. 8, a 13× phosphotriester guide strand (G13b) is shown annealed to 13× phosphotriester passenger strands containing phosphotriester insertions located in different positions (P13a, P13b, P13c). Note the discrepancy with annealing efficiency (% Double Stranded) correlates with differences in phosphotriester insertion sites on the dsRNN backbone.

Summary of dsRNN Formation Efficiency with Various O-SATE ssRNN Combinations. FIG. 9 and FIG. 10 demonstrate that hybridization of the polynucleotide constructs of the disclosure is dependent on the type and spacing of the bioreversible groups. In these figures, the passenger strand (P) is 5'-CCACUACCUGAGCACCCAGUU-3' (SEQ ID NO: 27), and the guide strand (G) is 5'-CUGGGUGCUCA-GGUAGUGGUU-3' (SEQ ID NO: 28). The numbers indicate the location of the bioreversible groups (counted from the 5' end). The default bioreversible group is O-SATE; additional bioreversible groups are 4-formylbenzoate-SATE (A).

Following the protocol described in FIG. 8, various combinations of O-SATE ssRNN molecules were annealed and analyzed by densitometry of silver stained SDS-PAGE gels to determine efficiency of dsRNN formation (see FIG. 9). In FIG. 9, passenger strands (P) and guide strands (G) containing differing numbers and locations of O-SATE phosphotriesters were tested (see FIG. 9, bottom panel for nomenclature). Efficiency of dsRNN formation was grouped into five categories (>90%, >75%, ~50%, <10% or 0%). Note the ability of both wildtype passenger ($p^{WT}$) and guide strands ($G^{WT}$) to anneal efficiently to ssRNN molecules containing high numbers of O-SATE insertions (G16a and P15a, respectively) (see FIG. 9, top panel). Some combinations, however, do not lead to high amounts of hybridization (e.g., <50% hybridization). In some studies, no hybridization was measured. dsRNN formation is compromised when both strands reach a specific phosphotriester number and location (i.e., P15a/G16a dsRNN=0%) (see FIG. 9, top panel). Only dsRNN molecules that annealed at >90% efficiency were used for future studies.

Summary of dsRNN Formation for Aid-SATE ssRNN Oligonucleotides. Following the protocol described in FIG. 8, various combinations of Ald-SATE or SPTE ssRNN molecules were annealed and analyzed by densitometry of silver stained SDS-PAGE gels to determine efficiency of dsRNN formation (see FIG. 10). In FIG. 10, passenger strands (P) and guide strands (G) containing differing numbers and locations of Ald-SATE or SPTE phosphotriesters were tested (see FIG. 10, bottom panel for nomenclature). In contrast to the nucleic acids studied in FIG. 9, the passenger and guide strands presented in FIG. 10 included fewer functionalized polynucleotides (e.g., 3-6 phosphotriesters per strand). Efficiency of dsRNN formation was grouped into five categories (>90%, >75%, ~50%, <10% or 0%). Note all Ald-SATE containing dsRNN combinations displayed >90% dsRNN formation efficiency as determined by densitometry analysis of silver stained SDS-PAGE gels. All Ald-SATE dsRNN combinations were used for future conjugation and intracellular delivery studies.

Example of Reverse Phase HPLC Purification for ssRNN Oligonucleotides. Following oligonucleotide synthesis and deprotection, ssRNN oligonucleotides were isolated by Reverse Phase HPLC (RP-HPLC) (see FIG. 11). By hydrophobically interacting with the column, the desired oligo product was isolated from contaminants in the presence of triethylammonium acetate (TEAA) and an increasing acetonitrile gradient (see FIG. 11, top panel). Fractionation across the main product peak resulted in purification of desired oligo synthesis product (see FIG. 11, bottom panel). Note RP-HPLC fractions 6-8 contain the final oligo product at >95% purity.

Figure 12:
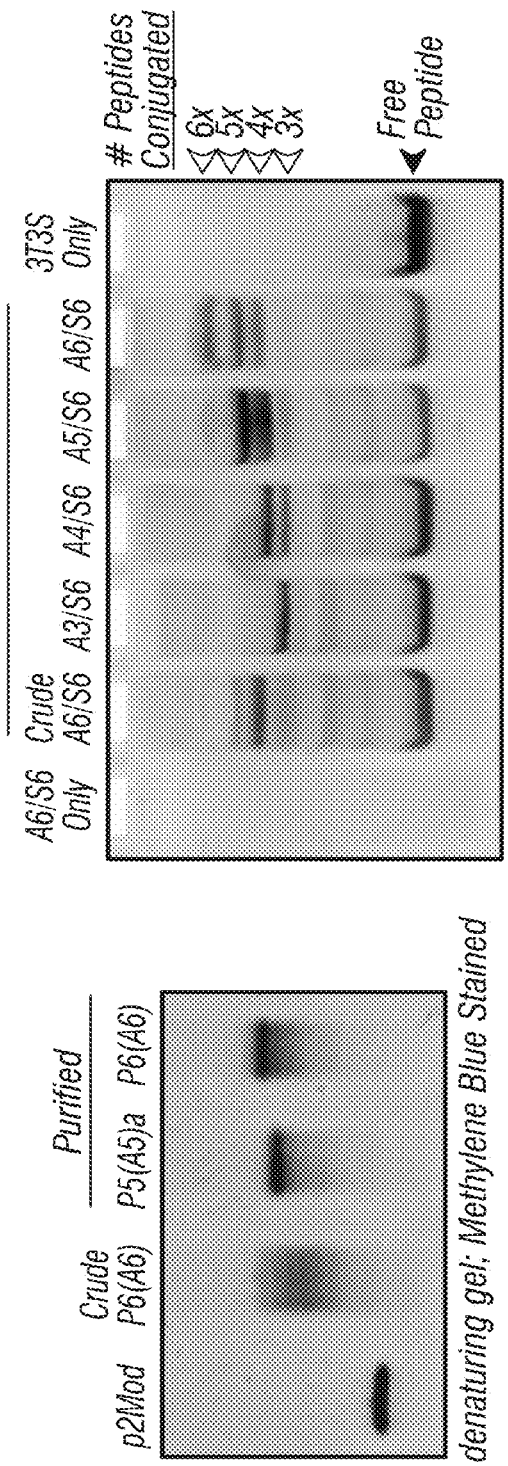
FIG. 12 shows that multiple PTD auxiliary moieties can be effectively conjugated to the nucleic acid constructs of the disclosure.

Peptide Conjugation of Aid-SATE Containing dsRNN Oligonucleotides. Following RP-HPLC purification, urea denaturing gels were used for the analysis of final ssRNN oligonucleotide products (see FIG. 12). Ald-SATE containing ssRNN oligonucleotides (P5(A5)a and P6(A6)a) were isolated to >95% purity (see FIG. 12, left panel). Following duplexing of various Ald-SATE passenger strands to a 6× SPTE-containing guide strand (G6(S6)a), dsRNN molecules were conjugated to the Peptide Transduction Domain 3T3S through free aldehydes on the Ald-SATE termini. Following peptide conjugation, conjugation efficiency was assessed by silver stained SDS-PAGE gels (see FIG. 12, middle panels). In FIG. 12, the ability of a siRNN oligonucleotide to conjugate to an increasing number of peptides based on the number of Ald-SATE insertions present is shown (see FIG. 12, right panel). It should be noted that there is near quantitative conjugation of Ald-SATE insertions to 3T3S peptide.

Figure 13:
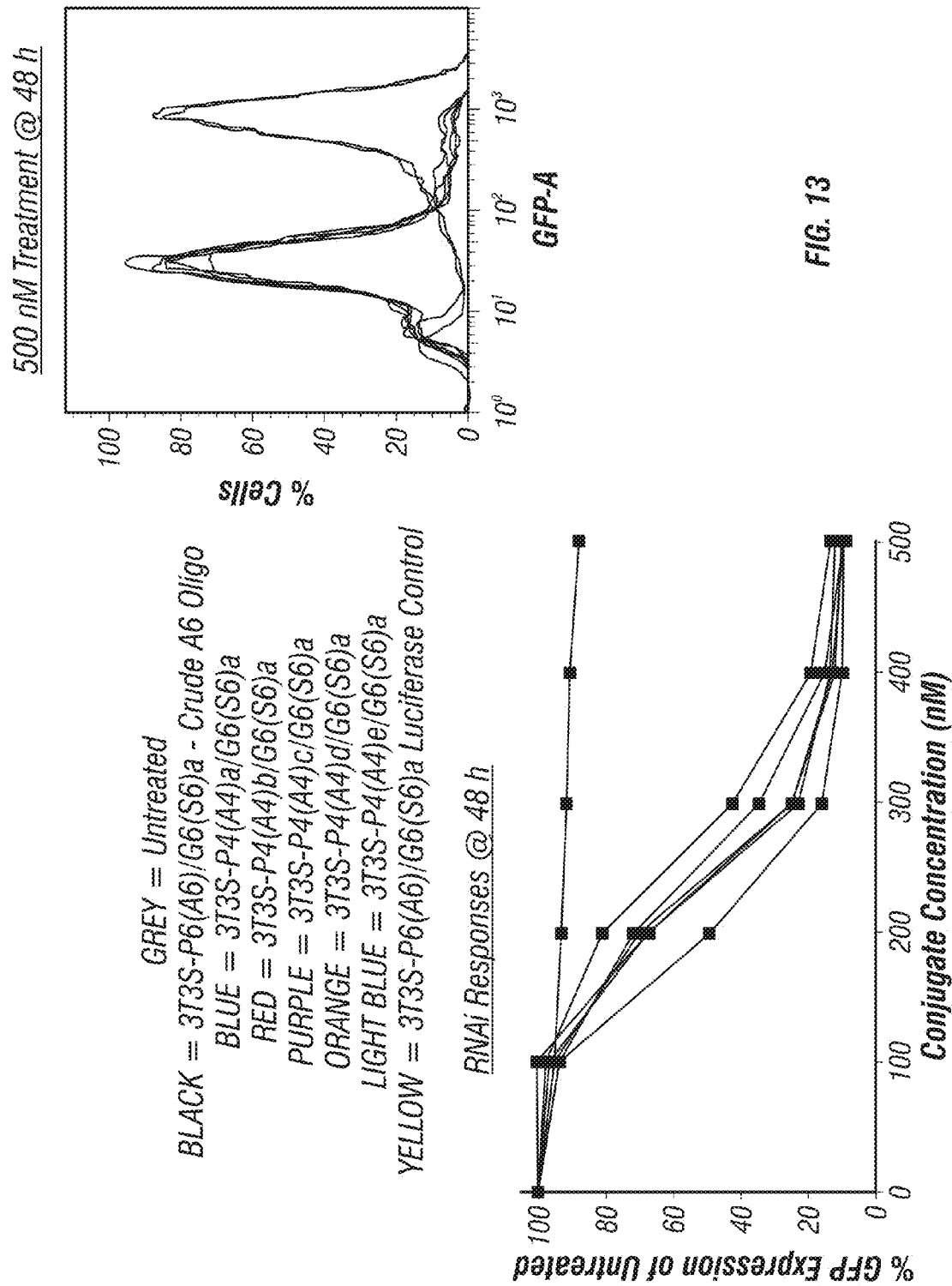
FIGS. 13-14 show that polynucleotide constructs of the disclosure having PTDs auxiliary moieties conjugated to bioreversible groups allow for effective intracellular delivery of polynucleotides into H1299 cells. These polynucleotide constructs are shown to reduce the expression of GFP in vitro at concentrations ranging from 200 nM to 500 nM.

Comparison of Self-Delivery of TAT PTD-siRNNs. Using the siRNN nomenclature abbreviations from FIG. 9 and FIG. 10, Ald-SATE and tBut-SATE phosphotriesters were placed in varying indicated positions on siRNNs, conjugated to TAT delivery peptides, purified and analyzed for self-delivery (see FIG. 13). The induction of GFP RNAi responses in H1299 constitutively expressing GFP cells was measure by flow cytometry at 48 hours post-self delivery and compared with the non-targeting control Luciferase siRNN. A FACS histogram (see FIG. 13, top right panel) and dose curve normalized to mock treated GFP cells (see FIG. 13, bottom panel) are presented.

Figure 14:
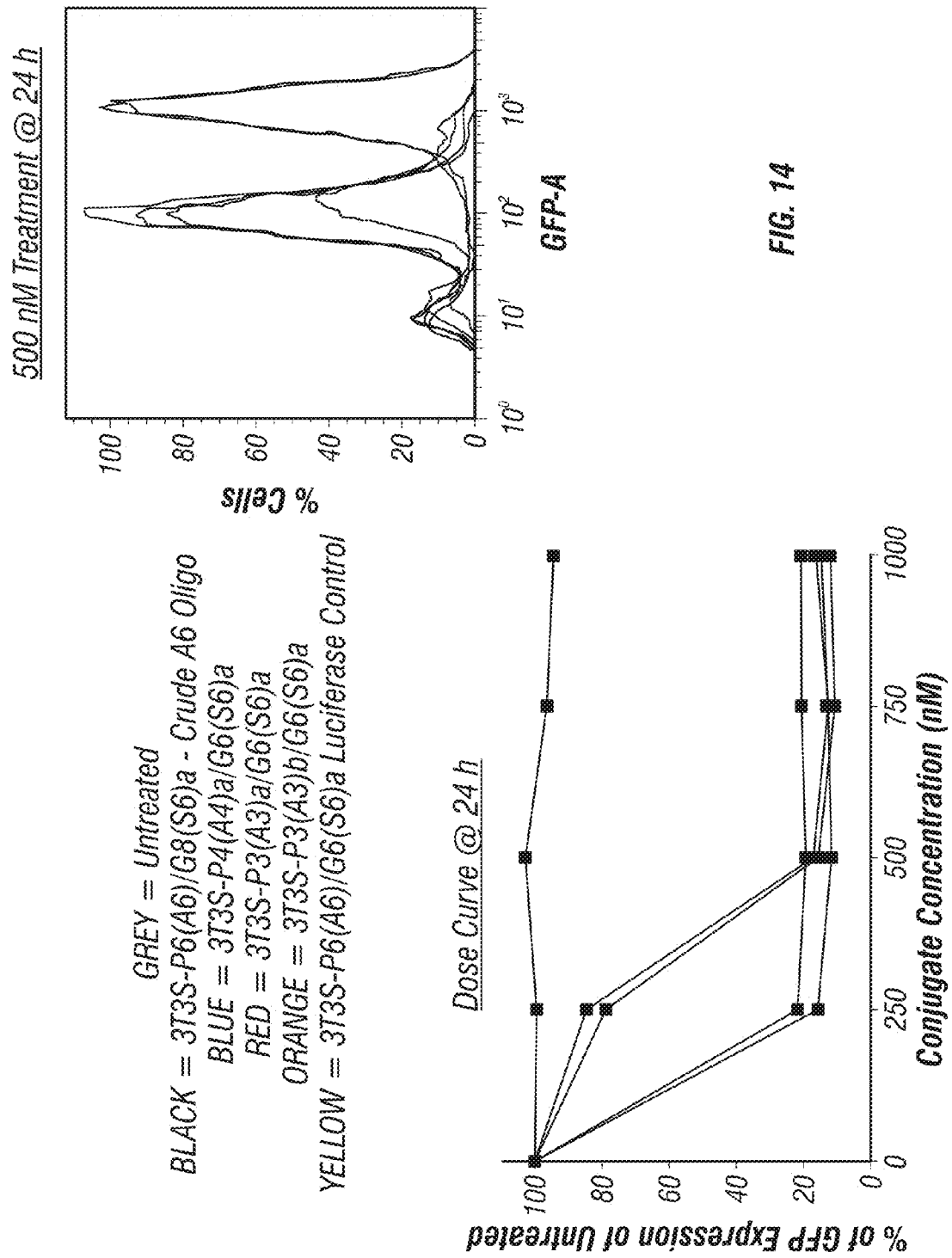

Comparison of Self-Delivery of TAT PTD-siRNNs by Limiting Ald-SATE Phosphotriester Numbers. Similar to FIG. 13 above, FIG. 14 shows the induction of RNAi responses by self-delivering siRNNs and controls targeting constitutively expressed GFP in H1299 cells. By varying the numbers and locations of Ald-ASTE phosphotriester groups on the passenger strand (see FIG. 14, top panel) (see nomenclature from FIG. 9 and FIG. 10 for specific locations), differences in RNAi responses could be detected in comparison to non-targeting control Luciferase siRNN. A FACS histogram (see FIG. 14, top right panel) and dose curve normalized to mock treated GFP cells (see FIG. 14, bottom panel) are presented.

Figure 15:
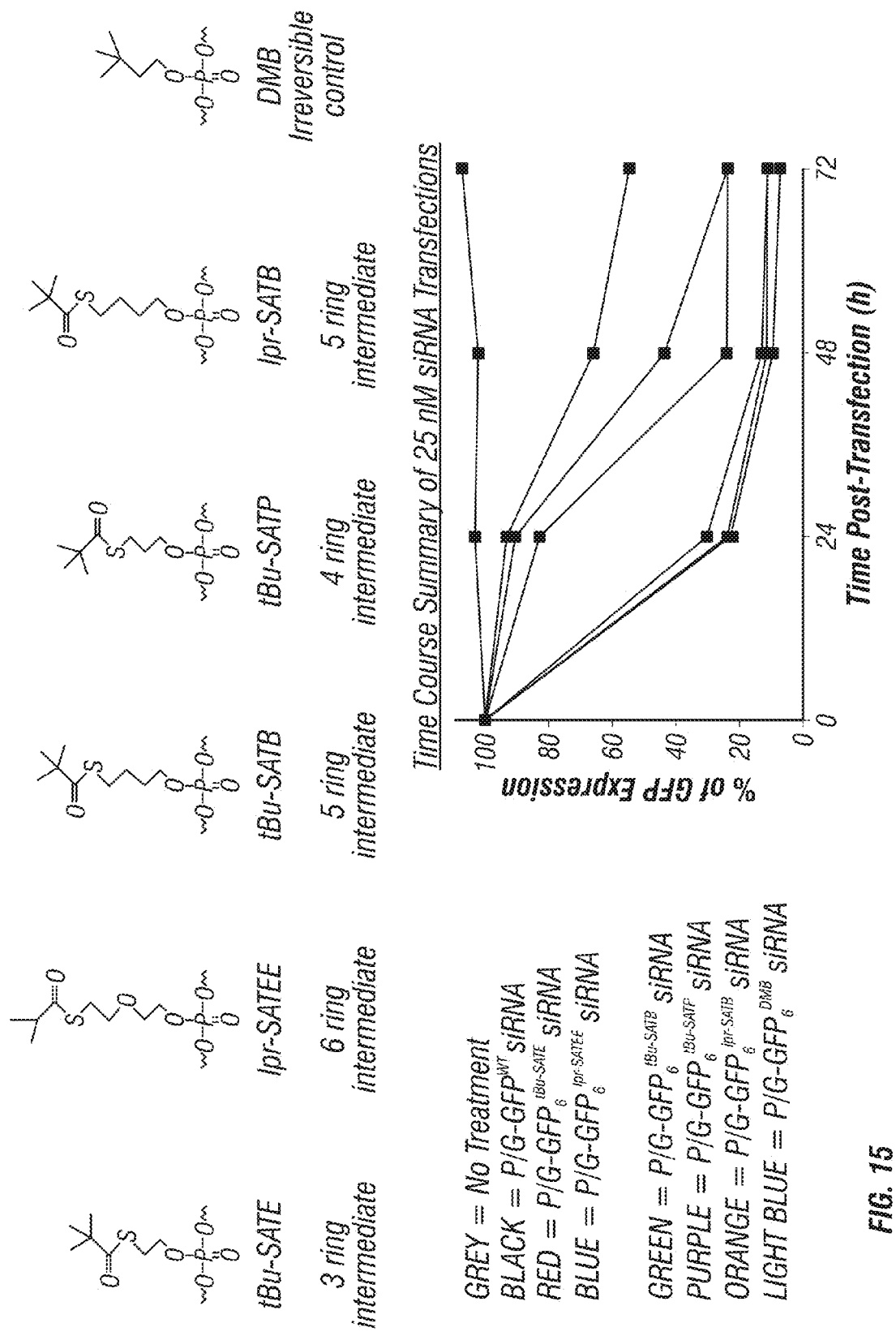
FIG. 15 shows the effect of linker length on the RNAi response for six different polynucleotide constructs having different bioreversible groups.

Comparison of Phosphotriester Linker-1 Length. To investigate the contribution of the Linker-1 ($L^1$) length to complete phosphotriester kick-out second step after thioesterase cleavage of the thioester bond (first step), guide strand RNNs were synthesized which targeted GFP, wherein the RNNs contained phosphotriester groups as are indicated (see FIG. 15, top diagrams) at all 6 Uridine internucleotide bridging groups (see sequence from FIG. 4) and wild type phosphodiester passenger strands. 25 nM siRNNs were transfected into constitutively expressing GFP H1299 cells and analyzed for GFP RNAi responses by FACS over time and normalized to mock treated GFP cells (see FIG. 15, bottom panel). tBut-SATE ($L^1$=ethyl), Ipr-SATB ($L^1$=butyl) induced GFP RNAi responses similar to wild type phosphodiester siRNAs, whereas control irreversible DMB phosphotriester siRNNs did not induce an RNAi response and tBut-SATP (L1=propyl) gave only a ~50% responses at 72 hours (see FIG. 15, bottom left panel). tBut-SATB ($L^1$=butyl) induced a delayed RNAi response compared to Ipr-SATB, demonstrating the influence of the $L^2$ and G groups on phosphotriester conversion rates. Ipr-SATEE ($L^1$=ethoxyethyl) also induced a delayed and poor RNAi response (see FIG. 15, bottom left panel). Accordingly, FIG. 15 provides that RNAi responses similar to wild-type were achieved with siRNNs that include the tBu-SATE and the iPR-SATB phosphotriesters which form, respectively, three- and five-membered ring intermediates. Delayed and/or incomplete RNAi responses were observed with siRNN that included SATP (four-membered intermediate) or the SATEE (five-membered intermediate with a heteroatom in the linker) phosphotriesters. The sterics of the thioester group can also influence the RNAi response, as the tBuSATB showed a delayed response relative to the iPrSATB phosphotriester.

Various modifications and variations of the described method and system of the disclosure will be apparent to those skilled in the art without departing from the scope and spirit of the disclosure. Although the disclosure has been described in connection with specific desired embodiments, it should be understood that the disclosure as claimed should not be unduly limited to such specific embodiments. Indeed, various modifications of the described modes for carrying out the disclosure that are obvious to those skilled in the fields of medicine, pharmacology, or related fields are intended to be within the scope of the disclosure.

The invention claimed is:

1. A polynucleotide construct comprising a component (i) selected from the group consisting of a peptide, a polypeptide, a carbohydrate, a neutral organic polymer, a positively charged polymer, a therapeutic agent, a targeting moiety, and any combination thereof,
wherein component (i) is linked to the polynucleotide construct through a bioreversible group attached to an internucleotide bridging group, and
wherein
the component (i) comprises a delivery domain that comprises one or more peptide transduction domains (PTDs); or
the component (i) comprises the targeting moiety, which is a ligand, carbohydrate, antibody, Fab, scFv, or single-domain antibody.

2. The polynucleotide construct of claim 1, further comprising at least one second component (ii) selected from the group consisting of a bioreversible group which comprises a hydrophilic functional group, a bioreversible group which comprises a conjugating moiety, and a bioreversible group which comprises a conjugating moiety and a hydrophilic group,
wherein the conjugating moiety may further comprise a protecting group.

3. The polynucleotide construct of claim 1, wherein the bioreversible group comprises a thioester.

4. The polynucleotide construct of claim 1, wherein the component (i) allows the polynucleotide construct to be transported intracellularly, whereupon the bioreversible group is cleaved.

5. The polynucleotide construct of claim 1, further comprising at least one third component (iii) selected from the group consisting of a small molecule, a peptide, a polypeptide, a carbohydrate, a neutral organic polymer, a positively charged polymer, a therapeutic agent, a targeting moiety, an endosomal escape moiety, or any combination thereof, wherein the component (iii) is conjugated to an internucleotide bridging group or terminal nucleotide group intracellularly bioreversible group.

6. The polynucleotide construct of claim 5, wherein component (iii) is the small molecule.

7. The polynucleotide construct of claim 6, wherein the small molecule is an optionally substituted $C_{1-6}$ alkyl.

8. The polynucleotide construct of claim 1, having the structure of Formula II:

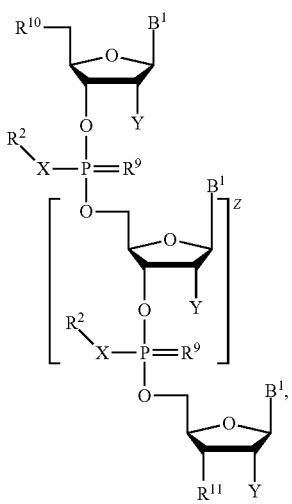

Formula II or a salt thereof,
wherein one $R^2$ comprises the component (i),
Z is a number from 0 to 150;
each $B^1$ is individually a nucleobase;
each X is individually selected from the group consisting of O, S and $NR^5$;
each Y is individually selected from the group consisting of a hydrogen, hydroxyl, halo, optionally substituted $C_{1-6}$ alkoxy, or a protected hydroxyl group;
each $R^2$ is individually absent, a hydrogen, or a first bioreversible group that comprises a hydrophilic functional group, a second bioreversible group that comprises a conjugating moiety, or a third bioreversible group that comprises an auxiliary moiety selected from the group consisting of a small molecule, a peptide, a polypeptide, a carbohydrate, a neutral organic polymer, a positively charged polymer, a therapeutic agent, a targeting moiety, and combinations thereof, wherein the conjugating moiety or the hydrophilic functional is optionally protected with a protecting group;
each $R^5$ is individually selected from the group consisting of H, an optionally substituted $C_{1-6}$ alkyl, S-pivaloyl thioethanol, hydroxyl, an optionally substituted $C_{1-6}$ alkoxy, an optionally substituted $C_{3-8}$ cycloalkyl, an optionally substituted $C_{6-12}$ aryl, and an optionally substituted $C_{2-9}$ heterocyclyl;
each $R^9$ is individually either an O or S;
$R^{10}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, a 5' cap, phosphothiol, an optionally substituted $C_{1-6}$ alkyl, an amino containing group, a biotin containing group, a digoxigenin containing group, a cholesterol containing group, a dye containing group, a quencher containing group, a peptide, a polypeptide, a carbohydrate, a neutral organic polymer, a positively charged polymer, a therapeutic agent, a targeting moiety, an endosomal escape moiety, and any combination thereof; and
$R^{11}$ is selected from the group consisting of H, hydroxyl, optionally substituted $C_{1-6}$ alkoxy, a protected hydroxyl group, a monophosphate, a disphosphate, a triphosphate, a tetraphosphate, a pentaphosphate, an optionally substituted $C_{1-6}$ alkyl, an amino containing group, a biotin containing group, a digoxigenin containing group, a cholesterol containing group, a dye containing group, a quencher containing group, a phosphothiol, a peptide, a polypeptide, a carbohydrate, a neutral organic polymer, a positively charged polymer, a therapeutic agent, a targeting moiety, an endosomal escape moiety, and any combination thereof.

9. The polynucleotide construct of claim 8, comprising one or more strands of nucleotides having the structure of Formula II(a):

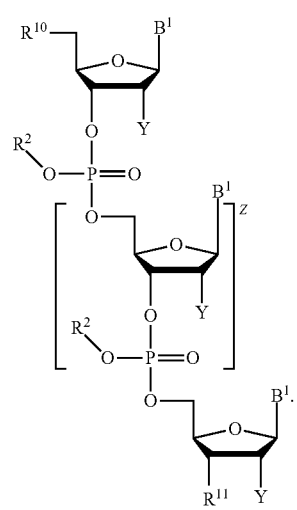

Formula II(a)

10. The polynucleotide construct of claim 8, wherein, for a nucleotide in which $R^2$ is the first, second, or third bioreversible group, Y is F or OMe.

11. The polynucleotide construct of claim 1, wherein component (i) bound to the bioreversible group has structural Formula V:

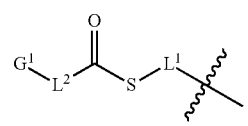

Formula V wherein,
$G^1$ is the peptide, the polypeptide, the carbohydrate, the neutral organic polymer, the positively charged polymer, the therapeutic agent, the targeting moiety, or combination thereof;
$L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and
$L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S.

12. The polynucleotide construct of claim 2, wherein component (ii) bound to the bioreversible group has structural Formula V:

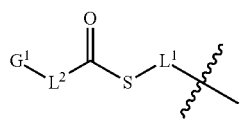

Formula V wherein,
- $G^1$ is the conjugating moiety or hydrophilic functional group;
- $L^1$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and
- $L^2$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S.

13. The polynucleotide construct of claim 11, wherein $L^1$ is

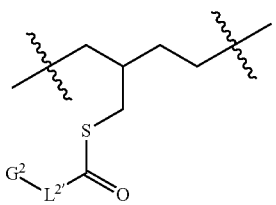

wherein $L^{2'}$ is a covalent bond or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S;

$G^2$ is a conjugating moiety, a hydrophilic functional group, a small molecule, a peptide, a polypeptide, a carbohydrate, a neutral organic polymer, a positively charged polymer, a therapeutic agent, a targeting moiety, or combination thereof.

14. The polynucleotide construct of claim 11, further comprising a structure of Formula V':

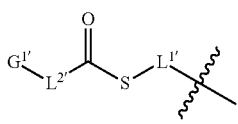

Formula V' wherein,
- $G^{1'}$ is a conjugating moiety, a hydrophilic functional group, a small molecule, a peptide, a polypeptide, a carbohydrate, a neutral organic polymer, a positively charged polymer, a therapeutic agent, a targeting moiety, or combination thereof;
- $L^{1'}$ is an optionally substituted $C_{2-10}$ alkylene, optionally substituted $C_{2-10}$ alkenylene, or optionally substituted $C_{2-10}$ alkynylene, wherein each of alkylene, alkenylene, or alkynylene is optionally interrupted with 1-10 heteroatoms selected from O, N, and S; and
- $L^{2'}$ is a covalent bond, or is selected from optionally substituted $C_{1-10}$ alkylene; optionally substituted $C_{2-10}$ alkenylene; optionally substituted $C_{2-10}$ alkynylene; and optionally substituted $C_{6-12}$ arylene, wherein each of alkylene, alkenylene, or alkynylene is optionally interrupted with 1-10 heteroatoms selected from O, N, and S.

15. The polynucleotide construct of claim 11, wherein structural Formula V is selected from the group consisting of:

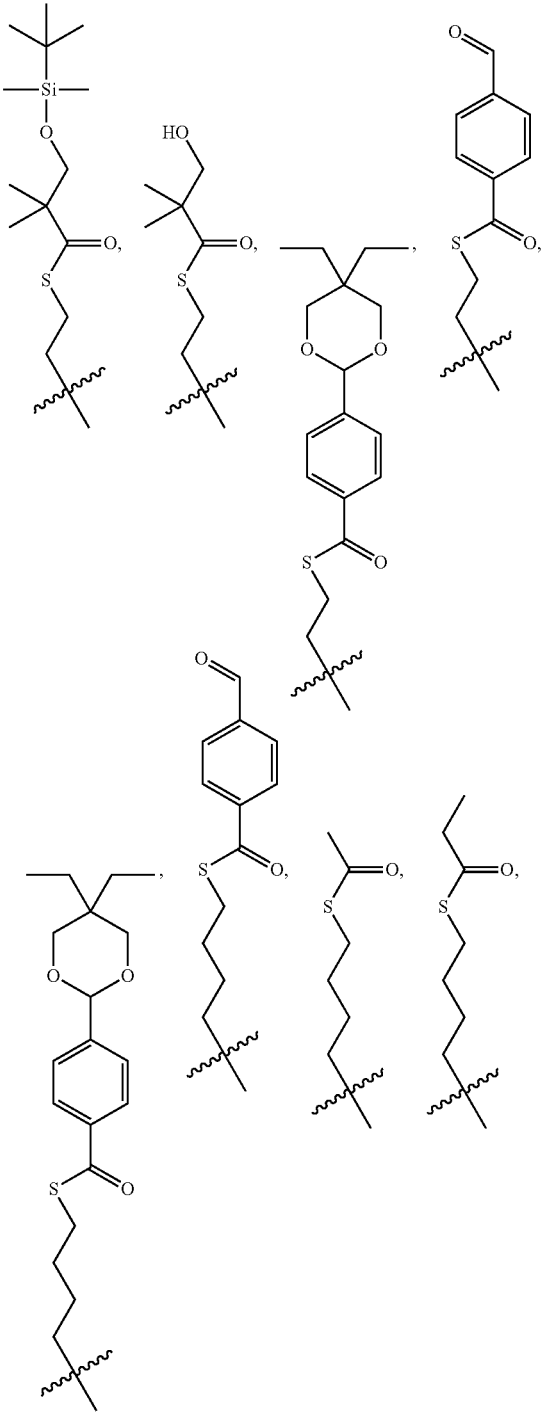

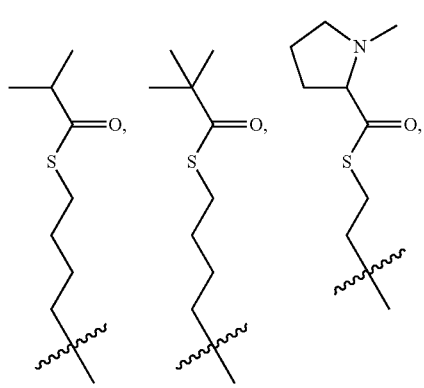
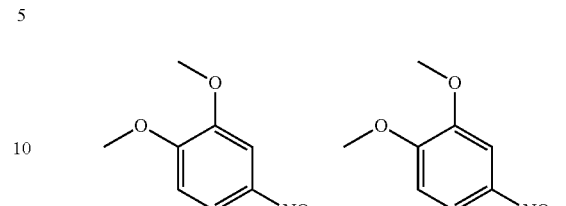
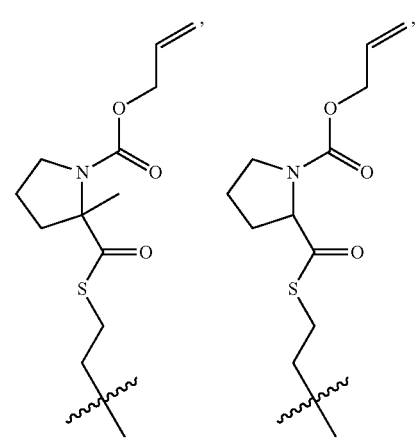
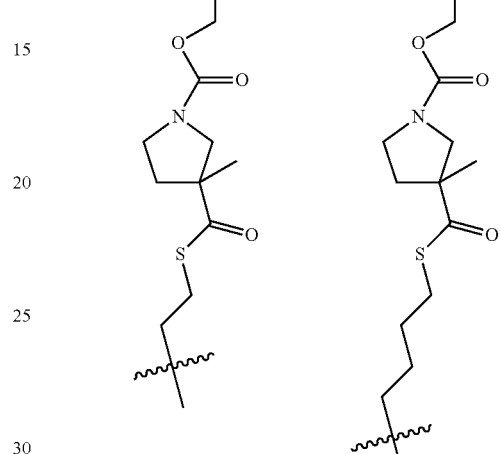
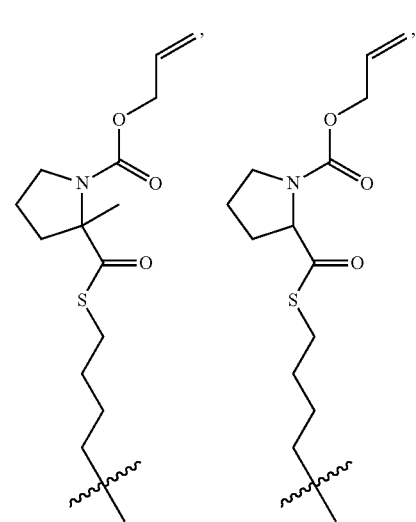
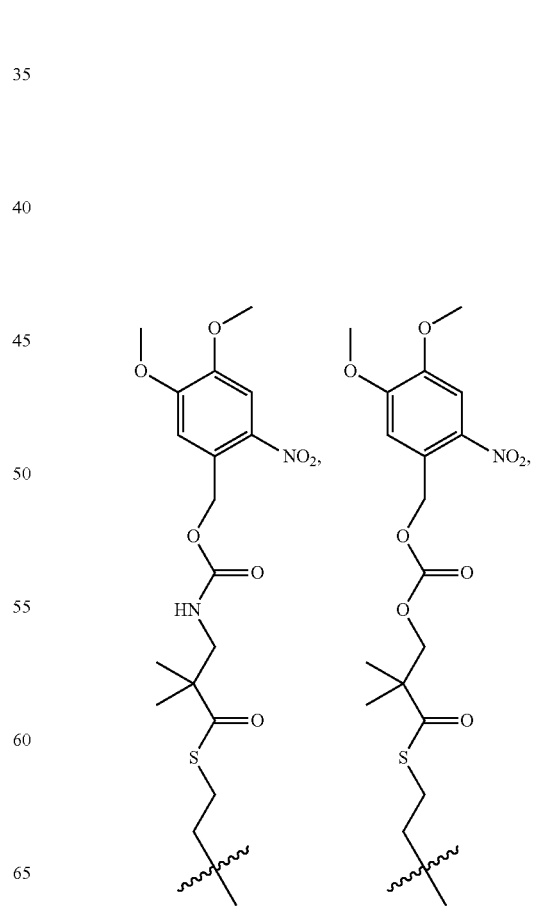

-continued
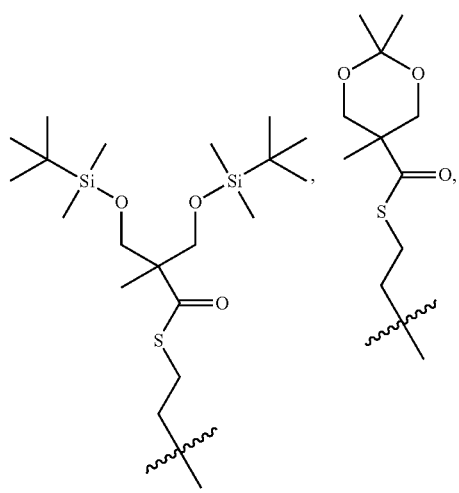
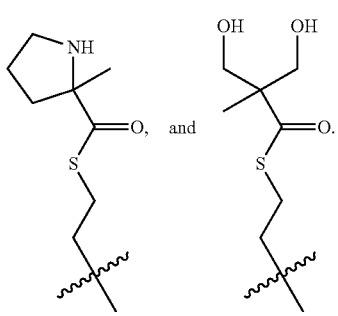 [SMILES: *CCSC(=O)C1(C)CCCN1 ; "and" ; *CCSC(=O)C(C)(CO)CO]
16. The polynucleotide construct of claim 15, wherein structural Formula V is selected from the group consisting of:
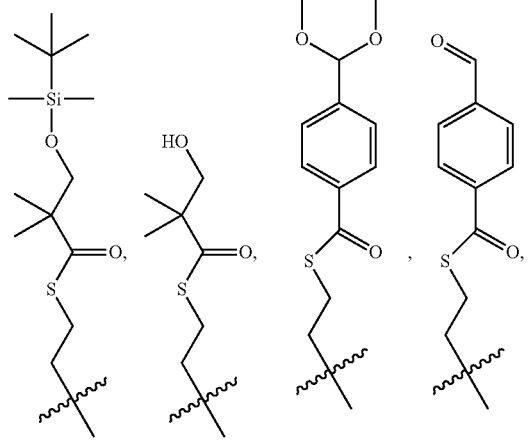
-continued
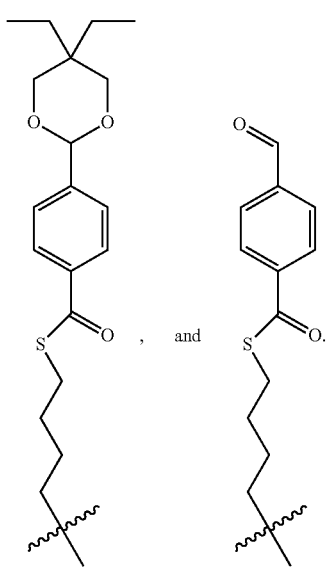
17. The polynucleotide construct of claim 15, wherein structural Formula V is selected from the group consisting of:
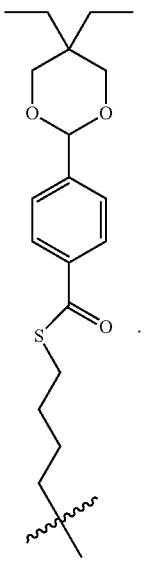
18. The polynucleotide construct of claim 15, wherein structural Formula V is selected from the group consisting of:

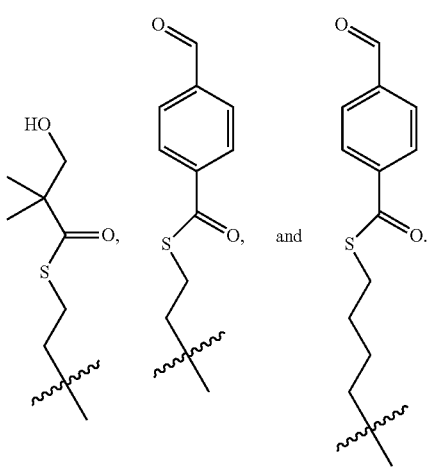

19. The polynucleotide construct of claim 14, wherein structural Formula V' is selected from the group consisting of:

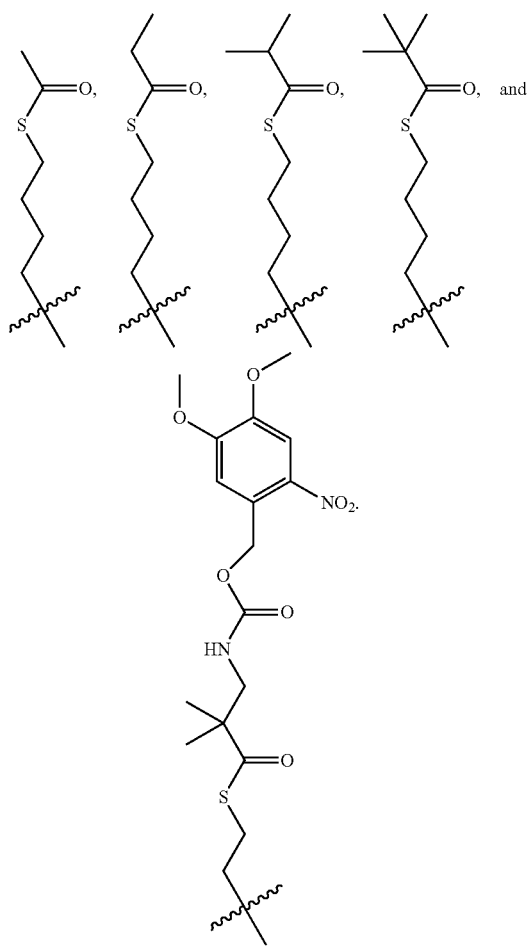

20. The polynucleotide construct of claim 11, wherein $L^1$ is optionally substituted $C_{2-10}$ alkylene.

21. The polynucleotide construct of claim 11, wherein $L^2$ is a covalent bond.

22. The polynucleotide construct of claim 11, wherein $L^2$ is optionally substituted $C_{1-10}$ alkylene or optionally substituted $C_{6-12}$ arylene.

23. The polynucleotide construct of claim 12 or 20, wherein $G^1$ is hydroxyl.

24. The polynucleotide construct of claim 12 or 20, wherein $G^1$ is the conjugating moiety.

25. The polynucleotide construct of claim 24, wherein the conjugating moiety is —CHO, thiol, or —$N_3$.

26. The polynucleotide construct of claim 11, wherein $G^1$ comprises the peptide, the polypeptide, the carbohydrate, the neutral organic polymer, the positively charged polymer, the therapeutic agent, the targeting moiety, or any combination thereof.

27. The polynucleotide construct of claim 26, wherein $L^2$ is not a bond, and $G^1$ is bound to $L^2$ via a bond formed by a reaction selected from the group consisting of a pericyclic reaction; an alkylation or arylation of a hydroxyl, thiol, or amino moiety; and a reaction of a hydroxyl, thiol, or amino nucleophile with an electrophile.

28. The polynucleotide construct of claim 26, wherein $L^2$ is not a bond, and $G^1$ is bound to $L^2$ via an amide bond, a sulfonamide bond, a carboxylic ester, a thioester, an optionally substituted $C_{6-12}$ aryl or $C_{2-9}$ heteroaryl; an imine; a hydrazone; an oxime; or a succinimide.

29. The polynucleotide construct of claim 12, wherein one or more hydrophilic functional groups and/or conjugating moieties of $R^2$ are protected with protecting groups.

30. The polynucleotide construct of claim 1, wherein the peptide, the polypeptide, the protein, the carbohydrate, the neutral organic polymer, the positively charged polymer, the therapeutic agent, the targeting moiety, or combination thereof is linked to the bioreversible group through a condensation reaction with an aldehyde conjugating moiety to form an imine, enamine or hydrazone bond.

31. The polynucleotide construct of claim 1, wherein the peptide, the polypeptide, the protein, the carbohydrate, the neutral organic polymer, the positively charged polymer, the therapeutic agent, the targeting moiety, or combination thereof is linked to the bioreversible group by one or more nitrogen containing conjugating moieties having the structure of Formula III:

(Formula III)

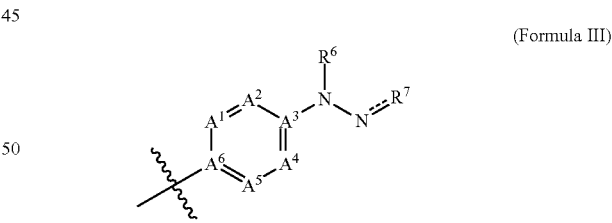

wherein,
$A^1$, $A^2$, $A^4$, and $A^5$ are each individually a N or $CR^8$;
$A^3$ and $A^6$ are C;
$R^6$-$R^7$ are each individually a H, optionally substituted $C_{1-6}$ alkyl, optionally substituted $C_{2-6}$ alkenyl, optionally substituted imine, and optionally substituted enamine; and
each $R^8$ is individually a H, optionally substituted $C_{1-6}$ alkyl, optionally substituted $C_{2-6}$ alkenyl, optionally substituted $C_{2-6}$ alkynyl, halo, hydroxyl, —CHO, optionally substituted $C_{1-6}$ acyl, carboxyl, cyano, nitro, optionally substituted amino, thiol, optionally substituted $C_{2-9}$ heterocyclyl, optionally substituted $C_{6-12}$ aryl, optionally substituted $C_{3-8}$ cycloalkyl, and optionally substituted $C_{4-8}$ cycloalkenyl.

32. The polynucleotide construct of claim 1, wherein at most 90% of the bioreversible groups are linked to the peptide, the polypeptide, the carbohydrate, the neutral organic polymer, the positively charged polymer, the therapeutic agent, the targeting moiety, or combination thereof.

33. The polynucleotide construct of claim 1, wherein the component (i) comprises a delivery domain.

34. The polynucleotide construct of claim 33, wherein the delivery domain comprises one or more a peptide transduction domains (PTDs).

35. The polynucleotide construct of claim 33, wherein the one or more PTDs are linked to the bioreversible group through an imine, enamine, or hydrazone bond.

36. The polynucleotide construct of claim 33, wherein the one or more PTDs are linked to the bioreversible group to form structural Formula IV:

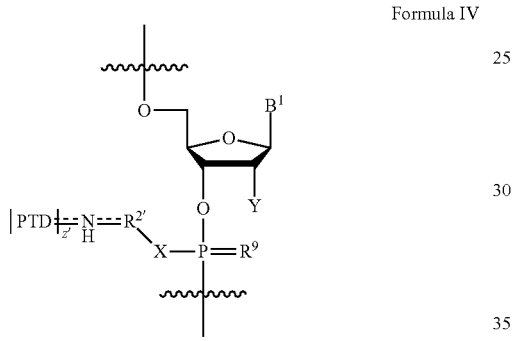

Formula IV wherein,
R$^{2'}$ is the residue of the bioreversible group bound to the PTD;
z' is a number from 1 to 10, wherein, when z' is greater than 1, the PTDs may be linked together through poly($C_{1-4}$ alkyleneoxide) groups having 1-10 repeating units.

37. The polynucleotide construct of claim 34, wherein the one or more PTDs are trans-activating transcriptional activator (TAT) peptides.

38. The polynucleotide construct of claim 34, wherein the PTD is linked to the bioreversible group through a complementary conjugating moiety comprising the structure of Formula III:

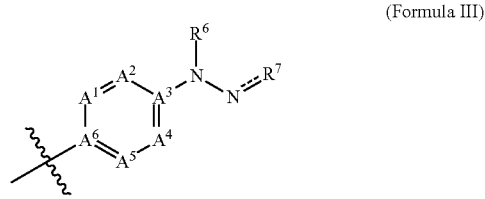

(Formula III)

wherein,
A$^1$, A$^2$, A$^4$, and A$^5$ are each individually a N or CR$^8$;
A$^3$ and A$^6$ are C;

R$^6$-R$^7$ are each individually a H, optionally substituted $C_{1-6}$ alkyl, optionally substituted $C_{2-6}$ alkenyl, optionally substituted imine, and optionally substituted enamine; and each R$^8$ is individually a H, optionally substituted $C_{1-6}$ alkyl, optionally substituted $C_{2-6}$ alkenyl, optionally substituted $C_{2-6}$ alkynyl, halo, hydroxyl, —CHO, optionally substituted $C_{1-6}$ acyl, carboxyl, cyano, nitro, optionally substituted amino, thiol, optionally substituted $C_{2-9}$ heterocyclyl, optionally substituted $C_{6-12}$ aryl, optionally substituted $C_{3-8}$ cycloalkyl, and optionally substituted $C_{4-8}$ cycloalkenyl.

39. The polynucleotide construct of claim 38, wherein the bioreversible group prior to conjugation is selected from the group consisting of:

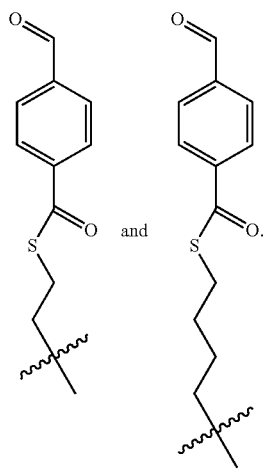 [SMILES: *CCSC(=O)c1ccc(C=O)cc1 ; "and" ; *CCCCSC(=O)c1ccc(C=O)cc1]

40. The polynucleotide construct of claim 34, wherein the PTD comprises a cationic peptide sequence having 5-10 arginine and/or lysine residues over 5-15 amino acids.

41. The polynucleotide construct of claim 34, wherein the PTD comprises the sequence RKKRRQRRR (SEQ ID NO:1).

42. The polynucleotide construct of claim 33, wherein component (i) comprises a protein transduction domain (PTD) conjugated to poly(ethylene glycol) (PEG) having 1-10 repeating units.

43. The polynucleotide construct of claim 42, wherein component (i) comprises a sequence selected from the group consisting of:
PEG-(PTD);
GG-(PTD)-PEG-(PTD);
PEG-(PTD)-PEG-(PTD);
GG-(PTD)-PEG-PEG-PEG-(PTD);
PEG-(PTD)-PEG-PEG-PEG-(PTD);
GG-(PTD)-PEG-(PTD)-PEG-(PTD); and
GG-(PTD)-PEG-PEG-PEG-(PTD)-PEG-PEG-PEG-(PTD);
wherein PEG is a poly(ethyleneglycol) linker having one to ten repeat units.

44. The polynucleotide construct of claim 1, wherein component (i) comprises the targeting moiety.

45. The polynucleotide construct of claim 44, wherein the targeting moiety is a ligand, carbohydrate, antibody, FAb, ScFv, or single-domain antibody.

46. The polynucleotide construct of claim 1, comprising a non-natural nucleobase.

47. The polynucleotide construct of claim 1, comprising only naturally occurring nucleobases.

48. The polynucleotide construct of claim 46, wherein the nucleobases are selected from cytosine, guanine, adenine, uracil, and thymidine.

49. The polynucleotide construct of claim 1, wherein no more than 75% of the nucleotides in the polynucleotide construct have the bioreversible group.

50. The polynucleotide construct of claim 1, wherein no more than 65% of the nucleotides in the polynucleotide construct have the bioreversible group.

51. The polynucleotide construct of claim 1, wherein the polynucleotide construct comprises 2-40 bioreversible groups.

52. The polynucleotide construct of claim 1, wherein the polynucleotide construct has 10-32 nucleotides.

53. The polynucleotide construct of claim 1, having the structure of Formula II(a):

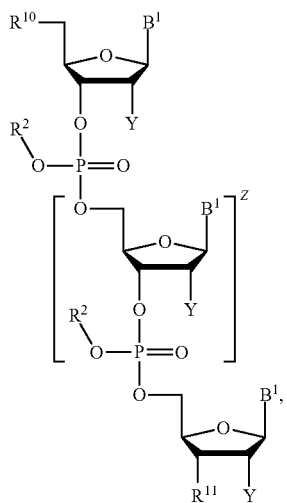

Formula II(a)

or a salt thereof,
wherein one $R^2$ comprises the component (i),
Z is a number from 0 to 30;
each $B^1$ is individually a nucleobase;
each Y is individually selected from the group consisting of hydroxyl, halo, or $C_{1-6}$ alkoxy;
each $R^2$ is individually absent; a hydrogen; a group of formula V:

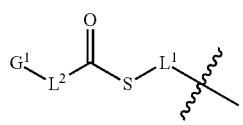

Formula V wherein,
$G^1$ is the peptide, the polypeptide, the neutral organic polymer, or any combination thereof;
$L^1$ is an optionally substituted $C_{2-6}$ alkylene, optionally substituted $C_{2-6}$ alkenylene, or optionally substituted $C_{2-6}$ alkynylene, wherein each of alkylene, alkenylene, or alkynylene is optionally interrupted with 1 or 2 oxygen atoms; and
$L^2$ is a covalent bond, or is selected from optionally substituted $C_{1-6}$ alkylene; optionally substituted $C_{2-6}$ alkenylene; optionally substituted $C_{2-6}$ alkynylene; and optionally substituted $C_{6-10}$ arylene; or
a group of Formula V':

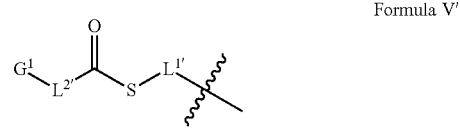

Formula V' wherein,
$G^{1'}$ is hydrogen, aldehyde or protected aldehyde, hydroxyl, protected hydroxyl, amine, protected amine, or 5- or 6-membered heterocyclic amine optionally substituted with a protecting group or $C_{1-6}$ alkyl;
$L^{1'}$ is an optionally substituted $C_{2-6}$ alkylene, wherein each alkylene is optionally interrupted with 1 or 2 oxygen atoms; and
$L^{2'}$ is a covalent bond, or is selected from optionally substituted $C_{1-6}$ alkylene and optionally substituted $C_{6-10}$ arylene;
$R^{10}$ is selected from the group consisting of H, hydroxyl, optionally substituted $C_{1-6}$ alkoxy, a protected hydroxyl group, a monophosphate, a disphosphate, a triphosphate, a 5' cap, phosphothiol, an optionally substituted $C_{1-6}$ alkyl, an amino containing group, a peptide, a polypeptide, a neutral organic polyemer, and any combination of peptide, polypeptide, and neutral organic polymer; and
$R^{11}$ is selected from the group consisting of H, hydroxyl, optionally substituted $C_{1-6}$ alkoxy, a protected hydroxyl group, a monophosphate, a disphosphate, a triphosphate, an optionally substituted $C_{1-6}$ alkyl, a peptide, a polypeptide, a neutral organic polyemer, and any combination of peptide, polypeptide, and neutral organic polymer.

54. The polynucleotide construct of claim 53, wherein, for a nucleotide in which $R^2$ is a group of formula V or V', Y is F or OMe.

55. The polynucleotide construct of claim 53, wherein structural Formula V' is selected from the group consisting of:

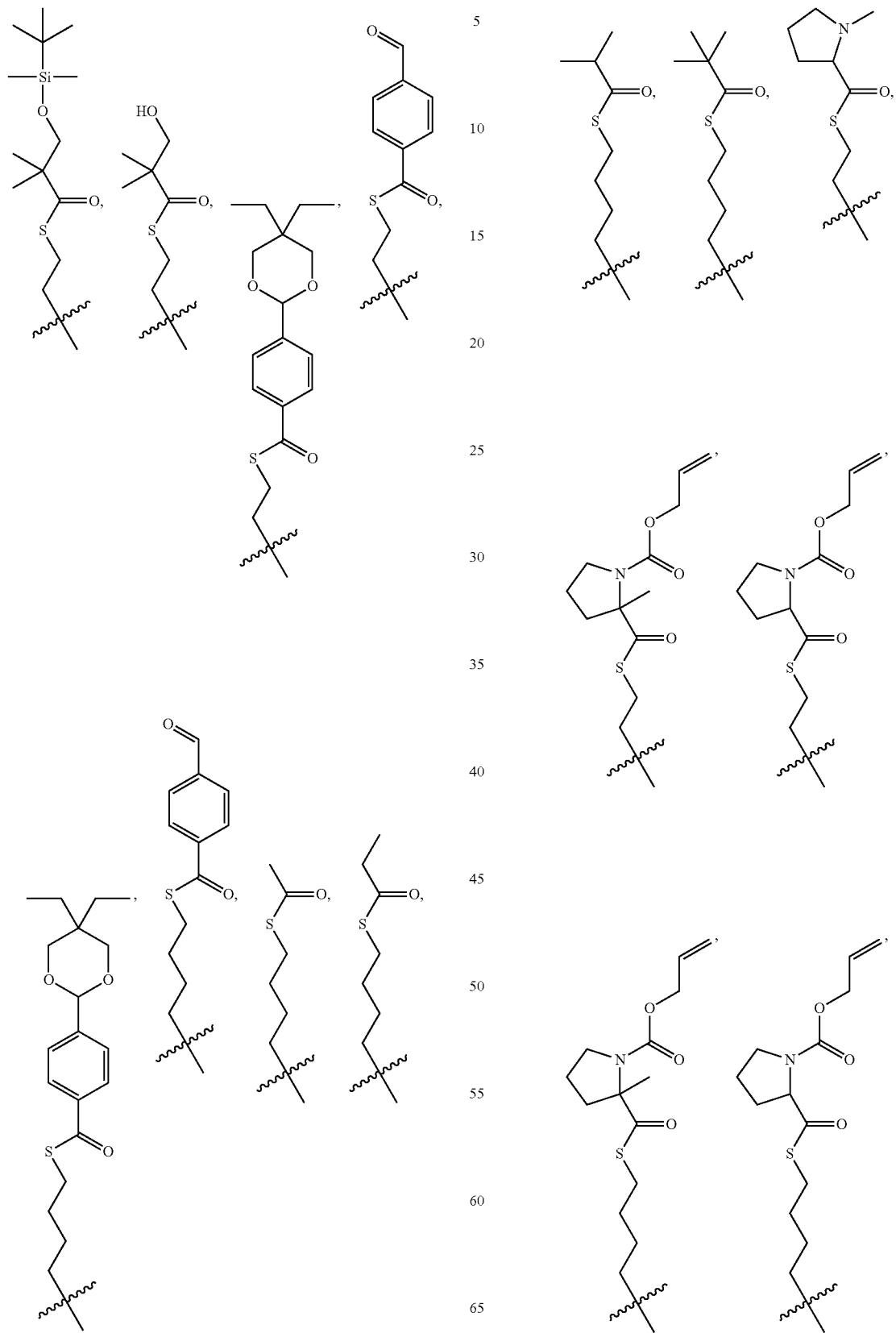

131
-continued

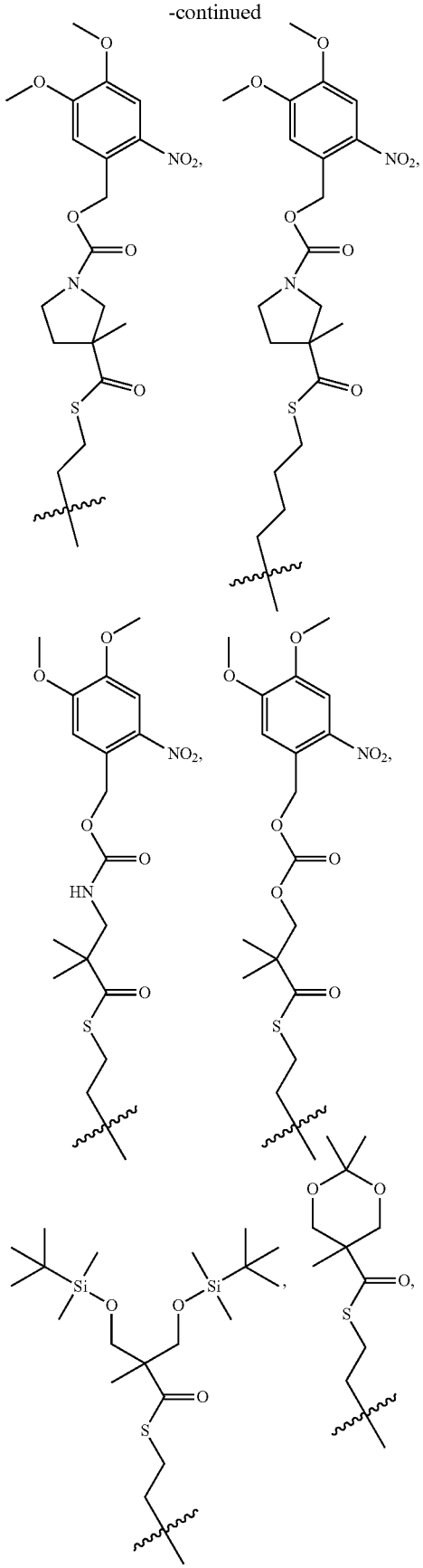

132
-continued

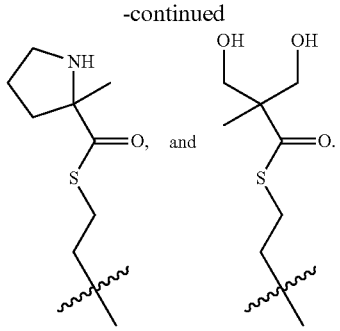

56. The polynucleotide construct of claim 53, wherein $G^1$ comprises a delivery domain.

57. The polynucleotide construct of claim 56, wherein the delivery domain comprises one or more a peptide transduction domains (PTDs).

58. The polynucleotide construct of claim 53, wherein the neutral organic polymer of $G^1$, $R^{10}$, or $R^{11}$ is poly(ethyleneglycol).

59. A hybridized polynucleotide comprising the polynucleotide construct of claim 1 hybridized to a complementary polynucleotide.

60. The polynucleotide of claim 59, wherein the complementary polynucleotide comprises an intracellularly bioreversible group conjugated to an internucleotide bridging group or a terminal nucleotide group.

61. The polynucleotide of claim 59, wherein no more than 75% of the total number of nucleotides have bioreversible groups.

62. The polynucleotide of claim 59, wherein the hybridized polynucleotide is a siRNA.

63. The polynucleotide of claim 62, wherein a polynucleotide construct comprising a component (i) selected from the group consisting of a peptide, a polypeptide, a carbohydrate, a neutral organic polymer, a positively charged polymer, a therapeutic agent, a targeting moiety, and any combination thereof, is the guide strand, and the complementary polynucleotide is the passenger strand, wherein component (i) is linked to the polynucleotide construct through a bioreversible group attached to an internucleotide bridging group.

64. The polynucleotide of claim 63, wherein the passenger strand comprises a phosphotriester having a moiety that is not cleavable by an intracellular enzyme.

65. The polynucleotide of claim 64, wherein the moiety that is not cleavable by the intracellular enzyme is optionally substituted $C_{1-6}$ alkyl.

66. A pharmaceutical composition comprising the polynucleotide construct or polynucleotide of claim 1 and a pharmaceutically acceptable excipient.

67. A method of reducing the expression of a protein, comprising administering the construct or hybridized polynucleotide of claim 1 to a cell in an amount sufficient to induce an antisense or RNAi mediated reduction of gene expression.

* * * * *